United States Patent
Lipford et al.

(10) Patent No.: US 9,428,536 B2
(45) Date of Patent: *Aug. 30, 2016

(54) IMMUNOSTIMULATORY G, U-CONTAINING OLIGORIBONUCLEOTIDES

(71) Applicant: Zoetis Belgium SA, Louvain-la-Neuve (BE)

(72) Inventors: Grayson B. Lipford, Watertown, MA (US); Stefan Bauer, Marburg-Michelbach (DE); Hermann Wagner, Eching (DE)

(73) Assignee: Zoetis Belgium SA, Louvain-la-Neuve (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/159,916

(22) Filed: Jan. 21, 2014

(65) Prior Publication Data

US 2014/0135487 A1 May 15, 2014

Related U.S. Application Data

(63) Continuation of application No. 11/368,333, filed on Mar. 3, 2006, now Pat. No. 8,658,607, which is a continuation of application No. 10/407,952, filed on Apr. 4, 2003, now Pat. No. 8,153,141.

(60) Provisional application No. 60/421,966, filed on Oct. 29, 2002, provisional application No. 60/370,515, filed on Apr. 4, 2002.

(51) Int. Cl.
| | |
|---|---|
| A61K 45/00 | (2006.01) |
| A61K 39/00 | (2006.01) |
| A61K 9/127 | (2006.01) |
| A61K 47/00 | (2006.01) |
| C12N 5/00 | (2006.01) |
| C12N 5/02 | (2006.01) |
| C07H 21/02 | (2006.01) |
| A61K 31/205 | (2006.01) |
| A61K 31/7105 | (2006.01) |
| A61K 31/7115 | (2006.01) |
| A61K 31/712 | (2006.01) |
| A61K 31/7125 | (2006.01) |
| A61K 39/395 | (2006.01) |
| A61K 45/06 | (2006.01) |
| C12N 15/117 | (2010.01) |
| G01N 33/566 | (2006.01) |
| A61K 39/39 | (2006.01) |

(52) U.S. Cl.
CPC .............. *C07H 21/02* (2013.01); *A61K 31/205* (2013.01); *A61K 31/712* (2013.01); *A61K 31/7105* (2013.01); *A61K 31/7115* (2013.01); *A61K 31/7125* (2013.01); *A61K 39/39* (2013.01); *A61K 39/395* (2013.01); *A61K 45/06* (2013.01); *C12N 15/117* (2013.01); *G01N 33/566* (2013.01); *A61K 2039/55555* (2013.01); *C12N 2310/17* (2013.01)

(58) Field of Classification Search
USPC .................. 424/278.1, 184.1, 450; 435/325; 514/44 R See application file for complete search history.

(56) References Cited

U.S. PATENT DOCUMENTS

| | | |
|---|---|---|
| 3,906,092 A | 9/1975 | Hilleman et al. |
| 4,469,863 A | 9/1984 | Ts'o et al. |
| 4,689,338 A | 8/1987 | Gerster |
| 4,929,624 A | 5/1990 | Gerster et al. |
| 5,023,243 A | 6/1991 | Tullis |
| 5,238,944 A | 8/1993 | Wick et al. |
| 5,266,575 A | 11/1993 | Gerster et al. |
| 5,268,376 A | 12/1993 | Gester |
| 5,346,905 A | 9/1994 | Gerster |
| 5,352,784 A | 10/1994 | Nikolaides et al. |
| 5,389,640 A | 2/1995 | Gerster et al. |
| 5,395,937 A | 3/1995 | Nikolaides et al. |
| 5,482,936 A | 1/1996 | Lindstrom |
| 5,488,039 A | 1/1996 | Masor et al. |
| 5,492,899 A | 2/1996 | Masor et al. |
| 5,494,916 A | 2/1996 | Lindstrom et al. |
| 5,525,612 A | 6/1996 | Gerster |
| 5,602,109 A | 2/1997 | Masor et al. |
| 5,612,060 A | 3/1997 | Alexander |
| 5,663,153 A | 9/1997 | Hutcherson et al. |
| 5,700,590 A | 12/1997 | Masor et al. |
| 5,712,256 A | 1/1998 | Kulkarni et al. |
| 5,723,335 A | 3/1998 | Hutcherson et al. |
| 6,039,969 A | 3/2000 | Tomai et al. |

(Continued)

FOREIGN PATENT DOCUMENTS

| | | |
|---|---|---|
| EP | 0092574 A1 | 11/1983 |
| EP | 0216133 A1 | 4/1987 |

(Continued)

OTHER PUBLICATIONS

[No Author Listed] Raw Materials for Cosmetics. Handbook for Cosmetics. Nov. 1, 1996. p. 126-144.

(Continued)

*Primary Examiner* — Maria Leavitt
(74) *Attorney, Agent, or Firm* — Wolf, Greenfield & Sacks, P.C.

(57) ABSTRACT

Compositions and methods relating to immunostimulatory RNA oligomers are provided. The immunostimulatory RNA molecules are believed to represent natural ligands of one or more Toll-like receptors, including Toll-like receptor 7 (TLR7) and Toll-like receptor 8 (TLR8). The compositions and methods are useful for stimulating immune activation. Methods useful for screening candidate immunostimulatory compounds are also provided.

7 Claims, 19 Drawing Sheets

(56) References Cited

U.S. PATENT DOCUMENTS

| | | |
|---|---|---|
| 6,110,929 A | 8/2000 | Gerster et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,239,116 B1 | 5/2001 | Krieg et al. |
| 6,339,068 B1 | 1/2002 | Davis et al. |
| 6,346,614 B1 | 2/2002 | Metelev et al. |
| 6,395,713 B1 | 5/2002 | Beigelman et al. |
| 6,399,630 B1 | 6/2002 | Macfarlane |
| 6,406,705 B1 | 6/2002 | Davis et al. |
| 6,429,199 B1 | 8/2002 | Krieg et al. |
| 6,479,504 B1 | 11/2002 | Macfarlane et al. |
| 6,514,948 B1 | 2/2003 | Raz et al. |
| 6,521,637 B2 | 2/2003 | Macfarlane |
| 6,562,798 B1 | 5/2003 | Schwartz et al. |
| 6,653,292 B1 | 11/2003 | Krieg et al. |
| 6,727,230 B1 | 4/2004 | Hutcherson et al. |
| 6,821,957 B2 | 11/2004 | Davis et al. |
| 6,852,705 B2 | 2/2005 | Audonnet et al. |
| 6,943,240 B2 | 9/2005 | Bauer et al. |
| 6,949,520 B1 | 9/2005 | Hartmann et al. |
| 7,001,890 B1 | 2/2006 | Wagner et al. |
| 7,223,741 B2 | 5/2007 | Krieg |
| 7,271,156 B2 | 9/2007 | Krieg et al. |
| 7,354,711 B2 | 4/2008 | Macfarlane |
| 7,402,572 B2 | 7/2008 | Krieg et al. |
| 7,410,975 B2 | 8/2008 | Lipford et al. |
| 7,488,490 B2 | 2/2009 | Davis et al. |
| 7,517,861 B2 | 4/2009 | Krieg et al. |
| 7,524,828 B2 | 4/2009 | Krieg et al. |
| 7,534,772 B2 | 5/2009 | Weiner et al. |
| 7,566,703 B2 | 7/2009 | Krieg et al. |
| 7,569,553 B2 | 8/2009 | Krieg |
| 7,576,066 B2 | 8/2009 | Krieg |
| 7,585,847 B2 | 9/2009 | Bratzler et al. |
| 7,605,138 B2 | 10/2009 | Krieg |
| 7,615,539 B2 | 11/2009 | Uhlmann et al. |
| 7,674,777 B2 | 3/2010 | Krieg et al. |
| 7,713,529 B2 | 5/2010 | Krieg et al. |
| 7,723,022 B2 | 5/2010 | Krieg et al. |
| 7,723,500 B2 | 5/2010 | Krieg et al. |
| 7,776,344 B2 | 8/2010 | Hartmann et al. |
| 7,795,235 B2 | 9/2010 | Krieg et al. |
| 7,807,803 B2 | 10/2010 | Krieg |
| 7,820,379 B2 | 10/2010 | Bauer et al. |
| 7,879,810 B2 | 2/2011 | Krieg et al. |
| 7,888,327 B2 | 2/2011 | Krieg et al. |
| 7,935,675 B1 | 5/2011 | Krieg et al. |
| 7,956,043 B2 | 6/2011 | Krieg et al. |
| 7,998,492 B2 | 8/2011 | Ahluwalia et al. |
| 8,008,266 B2 | 8/2011 | Krieg et al. |
| 8,153,141 B2 | 4/2012 | Lipford et al. |
| 8,658,607 B2 | 2/2014 | Lipford et al. |
| 2001/0044416 A1 | 11/2001 | McCluskie et al. |
| 2002/0064515 A1 | 5/2002 | Krieg et al. |
| 2002/0091097 A1 | 7/2002 | Bratzler et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0198165 A1 | 12/2002 | Bratzler et al. |
| 2003/0026782 A1 | 2/2003 | Krieg et al. |
| 2003/0026801 A1 | 2/2003 | Weiner et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0064945 A1 | 4/2003 | Akhtar et al. |
| 2003/0087848 A1 | 5/2003 | Bratzler et al. |
| 2003/0091599 A1 | 5/2003 | Davis et al. |
| 2003/0100527 A1 | 5/2003 | Krieg et al. |
| 2003/0104523 A1 | 6/2003 | Bauer et al. |
| 2003/0139364 A1 | 7/2003 | Krieg et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0170273 A1 | 9/2003 | O'Hagan et al. |
| 2003/0181406 A1 | 9/2003 | Schetter et al. |
| 2003/0191079 A1 | 10/2003 | Krieg et al. |
| 2003/0212026 A1 | 11/2003 | Krieg et al. |
| 2003/0219157 A1 | 11/2003 | Koide et al. |
| 2003/0224010 A1 | 12/2003 | Davis et al. |
| 2003/0232074 A1 | 12/2003 | Lipford et al. |
| 2004/0009949 A1 | 1/2004 | Krieg |
| 2004/0014779 A1 | 1/2004 | Gorden et al. |
| 2004/0030118 A1 | 2/2004 | Wagner et al. |
| 2004/0052763 A1 | 3/2004 | Mond et al. |
| 2004/0053880 A1 | 3/2004 | Krieg |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0091491 A1 | 5/2004 | Kedl et al. |
| 2004/0092472 A1 | 5/2004 | Krieg |
| 2004/0106568 A1 | 6/2004 | Krieg et al. |
| 2004/0131628 A1 | 7/2004 | Bratzler et al. |
| 2004/0132685 A1 | 7/2004 | Krieg et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0247662 A1 | 12/2004 | Dow et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0013812 A1 | 1/2005 | Dow et al. |
| 2005/0032734 A1 | 2/2005 | Krieg et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0048072 A1 | 3/2005 | Kedl et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartmann et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |

(56) References Cited

U.S. PATENT DOCUMENTS

| | | |
|---|---|---|
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250723 A1 | 11/2005 | Hoerr et al. |
| 2005/0250726 A1 | 11/2005 | Krieg et al. |
| 2005/0256073 A1 | 11/2005 | Lipford et al. |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188913 A1 | 8/2006 | Krieg et al. |
| 2006/0211639 A1 | 9/2006 | Bratzler et al. |
| 2006/0211644 A1 | 9/2006 | Krieg et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0224210 A1 | 9/2007 | Krieg et al. |
| 2007/0232622 A1 | 10/2007 | Lipford et al. |
| 2008/0009455 A9 | 1/2008 | Krieg et al. |
| 2008/0026011 A1 | 1/2008 | Krieg et al. |
| 2008/0031936 A1 | 2/2008 | Krieg et al. |
| 2008/0045473 A1 | 2/2008 | Uhlmann et al. |
| 2008/0113929 A1 | 5/2008 | Lipford et al. |
| 2008/0226649 A1 | 9/2008 | Schetter et al. |
| 2009/0017021 A1 | 1/2009 | Davis et al. |
| 2009/0060927 A1 | 3/2009 | Wagner et al. |
| 2009/0117132 A1 | 5/2009 | Readett et al. |
| 2009/0137519 A1 | 5/2009 | Krieg et al. |
| 2009/0142362 A1 | 6/2009 | Krieg et al. |
| 2009/0155212 A1 | 6/2009 | Bratzler et al. |
| 2009/0155307 A1 | 6/2009 | Davis et al. |
| 2009/0191188 A1 | 7/2009 | Krieg et al. |
| 2009/0202575 A1 | 8/2009 | Krieg et al. |
| 2009/0214578 A1 | 8/2009 | Bauer |
| 2009/0306177 A1 | 12/2009 | Uhlmann et al. |
| 2009/0311277 A1 | 12/2009 | Krieg |
| 2010/0125101 A1 | 5/2010 | Krieg et al. |
| 2010/0166780 A1 | 7/2010 | Debelak et al. |
| 2010/0183639 A1 | 7/2010 | Uhlmann et al. |
| 2010/0285041 A1 | 11/2010 | Uhlmann et al. |
| 2011/0033421 A1 | 2/2011 | Hartmann et al. |
| 2011/0081366 A1 | 4/2011 | Krieg |
| 2011/0098456 A1 | 4/2011 | Uhlmann et al. |
| 2011/0135605 A1 | 6/2011 | Ahluwalia et al. |
| 2011/0201672 A1 | 8/2011 | Krieg et al. |

FOREIGN PATENT DOCUMENTS

| | | |
|---|---|---|
| EP | 0286224 A2 | 10/1988 |
| EP | 0360257 A2 | 3/1990 |
| EP | 1167378 A2 | 1/2002 |
| JP | 09323979 | 12/1997 |
| WO | WO-93/23569 A1 | 11/1993 |
| WO | WO-98/32462 A1 | 7/1998 |
| WO | WO-98/40100 A1 | 9/1998 |
| WO | WO-99/37151 A1 | 7/1999 |
| WO | WO-99/56755 A1 | 11/1999 |
| WO | WO-99/58118 A2 | 11/1999 |
| WO | WO-99/61056 A2 | 12/1999 |
| WO | WO-00/06588 A1 | 2/2000 |
| WO | WO-00/14217 A2 | 3/2000 |
| WO | WO-00/67023 A1 | 11/2000 |
| WO | WO-01/22972 A2 | 4/2001 |
| WO | WO-01/22990 A2 | 4/2001 |
| WO | WO-0136641 A2 | 5/2001 |
| WO | WO-01/45750 A1 | 6/2001 |
| WO | WO-0193902 A2 | 12/2001 |
| WO | WO-02/22125 A1 | 3/2002 |
| WO | WO-02/22809 A2 | 3/2002 |
| WO | WO-02/069369 A2 | 9/2002 |
| WO | WO-03/043572 A2 | 5/2003 |
| WO | WO-03/059381 A2 | 7/2003 |
| WO | WO-03/086280 A2 | 10/2003 |
| WO | WO-2004/007743 A2 | 1/2004 |
| WO | WO-2004/026888 A2 | 4/2004 |
| WO | WO-2004/094671 A2 | 11/2004 |
| WO | WO-2006/063252 A2 | 6/2006 |
| WO | WO-2006/092607 A1 | 9/2006 |
| WO | WO-2008/030455 A2 | 3/2008 |
| WO | WO-2008/033432 A2 | 3/2008 |
| WO | WO-2008/039538 A2 | 4/2008 |
| WO | WO-2008/068638 A2 | 6/2008 |
| WO | WO-2008/139262 A2 | 11/2008 |

OTHER PUBLICATIONS

Aderem A et al., Toll-like receptors in the induction of the innate immune response. Nature. Aug. 17, 2000;406(6797):782-7.

Agrawal, S. and Kandimalla, E.R. Role of Toll-like receptors in antisense and siRNA [corrected] Nat Biotechnol. Dec. 2004;22(12)1 533-7. Review. Erratum in: Nat Biotechnol. Jan. 2005;23(1):1 17.

Alexopoulou L et al., Recognition of double-stranded RNA and activation of NF-kappaB by Toll-like receptor 3. Nature. Oct. 18, 2001 ;413(6857):732-8.

Aliprantis AO et al., Cell activation and apoptosis by bacterial lipoproteins through toll-like receptor-2. Science. Jul. 30, 1999;285(5428):736-9.

Audouy et al., Cationic lipid-mediated transfection in vitro and in vivo (review). Mol Membr Biol. Apr.-Jun. 2001 ; 18(2):129-43.

Bauer S et al., Human TLR9 confers responsiveness to bacterial DNA via species-specific CpG motif recognition. Proc Natl Acad Sci U S A. Jul. 31, 2001;98(16):9237-42.

Beaucage SL et al., Deoxynucleoside phosporamidites—a new class of key intermediates for deoxypolynucleotide synthesis. Tetrahedron Lett. 1981;22:1859-62.

Beignon, A.S. et al., Endocytosis of HIV-1 activates plasmacytoid dendritic cells via Toll-like receptor-viral RNA interactions. J Clin Invest. Nov. 2005;115(11):3265-75. Epub Oct. 13, 2005.

Berger SL et al., Inhibition of intractable nucleases with ribonucleoside—vanadyl complexes: isolation of messenger ribonucleic acid from resting lymphocytes. Biochemistry. Nov. 13, 1979;18(23):5143-9.

Beutler et al., Synergy between TLR2 and TLR4: a safety mechanism. Blood Cells Mol Dis. Jul.-Aug. 2001 ;27(4):728-30.

Boczkowski D et al., Dendritic cells pulsed with Rna are potent antigen-presenting cells in vitro and in vivo. J Exp Med. Aug. 1, 1996;184(2):465-72.

Bragonzi et al., Comparison between cationic polymers and lipids in mediating systemic gene delivery to the lungs. Gene Ther. Dec. 1999;6(12):1995-2004.

Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules inToll-like receptor 2 signaling. J Immunol. Jul. 15, 2001;167(2):987-94.

(56) References Cited

OTHER PUBLICATIONS

Bushell et al., Hijacking the translation apparatus by RNA viruses. J Cell Biol. Aug. 5, 2002;158(3):395-9. Epub Aug. 5, 2002.
Cella et al., Maturation, activation, and protection of dendritic cells induced by double-stranded RNA. J Exp Med. Mar. 1, 1999;189(5):821-9.
Chisholm et al., High efficiency gene transfer into mammalian cells. Chapter 1 in DNA Cloning 4: Mammalian Systems. A Practical Approach. Ed. Glover et al. IRL Press, 1995:1-41.
Chiu et al., siRNA function in RNAi: a chemical modification analysis. RNA. Sep. 2003;9(9):1034-48.
Chuang TH et al., Cloning and characterization of a sub-family of human toll-like receptors:: hTLR7, hTLR8 and hTLR9. Eur Cytokine Netw. Sep. 2000;11(3):372-8.
Clark et al., Cationic lipid-mediated gene transfer: current concepts. Curr Opin Mol Ther. Apr. 1999;1(2):158-76.
Cohen PA et al.; CD4+ T-cells from mice immunized to syngeneic sarcomas recognize distinct, non-shared tumor antigens. Cancer Res. Feb. 15, 1994;54(4)1 055-8.
Crook et al., Inclusion of cholesterol in DOTAP transfection complexes increases the delivery of DNA to cells in vitro in the presence of serum. Gene Ther. Jan. 1998;5(1)137-43.
Czauderna et al., Structural variations and stabilising modifications of synthetic siRNAs in mammalian cells. Nucleic Acids Res. Jun. 1, 2003;31(11):2705-16.
Diamantstein, T. et al., Specific binding of poly(I)-poly(C) to the membrane of murine B lymphocyte subsets. Eur J Immunol. Dec. 1978;8(12):896-9.
Diebold SS et al., Innate antiviral responses by means of TLR7-mediated recognition of single-RNA. Science. Mar. 5, 2004;303(5663):1529-31. Epub Feb. 19, 2004.
Djukanovic R et al., Mucosal inflammation in asthma. Am Rev Respir Dis. Aug. 1990;142(2):434-57.
Elliott et al., Probing the TRAP-RNA interaction with nucleoside analogs. RNA. Oct. 1999;5(10):1277-89.
Ewel, C.H. et al., Polyinosinic-polycytidylic acid complexed with poly-L-lysine and carboxymethylcellulose in combination with interleukin 2 in patients with cancer: clinical and immunological effects. Cancer Res. Jun. 1, 1992;52(11):3005-10.
Fanslow, W.C. et al., Effect of nucleotide restriction and supplementation on resistance to experimental murine candidiasis. JPEN J Parenter Enteral Nutr. Jan.-Feb. 1988;12(1):49-52 Abstract.
Feigner et al., Enhanced gene delivery and mechanism studies with a novel series of cationic lipid formulations. J Biol Chem. Jan. 28, 1994;269(4):2550-61.
Forsbach et al., Identification of RNA sequence motifs stimulating sequence-specific TLR8-dependent immune responses. J Immunol. Mar. 15, 2008;180(6):3729-38.
Fraley R et al., New generation liposomes: the engineering of an efficient vehicle for intracellular delivery of nucleic acids. Trends Biochem Sci. Mar. 1981;6:77-80.
Froehler BC et al., Synthesis of DNA via deoxynucleoside H-phosphonate intermediates. Nucleic Acids Res. Jul. 11, 1986;14(13):5399-407.
Gaffney BL et al., Large-scale oligonucleotide synthesis by the H-phosphonate method. Tetrahedron Lett. 1988;29:2619-22.
Garegg et al., Nucleoside H-phosphonates. IV. Automated solid phase synthesis of oligoribonucleotides by the hydrogenphosphonate approach. Tetrahedron Lett. 1986; 27(34):4055-8.
Garegg PJ et al., Nucleoside H-phosphonates. III. Chemical synthesis of oligodeoxyribonucleotides by the hydrogenphosphonate method. Tetrahedron Lett. 1986;27:4051-4.
Ghisolfi-Nieto, L. et al., Nucleolin is a sequence-specific RNA-binding protein: characterization of targets on pre-ribosomal RNA. J Mol Biol. Jul. 5, 1996;260(1):34-53.
Goodchild J, Conjugates of oligonucleotides and modified oligonucleotides: a review of their synthesis and properties. Bioconjug Chem. May-Jun. 1990;1(3):165-87.
Goodman MG et al., Selective modulation of elements of the immune system by low molecular weight nucleosides. J Pharmacol Exp Ther. Sep. 1995;274(3):1552-7.
Goodman, M.G. Cellular and biochemical studies of substituted guanine ribonucleoside immunostimulants. Immunopharmacology. Jan.-Feb. 1991;21(1):51-68.
Goodman, M.G. Mechanism of synergy between T cell signals and C8-substituted guanine nucleosides in humoral immunity: B lymphotropic cytokines induce responsiveness to 8-mercaptoguanosine. J Immunol. May 1, 1986;136(9):3335-40.
Goodman, M.G. Role of salvage and phosphorylation in the immunostimulatory activity of C8-substituted guanine ribonucleosides. J Immunol. Oct. 1, 1988;141(7):2394-9.
Gregoriadis G, Liposomes for drugs and vaccines. Trends Biotechnol. 1985;3(9):235-41.
Hacker H et al., Immune cell activation by bacterial CpG-DNA through myeloid differentiation marker 88 and tumor necrosis factor receptor-associated factor (TRAF)6. J Exp Med. Aug. 21, 2000;192(4):595-600.
Hadden, J.W. and Smith, D.L. Immunopharmacology. Immunomodulation and immunotherapy. JAMA. Nov. 25, 1992;268(20):2964-9.
Hadden, J.W. Immunostimulants. Trends Pharmacol Sci. May 1993;14(5):169-74.
Hamada et al., Effects on RNA interference in gene expression (RNAi) in cultured mammalian cells of mismatches and the introduction of chemical modifications at the 3'-ends of siRNAs. Antisense Nucleic Acid Drug Dev. Oct. 2002;12(5):301-9.
Handa et al., Structural basis for recognition of the tra mRNA precursor by the Sex-lethal protein. Nature. Apr. 15, 1999;398(6728):579-85.
Hannon GJ, RNA interference. Nature Jul. 11, 2002;418(6894):244-51.
Hayashi F et al., The innate immune response to bacterial flagellin is mediated by Toll-like receptor 5. Nature. Apr. 26, 2001;410(6832):1099-103.
Heil F et al., Species-specific recognition of single-stranded RNA via toll-like receptor 7 and 8. Science. Mar. 5, 2004;303(5663):1526-9. Epub Feb. 19, 2004.
Hellen CU et al., Internal ribosome entry sites in eukaryotic mRNA molecules. Genes Dev. Jul. 1, 2001;15(13):1593-612.
Hemmi H et al., A Toll-like receptor recognizes bacterial DNA. Nature. Dec. 7, 2000;408(6813):740-5.
Hemmi H et al., Small anti-viral compounds activate immune cells via the TLR7 MyD88-dependent signaling pathway. Nat Immunol. Feb. 2002;3(2):196-200.
Hoerr et al., In vivo application of RNA leads to induction of specific cytotoxic T lymphocytes and antibodies. Eur J Immunol. Jan. 2000;30(1):1-7.
Hornung, V. et al., Sequence-specific potent induction of IFN-alpha by short interfering RNA in plasmacytoid dendritic cells through TLR7. Nat Med. Mar. 2005;11(3):263-70. Epub Feb. 20, 2005.
Hoshino K et al., Cutting edge: Toll-like receptor 4 (TLR4)-deficient mice are hyporesponsive to lipopolysaccharide: evidence for TLR4 as the lps gene product. J Immunol. Apr. 1, 1999;162(7):3749-52.
Hunt et al., unr, a cellular cytoplasmic RNA-binding protein with five cold-shock domains, is required for internal initiation of translation of human rhinovirus RNA. Genes Dev. Feb. 15, 1999;13(4):437-48.
Ito et al., Interferon-alpha and interleukin-12 are induced differentially by Toll-like receptor 7 ligands in human blood dendritic cell subsets. J Exp Med. Jun. 3, 2002;195(11):1507-12.
Jackson RJ et al., Internal initiation of translation in eukaryotes: the picornavirus paradigm and beyond. RNA. Dec. 1995;1(10):985-1000.
Jackson RJ et al., The novel mechanism of initiation of picornavirus RNA translation. Trends Biochem Sci. Dec. 1990;15(12):477-83.
Jeffries AC et al., A catalytic 13-mer ribozyme. Nucleic Acids Res Feb. 25, 1989;17(4):1371-7.

(56) References Cited

OTHER PUBLICATIONS

Johnson et al., Non-specific resistance against microbial infections induced by polyribonucleotide complexes. In: Immunopharmacology of infection diseases: Vaccine adjuvants and modulators of non-specific resistance. 1987: 291-301.
Jurk M et al., Human TLR7 or TLR8 independently confer responsiveness to the antiviral compound R-848. Nat Immunol. Jun. 2002;3(6):499.
Jyonouchi, H. et al., Immunomodulating actions of nucleotides: enhancement of immunoglobulin production by human cord blood lymphocytes. Pediatr Res. Nov. 1993;34(5):565-71.
Kadowacki N et al., Subsets of human dendritic cell precursors express different toll-like receptors and respond to different microbial antigens. J Exp Med. Sep. 17, 2001;194(6):863-9.
Kaisho et al., Toll-like receptors as adjuvant receptors. Biochim Biophys Acta. Feb. 13, 2002;1589(1):1-13. Review.
Kariko et al., Small interfering RNAs mediate sequence-independent gene suppression and induce immune activation by signaling through toll-like receptor 3. J Immunol. Jan. 1, 2004;172(11):6545-9.
Kariko, K. et al., Suppression of RNA recognition by Toll-like receptors: the impact of nucleoside modification and the evolutionary origin of RNA. Immunity. Aug. 2005;23(2):165-75.
Katsel et al., Eukaryotic gene transfer with liposomes: effect of differences in lipid structure. Biotechnol Annu Rev. 2000,5:197-220.
Khan, A.L. et al., Polyadenylic-polyuridylic acid enhances the natural cell-mediated cytotoxicity in patients with breast cancer undergoing mastectomy. Surgery. Sep. 1995;118(3):531-8.
Kieft JS et al., The hepatitis C virus internal ribosome entry site adopts an ion-dependent tertiary fold: J Mol Biol. Sep. 24, 1999;292(3):513-29.
Klinck R et al., A potential RNA drug target in the hepatitis C virus internal ribosomal entry site. RNA. Oct. 2000;6(10):1423-31.
Lacour, J. Clinical trials using polyadenylic-polyuridylic acid as an adjuvant to surgery in treating different human tumors. J Biol Response Mod. Oct. 1985;4(5):538-43.
Liu et al., Cationic liposome-mediated intravenous gene delivery. J Biol Chem. Oct. 20, 1995;270(42):24864-70.
Löseke, S et al., In vitro-generated viral double-stranded RNA in contrast to polyinosinic:polycytidylic acid induces interferon-alpha in human plasmacytoid dendritic cells. Scand J Immunol. Apr. 2006;63(4):264-74.
Lund JM et al., Recognition of single-stranded RNA viruses by Toll-like receptor 7. Proc Natl Acad Sci U S A. Apr. 13, 2004;101(15):5598-603. Epub Mar. 19, 2004.
Marino et al., Determination of γ and stereospecific assignment of H5' protons by measurement of $^2J$ and $^3J$ coupling constants in uniformly $^{13}C$ labeled RNA. J Am Chem Soc. 1996;118:4388-95.
Medzhitov R et al., MyD88 is an adaptor protein in the hToll/IL-1 receptor family signaling pathways. Mol Cell. Aug. 1998;2(2):253-8.
Michelson, A.M. et al., Poly(A).poly(U) as adjuvant in cancer treatment distribution and pharmacokinetics in rabbits. Proc Soc Exp Biol Med. Jun. 1985;179(2):180-6.
Mitchell DA et al., RNA transfected dendritic cells as cancer vaccines. Curr Opin Mol Ther. Apr. 2000;2(2):176-81.
O'Neill, TLR-7 and antiviral immunity. Trends in Immunology. May 2002;23(5):234.
Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.
Ozinsky A et al., The repertoire for pattern recognition of pathogens by the innate immune system is defined by cooperation between toll-like receptors. Proc Natl Acad Sci U S A. Dec. 5, 2000;97(25):13766-71.
Park, S.J. et al., Adjuvant effect of polyadenylic.polyuridylic acid on antibody production of recombinant hepatitis B surface antigen in mice. Int J Immunopharmacol. Jun. 1995;17(6):513-6.

Parrish et al., Functional anatomy of a dsRNA trigger: differential requirement for the two trigger strands in RNA interference. Mol Cell. Nov. 2000;6(5):1077-87.
Pilipenko et al., Cell-specific proteins regulate viral RNA translation and virus-induced disease. EMBO J. Dec. 3, 2001;20(23):6899-908.
Poltorak A et al., Defective LPS signaling in C3H/HeJ and C57BL/10ScCr mice: mutations in Tl r4 gene. Science. Dec. 11, 1998;282(5396):2085-8.
Prasmickaite L et al., Intracellular metabolism of a 2'-O-methyl-stabilized ribozyme after uptake by DOTAP transfection or as free ribozyme. A study by capillary electrophoresis. Nucleic Acids Res Sep. 15, 1998;26(18):4241-8.
Puskas RS et al., Effect of ribonucleoside-vanadyl complexes on enzyme-catalyzed reactions central to recombinant deoxyribonucleic acid technology. Biochemistry. Sep. 14, 1982;21 (19):4602-8.
Reitz AB et al., Small-molecule immunostimulants. Synthesis and activity of 7,8-disubstituted. Synthesis and activity of 7,8-disubstituted guanosines and structurally related compounds. J Med Chem. Oct. 14, 1994: 37(21):3561-78.
Reynolds JE et al., Internal initiation of translation of hepatitis C virus RNA: the ribosome entry site is at the authentic initiation codon. RNA. Sep. 1996;2(9):867-78.
Robinson DS et al., Predominant TH2-like bronchoalveolar T-lymphocyte population in atopic asthma. N Engl J Med. Jan. 30, 1992;326(5):298-304.
Russell RS et al., Deficient dimerization of human immunodeficiency virus type 1 RNA caused by mutations of the u5 RNA sequences. Virology. Nov. 10, 2002;303(1):152-63.
Scheel B et al., Immunostimulating capacities of stabilized RNA molecules. Eur J Immunol. Feb. 2004;34(2):537-47.
Schroeder SJ et al., Factors affecting the thermodynamic stability of small asymmetric internal loops in RNA. Biochemistry Aug. 24, 2000; 39(31):9257-74.
Sioud, M. Innate sensing of self and non-self RNAs by Toll-like receptors. Trends Mol Med. Apr. 2006;12(4):167-76. Epub Mar. 10, 2006.
Sioud, M. Single-stranded small interfering RNA are more immunostimulatory than their double-stranded counterparts: a central role for 2'-hydroxyl uridines in immune responses. Eur J Immunol. May 2006;36(5):1222-30.
Sledz et al., Activation of the interferon system by short-interfering RNAs. Nat Cell Biol. Sep. 2003;5(9):834-9. Epub Aug. 24, 2003.
Srinivasan et al., Continuum solvent studies of the stability of RNA hairpin loops and helices. J Biomol Struct Dyn. Dec. 1998;16(3):671-82.
Stull, R.A. and Szoka, F.C. Jr. Antigene, ribozyme and aptamer nucleic acid drugs: progress and prospects. Pharm Res. Apr. 1995;12(4):465-83.
Sugiyama, T. et al., CpG RNA: identification of novel single-stranded RNA that stimulates human CD14+CD11c+ monocytes. J Immunol. Feb. 15, 2005;174(4):2273-9. Erratum in: J Immunol. Aug. 1, 2005;175(3):2026.
Takeuchi O et al., Discrimination of bacterial lipoproteins by Toll-like receptor 6. Int Immunol. Jul. 2001 ;13(7):933-40.
Talmadge, J.E. et al., Immunomodulatory effects in mice of polyinosinic-polycytidylic acid complexed with poly-L-lysine and carboxymethylcellulose. Cancer Res. Mar. 1985;45(3)1058-65.
Thompson, R.A. and Ballas, Z. K. Lymphokine-activated killer (LAK) cells. V. 8-Mercaptoguanosine as an IL-2-sparing agent in LAK generation. J Immunol. Nov. 15, 1990;145(10):3524-31.
Tsai et al., In vitro selection of RNA epitopes using autoimmune patient serum. J Immunol. Feb. 1, 1993;150(3):1137-45.
Tsui et al., Molecular dynamics simulations of nucleic acids with a generalized born solvation model. J Am Chem Soc. 2000; 22:2489-98. doi: 10.1021/ja9939385.
Tursz et al., Poly A-poly U: An updated review. In: Immunotherapeutic Prospects of Infectious Diseases. 1990:263-72.
Uhlmann E et al., Antisense oligonucleotides: a new therapeutic principle. Chem Rev. 1990;90:543-84.
Underhill et al., Toll-like receptors: key mediators of microbe detection. Curr Opin Immunol. Feb. 2002;14(1):103-10.

(56) References Cited

OTHER PUBLICATIONS

Vabulas et al., Heat shock proteins as ligands of toll-like receptors. Curr Top Microbiol Immunol. 2002;270:169-84.

Vollmer et al., Immune stimulation mediated by autoantigen binding sites within small nuclear RNAs involves Toll-like receptors 7 and 8. J Exp Med. Dec. 5, 2005;202(11):1575-85.

Vollmer, J. et al., Modulation of CpG oligodeoxynucleotide-mediated immune stimulation by locked nucleic acid (LNA). Oligonucleotides. 2004 Spring;14(1):23-31.

Wagner RW et al., Potent and selective inhibition of gene expression by an antisense heptanucleotide. Nat Biotechnol. Jul. 1996;14(7):840-4.

Whitmore, M.M. et al., Synergistic activation of innate immunity by double-stranded RNA and CpG DNA promotes enhanced antitumor activity. Cancer Res. Aug. 15, 2004;64(16):5850-60.

Wiltrout, R.H. et al., Immunomodulation of natural killer activity by polyribonucleotides. J Biol Response Mod. Oct. 1985;4(5):512-7.

Wollmer et al., Immune stimulation mediated by autoantigen binding sites within small nuclear RNAs involves Toll-like receptors 7 and 8 JEM.COPYRGT. The Rockefeller University Press vol. 202, No. 11, Dec. 5, 2005 1575-85.

Yoshimura A et al., Cutting edge: recognition of Gram-positive bacterial cell wall components by the innate immune system occurs via Toll-like receptor 2. J Immunol. Jul. 1, 1999;163(1):1-5.

Zhao Q et al., Site of chemical modifications in CpG containing phosphorothioate oligodeoxynucleotide modulates its immunostimulatory activity. Bioorg Med Chem Lett. Dec. 20, 1999;9(24):3453-8.

TLR7 AND TLR8 HAVE TLR9-LIKE NUCLEIC ACID BINDING DOMAINS

```
CXXC motif          GNCXXCXXXXXXCXXC
Human TLR9          GNCRRCDHAPNPCMEC
Murine TLR9         GNCRRCDHAPNPCMIC
Human TLR8          GNCPRCFNAPFPCVPC
Human TLR7          GNCPRCYNAPFPCAPC MBD motif
          *         *    *  *  *              * *
MBD-1   V-X-R-XXXX-T-XX-R-X-D-X-Y-XXXXXXXXX-R-S
hTLR9   G-X-Q-XXXX-S-XX-K-X-D-X-Y-XXXXXXXXX-R-L
hTLR8   H-X-K-XXXX-T-XX-R-X-D-X-D-XXXXXXXXX-D-L
hTLR7   E-X-R-XXXX-S-XX-R-X-D-X-L-XXXXXXXXX-K-L
```

Fig. 9

```
                         SEQUENCE LISTING

<160> NUMBER OF SEQ ID NOS: 39

<210> SEQ ID NO 1
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 1
guugugguug ugguugug                                                    18

<210> SEQ ID NO 2
<211> LENGTH: 10
<212> TYPE: RNA
<213> ORGANISM: Artificial sequence
<220> FEATURE:
<223> OTHER INFORMATION: Synthetic oligonucleotide

<400> SEQUENCE: 2
guagugugug                                                             10

<210> SEQ ID NO 3
<211> LENGTH: 12
<212> TYPE: RNA
<213> ORGANISM: Artificial sequence
<220> FEATURE:
<223> OTHER INFORMATION: Synthetic oligonucleotide

<400> SEQUENCE: 3
gucuguugug ug                                                          12

<210> SEQ ID NO 4
<211> LENGTH: 27
<212> TYPE: RNA
<213> ORGANISM: Artificial sequence
<220> FEATURE:
<223> OTHER INFORMATION: Synthetic oligonucleotide

<400> SEQUENCE: 4
gccgaguagu guugggucgc gaaaggc                                          27

<210> SEQ ID NO 5
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 5
attgaagagt ttgatcatgg ctcagattga acg                                   33

<210> SEQ ID NO 6
<211> LENGTH: 27
```

```
<212> TYPE: DNA
<213> ORGANISM: Artificial sequence
<220> FEATURE:
<223> OTHER INFORMATION: Synthetic oligonucleotide

<400> SEQUENCE: 6
taaggaggtg atccaaccgc aggttcc                                         27

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
tccatgacgt tcctgatgct                                                 20

<210> SEQ ID NO 8
<211> LENGTH: 26
<212> TYPE: RNA
<213> ORGANISM: Artificial sequence
<220> FEATURE:
<223> OTHER INFORMATION: Synthetic oligonucleotide

<400> SEQUENCE: 8
uccgcaaugg acgaaagucu gacgga                                          26

<210> SEQ ID NO 9
<211> LENGTH: 26
<212> TYPE: RNA
<213> ORGANISM: Artificial sequence
<220> FEATURE:
<223> OTHER INFORMATION: Synthetic oligonucleotide

<400> SEQUENCE: 9
gagaugggug cgagagcguc aguauu                                          26

<210> SEQ ID NO 10
<211> LENGTH: 40
<212> TYPE: RNA
<213> ORGANISM: Artificial sequence
<220> FEATURE:
<223> OTHER INFORMATION: Synthetic oligonucleotide

<400> SEQUENCE: 10
cacacacugc uuaagcgcuu gccugcuuaa guagugugug                           40

<210> SEQ ID NO 11
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: combined DNA/RNA sequence
<220> FEATURE:
<221> NAME/KEY: misc_feature
<222> LOCATION: (1)..(8)
<223> OTHER INFORMATION: RNA sequence
<220> FEATURE:
<221> NAME/KEY: misc_feature
<222> LOCATION: (9)..(14)
<223> OTHER INFORMATION: DNA sequence

<400> SEQUENCE: 11
```
gugugugugg gggg                                                          14

<210> SEQ ID NO 12
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: combined DNA/RNA sequence
<220> FEATURE:
<221> NAME/KEY: misc_feature
<222> LOCATION: (1)..(5)
<223> OTHER INFORMATION: DNA sequence
<220> FEATURE:
<221> NAME/KEY: misc_feature
<222> LOCATION: (6)..(13)
<223> OTHER INFORMATION: RNA sequence

<400> SEQUENCE: 12 gggggugug ugu                                                            13

<210> SEQ ID NO 13
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: combined DNA/RNA sequence
<220> FEATURE:
<221> NAME/KEY: misc_feature
<222> LOCATION: (1)..(8)
<223> OTHER INFORMATION: RNA sequence
<220> FEATURE:
<221> NAME/KEY: misc_feature
<222> LOCATION: (9)..(14)
<223> OTHER INFORMATION: DNA sequence

<400> SEQUENCE: 13
gugugugutt tttt                                                          14

<210> SEQ ID NO 14
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: combined DNA/RNA sequence
<220> FEATURE:
<221> NAME/KEY: misc_feature
<222> LOCATION: (1)..(5)
<223> OTHER INFORMATION: DNA sequence
<220> FEATURE:
<221> NAME/KEY: misc_feature
<222> LOCATION: (6)..(13)
<223> OTHER INFORMATION: RNA sequence

<400> SEQUENCE: 14
tttttgugug ugu                                                           13

<210> SEQ ID NO 15
<211> LENGTH: 24
<212> TYPE: DNA
<213> ORGANISM: Artificial sequence

```
<220> FEATURE:
<223> OTHER INFORMATION: Synthetic oligonucleotide

<400> SEQUENCE: 15
cacctctcat gctctgctct cttc                                              24

<210> SEQ ID NO 16
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 16
gctagaccgt ttccttgaac acctg                                             25

<210> SEQ ID NO 17
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 17
ctgcgctgct gcaagttacg gaatg                                             25

<210> SEQ ID NO 18
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 18
gcgcgaaatc atgacttaac gtcag                                             25

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: all deoxyribonucleic acid nucleotides

<400> SEQUENCE: 19 gugugguug ugguugug                                                      18

<210> SEQ ID NO 20
<211> LENGTH: 904
<212> TYPE: PRT
<213> ORGANISM: Homo sapiens

<400> SEQUENCE: 20

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
                20                  25                  30

Glu Val Ala Asp Cys Ser His Leu Lys Leu Thr Gln Val Pro Asp Asp
            35                  40                  45

Leu Pro Thr Asn Ile Thr Val Leu Asn Leu Thr His Asn Gln Leu Arg
        50                  55                  60
```

```
Arg Leu Pro Ala Ala Asn Phe Thr Arg Tyr Ser Gln Leu Thr Ser Leu
 65                  70                  75                  80

Asp Val Gly Phe Asn Thr Ile Ser Lys Leu Glu Pro Glu Leu Cys Gln
                 85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
                180                 185                 190

Ile Phe Ala Asn Ser Ser Leu Lys Lys Leu Glu Leu Ser Ser Asn Gln
            195                 200                 205

Ile Lys Glu Phe Ser Pro Gly Cys Phe His Ala Ile Gly Arg Leu Phe
        210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
                260                 265                 270

Trp Thr Asn Leu Thr Met Leu Asp Leu Ser Tyr Asn Asn Leu Asn Val
            275                 280                 285

Val Gly Asn Asp Ser Phe Ala Trp Leu Pro Gln Leu Glu Tyr Phe Phe
        290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
        355                 360                 365

Gly Ile Lys Ser Asn Met Phe Thr Gly Leu Ile Asn Leu Lys Tyr Leu
    370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
        435                 440                 445

Gly Gln Glu Trp Arg Gly Leu Glu Asn Ile Phe Glu Ile Tyr Leu Ser
    450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
```

-continued

```
                485                 490                 495
Ser Ser Pro Ser Pro Phe Gln Pro Leu Arg Asn Leu Thr Ile Leu Asp
            500                 505                 510
Leu Ser Asn Asn Ile Ala Asn Ile Asn Asp Asp Met Leu Glu Gly
            515                 520                 525
Leu Glu Lys Leu Glu Ile Leu Asp Leu Gln His Asn Asn Leu Ala Arg
            530                 535                 540
Leu Trp Lys His Ala Asn Pro Gly Gly Pro Ile Tyr Phe Leu Lys Gly
545                 550                 555                 560
Leu Ser His Leu His Ile Leu Asn Leu Glu Ser Asn Gly Phe Asp Glu
                565                 570                 575
Ile Pro Val Glu Val Phe Lys Asp Leu Phe Glu Leu Lys Ile Ile Asp
            580                 585                 590
Leu Gly Leu Asn Asn Leu Asn Thr Leu Pro Ala Ser Val Phe Asn Asn
            595                 600                 605
Gln Val Ser Leu Lys Ser Leu Asn Leu Gln Lys Asn Leu Ile Thr Ser
            610                 615                 620
Val Glu Lys Lys Val Phe Gly Pro Ala Phe Arg Asn Leu Thr Glu Leu
625                 630                 635                 640
Asp Met Arg Phe Asn Pro Phe Asp Cys Thr Cys Glu Ser Ile Ala Trp
                645                 650                 655
Phe Val Asn Trp Ile Asn Glu Thr His Thr Asn Ile Pro Glu Leu Ser
                660                 665                 670
Ser His Tyr Leu Cys Asn Thr Pro Pro His Tyr His Gly Phe Pro Val
                675                 680                 685
Arg Leu Phe Asp Thr Ser Ser Cys Lys Asp Ser Ala Pro Phe Glu Leu
            690                 695                 700
Phe Phe Met Ile Asn Thr Ser Ile Leu Leu Ile Phe Ile Phe Ile Val
705                 710                 715                 720
Leu Leu Ile His Phe Glu Gly Trp Arg Ile Ser Phe Tyr Trp Asn Val
                725                 730                 735
Ser Val His Arg Val Leu Gly Phe Lys Glu Ile Asp Arg Gln Thr Glu
            740                 745                 750
Gln Phe Glu Tyr Ala Ala Tyr Ile Ile His Ala Tyr Lys Asp Lys Asp
            755                 760                 765
Trp Val Trp Glu His Phe Ser Ser Met Glu Lys Glu Asp Gln Ser Leu
            770                 775                 780
Lys Phe Cys Leu Glu Glu Arg Asp Phe Glu Ala Gly Val Phe Glu Leu
785                 790                 795                 800
Glu Ala Ile Val Asn Ser Ile Lys Arg Ser Arg Lys Ile Ile Phe Val
                805                 810                 815
Ile Thr His His Leu Leu Lys Asp Pro Leu Cys Lys Arg Phe Lys Val
            820                 825                 830
His His Ala Val Gln Gln Ala Ile Glu Gln Asn Leu Asp Ser Ile Ile
            835                 840                 845
Leu Val Phe Leu Glu Glu Ile Pro Asp Tyr Lys Leu Asn His Ala Leu
            850                 855                 860
Cys Leu Arg Arg Gly Met Phe Lys Ser His Cys Ile Leu Asn Trp Pro
865                 870                 875                 880
Val Gln Lys Glu Arg Ile Gly Ala Phe Arg His Lys Leu Gln Val Ala
                885                 890                 895
Leu Gly Ser Lys Asn Ser Val His
            900
```

<210> SEQ ID NO 21
<211> LENGTH: 3057
<212> TYPE: DNA
<213> ORGANISM: Homo sapiens

<400> SEQUENCE: 21

| | | | | | |
|---|---|---|---|---|---|
| cactttcgag | agtgccgtct | atttgccaca | cacttccctg | atgaaatgtc | tggatttgga | 60 |
| ctaaagaaaa | aaggaaaggc | tagcagtcat | ccaacagaat | catgagacag | actttgcctt | 120 |
| gtatctactt | ttgggggggc | cttttgccct | ttgggatgct | gtgtgcatcc | tccaccacca | 180 |
| agtgcactgt | tagccatgaa | gttgctgact | gcagccacct | gaagttgact | caggtacccg | 240 |
| atgatctacc | cacaaacata | acagtgttga | accttaccca | taatcaactc | agaagattac | 300 |
| cagccgccaa | cttcacaagg | tatagccagc | taactagctt | ggatgtagga | tttaacacca | 360 |
| tctcaaaact | ggagccagaa | ttgtgccaga | aacttcccat | gttaaaagtt | ttgaacctcc | 420 |
| agcacaatga | gctatctcaa | cttctctgata | aaaccttttgc | cttctgcacg | aatttgactg | 480 |
| aactccatct | catgtccaac | tcaatccaga | aaattaaaaa | taatcccttt | gtcaagcaga | 540 |
| agaatttaat | cacattagat | ctgtctcata | atggcttgtc | atctacaaaa | ttaggaactc | 600 |
| aggttcagct | ggaaaatctc | caagagcttc | tattatcaaa | caataaaatt | caagcgctaa | 660 |
| aaagtgaaga | actggatatc | tttgccaatt | catctttaaa | aaaattagag | ttgtcatcga | 720 |
| atcaaattaa | agagttttct | ccagggtgtt | ttcacgcaat | tggaagatta | tttggcctct | 780 |
| ttctgaacaa | tgtccagctg | ggtcccagcc | ttacagagaa | gctatgtttg | gaattagcaa | 840 |
| acacaagcat | tcggaatctg | tctctgagta | acagccagct | gtccaccacc | agcaatacaa | 900 |
| ctttcttggg | actaaagtgg | acaaatctca | ctatgctcga | tctttcctac | aacaacttaa | 960 |
| atgtggttgg | taacgattcc | tttgcttggc | ttccacaact | agaatatttc | ttcctagagt | 1020 |
| ataataatat | acagcatttg | ttttctcact | cttttgcacgg | gcttttcaat | gtgaggtacc | 1080 |
| tgaatttgaa | acggtctttt | actaaacaaa | gtatttccct | tgcctcactc | cccaagattg | 1140 |
| atgattttc | ttttcagtgg | ctaaaatgtt | tggagcacct | taacatggaa | gataatgata | 1200 |
| ttccaggcat | aaaaagcaat | atgttcacag | gattgataaa | cctgaaatac | ttaagtctat | 1260 |
| ccaactcctt | tacaagtttg | cgaactttga | caaatgaaac | atttgtatca | cttgctcatt | 1320 |
| ctcccttaca | catactcaac | ctaaccaaga | ataaaatctc | aaaaatagag | agtgatgctt | 1380 |
| tctcttggtt | gggccaccta | gaagtacttg | acctgggcct | taatgaaatt | gggcaagaac | 1440 |
| tcacaggcca | ggaatggaga | ggtctagaaa | atatttttcga | aatctatctt | tcctacaaca | 1500 |
| agtacctgca | gctgactagg | aactcctttg | ccttggtccc | aagccttcaa | cgactgatgc | 1560 |
| tccgaagggt | ggcccttaaa | aatgtggata | gctctccttc | accattccag | cctcttcgta | 1620 |
| acttgaccat | tctggatcta | agcaacaaca | acatagccaa | cataaatgat | gacatgttgg | 1680 |
| agggtcttga | gaaactagaa | attctcgatt | tgcagcataa | caacttagca | cggctctgga | 1740 |
| aacacgcaaa | ccctggtggt | cccatttatt | tcctaaaggg | tctgtctcac | ctccacatcc | 1800 |
| ttaacttgga | gtccaacggc | tttgacgaga | tcccagttga | ggtcttcaag | gatttatttg | 1860 |
| aactaaagat | catcgattta | ggattgaata | atttaaacac | acttccagca | tctgtctttta | 1920 |
| ataatcaggt | gtctctaaag | tcattgaacc | ttcagaagaa | tctcataaca | tccgttgaga | 1980 |
| agaaggtttt | cggccagct | ttcaggaacc | tgactgagtt | agatatgcgc | tttaatccct | 2040 |
| ttgattgcac | gtgtgaaagt | attgcctggt | ttgttaattg | gattaacgag | acccatacca | 2100 |

```
acatccctga gctgtcaagc cactaccttt gcaacactcc acctcactat catgggttcc    2160
cagtgagact ttttgataca tcatcttgca aagacagtgc cccctttgaa ctctttttca    2220
tgatcaatac cagtatcctg ttgattttta tctttattgt acttctcatc cactttgagg    2280
gctggaggat atcttttat tggaatgttt cagtacatcg agttcttggt ttcaaagaaa     2340
tagacagaca gacagaacag tttgaatatg cagcatatat aattcatgcc tataaagata    2400
aggattgggt ctgggaacat ttctcttcaa tggaaaagga agaccaatct ctcaaatttt    2460
gtctggaaga aagggacttt gaggcgggtg tttttgaact agaagcaatt gttaacagca    2520
tcaaaagaag cagaaaaatt attttttgtta aacacaccca tctattaaaa gacccattat   2580
gcaaaagatt caaggtacat catgcagttc aacaagctat tgaacaaaat ctggattcca    2640
ttatattggt tttccttgag gagattccag attataaact gaaccatgca ctctgtttgc    2700
gaagaggaat gtttaaatct cactgcatct tgaactggcc agttcagaaa gaacggatag    2760
gtgcctttcg tcataaattg caagtagcac ttggatccaa aaactctgta cattaaattt    2820
atttaaatat tcaattagca aaggagaaac tttctcaatt taaaaagttc tatggcaaat    2880
ttaagttttc cataaaggtg ttataatttg tttattcata tttgtaaatg attatattct    2940
atcacaatta catctcttct aggaaaatgt gtctccttat tcaggccta tttttgacaa     3000
ttgacttaat tttacccaaa ataaaacata taagcacgta aaaaaaaaa aaaaaaa        3057

<210> SEQ ID NO 22
<211> LENGTH: 905
<212> TYPE: PRT
<213> ORGANISM: Mus musculus

<400> SEQUENCE: 22

Met Lys Gly Cys Ser Ser Tyr Leu Met Tyr Ser Phe Gly Gly Leu Leu
1               5                   10                  15

Ser Leu Trp Ile Leu Leu Val Ser Ser Thr Asn Gln Cys Thr Val Arg
            20                  25                  30

Tyr Asn Val Ala Asp Cys Ser His Leu Lys Leu Thr His Ile Pro Asp
        35                  40                  45

Asp Leu Pro Ser Asn Ile Thr Val Leu Asn Leu Thr His Asn Gln Leu
    50                  55                  60

Arg Arg Leu Pro Pro Thr Asn Phe Thr Arg Tyr Ser Gln Leu Ala Ile
65                  70                  75                  80

Leu Asp Ala Gly Phe Asn Ser Ile Ser Lys Leu Glu Pro Glu Leu Cys
                85                  90                  95

Gln Ile Leu Pro Leu Leu Lys Val Leu Asn Leu Gln His Asn Glu Leu
            100                 105                 110

Ser Gln Ile Ser Asp Gln Thr Phe Val Phe Cys Thr Asn Leu Thr Glu
        115                 120                 125

Leu Asp Leu Met Ser Asn Ser Ile His Lys Ile Lys Ser Asn Pro Phe
    130                 135                 140

Lys Asn Gln Lys Asn Leu Ile Lys Leu Asp Leu Ser His Asn Gly Leu
145                 150                 155                 160

Ser Ser Thr Lys Leu Gly Thr Gly Val Gln Leu Glu Asn Leu Gln Glu
                165                 170                 175

Leu Leu Leu Ala Lys Asn Lys Ile Leu Ala Leu Arg Ser Glu Glu Leu
            180                 185                 190

Glu Phe Leu Gly Asn Ser Ser Leu Arg Lys Leu Asp Leu Ser Ser Asn
        195                 200                 205
```

-continued

```
Pro Leu Lys Glu Phe Ser Pro Gly Cys Phe Gln Thr Ile Gly Lys Leu
    210                 215                 220

Phe Ala Leu Leu Leu Asn Asn Ala Gln Leu Asn Pro His Leu Thr Glu
225                 230                 235                 240

Lys Leu Cys Trp Glu Leu Ser Asn Thr Ser Ile Gln Asn Leu Ser Leu
                245                 250                 255

Ala Asn Asn Gln Leu Leu Ala Thr Ser Glu Ser Thr Phe Ser Gly Leu
                260                 265                 270

Lys Trp Thr Asn Leu Thr Gln Leu Asp Leu Ser Tyr Asn Asn Leu His
            275                 280                 285

Asp Val Gly Asn Gly Ser Phe Ser Tyr Leu Pro Ser Leu Arg Tyr Leu
    290                 295                 300

Ser Leu Glu Tyr Asn Asn Ile Gln Arg Leu Ser Pro Arg Ser Phe Tyr
305                 310                 315                 320

Gly Leu Ser Asn Leu Arg Tyr Leu Ser Leu Lys Arg Ala Phe Thr Lys
                325                 330                 335

Gln Ser Val Ser Leu Ala Ser His Pro Asn Ile Asp Asp Phe Ser Phe
                340                 345                 350

Gln Trp Leu Lys Tyr Leu Glu Tyr Leu Asn Met Asp Asp Asn Asn Ile
            355                 360                 365

Pro Ser Thr Lys Ser Asn Thr Phe Thr Gly Leu Val Ser Leu Lys Tyr
    370                 375                 380

Leu Ser Leu Ser Lys Thr Phe Thr Ser Leu Gln Thr Leu Thr Asn Glu
385                 390                 395                 400

Thr Phe Val Ser Leu Ala His Ser Pro Leu Leu Thr Leu Asn Leu Thr
                405                 410                 415

Lys Asn His Ile Ser Lys Ile Ala Asn Gly Thr Phe Ser Trp Leu Gly
            420                 425                 430

Gln Leu Arg Ile Leu Asp Leu Gly Leu Asn Glu Ile Glu Gln Lys Leu
        435                 440                 445

Ser Gly Gln Glu Trp Arg Gly Leu Arg Asn Ile Phe Glu Ile Tyr Leu
    450                 455                 460

Ser Tyr Asn Lys Tyr Leu Gln Leu Ser Thr Ser Ser Phe Ala Leu Val
465                 470                 475                 480

Pro Ser Leu Gln Arg Leu Met Leu Arg Arg Val Ala Leu Lys Asn Val
                485                 490                 495

Asp Ile Ser Pro Ser Pro Phe Arg Pro Leu Arg Asn Leu Thr Ile Leu
            500                 505                 510

Asp Leu Ser Asn Asn Asn Ile Ala Asn Ile Asn Glu Asp Leu Leu Glu
        515                 520                 525

Gly Leu Glu Asn Leu Glu Ile Leu Asp Phe Gln His Asn Asn Leu Ala
    530                 535                 540

Arg Leu Trp Lys Arg Ala Asn Pro Gly Gly Pro Val Asn Phe Leu Lys
545                 550                 555                 560

Gly Leu Ser His Leu His Ile Leu Asn Leu Glu Ser Asn Gly Leu Asp
                565                 570                 575

Glu Ile Pro Val Gly Val Phe Lys Asn Leu Phe Glu Leu Lys Ser Ile
            580                 585                 590

Asn Leu Gly Leu Asn Asn Leu Asn Lys Leu Glu Pro Phe Ile Phe Asp
        595                 600                 605

Asp Gln Thr Ser Leu Arg Ser Leu Asn Leu Gln Lys Asn Leu Ile Thr
    610                 615                 620

Ser Val Glu Lys Asp Val Phe Gly Pro Pro Phe Gln Asn Leu Asn Ser
```

```
                625                 630                 635                 640
Leu Asp Met Arg Phe Asn Pro Phe Asp Cys Thr Cys Glu Ser Ile Ser
                        645                 650                 655
Trp Phe Val Asn Trp Ile Asn Gln Thr His Thr Asn Ile Phe Glu Leu
                660                 665                 670
Ser Thr His Tyr Leu Cys Asn Thr Pro His His Tyr Tyr Gly Phe Pro
                675                 680                 685
Leu Lys Leu Phe Asp Thr Ser Ser Cys Lys Asp Ser Ala Pro Phe Glu
                690                 695                 700
Leu Leu Phe Ile Ile Ser Thr Ser Met Leu Leu Val Phe Ile Leu Val
705                 710                 715                 720
Val Leu Leu Ile His Ile Glu Gly Trp Arg Ile Ser Phe Tyr Trp Asn
                725                 730                 735
Val Ser Val His Arg Ile Leu Gly Phe Lys Glu Ile Asp Thr Gln Ala
                740                 745                 750
Glu Gln Phe Glu Tyr Thr Ala Tyr Ile Ile His Ala His Lys Asp Arg
                755                 760                 765
Asp Trp Val Trp Glu His Phe Ser Pro Met Glu Glu Gln Asp Gln Ser
                770                 775                 780
Leu Lys Phe Cys Leu Glu Arg Asp Phe Glu Ala Gly Val Leu Gly
785                 790                 795                 800
Leu Glu Ala Ile Val Asn Ser Ile Lys Arg Ser Arg Lys Ile Ile Phe
                805                 810                 815
Val Ile Thr His His Leu Leu Lys Asp Pro Leu Cys Arg Arg Phe Lys
                820                 825                 830
Val His His Ala Val Gln Gln Ala Ile Glu Gln Asn Leu Asp Ser Ile
                835                 840                 845
Ile Leu Ile Phe Leu Gln Asn Ile Pro Asp Tyr Lys Leu Asn His Ala
                850                 855                 860
Leu Cys Leu Arg Arg Gly Met Phe Lys Ser His Cys Ile Leu Asn Trp
865                 870                 875                 880
Pro Val Gln Lys Glu Arg Ile Asn Ala Phe His His Lys Leu Gln Val
                885                 890                 895
Ala Leu Gly Ser Arg Asn Ser Ala His
                900                 905

<210> SEQ ID NO 23
<211> LENGTH: 3310
<212> TYPE: DNA
<213> ORGANISM: Mus musculus

<400> SEQUENCE: 23
tagaatatga tacagggatt gcacccataa tctgggctga atcatgaaag ggtgttcctc     60
ttatctaatg tactcctttg ggggactttt gtccctatgg attcttctgg tgtcttccac    120
aaaccaatgc actgtgagat acaacgtagc tgactgcagc catttgaagc taacacacat    180
acctgatgat cttccctcta acataacagt gttgaatctt actcacaacc aactcagaag    240
attaccacct accaacttta caagatacag ccaacttgct atcttggatg caggatttaa    300
ctccatttca aaactggagc cagaactgtg ccaaatactc cctttgttga agtattgaa    360 cctgcaacat aatgagctct ctcagatttc tgatcaaacc tttgtcttct gcacgaacct    420
gacagaactc gatctaatgt ctaactcaat acacaaaatt aaaagcaacc ctttcaaaaa    480
ccagaagaat ctaatcaaat tagatttgtc tcataatggt ttatcatcta caaagttggg    540
```

```
aacgggggtc caactggaga acctccaaga actgctctta gcaaaaaata aaatccttgc    600
gttgcgaagt gaagaacttg agtttcttgg caattcttct ttacgaaagt tggacttgtc    660
atcaaatcca cttaaagagt tctccccggg gtgtttccag acaattggca agttattcgc    720
cctcctcttg aacaacgccc aactgaaccc ccacctcaca gagaagcttt gctgggaact    780
ttcaaacaca agcatccaga atctctctct ggctaacaac cagctgctgg ccaccagcga    840
gagcactttc tctgggctga agtggacaaa tctcacccag ctcgatcttt cctacaacaa    900
cctccatgat gtcggcaacg gttccttctc ctatctccca agcctgaggt atctgtctct    960
ggagtacaac aatatacagc gtctgtcccc tcgctctttt tatggactct ccaacctgag   1020
gtacctgagt ttgaagcgag catttactaa gcaaagtgtt tcacttgctt cacatcccaa   1080
cattgacgat ttttcctttc aatggttaaa atatttggaa tatctcaaca tggatgacaa   1140
taatattcca agtaccaaaa gcaataccct cacgggattg gtgagtctga agtacctaag   1200
tctttccaaa actttcacaa gtttgcaaac tttaacaaat gaaacatttg tgtcacttgc   1260
tcattctccc ttgctcactc tcaacttaac gaaaaatcac atctcaaaaa tagcaaatgg   1320
tactttctct tggttaggcc aactcaggat acttgatctc ggccttaatg aaattgaaca   1380
aaaactcagc ggccaggaat ggagaggtct gagaaatata tttgagatct acctatccta   1440
taacaaatac ctccaactgt ctaccagttc ctttgcattg gtccccagcc ttcaaagact   1500
gatgctcagg agggtggccc ttaaaaatgt ggatatctcc ccttcacctt tccgccctct   1560
tcgtaacttg accattctgg acttaagcaa caacaacata gccaacataa atgaggactt   1620
gctggagggt cttgagaatc tagaaatcct ggattttcag cacaataact agccaggct    1680
ctggaaacgc gcaaaccccg gtggtcccgt taatttcctg aagggctgt ctcacctcca    1740
catcttgaat ttagagtcca acggcttaga tgaaatccca gtcggggttt tcaagaactt   1800
attcgaacta aagagcatca atctaggact gaataactta aacaaacttg aaccattcat   1860
ttttgatgac cagacatctc taaggtcact gaacctccag aagaacctca taacatctgt   1920
tgagaaggat gttttcgggc cgccttttca aaacctgaac agtttagata tgcgcttcaa   1980
tccgttcgac tgcacgtgtg aaagtatttc ctggtttgtt aactggatca accagaccca   2040
cactaatatc tttgagctgt ccactcacta cctctgtaac actccacatc attattatgg   2100
cttcccctg aagcttttcg atacatcatc ctgtaaagac agcgcccct ttgaactcct    2160
cttcataatc agcaccagta tgctcctggt ttttatactt gtggtactgc tcattcacat   2220
cgagggctgg aggatctctt tttactggaa tgtttcagtg catcggattc ttggtttcaa   2280
ggaaatagac acacaggctg agcagtttga atatacagcc tacataattc atgcccataa   2340
agacagagac tgggtctggg aacatttctc cccaatggaa gaacaagacc aatctctcaa   2400
atttttgccta gaagaaaggg actttgaagc aggcgtcctt ggacttgaag caattgttaa   2460
tagcatcaaa agaagccgaa aaatcatttt cgttatcaca caccatttat taaaagaccc   2520
tctgtgcaga agattcaagg tacatcacgc agttcagcaa gctattgagc aaaatctgga   2580
ttcaattata ctgatttttc tccagaatat tccagattat aaactaaacc atgcactctg   2640
tttgcgaaga ggaatgttta atctcattg catcttgaac tggccagttc agaaagaacg    2700
gataaatgcc tttcatcata aattgcaagt agcacttgga tctcggaatt cagcacatta   2760
aactcatttg aagatttgga gtcggtaaag ggatagatcc aatttataaa ggtccatcat   2820
gaatctaagt tttacttgaa agttttgtat atttattat atgtatagat gatgatatta    2880
catcacaatc caatctcagt tttgaaatat ttcggcttat ttcattgaca tctggtttat   2940
```

```
tcactccaaa taaacacatg ggcagttaaa aacatcctct attaatagat tacccattaa    3000
ttcttgaggt gtatcacagc tttaaagggt tttaaatatt tttatataaa taagactgag    3060
agttttataa atgtaattt  ttaaaactcg agtcttactg tgtagctcag aaaggcctgg    3120
aaattaatat attagagagt catgtcttga acttatttat ctctgcctcc ctctgtctcc    3180
agagtgttgc ttttaagggc atgtagcacc acacccagct atgtacgtgt gggattttat    3240
aatgctcatt tttgagacgt ttatagaata aaagataatt gcttttatgg tataaggcta    3300
cttgaggtaa                                                          3310
```

<210> SEQ ID NO 24
<211> LENGTH: 1049
<212> TYPE: PRT
<213> ORGANISM: Homo sapiens

<400> SEQUENCE: 24

```
Met Val Phe Pro Met Trp Thr Leu Lys Arg Gln Ile Leu Ile Leu Phe
1               5                  10                  15

Asn Ile Ile Leu Ile Ser Lys Leu Leu Gly Ala Arg Trp Phe Pro Lys
            20                  25                  30

Thr Leu Pro Cys Asp Val Thr Leu Asp Val Pro Lys Asn His Val Ile
        35                  40                  45

Val Asp Cys Thr Asp Lys His Leu Thr Glu Ile Pro Gly Gly Ile Pro
    50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
        115                 120                 125

Leu Lys Ser Leu Tyr Leu Asp Gly Asn Gln Leu Leu Glu Ile Pro Gln
    130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser
            180                 185                 190

Tyr Ser Ile Glu Lys Asp Ala Phe Leu Asn Leu Thr Lys Leu Lys Val
        195                 200                 205

Leu Ser Leu Lys Asp Asn Asn Val Thr Ala Val Pro Thr Val Leu Pro
    210                 215                 220

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Ala Pro
            260                 265                 270

Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
    290                 295                 300
```

-continued

```
Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
            325                 330                 335

His Phe Leu Pro Ser Leu Ile Gln Leu Asp Leu Ser Phe Asn Phe Glu
                340                 345                 350

Leu Gln Val Tyr Arg Ala Ser Met Asn Leu Ser Gln Ala Phe Ser Ser
        355                 360                 365

Leu Lys Ser Leu Lys Ile Leu Arg Ile Arg Gly Tyr Val Phe Lys Glu
    370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
            405                 410                 415

Phe Lys Gln Phe Lys Arg Leu Lys Val Ile Asp Leu Ser Val Asn Lys
                420                 425                 430

Ile Ser Pro Ser Gly Asp Ser Glu Val Gly Phe Cys Ser Asn Ala
        435                 440                 445

Arg Thr Ser Val Glu Ser Tyr Glu Pro Gln Val Leu Glu Gln Leu His
    450                 455                 460

Tyr Phe Arg Tyr Asp Lys Tyr Ala Arg Ser Cys Arg Phe Lys Asn Lys
465                 470                 475                 480

Glu Ala Ser Phe Met Ser Val Asn Glu Ser Cys Tyr Lys Tyr Gly Gln
            485                 490                 495

Thr Leu Asp Leu Ser Lys Asn Ser Ile Phe Phe Val Lys Ser Ser Asp
                500                 505                 510

Phe Gln His Leu Ser Phe Leu Lys Cys Leu Asn Leu Ser Gly Asn Leu
        515                 520                 525

Ile Ser Gln Thr Leu Asn Gly Ser Glu Phe Gln Pro Leu Ala Glu Leu
    530                 535                 540

Arg Tyr Leu Asp Phe Ser Asn Asn Arg Leu Asp Leu Leu His Ser Thr
545                 550                 555                 560

Ala Phe Glu Glu Leu His Lys Leu Glu Val Leu Asp Ile Ser Ser Asn
            565                 570                 575

Ser His Tyr Phe Gln Ser Glu Gly Ile Thr His Met Leu Asn Phe Thr
                580                 585                 590

Lys Asn Leu Lys Val Leu Gln Lys Leu Met Met Asn Asp Asn Asp Ile
        595                 600                 605

Ser Ser Ser Thr Ser Arg Thr Met Glu Ser Glu Ser Leu Arg Thr Leu
    610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Lys Leu Glu Glu Leu Asp
            645                 650                 655

Ile Ser Lys Asn Ser Leu Ser Phe Leu Pro Ser Gly Val Phe Asp Gly
                660                 665                 670

Met Pro Pro Asn Leu Lys Asn Leu Ser Leu Ala Lys Asn Gly Leu Lys
        675                 680                 685

Ser Phe Ser Trp Lys Lys Leu Gln Cys Leu Lys Asn Leu Glu Thr Leu
    690                 695                 700

Asp Leu Ser His Asn Gln Leu Thr Thr Val Pro Glu Arg Leu Ser Asn
705                 710                 715                 720
```

```
Cys Ser Arg Ser Leu Lys Asn Leu Ile Leu Lys Asn Asn Gln Ile Arg
                725                 730                 735

Ser Leu Thr Lys Tyr Phe Leu Gln Asp Ala Phe Gln Leu Arg Tyr Leu
            740                 745                 750

Asp Leu Ser Ser Asn Lys Ile Gln Met Ile Gln Lys Thr Ser Phe Pro
        755                 760                 765

Glu Asn Val Leu Asn Asn Leu Lys Met Leu Leu Leu His His Asn Arg
    770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

Cys Glu Leu Asp Leu Thr Asn Leu Ile Leu Phe Ser Leu Ser Ile Ser
        835                 840                 845

Val Ser Leu Phe Leu Met Val Met Met Thr Ala Ser His Leu Tyr Phe
    850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
        915                 920                 925

Glu Glu Arg Asp Trp Leu Pro Gly Gln Pro Val Leu Glu Asn Leu Ser
    930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
                965                 970                 975

Arg Leu Met Asp Glu Lys Val Asp Val Ile Leu Ile Phe Leu Glu
            980                 985                 990

Lys Pro Phe Gln Lys Ser Lys Phe  Leu Gln Leu Arg Lys  Arg Leu Cys
    995                 1000                1005

Gly Ser  Ser Val Leu Glu Trp  Pro Thr Asn Pro Gln  Ala His Pro
   1010                1015                1020

Tyr Phe  Trp Gln Cys Leu Lys  Asn Ala Leu Ala Thr  Asp Asn His
   1025                1030                1035

Val Ala  Tyr Ser Gln Val Phe  Lys Glu Thr Val
   1040                1045

<210> SEQ ID NO 25
<211> LENGTH: 5007
<212> TYPE: DNA
<213> ORGANISM: Homo sapiens

<400> SEQUENCE: 25
actccagata taggatcact ccatgccatc aagaaagttg atgctattgg gcccatctca    60
agctgatctt ggcacctctc atgctctgct ctcttcaacc agacctctac attccatttt   120
ggaagaagac taaaaatggt gtttccaatg tggacactga agagacaaat tcttatcctt   180
tttaacataa tcctaatttc caaactcctt ggggctagat ggtttcctaa aactctgccc   240
```

```
tgtgatgtca ctctggatgt tccaaagaac catgtgatcg tggactgcac agacaagcat    300
ttgacagaaa ttcctggagg tattcccacg aacaccacga acctcaccct caccattaac    360
cacataccag acatctcccc agcgtccttt cacagactgg accatctggt agagatcgat    420
ttcagatgca actgtgtacc tattccactg gggtcaaaaa acaacatgtg catcaagagg    480
ctgcagatta acccagaag  ctttagtgga ctcacttatt taaaatccct ttacctggat    540
ggaaaccagc tactagagat accgcagggc ctcccgccta gcttacagct tctcagcctt    600
gaggccaaca acatctttc  catcagaaaa gagaatctaa cagaactggc aacatagaa     660 atactctacc tgggccaaaa ctgttattat cgaaatcctt gttatgtttc atattcaata    720
gagaaagatg ccttcctaaa cttgacaaag ttaaagtgc  tctccctgaa agataacaat    780
gtcacagccg tccctactgt tttgccatct actttaacag aactatatct ctacaacaac    840
atgattgcaa aaatccaaga agatgatttt aataacctca accaattaca aattcttgac    900
ctaagtggaa attgccctcg ttgttataat gccccatttc cttgtgcgcc gtgtaaaaat    960
aattctcccc tacagatccc tgtaaatgct tttgatgcgc tgacagaatt aaaagtttta   1020
cgtctacaca gtaactctct tcagcatgtg ccccccaagat ggtttaagaa catcaacaaa   1080
ctccaggaac tggatctgtc ccaaaacttc ttggccaaag aaattgggga tgctaaattt   1140
ctgcattttc tccccagcct catccaattg gatctgtctt tcaatttga  acttcaggtc   1200 tatcgtgcat ctatgaatct atcacaagca ttttcttcac tgaaaagcct gaaaattctg   1260
cggatcagag atatgtcttt aaagagttg  aaaagcttta acctctcgcc attacataat   1320
cttcaaaatc ttgaagttct tgatcttggc actaacttta taaaaattgc taacctcagc   1380
atgtttaaac aatttaaaag actgaaagtc atagatcttt cagtgaataa aatatcacct   1440
tcaggagatt caagtgaagt tggcttctgc tcaaatgcca gaacttctgt agaaagttat   1500
gaaccccagg tcctggaaca attacattat tcagatatg  ataagtatgc aaggagttgc   1560
agattcaaaa acaagaggc  ttctttcatg tctgttaatg aaagctgcta caagtatggg   1620
cagaccttgg atctaagtaa aaatagtata tttttttgtca agtcctctga ttttcagcat   1680 cttttctttcc tcaaatgcct gaatctgtca ggaaatctca ttagccaaac tcttaatggc   1740
agtgaattcc aacctttagc agagctgaga tatttggact tctccaacaa ccggcttgat   1800
ttactccatt caacagcatt tgaagagctt cacaaactgg aagttctgga tataagcagt   1860
aatagccatt atttcaatc  agaaggaatt actcatatgc taaactttac caagaaccta   1920
aaggttctgc agaaactgat gatgaacgac aatgacatct cttcctccac cagcaggacc   1980
atggagagtg agtctcttag aactctggaa ttcagaggaa atcacttaga tgttttatgg   2040
agagaaggtg ataacagata cttacaatta ttcaagaatc tgctaaaatt agaggaatta   2100
gacatctcta aaaattccct aagtttcttg ccttctggag ttttgatgg  tatgcctcca   2160 aatctaaaga atctctcttt ggccaaaaat gggctcaaat ctttcagttg gaagaaactc   2220
cagtgtctaa agaacctgga aactttggac ctcagccaca accaactgac cactgtccct   2280
gagagattat ccaactgttc cagaagcctc aagaatctga ttcttaagaa taatcaaatc   2340
aggagtctga cgaagtattt tctacaagat gccttccagt gcgatatct  ggatctcagc   2400 tcaaataaaa tccagatgat ccaaaagacc agcttcccag aaaatgtcct caacaatctg   2460
aagatgttgc ttttgcatca taatcggttt ctgtgcacct gtgatgctgt gtggtttgtc   2520
tggtgggtta accatacgga ggtgactatt ccttacctgg ccacagatgt gacttgtgtg   2580
gggccaggag cacacaaggg ccaaagtgtg atctccctgg atctgtacac ctgtgagtta   2640
```

```
gatctgacta acctgattct gttctcactt tccatatctg tatctctctt tctcatggtg   2700
atgatgacag caagtcacct ctatttctgg gatgtgtggt atatttacca tttctgtaag   2760
gccaagataa aggggtatca gcgtctaata tcaccagact gttgctatga tgcttttatt   2820
gtgtatgaca ctaaagaccc agctgtgacc gagtgggttt tggctgagct ggtggccaaa   2880
ctggaagacc caagagagaa acattttaat ttatgtctcg aggaaaggga ctggttacca   2940
gggcagccag ttctggaaaa cctttcccag agcatacagc ttagcaaaaa gacagtgttt   3000
gtgatgacag acaagtatgc aaagactgaa aattttaaga tagcatttta cttgtcccat   3060
cagaggctca tggatgaaaa agttgatgtg attatcttga tatttcttga gaagcccttt   3120
cagaagtcca agttcctcca gctccggaaa aggctctgtg ggagttctgt ccttgagtgg   3180
ccaacaaacc cgcaagctca cccatacttc tggcagtgtc taaagaacgc cctgccaca   3240
gacaatcatg tggcctatag tcaggtgttc aaggaaacgg tctagcccctt ctttgcaaaa   3300
cacaactgcc tagtttacca aggagaggcc tggctgttta aattgttttc atatatatca   3360
caccaaaagc gtgttttgaa attcttcaag aaatgagatt gcccatattt caggggagcc   3420
accaacgtct gtcacaggag ttggaaagat ggggtttata taatgcatca agtcttcttt   3480
cttatctctc tgtgtctcta tttgcacttg agtctctcac ctcagctcct gtaaaagagt   3540
ggcaagtaaa aaacatgggg ctctgattct cctgtaattg tgataattaa atatacacac   3600
aatcatgaca ttgagaagaa ctgcatttct acccttaaaa agtactggta tatacagaaa   3660
tagggttaaa aaaaactcaa gctctctcta tatgagacca aaatgtacta gagttagttt   3720
agtgaaataa aaaaccagtc agctggccgg gcatggtggc tcatgcttgt aatcccagca   3780
ctttgggagg ccgaggcagg tggatcacga ggtcaggagt ttgagaccag tctggccaac   3840
atggtgaaac cccgtctgta ctaaaaatac aaaaattagc tgggcgtggt ggtgggtgcc   3900
tgtaatccca gctacttggg aggctgaggc aggagaatcg cttgaacccg ggaggtggag   3960
gtggcagtga gccgagatca cgccactgca atgcagcccg gcaacagag ctagactgtc   4020
tcaaagaac aaaaaaaaaa aaacacaaaa aaactcagtc agcttcttaa ccaattgctt   4080
ccgtgtcatc cagggcccca ttctgtgcag attgagtgtg gcaccacac aggtggttgc   4140
tgcttcagtg cttcctgctc ttttttcttg ggcctgcttc tgggttccat agggaaacag   4200
taagaaagaa agacacatcc ttaccataaa tgcatatggt ccacctacaa atagaaaat   4260
atttaaatga tctgccttta tacaaagtga tattctctac ctttgataat ttacctgctt   4320
aaatgttttt atctgcactg caaagtactg tatccaaagt aaaatttcct catccaatat   4380
ctttcaaact gttttgttaa ctaatgccat atatttgtaa gtatctgcac acttgataca   4440
gcaacgttag atggttttga tggtaaaccc taaaggagga ctccaagagt gtgtatttat   4500
ttatagtttt atcagagatg acaattattt gaatgccaat tatatggatt cctttcatt   4560
tttgctggag gatgggagaa gaaaccaaag tttatagacc ttcacattga gaaagcttca   4620
gttttgaact tcagctatca gattcaaaaa caacagaaag aaccaagaca ttcttaagat   4680
gcctgtactt tcagctgggt ataaattcat gagttcaaag attgaaacct gaccaatttg   4740
ctttatttca tggaagaagt gatctacaaa ggtgtttgtg ccatttggaa aacagcgtgc   4800
atgtgttcaa gccttagatt ggcgatgtcg tattttcctc acgtgtggca atgccaaagg   4860
ctttacttta cctgtgagta cacactatat gaattatttc caacgtacat ttaatcaata   4920
agggtcacaa attcccaaat caatctctgg aataaataga gaggtaatta aattgctgga   4980
```

-continued

```
gccaactatt tcacaacttc tgtaagc                                    5007
```

<210> SEQ ID NO 26
<211> LENGTH: 1050
<212> TYPE: PRT
<213> ORGANISM: Mus musculus

<400> SEQUENCE: 26

| Met | Val | Phe | Ser | Met | Trp | Thr | Arg | Lys | Arg | Gln | Ile | Leu | Ile | Phe | Leu |
|---|---|---|---|---|---|---|---|---|---|---|---|---|---|---|---|
| 1 | | | | 5 | | | | | 10 | | | | | 15 | |

| Asn | Met | Leu | Leu | Val | Ser | Arg | Val | Phe | Gly | Phe | Arg | Trp | Phe | Pro | Lys |
|---|---|---|---|---|---|---|---|---|---|---|---|---|---|---|---|
| | | | 20 | | | | | 25 | | | | | 30 | | |

| Thr | Leu | Pro | Cys | Glu | Val | Lys | Val | Asn | Ile | Pro | Glu | Ala | His | Val | Ile |
|---|---|---|---|---|---|---|---|---|---|---|---|---|---|---|---|
| | | 35 | | | | | 40 | | | | | 45 | | | |

| Val | Asp | Cys | Thr | Asp | Lys | His | Leu | Thr | Glu | Ile | Pro | Glu | Gly | Ile | Pro |
|---|---|---|---|---|---|---|---|---|---|---|---|---|---|---|---|
| 50 | | | | | 55 | | | | | 60 | | | | | |

| Thr | Asn | Thr | Thr | Asn | Leu | Thr | Leu | Thr | Ile | Asn | His | Ile | Pro | Ser | Ile |
|---|---|---|---|---|---|---|---|---|---|---|---|---|---|---|---|
| 65 | | | | | 70 | | | | | 75 | | | | | 80 |

| Ser | Pro | Asp | Ser | Phe | Arg | Arg | Leu | Asn | His | Leu | Glu | Glu | Ile | Asp | Leu |
|---|---|---|---|---|---|---|---|---|---|---|---|---|---|---|---|
| | | | | 85 | | | | | 90 | | | | | 95 | |

| Arg | Cys | Asn | Cys | Val | Pro | Val | Leu | Leu | Gly | Ser | Lys | Ala | Asn | Val | Cys |
|---|---|---|---|---|---|---|---|---|---|---|---|---|---|---|---|
| | | | 100 | | | | | 105 | | | | | 110 | | |

| Thr | Lys | Arg | Leu | Gln | Ile | Arg | Pro | Gly | Ser | Phe | Ser | Gly | Leu | Ser | Asp |
|---|---|---|---|---|---|---|---|---|---|---|---|---|---|---|---|
| | | 115 | | | | | 120 | | | | | 125 | | | |

| Leu | Lys | Ala | Leu | Tyr | Leu | Asp | Gly | Asn | Gln | Leu | Leu | Glu | Ile | Pro | Gln |
|---|---|---|---|---|---|---|---|---|---|---|---|---|---|---|---|
| 130 | | | | | 135 | | | | | 140 | | | | | |

| Asp | Leu | Pro | Ser | Ser | Leu | His | Leu | Leu | Ser | Leu | Glu | Ala | Asn | Asn | Ile |
|---|---|---|---|---|---|---|---|---|---|---|---|---|---|---|---|
| 145 | | | | | 150 | | | | | 155 | | | | | 160 |

| Phe | Ser | Ile | Thr | Lys | Glu | Asn | Leu | Thr | Glu | Leu | Val | Asn | Ile | Glu | Thr |
|---|---|---|---|---|---|---|---|---|---|---|---|---|---|---|---|
| | | | | 165 | | | | | 170 | | | | | 175 | |

| Leu | Tyr | Leu | Gly | Gln | Asn | Cys | Tyr | Tyr | Arg | Asn | Pro | Cys | Asn | Val | Ser |
|---|---|---|---|---|---|---|---|---|---|---|---|---|---|---|---|
| | | | 180 | | | | | 185 | | | | | 190 | | |

| Tyr | Ser | Ile | Glu | Lys | Asp | Ala | Phe | Leu | Val | Met | Arg | Asn | Leu | Lys | Val |
|---|---|---|---|---|---|---|---|---|---|---|---|---|---|---|---|
| | | 195 | | | | | 200 | | | | | 205 | | | |

| Leu | Ser | Leu | Lys | Asp | Asn | Asn | Val | Thr | Ala | Val | Pro | Thr | Thr | Leu | Pro |
|---|---|---|---|---|---|---|---|---|---|---|---|---|---|---|---|
| 210 | | | | | 215 | | | | | 220 | | | | | |

| Pro | Asn | Leu | Leu | Glu | Leu | Tyr | Leu | Tyr | Asn | Asn | Ile | Ile | Lys | Lys | Ile |
|---|---|---|---|---|---|---|---|---|---|---|---|---|---|---|---|
| 225 | | | | | 230 | | | | | 235 | | | | | 240 |

| Gln | Glu | Asn | Asp | Phe | Asn | Asn | Leu | Asn | Glu | Leu | Gln | Val | Leu | Asp | Leu |
|---|---|---|---|---|---|---|---|---|---|---|---|---|---|---|---|
| | | | | 245 | | | | | 250 | | | | | 255 | |

| Ser | Gly | Asn | Cys | Pro | Arg | Cys | Tyr | Asn | Val | Pro | Tyr | Pro | Cys | Thr | Pro |
|---|---|---|---|---|---|---|---|---|---|---|---|---|---|---|---|
| | | | 260 | | | | | 265 | | | | | 270 | | |

| Cys | Glu | Asn | Asn | Ser | Pro | Leu | Gln | Ile | His | Asp | Asn | Ala | Phe | Asn | Ser |
|---|---|---|---|---|---|---|---|---|---|---|---|---|---|---|---|
| | | 275 | | | | | 280 | | | | | 285 | | | |

| Leu | Thr | Glu | Leu | Lys | Val | Leu | Arg | Leu | His | Ser | Asn | Ser | Leu | Gln | His |
|---|---|---|---|---|---|---|---|---|---|---|---|---|---|---|---|
| | 290 | | | | | 295 | | | | | 300 | | | | |

| Val | Pro | Pro | Thr | Trp | Phe | Lys | Asn | Met | Arg | Asn | Leu | Gln | Glu | Leu | Asp |
|---|---|---|---|---|---|---|---|---|---|---|---|---|---|---|---|
| 305 | | | | | 310 | | | | | 315 | | | | | 320 |

| Leu | Ser | Gln | Asn | Tyr | Leu | Ala | Arg | Glu | Ile | Glu | Glu | Ala | Lys | Phe | Leu |
|---|---|---|---|---|---|---|---|---|---|---|---|---|---|---|---|
| | | | | 325 | | | | | 330 | | | | | 335 | |

| His | Phe | Leu | Pro | Asn | Leu | Val | Glu | Leu | Asp | Phe | Ser | Phe | Asn | Tyr | Glu |
|---|---|---|---|---|---|---|---|---|---|---|---|---|---|---|---|
| | | | 340 | | | | | 345 | | | | | 350 | | |

| Leu | Gln | Val | Tyr | His | Ala | Ser | Ile | Thr | Leu | Pro | His | Ser | Leu | Ser | Ser |
|---|---|---|---|---|---|---|---|---|---|---|---|---|---|---|---|
| | | 355 | | | | | 360 | | | | | 365 | | | |

```
Leu Glu Asn Leu Lys Ile Leu Arg Val Lys Gly Tyr Val Phe Lys Glu
        370                 375                 380
Leu Lys Asn Ser Ser Leu Ser Val Leu His Lys Leu Pro Arg Leu Glu
385                 390                 395                 400
Val Leu Asp Leu Gly Thr Asn Phe Ile Lys Ile Ala Asp Leu Asn Ile
                405                 410                 415
Phe Lys His Phe Glu Asn Leu Lys Leu Ile Asp Leu Ser Val Asn Lys
            420                 425                 430
Ile Ser Pro Ser Glu Glu Ser Arg Glu Val Gly Phe Cys Pro Asn Ala
        435                 440                 445
Gln Thr Ser Val Asp Arg His Gly Pro Gln Val Leu Glu Ala Leu His
450                 455                 460
Tyr Phe Arg Tyr Asp Glu Tyr Ala Arg Ser Cys Arg Phe Lys Asn Lys
465                 470                 475                 480
Glu Pro Pro Ser Phe Leu Pro Leu Asn Ala Asp Cys His Ile Tyr Gly
                485                 490                 495
Gln Thr Leu Asp Leu Ser Arg Asn Asn Ile Phe Phe Ile Lys Pro Ser
            500                 505                 510
Asp Phe Gln His Leu Ser Phe Leu Lys Cys Leu Asn Leu Ser Gly Asn
        515                 520                 525
Thr Ile Gly Gln Thr Leu Asn Gly Ser Glu Leu Trp Pro Leu Arg Glu
530                 535                 540
Leu Arg Tyr Leu Asp Phe Ser Asn Asn Arg Leu Asp Leu Leu Tyr Ser
545                 550                 555                 560
Thr Ala Phe Glu Glu Leu Gln Ser Leu Glu Val Leu Asp Leu Ser Ser
                565                 570                 575
Asn Ser His Tyr Phe Gln Ala Glu Gly Ile Thr His Met Leu Asn Phe
            580                 585                 590
Thr Lys Lys Leu Arg Leu Leu Asp Lys Leu Met Met Asn Asp Asn Asp
        595                 600                 605
Ile Ser Thr Ser Ala Ser Arg Thr Met Glu Ser Asp Ser Leu Arg Ile
610                 615                 620
Leu Glu Phe Arg Gly Asn His Leu Asp Val Leu Trp Arg Ala Gly Asp
625                 630                 635                 640
Asn Arg Tyr Leu Asp Phe Phe Lys Asn Leu Phe Asn Leu Glu Val Leu
                645                 650                 655
Asp Ile Ser Arg Asn Ser Leu Asn Ser Leu Pro Pro Glu Val Phe Glu
            660                 665                 670
Gly Met Pro Pro Asn Leu Lys Asn Leu Ser Leu Ala Lys Asn Gly Leu
        675                 680                 685
Lys Ser Phe Phe Trp Asp Arg Leu Gln Leu Leu Lys His Leu Glu Ile
690                 695                 700
Leu Asp Leu Ser His Asn Gln Leu Thr Lys Val Pro Glu Arg Leu Ala
705                 710                 715                 720
Asn Cys Ser Lys Ser Leu Thr Thr Leu Ile Leu Lys His Asn Gln Ile
                725                 730                 735
Arg Gln Leu Thr Lys Tyr Phe Leu Glu Asp Ala Leu Gln Leu Arg Tyr
            740                 745                 750
Leu Asp Ile Ser Ser Asn Lys Ile Gln Val Ile Gln Lys Thr Ser Phe
        755                 760                 765
Pro Glu Asn Val Leu Asn Asn Leu Glu Met Leu Val Leu His His Asn
770                 775                 780
Arg Phe Leu Cys Asn Cys Asp Ala Val Trp Phe Val Trp Trp Val Asn
```

```
                785                 790                 795                 800
        His Thr Asp Val Thr Ile Pro Tyr Leu Ala Thr Asp Val Thr Cys Val
                        805                 810                 815

Gly Pro Gly Ala His Lys Gly Gln Ser Val Ile Ser Leu Asp Leu Tyr
                    820                 825                 830

Thr Cys Glu Leu Asp Leu Thr Asn Leu Ile Leu Phe Ser Val Ser Ile
                835                 840                 845

Ser Ser Val Leu Phe Leu Met Val Val Met Thr Thr Ser His Leu Phe
            850                 855                 860

Phe Trp Asp Met Trp Tyr Ile Tyr Tyr Phe Trp Lys Ala Lys Ile Lys
        865                 870                 875                 880

Gly Tyr Gln His Leu Gln Ser Met Glu Ser Cys Tyr Asp Ala Phe Ile
                        885                 890                 895

Val Tyr Asp Thr Lys Asn Ser Ala Val Thr Glu Trp Val Leu Gln Glu
                    900                 905                 910

Leu Val Ala Lys Leu Glu Asp Pro Arg Glu Lys His Phe Asn Leu Cys
                915                 920                 925

Leu Glu Glu Arg Asp Trp Leu Pro Gly Gln Pro Val Leu Glu Asn Leu
            930                 935                 940

Ser Gln Ser Ile Gln Leu Ser Lys Lys Thr Val Phe Val Met Thr Gln
        945                 950                 955                 960

Lys Tyr Ala Lys Thr Glu Ser Phe Lys Met Ala Phe Tyr Leu Ser His
                        965                 970                 975

Gln Arg Leu Leu Asp Glu Lys Val Asp Val Ile Ile Leu Ile Phe Leu
                    980                 985                 990

Glu Lys Pro Leu Gln Lys Ser Lys  Phe Leu Gln Leu Arg  Lys Arg Leu
                995                 1000                1005

Cys Arg  Ser Ser Val Leu Glu  Trp Pro Ala Asn Pro  Gln Ala His
            1010                1015                1020

Pro Tyr  Phe Trp Gln Cys Leu  Lys Asn Ala Leu Thr  Thr Asp Asn
            1025                1030                1035

His Val  Ala Tyr Ser Gln Met  Phe Lys Glu Thr Val
            1040                1045                1050

<210> SEQ ID NO 27
<211> LENGTH: 3243
<212> TYPE: DNA
<213> ORGANISM: Mus musculus

<400> SEQUENCE: 27
attctcctcc accagacctc ttgattccat tttgaaagaa aactgaaaat ggtgttttcg     60
atgtggacac ggaagagaca aattttgatc tttttaaata tgctcttagt ttctagagtc    120
tttgggtttc gatggtttcc taaaactcta ccttgtgaag ttaaagtaaa tatcccagag    180
gcccatgtga tcgtggactg cacagacaag catttgacag aaatccctga gggcattccc    240
actaacacca ccaatcttac ccttaccatc aaccacatac caagcatctc tccagattcc    300
ttccgtaggc tgaaccatct ggaagaaatc gatttaagat gcaattgtgt acctgttcta    360
ctggggtcca agccaatgt gtgtaccaag aggctgcaga ttagacctgg aagctttagt    420
ggactctctg acttaaaagc cctttacctg gatggaaacc aacttctgga taccacag     480 gatctgccat ccagcttaca tcttctgagc cttgaggcta acaacatctt ctccatcacg    540
aaggagaata taacagaact ggtcaacatt gaaacactct acctgggtca aaactgttat    600
tatcgaaatc cttgcaatgt ttcctattct attgaaaaag atgctttcct agttatgaga    660
```

```
aatttgaagg ttctctcact aaaagataac aatgtcacag ctgtccccac cactttgcca    720
cctaatttac tagagctcta tctttataac aatatcatta agaaaatcca agaaaatgat    780
tttaataacc tcaatgagtt gcaagttctt gacctaagtg gaaattgccc tcgatgttat    840
aatgtcccat atccgtgtac accgtgtgaa aataattccc ccttacagat ccatgacaat    900
gctttcaatt cattgacaga attaaaagtt ttacgtttac acagtaattc tcttcagcat    960
gtgcccccaa catggtttaa aaacatgaga acctccagg aactagacct ctcccaaaac    1020
tacttggcca gagaaattga ggaggccaaa ttttttgcatt ttcttcccaa ccttgttgag    1080
ttggattttt ctttcaatta tgagctgcag gtctaccatg catctataac tttaccacat    1140
tcactctctt cattggaaaa cttgaaaatt ctgcgtgtca aggggtatgt ctttaaagag    1200
ctgaaaaact ccagtctttc tgtattgcac aagcttccca ggctggaagt tcttgacctt    1260
ggcactaact tcataaaaat tgctgacctc aacatattca aacattttga aaacctcaaa    1320
ctcatagacc tttcagtgaa taagatatct ccttcagaag agtcaagaga gttggctttt    1380
tgtcctaatg ctcaaacttc tgtagaccgt catgggcccc aggtccttga ggccttacac    1440
tatttccgat acgatgaata tgcacggagc tgcaggttca aaaacaaaga gccaccttct    1500
ttcttgcctt tgaatgcaga ctgccacata tatgggcaga ccttagactt aagtagaaat    1560
aacatatttt ttattaaacc ttctgatttt cagcatcttt cattcctcaa atgcctcaac    1620
ttatcaggaa acaccattgg ccaaactctt aatggcagtg aactctggcc gttgagagag    1680
ttgcggtact tagacttctc caacaaccgg cttgatttac tctactcaac agcctttgaa    1740
gagctccaga gtcttgaagt tctggatcta agtagtaaca gccactattt tcaagcagaa    1800
ggaattactc acatgctaaa ctttaccaag aaattacggc ttctggacaa actcatgatg    1860
aatgataatg acatctctac ttcggccagc aggaccatgg aaagtgactc tcttcgaatt    1920
ctggagttca gaggcaacca tttagatgtt ctatggagag ccggtgataa cagatacttg    1980
gacttcttca agaatttgtt caatttagag gtattagata tctccagaaa ttccctgaat    2040
tccttgcctc ctgaggtttt tgagggtatg ccgccaaatc taaagaatct ctccttggcc    2100
aaaaatgggc tcaaatcttt cttttgggac agactccagt tactgaagca tttggaaatt    2160
ttggacctca gccataacca gctgacaaaa gtacctgaga gattggccaa ctgttccaaa    2220
agtctcacaa cactgattct taagcataat caaatcaggc aattgacaaa atattttcta    2280
gaagatgctt tgcaattgcg ctatctagac atcagttcaa ataaaatcca ggtcattcag    2340
aagactagct cccagaaaaa tgtcctcaac aatctggaga tgttggtttt acatcacaat    2400
cgctttcttt gcaactgtga tgctgtgtgg tttgtctggt gggttaacca tacagatgtt    2460
actattccat acctggccac tgatgtgact tgtgtaggtc caggagcaca caaaggtcaa    2520
agtgtcatat cccttgatct gtatacgtgt gagttagatc tcacaaacct gattctgttc    2580
tcagtttcca tatcatcagt cctctttctt atggtagtta tgacaacaag tcacctcttt    2640
ttctgggata tgtggtacat ttattatttt tggaaagcaa agataaaggg gtatcagcat    2700
ctgcaatcca tggagtcttg ttatgatgct tttattgtgt atgacactaa aaactcagct    2760
gtgacagaat gggttttgca ggagctggtg gcaaaattgg aagatccaag agaaaaacac    2820
ttcaatttgt gtctagaaga aagagactgg ctaccaggac agccagttct agaaaacctt    2880
tcccagagca tacagctcag caaaaagaca gtgtttgtga tgcacagaa atatgctaag    2940 actgagagtt ttaagatggc attttatttg tctcatcaga ggctcctgga tgaaaaagtg    3000
```

```
gatgtgatta tcttgatatt cttggaaaag cctcttcaga agtctaagtt tcttcagctc    3060
aggaagagac tctgcaggag ctctgtcctt gagtggcctg caaatccaca ggctcaccca    3120
tacttctggc agtgcctgaa aaatgccctg accacagaca atcatgtggc ttatagtcaa    3180
atgttcaagg aaacagtcta gctctctgaa gaatgtcacc acctaggaca tgccttgaat    3240
cga                                                                  3243
```

<210> SEQ ID NO 28
<211> LENGTH: 1041
<212> TYPE: PRT
<213> ORGANISM: Homo sapiens

<400> SEQUENCE: 28

```
Met Glu Asn Met Phe Leu Gln Ser Ser Met Leu Thr Cys Ile Phe Leu
1               5                   10                  15

Leu Ile Ser Gly Ser Cys Glu Leu Cys Ala Glu Glu Asn Phe Ser Arg
            20                  25                  30

Ser Tyr Pro Cys Asp Glu Lys Lys Gln Asn Asp Ser Val Ile Ala Glu
        35                  40                  45

Cys Ser Asn Arg Arg Leu Gln Glu Val Pro Gln Thr Val Gly Lys Tyr
    50                  55                  60

Val Thr Glu Leu Asp Leu Ser Asp Asn Phe Ile Thr His Ile Thr Asn
65                  70                  75                  80

Glu Ser Phe Gln Gly Leu Gln Asn Leu Thr Lys Ile Asn Leu Asn His
                85                  90                  95

Asn Pro Asn Val Gln His Gln Asn Gly Asn Pro Gly Ile Gln Ser Asn
            100                 105                 110

Gly Leu Asn Ile Thr Asp Gly Ala Phe Leu Asn Leu Lys Asn Leu Arg
        115                 120                 125

Glu Leu Leu Leu Glu Asp Asn Gln Leu Pro Gln Ile Pro Ser Gly Leu
    130                 135                 140

Pro Glu Ser Leu Thr Glu Leu Ser Leu Ile Gln Asn Asn Ile Tyr Asn
145                 150                 155                 160

Ile Thr Lys Glu Gly Ile Ser Arg Leu Ile Asn Leu Lys Asn Leu Tyr
                165                 170                 175

Leu Ala Trp Asn Cys Tyr Phe Asn Lys Val Cys Glu Lys Thr Asn Ile
            180                 185                 190

Glu Asp Gly Val Phe Glu Thr Leu Thr Asn Leu Glu Leu Leu Ser Leu
        195                 200                 205

Ser Phe Asn Ser Leu Ser His Val Pro Pro Lys Leu Pro Ser Ser Leu
    210                 215                 220

Arg Lys Leu Phe Leu Ser Asn Thr Gln Ile Lys Tyr Ile Ser Glu Glu
225                 230                 235                 240

Asp Phe Lys Gly Leu Ile Asn Leu Thr Leu Leu Asp Leu Ser Gly Asn
                245                 250                 255

Cys Pro Arg Cys Phe Asn Ala Pro Phe Pro Cys Val Pro Cys Asp Gly
            260                 265                 270

Gly Ala Ser Ile Asn Ile Asp Arg Phe Ala Phe Gln Asn Leu Thr Gln
        275                 280                 285

Leu Arg Tyr Leu Asn Leu Ser Ser Thr Ser Leu Arg Lys Ile Asn Ala
    290                 295                 300

Ala Trp Phe Lys Asn Met Pro His Leu Lys Val Leu Asp Leu Glu Phe
305                 310                 315                 320

Asn Tyr Leu Val Gly Glu Ile Ala Ser Gly Ala Phe Leu Thr Met Leu
```

```
            325                 330                 335
Pro Arg Leu Glu Ile Leu Asp Leu Ser Phe Asn Tyr Ile Lys Gly Ser
            340                 345                 350

Tyr Pro Gln His Ile Asn Ile Ser Arg Asn Phe Ser Lys Leu Leu Ser
            355                 360                 365

Leu Arg Ala Leu His Leu Arg Gly Tyr Val Phe Gln Glu Leu Arg Glu
            370                 375                 380

Asp Asp Phe Gln Pro Leu Met Gln Leu Pro Asn Leu Ser Thr Ile Asn
385                 390                 395                 400

Leu Gly Ile Asn Phe Ile Lys Gln Ile Asp Phe Lys Leu Phe Gln Asn
                    405                 410                 415

Phe Ser Asn Leu Glu Ile Ile Tyr Leu Ser Glu Asn Arg Ile Ser Pro
                420                 425                 430

Leu Val Lys Asp Thr Arg Gln Ser Tyr Ala Asn Ser Ser Ser Phe Gln
            435                 440                 445

Arg His Ile Arg Lys Arg Ser Thr Asp Phe Glu Phe Asp Pro His
            450                 455                 460

Ser Asn Phe Tyr His Phe Thr Arg Pro Leu Ile Lys Pro Gln Cys Ala
465                 470                 475                 480

Ala Tyr Gly Lys Ala Leu Asp Leu Ser Leu Asn Ser Ile Phe Phe Ile
                    485                 490                 495

Gly Pro Asn Gln Phe Glu Asn Leu Pro Asp Ile Ala Cys Leu Asn Leu
                500                 505                 510

Ser Ala Asn Ser Asn Ala Gln Val Leu Ser Gly Thr Glu Phe Ser Ala
            515                 520                 525

Ile Pro His Val Lys Tyr Leu Asp Leu Thr Asn Asn Arg Leu Asp Phe
530                 535                 540

Asp Asn Ala Ser Ala Leu Thr Glu Leu Ser Asp Leu Glu Val Leu Asp
545                 550                 555                 560

Leu Ser Tyr Asn Ser His Tyr Phe Arg Ile Ala Gly Val Thr His His
                565                 570                 575

Leu Glu Phe Ile Gln Asn Phe Thr Asn Leu Lys Val Leu Asn Leu Ser
                580                 585                 590

His Asn Asn Ile Tyr Thr Leu Thr Asp Lys Tyr Asn Leu Glu Ser Lys
            595                 600                 605

Ser Leu Val Glu Leu Val Phe Ser Gly Asn Arg Leu Asp Ile Leu Trp
            610                 615                 620

Asn Asp Asp Asp Asn Arg Tyr Ile Ser Ile Phe Lys Gly Leu Lys Asn
625                 630                 635                 640

Leu Thr Arg Leu Asp Leu Ser Leu Asn Arg Leu Lys His Ile Pro Asn
                    645                 650                 655

Glu Ala Phe Leu Asn Leu Pro Ala Ser Leu Thr Glu Leu His Ile Asn
                660                 665                 670

Asp Asn Met Leu Lys Phe Phe Asn Trp Thr Leu Leu Gln Gln Phe Pro
            675                 680                 685

Arg Leu Glu Leu Leu Asp Leu Arg Gly Asn Lys Leu Leu Phe Leu Thr
            690                 695                 700

Asp Ser Leu Ser Asp Phe Thr Ser Ser Leu Arg Thr Leu Leu Leu Ser
705                 710                 715                 720

His Asn Arg Ile Ser His Leu Pro Ser Gly Phe Leu Ser Glu Val Ser
                    725                 730                 735

Ser Leu Lys His Leu Asp Leu Ser Ser Asn Leu Leu Lys Thr Ile Asn
                740                 745                 750
```

Lys Ser Ala Leu Glu Thr Lys Thr Thr Thr Lys Leu Ser Met Leu Glu
        755                 760                 765

Leu His Gly Asn Pro Phe Glu Cys Thr Cys Asp Ile Gly Asp Phe Arg
    770                 775                 780

Arg Trp Met Asp Glu His Leu Asn Val Lys Ile Pro Arg Leu Val Asp
785                 790                 795                 800

Val Ile Cys Ala Ser Pro Gly Asp Gln Arg Gly Lys Ser Ile Val Ser
            805                 810                 815

Leu Glu Leu Thr Thr Cys Val Ser Asp Val Thr Ala Val Ile Leu Phe
        820                 825                 830

Phe Phe Thr Phe Phe Ile Thr Thr Met Val Met Leu Ala Ala Leu Ala
        835                 840                 845

His His Leu Phe Tyr Trp Asp Val Trp Phe Ile Tyr Asn Val Cys Leu
    850                 855                 860

Ala Lys Val Lys Gly Tyr Arg Ser Leu Ser Thr Ser Gln Thr Phe Tyr
865                 870                 875                 880

Asp Ala Tyr Ile Ser Tyr Asp Thr Lys Asp Ala Ser Val Thr Asp Trp
            885                 890                 895

Val Ile Asn Glu Leu Arg Tyr His Leu Glu Glu Ser Arg Asp Lys Asn
        900                 905                 910

Val Leu Leu Cys Leu Glu Glu Arg Asp Trp Asp Pro Gly Leu Ala Ile
    915                 920                 925

Ile Asp Asn Leu Met Gln Ser Ile Asn Gln Ser Lys Lys Thr Val Phe
930                 935                 940

Val Leu Thr Lys Lys Tyr Ala Lys Ser Trp Asn Phe Lys Thr Ala Phe
945                 950                 955                 960

Tyr Leu Ala Leu Gln Arg Leu Met Asp Glu Asn Met Asp Val Ile Ile
            965                 970                 975

Phe Ile Leu Leu Glu Pro Val Leu Gln His Ser Gln Tyr Leu Arg Leu
        980                 985                 990

Arg Gln Arg Ile Cys Lys Ser Ser Ile Leu Gln Trp Pro Asp Asn Pro
    995                 1000                1005

Lys Ala Glu Gly Leu Phe Trp Gln Thr Leu Arg Asn Val Val Leu
    1010                1015                1020

Thr Glu Asn Asp Ser Arg Tyr Asn Asn Met Tyr Val Asp Ser Ile
    1025                1030                1035

Lys Gln Tyr
    1040

<210> SEQ ID NO 29
<211> LENGTH: 3311
<212> TYPE: DNA
<213> ORGANISM: Homo sapiens

<400> SEQUENCE: 29
ttctgcgctg ctgcaagtta cggaatgaaa aattagaaca acagaaacat ggaaacatg      60 ttccttcagt cgtcaatgct gacctgcatt ttcctgctaa tatctggttc ctgtgagtta    120
tgcgccgaag aaaatttttc tagaagctat ccttgtgatg agaaaagca aaatgactca    180 gttattgcag agtgcagcaa tcgtcgacta caggaagttc cccaaacggt gggcaaatat    240
gtgacagaac tagacctgtc tgataatttc atcacacaca taacgaatga atcatttcaa    300
gggctgcaaa atctcactaa aataaatcta accacaacc ccaatgtaca gcaccagaac    360
ggaaatcccg gtatacaatc aaatggcttg aatatcacag acggggcatt cctcaaccta    420

```
aaaaacctaa gggagttact gcttgaagac aaccagttac cccaaatacc ctctggtttg    480
ccagagtctt tgacagaact tagtctaatt caaaacaata tatacaacat aactaaagag    540
ggcatttcaa gacttataaa cttgaaaaat ctctatttgg cctgaactg ctattttaac     600 aaagtttgcg agaaaactaa catagaagat ggagtatttg aaacgctgac aaatttggag    660
ttgctatcac tatctttcaa ttctctttca cacgtgccac ccaaactgcc aagctcccta    720
cgcaaacttt ttctgagcaa cacccagatc aaatacatta gtgaagaaga tttcaaggga    780
ttgataaatt taacattact agatttaagc gggaactgtc cgaggtgctt caatgcccca    840
tttccatgcg tgccttgtga tggtggtgct tcaattaata tagatcgttt tgcttttcaa    900
aacttgaccc aacttcgata cctaaacctc tctagcactt ccctcaggaa gattaatgct    960
gcctggttta aaaatatgcc tcatctgaag gtgctggatc ttgaattcaa ctatttagtg   1020
ggagaaatag cctctggggc attttttaacg atgctgcccc gcttagaaat acttgacttg   1080
tcttttaact atataaaggg gagttatcca cagcatatta atatttccag aaacttctct   1140
aaacttttgt ctctacgggc attgcattta agaggttatg tgttccagga actcagagaa   1200
gatgatttcc agcccctgat gcagcttcca aacttatcga ctatcaactt gggtattaat   1260
tttattaagc aaatcgattt caaacttttc caaaatttct ccaatctgga aattatttac   1320
ttgtcagaaa acagaatatc accgttggta aaagatacccc ggcagagtta tgcaaatagt   1380
tcctcttttc aacgtcatat ccggaaacga cgctcaacag attttgagtt tgacccacat   1440
tcgaactttt atcatttcac ccgtccttta ataaagccac aatgtgctgc ttatggaaaa   1500
gccttagatt taagcctcaa cagtattttc ttcattgggc caaaccaatt tgaaaatctt   1560
cctgacattg cctgtttaaa tctgtctgca aatagcaatg ctcaagtgtt aagtggaact   1620
gaattttcag ccattcctca tgtcaaatat ttggatttga caaacaatag actagacttt   1680
gataatgcta gtgctcttac tgaattgtcc gacttggaag ttctagatct cagctataat   1740
tcacactatt tcagaatagc aggcgtaaca catcatctag aatttattca aaatttcaca   1800
aatctaaaag ttttaaactt gagccacaac aacatttata ctttaacaga taagtataac   1860
ctggaaagca agtccctggt agaattagtt ttcagtggca atcgccttga cattttgtgg   1920
aatgatgatg acaacaggta tatctccatt ttcaaaggtc tcaagaatct gacacgtctg   1980
gatttatccc ttaataggct gaagcacatc ccaaatgaag cattccttaa tttgccagcg   2040
agtctcactg aactacatat aaatgataat atgttaaagt tttttaactg gacattactc   2100
cagcagttcc ctcgtctcga gttgcttgac ttacgtggaa acaaactact cttttttaact   2160 gatagcctat ctgactttac atcttccctt cggacactgc tgctgagtca taacaggatt   2220
tcccacctac cctctggctt tctttctgaa gtcagtagtc tgaagcacct cgatttaagt   2280
tccaatctgc taaaaacaat caacaaatcc gcacttgaaa ctaagaccac caccaaatta   2340
tctatgttgg aactacacgg aaaccccttt gaatgcacct gtgacattgg agatttccga   2400
agatggatgg atgaacatct gaatgtcaaa attcccagac tggtagatgt catttgtgcc   2460
agtcctgggg atcaaagagg gaagagtatt gtgagtctgg agctgacaac ttgtgtttca   2520
gatgtcactg cagtgatatt attttttcttc acgttcttta tcaccaccat ggttatgttg   2580
gctgccctgg ctcaccattt gttttactgg gatgtttggt ttatatataa tgtgtgttta   2640
gctaaggtaa aaggctacag gtctctttcc acatcccaaa cttttctatga tgcttacatt   2700 tcttatgaca ccaaagatgc ctctgttact gactgggtga taaatgagct gcgctaccac   2760
```

-continued

```
cttgaagaga gccgagacaa aaacgttctc ctttgtctag aggagaggga ttgggacccg    2820
ggattggcca tcatcgacaa cctcatgcag agcatcaacc aaagcaagaa aacagtattt    2880
gttttaacca aaaatatgc aaaaagctgg aactttaaaa cagcttttta cttggctttg    2940
cagaggctaa tggatgagaa catggatgtg attatattta tcctgctgga gccagtgtta    3000
cagcattctc agtatttgag gctacggcag cggatctgta agagctccat cctccagtgg    3060
cctgacaacc cgaaggcaga aggcttgttt tggcaaactc tgagaaatgt ggtcttgact    3120
gaaaatgatt cacggtataa caatatgtat gtcgattcca ttaagcaata ctaactgacg    3180
ttaagtcatg atttcgcgcc ataataaaga tgcaaaggaa tgacatttct gtattagtta    3240
tctattgcta tgtaacaaat tatcccaaaa cttagtggtt taaaacaaca catttgctgg    3300
cccacagttt t                                                        3311
```

<210> SEQ ID NO 30
<211> LENGTH: 1059
<212> TYPE: PRT
<213> ORGANISM: Homo sapiens

<400> SEQUENCE: 30

```
Met Lys Glu Ser Ser Leu Gln Asn Ser Ser Cys Ser Leu Gly Lys Glu
1               5                   10                  15

Thr Lys Lys Glu Asn Met Phe Leu Gln Ser Ser Met Leu Thr Cys Ile
            20                  25                  30

Phe Leu Leu Ile Ser Gly Ser Cys Glu Leu Cys Ala Glu Glu Asn Phe
        35                  40                  45

Ser Arg Ser Tyr Pro Cys Asp Glu Lys Lys Gln Asn Asp Ser Val Ile
    50                  55                  60

Ala Glu Cys Ser Asn Arg Arg Leu Gln Glu Val Pro Gln Thr Val Gly
65                  70                  75                  80

Lys Tyr Val Thr Glu Leu Asp Leu Ser Asp Asn Phe Ile Thr His Ile
                85                  90                  95

Thr Asn Glu Ser Phe Gln Gly Leu Gln Asn Leu Thr Lys Ile Asn Leu
            100                 105                 110

Asn His Asn Pro Asn Val Gln His Gln Asn Gly Asn Pro Gly Ile Gln
        115                 120                 125

Ser Asn Gly Leu Asn Ile Thr Asp Gly Ala Phe Leu Asn Leu Lys Asn
    130                 135                 140

Leu Arg Glu Leu Leu Leu Glu Asp Asn Gln Leu Pro Gln Ile Pro Ser
145                 150                 155                 160

Gly Leu Pro Glu Ser Leu Thr Glu Leu Ser Leu Ile Gln Asn Asn Ile
                165                 170                 175

Tyr Asn Ile Thr Lys Glu Gly Ile Ser Arg Leu Ile Asn Leu Lys Asn
            180                 185                 190

Leu Tyr Leu Ala Trp Asn Cys Tyr Phe Asn Lys Val Cys Glu Lys Thr
        195                 200                 205

Asn Ile Glu Asp Gly Val Phe Glu Thr Leu Thr Asn Leu Glu Leu Leu
    210                 215                 220

Ser Leu Ser Phe Asn Ser Leu Ser His Val Ser Pro Lys Leu Pro Ser
225                 230                 235                 240

Ser Leu Arg Lys Leu Phe Leu Ser Asn Thr Gln Ile Lys Tyr Ile Ser
                245                 250                 255

Glu Glu Asp Phe Lys Gly Leu Ile Asn Leu Thr Leu Leu Asp Leu Ser
            260                 265                 270
```

-continued

Gly Asn Cys Pro Arg Cys Phe Asn Ala Pro Phe Pro Cys Val Pro Cys
            275                 280                 285

Asp Gly Gly Ala Ser Ile Asn Ile Asp Arg Phe Ala Phe Gln Asn Leu
        290                 295                 300

Thr Gln Leu Arg Tyr Leu Asn Leu Ser Ser Thr Ser Leu Arg Lys Ile
305                 310                 315                 320

Asn Ala Ala Trp Phe Lys Asn Met Pro His Leu Lys Val Leu Asp Leu
                325                 330                 335

Glu Phe Asn Tyr Leu Val Gly Glu Ile Ala Ser Gly Ala Phe Leu Thr
            340                 345                 350

Met Leu Pro Arg Leu Glu Ile Leu Asp Leu Ser Phe Asn Tyr Ile Lys
        355                 360                 365

Gly Ser Tyr Pro Gln His Ile Asn Ile Ser Arg Asn Phe Ser Lys Pro
    370                 375                 380

Leu Ser Leu Arg Ala Leu His Leu Arg Gly Tyr Val Phe Gln Glu Leu
385                 390                 395                 400

Arg Glu Asp Asp Phe Gln Pro Leu Met Gln Leu Pro Asn Leu Ser Thr
                405                 410                 415

Ile Asn Leu Gly Ile Asn Phe Ile Lys Gln Ile Asp Phe Lys Leu Phe
            420                 425                 430

Gln Asn Phe Ser Asn Leu Glu Ile Ile Tyr Leu Ser Glu Asn Arg Ile
        435                 440                 445

Ser Pro Leu Val Lys Asp Thr Arg Gln Ser Tyr Ala Asn Ser Ser Ser
    450                 455                 460

Phe Gln Arg His Ile Arg Lys Arg Arg Ser Thr Asp Phe Glu Phe Asp
465                 470                 475                 480

Pro His Ser Asn Phe Tyr His Phe Thr Arg Pro Leu Ile Lys Pro Gln
                485                 490                 495

Cys Ala Ala Tyr Gly Lys Ala Leu Asp Leu Ser Leu Asn Ser Ile Phe
            500                 505                 510

Phe Ile Gly Pro Asn Gln Phe Glu Asn Leu Pro Asp Ile Ala Cys Leu
        515                 520                 525

Asn Leu Ser Ala Asn Ser Asn Ala Gln Val Leu Ser Gly Thr Glu Phe
    530                 535                 540

Ser Ala Ile Pro His Val Lys Tyr Leu Asp Leu Thr Asn Asn Arg Leu
545                 550                 555                 560

Asp Phe Asp Asn Ala Ser Ala Leu Thr Glu Leu Ser Asp Leu Glu Val
                565                 570                 575

Leu Asp Leu Ser Tyr Asn Ser His Tyr Phe Arg Ile Ala Gly Val Thr
            580                 585                 590

His His Leu Glu Phe Ile Gln Asn Phe Thr Asn Leu Lys Val Leu Asn
        595                 600                 605

Leu Ser His Asn Asn Ile Tyr Thr Leu Thr Asp Lys Tyr Asn Leu Glu
    610                 615                 620

Ser Lys Ser Leu Val Glu Leu Val Phe Ser Gly Asn Arg Leu Asp Ile
625                 630                 635                 640

Leu Trp Asn Asp Asp Asp Asn Arg Tyr Ile Ser Ile Phe Lys Gly Leu
                645                 650                 655

Lys Asn Leu Thr Arg Leu Asp Leu Ser Leu Asn Arg Leu Lys His Ile
            660                 665                 670

Pro Asn Glu Ala Phe Leu Asn Leu Pro Ala Ser Leu Thr Glu Leu His
        675                 680                 685

Ile Asn Asp Asn Met Leu Lys Phe Phe Asn Trp Thr Leu Leu Gln Gln

```
              690                 695                 700
Phe Pro Arg Leu Glu Leu Leu Asp Leu Arg Gly Asn Lys Leu Leu Phe
705                 710                 715                 720

Leu Thr Asp Ser Leu Ser Asp Phe Thr Ser Leu Arg Thr Leu Leu
                725                 730                 735

Leu Ser His Asn Arg Ile Ser His Leu Pro Ser Gly Phe Leu Ser Glu
                740                 745                 750

Val Ser Ser Leu Lys His Leu Asp Leu Ser Ser Asn Leu Leu Lys Thr
                755                 760                 765

Ile Asn Lys Ser Ala Leu Glu Thr Lys Thr Thr Thr Lys Leu Ser Met
770                 775                 780

Leu Glu Leu His Gly Asn Pro Phe Glu Cys Thr Cys Asp Ile Gly Asp
785                 790                 795                 800

Phe Arg Arg Trp Met Asp Glu His Leu Asn Val Lys Ile Pro Arg Leu
                805                 810                 815

Val Asp Val Ile Cys Ala Ser Pro Gly Asp Gln Arg Gly Lys Ser Ile
                820                 825                 830

Val Ser Leu Glu Leu Thr Thr Cys Val Ser Asp Val Thr Ala Val Ile
                835                 840                 845

Leu Phe Phe Phe Thr Phe Phe Ile Thr Thr Met Val Met Leu Ala Ala
850                 855                 860

Leu Ala His His Leu Phe Tyr Trp Asp Val Trp Phe Ile Tyr Asn Val
865                 870                 875                 880

Cys Leu Ala Lys Ile Lys Gly Tyr Arg Ser Leu Ser Thr Ser Gln Thr
                885                 890                 895

Phe Tyr Asp Ala Tyr Ile Ser Tyr Asp Thr Lys Asp Ala Ser Val Thr
                900                 905                 910

Asp Trp Val Ile Asn Glu Leu Arg Tyr His Leu Glu Glu Ser Arg Asp
                915                 920                 925

Lys Asn Val Leu Leu Cys Leu Glu Glu Arg Asp Trp Asp Pro Gly Leu
930                 935                 940

Ala Ile Ile Asp Asn Leu Met Gln Ser Ile Asn Gln Ser Lys Lys Thr
945                 950                 955                 960

Val Phe Val Leu Thr Lys Lys Tyr Ala Lys Ser Trp Asn Phe Lys Thr
                965                 970                 975

Ala Phe Tyr Leu Ala Leu Gln Arg Leu Met Asp Glu Asn Met Asp Val
                980                 985                 990

Ile Ile Phe Ile Leu Leu Glu Pro Val Leu Gln His Ser Gln Tyr Leu
                995                 1000                1005

Arg Leu Arg Gln Arg Ile Cys Lys Ser Ser Ile Leu Gln Trp Pro
1010                1015                1020

Asp Asn Pro Lys Ala Glu Gly Leu Phe Trp Gln Thr Leu Arg Asn
1025                1030                1035

Val Val Leu Thr Glu Asn Asp Ser Arg Tyr Asn Asn Met Tyr Val
1040                1045                1050

Asp Ser Ile Lys Gln Tyr
        1055

<210> SEQ ID NO 31
<211> LENGTH: 3367
<212> TYPE: DNA
<213> ORGANISM: Homo sapiens

<400> SEQUENCE: 31
```

-continued

```
ctcctgcata gagggtacca ttctgcgctg ctgcaagtta cggaatgaaa aattagaaca      60
acagaaacgt ggttctcttg acacttcagt gttagggaac atcagcaaga cccatcccag     120
gagaccttga aggaagcctt tgaaagggag aatgaaggag tcatctttgc aaaatagctc     180
ctgcagcctg ggaaggagaa ctaaaaagga aaacatgttc cttcagtcgt caatgctgac     240
ctgcattttc ctgctaatat ctggttcctg tgagttatgc gccgaagaaa attttttctag   300
aagctatcct tgtgatgaga aaaagcaaaa tgactcagtt attgcagagt gcagcaatcg     360
tcgactacag gaagttcccc aaacggtggg caaatatgtg acagaactag acctgtctga     420
taatttcatc acacacataa cgaatgaatc atttcaaggg ctgcaaaatc tcactaaaat     480
aaatctaaac cacaacccca atgtacagca ccagaacgga atcccggta tacaatcaaa     540
tggcttgaat atcacagacg gggcattcct caacctaaaa aacctaaggg agttactgct    600
tgaagacaac cagttacccc aaataccctc tggtttgcca gagtctttga cagaacttag    660
tctaattcaa aacaatatat acaacataac taaagagggc atttcaagac ttataaactt    720
gaaaaatctc tatttggcct ggaactgcta ttttaacaaa gtttgcgaga aaactaacat    780
agaagatgga gtatttgaaa cgctgacaaa tttggagttg ctatcactat ctttcaattc    840
tctttcacac gtgtcaccca aactgccaag ctccctacgc aaacttttc tgagcaacac    900
ccagatcaaa tacattagtg aagaagattt caagggattg ataaatttaa cattactaga   960
tttaagcggg aactgtccga ggtgcttcaa tgccccattt ccatgcgtgc cttgtgatgg  1020
tggtgcttca attaatatag atcgttttgc ttttcaaaac ttgacccaac ttcgatacct   1080
aaacctctct agcacttccc tcaggaagat taatgctgcc tggtttaaaa atatgcctca    1140
tctgaaggtg ctggatcttg aattcaacta tttagtggga gaaatagcct ctggggcatt   1200
tttaacgatg ctgccccgct tagaaatact tgacttgtct tttaactata taaaggggag   1260
ttatccacag catattaata tttccagaaa cttctctaaa cctttgtctc tacgggcatt    1320
gcatttaaga ggttatgtgt tccaggaact cagagaagat gatttccagc ccctgatgca    1380
gcttccaaac ttatcgacta tcaacttggg tattaatttt attaagcaaa tcgatttcaa    1440
acttttccaa aatttctcca atctggaaat tatttacttg tcagaaaaca gaatatcacc    1500
gttggtaaaa gatacccggc agagttatgc aaatagttcc tcttttcaac gtcatatccg    1560
gaaacgacgc tcaacagatt ttgagtttga cccacattcg aacttttatc atttcacccg    1620
tcctttaata aagccacaat gtgctgctta tggaaaagcc ttagatttaa gcctcaacag    1680
tattttcttc attgggccaa accaatttga aaatcttcct gacattgcct gtttaaatct    1740
gtctgcaaat agcaatgctc aagtgttaag tggaactgaa ttttcagcca ttcctcatgt   1800
caaatatttg gatttgacaa acaatagact agactttgat aatgctagtg ctcttactga   1860
attgtccgac ttggaagttc tagatctcag ctataattca cactatttca gaatagcagg    1920
cgtaacacat catctagaat ttattcaaaa tttcacaaat ctaaagttt taaacttgag     1980
ccacaacaac atttatactt taacagataa gtataacctg gaaagcaagt ccctggtaga   2040
attagttttc agtggcaatc gccttgacat tttgtggaat gatgatgaca acaggtatat   2100
ctccattttc aaaggtctca gaatctgac acgtctggat ttatccctta ataggctgaa   2160
gcacatccca aatgaagcat tccttaattt gccagcgagt ctcactgaac tacatataaa   2220
tgataatatg ttaaagtttt ttaactggac attactccag cagtttcctc gtctcgagtt  2280
gcttgactta cgtggaaaca aactactctt tttaactgat agcctatctg actttacatc   2340
ttccccttcgg acactgctgc tgagtcataa caggatttcc cacctaccct ctggctttct   2400
```

```
ttctgaagtc agtagtctga agcacctcga tttaagttcc aatctgctaa aaacaatcaa    2460
caaatccgca cttgaaacta agaccaccac caaattatct atgttggaac tacacggaaa    2520
cccctttgaa tgcacctgtg acattggaga tttccgaaga tggatggatg aacatctgaa    2580
tgtcaaaatt cccagactgg tagatgtcat ttgtgccagt cctggggatc aaagagggaa    2640
gagtattgtg agtctggagc taacaacttg tgtttcagat gtcactgcag tgatattatt    2700
tttcttcacg ttctttatca ccaccatggt tatgttggct gccctggctc accatttgtt    2760
ttactgggat gtttggttta tataatgt gtgtttagct aagataaaag gctacaggtc    2820
tctttccaca tcccaaactt tctatgatgc ttacatttct tatgacacca agatgcctc    2880 tgttactgac tgggtgataa atgagctgcg ctaccacctt gaagagagcc gagacaaaaa    2940
cgttctcctt tgtctagagg agagggattg ggacccggga ttggccatca tcgacaacct    3000
catgcagagc atcaaccaaa gcaagaaaac agtatttgtt ttaaccaaaa aatatgcaaa    3060
aagctggaac tttaaaacag cttttttactt ggctttgcag aggctaatgg atgagaacat    3120
ggatgtgatt atatttatcc tgctggagcc agtgttacag cattctcagt atttgaggct    3180
acggcagcgg atctgtaaga gctccatcct ccagtggcct gacaacccga aggcagaagg    3240
cttgttttgg caaactctga gaatgtggt cttgactgaa aatgattcac ggtataacaa    3300
tatgtatgtc gattccatta agcaatacta actgacgtta agtcatgatt tcgcgccata    3360
ataaaga                                                              3367
```

<210> SEQ ID NO 32
<211> LENGTH: 1032
<212> TYPE: PRT
<213> ORGANISM: Mus musculus

<400> SEQUENCE: 32

```
Met Glu Asn Met Pro Pro Gln Ser Trp Ile Leu Thr Cys Phe Cys Leu
1               5                   10                  15

Leu Ser Ser Gly Thr Ser Ala Ile Phe His Lys Ala Asn Tyr Ser Arg
            20                  25                  30

Ser Tyr Pro Cys Asp Glu Ile Arg His Asn Ser Leu Val Ile Ala Glu
        35                  40                  45

Cys Asn His Arg Gln Leu His Glu Val Pro Gln Thr Ile Gly Lys Tyr
    50                  55                  60

Val Thr Asn Ile Asp Leu Ser Asp Asn Ala Ile Thr His Ile Thr Lys
65                  70                  75                  80

Glu Ser Phe Gln Lys Leu Gln Asn Leu Thr Lys Ile Asp Leu Asn His
                85                  90                  95

Asn Ala Lys Gln Gln His Pro Asn Glu Asn Lys Asn Gly Met Asn Ile
            100                 105                 110

Thr Glu Gly Ala Leu Leu Ser Leu Arg Asn Leu Thr Val Leu Leu Leu
        115                 120                 125

Glu Asp Asn Gln Leu Tyr Thr Ile Pro Ala Gly Leu Pro Glu Ser Leu
    130                 135                 140

Lys Glu Leu Ser Leu Ile Gln Asn Asn Ile Phe Gln Val Thr Lys Asn
145                 150                 155                 160

Asn Thr Phe Gly Leu Arg Asn Leu Glu Arg Leu Tyr Leu Gly Trp Asn
                165                 170                 175

Cys Tyr Phe Lys Cys Asn Gln Thr Phe Lys Val Glu Asp Gly Ala Phe
            180                 185                 190
```

```
Lys Asn Leu Ile His Leu Lys Val Leu Ser Leu Ser Phe Asn Asn Leu
            195                 200                 205
Phe Tyr Val Pro Pro Lys Leu Pro Ser Ser Leu Arg Lys Leu Phe Leu
210                 215                 220
Ser Asn Ala Lys Ile Met Asn Ile Thr Gln Glu Asp Phe Lys Gly Leu
225                 230                 235                 240
Glu Asn Leu Thr Leu Leu Asp Leu Ser Gly Asn Cys Pro Arg Cys Tyr
            245                 250                 255
Asn Ala Pro Phe Pro Cys Thr Pro Cys Lys Glu Asn Ser Ser Ile His
            260                 265                 270
Ile His Pro Leu Ala Phe Gln Ser Leu Thr Gln Leu Leu Tyr Leu Asn
            275                 280                 285
Leu Ser Ser Thr Ser Leu Arg Thr Ile Pro Ser Thr Trp Phe Glu Asn
290                 295                 300
Leu Ser Asn Leu Lys Glu Leu His Leu Glu Phe Asn Tyr Leu Val Gln
305                 310                 315                 320
Glu Ile Ala Ser Gly Ala Phe Leu Thr Lys Leu Pro Ser Leu Gln Ile
                325                 330                 335
Leu Asp Leu Ser Phe Asn Phe Gln Tyr Lys Glu Tyr Leu Gln Phe Ile
                340                 345                 350
Asn Ile Ser Ser Asn Phe Ser Lys Leu Arg Ser Leu Lys Lys Leu His
            355                 360                 365
Leu Arg Gly Tyr Val Phe Arg Glu Leu Lys Lys His Phe Glu His
370                 375                 380
Leu Gln Ser Leu Pro Asn Leu Ala Thr Ile Asn Leu Gly Ile Asn Phe
385                 390                 395                 400
Ile Glu Lys Ile Asp Phe Lys Ala Phe Gln Asn Phe Ser Lys Leu Asp
                405                 410                 415
Val Ile Tyr Leu Ser Gly Asn Arg Ile Ala Ser Val Leu Asp Gly Thr
                420                 425                 430
Asp Tyr Ser Ser Trp Arg Asn Arg Leu Arg Lys Pro Leu Ser Thr Asp
            435                 440                 445
Asp Asp Glu Phe Asp Pro His Val Asn Phe Tyr His Ser Thr Lys Pro
450                 455                 460
Leu Ile Lys Pro Gln Cys Thr Ala Tyr Gly Lys Ala Leu Asp Leu Ser
465                 470                 475                 480
Leu Asn Asn Ile Phe Ile Ile Gly Lys Ser Gln Phe Glu Gly Phe Gln
                485                 490                 495
Asp Ile Ala Cys Leu Asn Leu Ser Phe Asn Ala Asn Thr Gln Val Phe
            500                 505                 510
Asn Gly Thr Glu Phe Ser Ser Met Pro His Ile Lys Tyr Leu Asp Leu
            515                 520                 525
Thr Asn Asn Arg Leu Asp Phe Asp Asn Asn Ala Phe Ser Asp Leu
530                 535                 540
His Asp Leu Glu Val Leu Asp Leu Ser His Asn Ala His Tyr Phe Ser
545                 550                 555                 560
Ile Ala Gly Val Thr His Arg Leu Gly Phe Ile Gln Asn Leu Ile Asn
                565                 570                 575
Leu Arg Val Leu Asn Leu Ser His Asn Gly Ile Tyr Thr Leu Thr Glu
            580                 585                 590
Glu Ser Glu Leu Lys Ser Ile Ser Leu Lys Glu Leu Val Phe Ser Gly
            595                 600                 605
Asn Arg Leu Asp His Leu Trp Asn Ala Asn Asp Gly Lys Tyr Trp Ser
```

```
            610                 615                 620
Ile Phe Lys Ser Leu Gln Asn Leu Ile Arg Leu Asp Leu Ser Tyr Asn
625                 630                 635                 640

Asn Leu Gln Gln Ile Pro Asn Gly Ala Phe Leu Asn Leu Pro Gln Ser
                645                 650                 655

Leu Gln Glu Leu Leu Ile Ser Gly Asn Lys Leu Arg Phe Phe Asn Trp
            660                 665                 670

Thr Leu Leu Gln Tyr Phe Pro His Leu His Leu Asp Leu Ser Arg
        675                 680                 685

Asn Glu Leu Tyr Phe Leu Pro Asn Cys Leu Ser Lys Phe Ala His Ser
    690                 695                 700

Leu Glu Thr Leu Leu Leu Ser His Asn His Phe Ser His Leu Pro Ser
705                 710                 715                 720

Gly Phe Leu Ser Glu Ala Arg Asn Leu Val His Leu Asp Leu Ser Phe
                725                 730                 735

Asn Thr Ile Lys Met Ile Asn Lys Ser Ser Leu Gln Thr Lys Met Lys
            740                 745                 750

Thr Asn Leu Ser Ile Leu Glu Leu His Gly Asn Tyr Phe Asp Cys Thr
        755                 760                 765

Cys Asp Ile Ser Asp Phe Arg Ser Trp Leu Asp Glu Asn Leu Asn Ile
    770                 775                 780

Thr Ile Pro Lys Leu Val Asn Val Ile Cys Ser Asn Pro Gly Asp Gln
785                 790                 795                 800

Lys Ser Lys Ser Ile Met Ser Leu Asp Leu Thr Thr Cys Val Ser Asp
                805                 810                 815

Thr Thr Ala Ala Val Leu Phe Phe Leu Thr Phe Leu Thr Thr Ser Met
            820                 825                 830

Val Met Leu Ala Ala Leu Val His His Leu Phe Tyr Trp Asp Val Trp
        835                 840                 845

Phe Ile Tyr His Met Cys Ser Ala Lys Leu Lys Gly Tyr Arg Thr Ser
    850                 855                 860

Ser Thr Ser Gln Thr Phe Tyr Asp Ala Tyr Ile Ser Tyr Asp Thr Lys
865                 870                 875                 880

Asp Ala Ser Val Thr Asp Trp Val Ile Asn Glu Leu Arg Tyr His Leu
                885                 890                 895

Glu Glu Ser Glu Asp Lys Ser Val Leu Leu Cys Leu Glu Glu Arg Asp
            900                 905                 910

Trp Asp Pro Gly Leu Pro Ile Ile Asp Asn Leu Met Gln Ser Ile Asn
        915                 920                 925

Gln Ser Lys Lys Thr Ile Phe Val Leu Thr Lys Lys Tyr Ala Lys Ser
    930                 935                 940

Trp Asn Phe Lys Thr Ala Phe Tyr Leu Ala Leu Gln Arg Leu Met Asp
945                 950                 955                 960

Glu Asn Met Asp Val Ile Ile Phe Ile Leu Leu Glu Pro Val Leu Gln
                965                 970                 975

Tyr Ser Gln Tyr Leu Arg Leu Arg Gln Arg Ile Cys Lys Ser Ser Ile
            980                 985                 990

Leu Gln Trp Pro Asn Asn Pro Lys  Ala Glu Asn Leu Phe Trp Gln Ser
        995                 1000                 1005

Leu Lys Asn Val Val Leu Thr  Glu Asn Asp Ser Arg  Tyr Asp Asp
    1010                1015                 1020

Leu Tyr  Ile Asp Ser Ile Arg  Gln Tyr
    1025                1030
```

<210> SEQ ID NO 33
<211> LENGTH: 3220
<212> TYPE: DNA
<213> ORGANISM: Mus musculus

<400> SEQUENCE: 33

| | | | | | |
|---|---|---|---|---|---|
| attcagagtt | ggatgttaag | agagaaacaa | acgttttacc | ttcctttgtc | tatagaacat | 60 |
| ggaaaacatg | cccctcagt | catggattct | gacgtgcttt | tgtctgctgt | cctctggaac | 120 |
| cagtgccatc | ttccataaag | cgaactattc | cagaagctat | ccttgtgacg | agataaggca | 180 |
| caactccctt | gtgattgcag | aatgcaacca | tcgtcaactg | catgaagttc | cccaaactat | 240 |
| aggcaagtat | gtgacaaaca | tagacttgtc | agacaatgcc | attacacata | taacgaaaga | 300 |
| gtcctttcaa | aagctgcaaa | acctcactaa | aatcgatctg | aaccacaatg | ccaaacaaca | 360 |
| gcacccaaat | gaaaataaaa | atggtatgaa | tattacagaa | ggggcacttc | tcagcctaag | 420 |
| aaatctaaca | gttttactgc | tggaagacaa | ccagttatat | actatacctg | ctgggttgcc | 480 |
| tgagtctttg | aaagaactta | gcctaattca | aaacaatata | tttcaggtaa | ctaaaaacaa | 540 |
| cacttttggg | cttaggaact | tggaaagact | ctatttgggc | tggaactgct | attttaaatg | 600 |
| taatcaaacc | tttaaggtag | aagatggggc | atttaaaaat | cttatacact | tgaaggtact | 660 |
| ctcattatct | ttcaataacc | ttttctatgt | gccccccaaa | ctaccaagtt | ctctaaggaa | 720 |
| acttttctg | agtaatgcca | aaatcatgaa | catcactcag | gaagacttca | aaggactgga | 780 |
| aaatttaaca | ttactagatc | tgagtggaaa | ctgtccaagg | tgttacaatg | ctccatttcc | 840 |
| ttgcacacct | tgcaaggaaa | actcatccat | ccacatacat | cctctggctt | ttcaaagtct | 900 |
| cacccaactt | ctctatctaa | acctttccag | cacttccctc | aggacgattc | cttctacctg | 960 |
| gtttgaaaat | ctgtcaaatc | tgaaggaact | ccatcttgaa | ttcaactatt | tagttcaaga | 1020 |
| aattgcctcg | ggggcatttt | taacaaaact | acccagttta | caaatccttg | atttgtcctt | 1080 |
| caactttcaa | tataaggaat | atttacaatt | tattaatatt | tcctcaaatt | tctctaagct | 1140 |
| tcgttctctc | aagaagttgc | acttaagagg | ctatgtgttc | cgagaactta | aaaagaagca | 1200 |
| tttcgagcat | ctccagagtc | ttccaaactt | ggcaaccatc | aacttgggca | ttaacttat | 1260 |
| tgagaaaatt | gatttcaaag | ctttccagaa | tttttccaaa | ctcgacgtta | tctatttatc | 1320 |
| aggaaatcgc | atagcatctg | tattagatgg | tacagattat | tcctcttggc | gaaatcgtct | 1380 |
| tcggaaacct | ctctcaacag | acgatgatga | gtttgatcca | cacgtgaatt | tttaccatag | 1440 |
| caccaaacct | ttaataaagc | cacagtgtac | tgcttatggc | aaggccttgg | atttaagttt | 1500 |
| gaacaatatt | ttcattattg | ggaaaagcca | atttgaaggt | ttcaggata | tcgcctgctt | 1560 |
| aaatctgtcc | ttcaatgcca | atactcaagt | gtttaatggc | acagaattct | cctccatgcc | 1620 |
| ccacattaaa | tatttggatt | taaccaacaa | cagactagac | tttgatgata | acaatgcttt | 1680 |
| cagtgatctt | cacgatctag | aagtgctgga | cctgagccac | aatgcacact | atttcagtat | 1740 |
| agcaggggta | acgcaccgtc | taggatttat | ccagaactta | ataaacctca | gggtgttaaa | 1800 |
| cctgagccac | aatggcattt | acaccctcac | agaggaaagt | gagctgaaaa | gcatctcact | 1860 |
| gaaagaattg | gttttcagtg | gaaatcgtct | tgaccatttg | tggaatgcaa | atgatggcaa | 1920 |
| atactggtcc | atttttaaaa | gtctccagaa | tttgatacgc | ctggacttat | catacaataa | 1980 |
| ccttcaacaa | atcccaaatg | gagcattcct | caatttgcct | cagagcctcc | aagagttact | 2040 |
| tatcagtggt | aacaaattac | gtttctttaa | ttggacatta | ctccagtatt | ttcctcacct | 2100 |

```
tcacttgctg gatttatcga gaaatgagct gtattttcta cccaattgcc tatctaagtt    2160
tgcacattcc ctggagacac tgctactgag ccataatcat ttctctcacc taccctctgg    2220
cttcctctcc gaagccagga atctggtgca cctggatcta agtttcaaca caataaagat    2280
gatcaataaa tcctccctgc aaaccaagat gaaaacgaac ttgtctattc tggagctaca    2340
tgggaactat tttgactgca cgtgtgacat aagtgatttt cgaagctggc tagatgaaaa    2400
tctgaatatc acaattccta aattggtaaa tgttatatgt tccaatcctg gggatcaaaa    2460
atcaaagagt atcatgagcc tagatctcac gacttgtgta tcggatacca ctgcagctgt    2520
cctgtttttc ctcacattcc ttaccacctc catggttatg ttggctgctc tggttcacca    2580
cctgttttac tgggatgttt ggtttatcta tcacatgtgc tctgctaagt taaaaggcta    2640
caggacttca tccacatccc aaactttcta tgatgcttat atttcttatg acaccaaaga    2700
tgcatctgtt actgactggg taatcaatga actgcgctac caccttgaag agagtgaaga    2760
caaaagtgtc ctcctttgtt tagaggagag ggattgggat ccaggattac ccatcattga    2820
taacctcatg cagagcataa accagagcaa gaaaacaatc tttgttttaa ccaagaaata    2880
tgccaagagc tggaacttta aaacagcttt ctacttggcc ttgcagaggc taatggatga    2940
gaacatggat gtgattattt tcatcctcct ggaaccagtg ttacagtact cacagtacct    3000
gaggcttcgg cagaggatct gtaagagctc catcctccag tggcccaaca atcccaaagc    3060
agaaaacttg ttttggcaaa gtctgaaaaa tgtggtcttg actgaaaatg attcacggta    3120
tgacgatttg tacattgatt ccattaggca atactagtga tgggaagtca cgactctgcc    3180
atcataaaaa cacacagctt ctccttacaa tgaaccgaat                          3220
```

<210> SEQ ID NO 34
<211> LENGTH: 1032
<212> TYPE: PRT
<213> ORGANISM: Homo sapiens

<400> SEQUENCE: 34

Met Gly Phe Cys Arg Ser Ala Leu His Pro Leu Ser Leu Leu Val Gln
1               5                   10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
    50                  55                  60

Val Thr Ser Leu Ser Leu Ser Ser Asn Arg Ile His His Leu His Asp
65                  70                  75                  80

Ser Asp Phe Ala His Leu Pro Ser Leu Arg His Leu Asn Leu Lys Trp
                85                  90                  95

Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
        115                 120                 125

Asn Leu Ser Tyr Asn Asn Ile Met Thr Val Pro Ala Leu Pro Lys Ser
    130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

-continued

Asn Cys Tyr Tyr Lys Asn Pro Cys Arg Gln Ala Leu Glu Val Ala Pro
                180                 185                 190

Gly Ala Leu Leu Gly Leu Gly Asn Leu Thr His Leu Ser Leu Lys Tyr
        195                 200                 205

Asn Asn Leu Thr Val Val Pro Arg Asn Leu Pro Ser Ser Leu Glu Tyr
        210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
                260                 265                 270

Pro Gln Leu His Pro Asp Thr Phe Ser His Leu Ser Arg Leu Glu Gly
        275                 280                 285

Leu Val Leu Lys Asp Ser Ser Leu Ser Trp Leu Asn Ala Ser Trp Phe
        290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
                340                 345                 350

His Leu Ser Leu Ala Pro Ser Phe Gly Ser Leu Val Ala Leu Lys Glu
        355                 360                 365

Leu Asp Met His Gly Ile Phe Phe Arg Ser Leu Asp Glu Thr Thr Leu
        370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
                420                 425                 430

Leu Thr Ala Thr Met Gly Glu Ala Asp Gly Gly Glu Lys Val Trp Leu
        435                 440                 445

Gln Pro Gly Asp Leu Ala Pro Ala Pro Val Asp Thr Pro Ser Ser Glu
        450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
                485                 490                 495

His Leu Gln Cys Leu Arg Leu Ser His Asn Cys Ile Ser Gln Ala Val
        500                 505                 510

Asn Gly Ser Gln Phe Leu Pro Leu Thr Gly Leu Gln Val Leu Asp Leu
        515                 520                 525

Ser His Asn Lys Leu Asp Leu Tyr His Glu His Ser Phe Thr Glu Leu
530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser
        580                 585                 590

Gln Gln Leu Cys Ser Thr Ser Leu Arg Ala Leu Asp Phe Ser Gly Asn

```
            595                 600                 605
Ala Leu Gly His Met Trp Ala Glu Gly Asp Leu Tyr Leu His Phe Phe
610                     615                 620
Gln Gly Leu Ser Gly Leu Ile Trp Leu Asp Leu Ser Gln Asn Arg Leu
625                     630                 635                 640
His Thr Leu Leu Pro Gln Thr Leu Arg Asn Leu Pro Lys Ser Leu Gln
                645                 650                 655
Val Leu Arg Leu Arg Asp Asn Tyr Leu Ala Phe Phe Lys Trp Trp Ser
            660                 665                 670
Leu His Phe Leu Pro Lys Leu Glu Val Leu Asp Leu Ala Gly Asn Gln
            675                 680                 685
Leu Lys Ala Leu Thr Asn Gly Ser Leu Pro Ala Gly Thr Arg Leu Arg
690                     695                 700
Arg Leu Asp Val Ser Cys Asn Ser Ile Ser Phe Val Ala Pro Gly Phe
705                     710                 715                 720
Phe Ser Lys Ala Lys Glu Leu Arg Glu Leu Asn Leu Ser Ala Asn Ala
                725                 730                 735
Leu Lys Thr Val Asp His Ser Trp Phe Gly Pro Leu Ala Ser Ala Leu
                740                 745                 750
Gln Ile Leu Asp Val Ser Ala Asn Pro Leu His Cys Ala Cys Gly Ala
            755                 760                 765
Ala Phe Met Asp Phe Leu Leu Glu Val Gln Ala Ala Val Pro Gly Leu
770                     775                 780
Pro Ser Arg Val Lys Cys Gly Ser Pro Gly Gln Leu Gln Gly Leu Ser
785                     790                 795                 800
Ile Phe Ala Gln Asp Leu Arg Leu Cys Leu Asp Glu Ala Leu Ser Trp
                805                 810                 815
Asp Cys Phe Ala Leu Ser Leu Leu Ala Val Ala Leu Gly Leu Gly Val
                820                 825                 830
Pro Met Leu His His Leu Cys Gly Trp Asp Leu Trp Tyr Cys Phe His
            835                 840                 845
Leu Cys Leu Ala Trp Leu Pro Trp Arg Gly Arg Gln Ser Gly Arg Asp
            850                 855                 860
Glu Asp Ala Leu Pro Tyr Asp Ala Phe Val Val Phe Asp Lys Thr Gln
865                     870                 875                 880
Ser Ala Val Ala Asp Trp Val Tyr Asn Glu Leu Arg Gly Gln Leu Glu
                885                 890                 895
Glu Cys Arg Gly Arg Trp Ala Leu Arg Leu Cys Leu Glu Glu Arg Asp
                900                 905                 910
Trp Leu Pro Gly Lys Thr Leu Phe Glu Asn Leu Trp Ala Ser Val Tyr
            915                 920                 925
Gly Ser Arg Lys Thr Leu Phe Val Leu Ala His Thr Asp Arg Val Ser
            930                 935                 940
Gly Leu Leu Arg Ala Ser Phe Leu Leu Ala Gln Gln Arg Leu Leu Glu
945                     950                 955                 960
Asp Arg Lys Asp Val Val Val Leu Val Ile Leu Ser Pro Asp Gly Arg
                965                 970                 975
Arg Ser Arg Tyr Val Arg Leu Arg Gln Arg Leu Cys Arg Gln Ser Val
                980                 985                 990
Leu Leu Trp Pro His Gln Pro Ser Gly Gln Arg Ser Phe Trp Ala Gln
            995                 1000                1005
Leu Gly Met Ala Leu Thr Arg Asp Asn His His Phe Tyr Asn Arg
            1010                1015                1020
```

Asn Phe Cys Gln Gly Pro Thr Ala Glu
    1025                1030

<210> SEQ ID NO 35
<211> LENGTH: 3257
<212> TYPE: DNA
<213> ORGANISM: Homo sapiens

<400> SEQUENCE: 35

| ccgctgctgc cctgtgggga agggacctcg agtgtgaagc atccttccct gtagctgctg | 60 |
| tccagtctgc ccgccagacc ctctggagaa gcccctgccc cccagcatgg gtttctgccg | 120 |
| cagcgccctg cacccgctgt ctctcctggt gcaggccatc atgctggcca tgaccctggc | 180 |
| cctgggtacc ttgcctgcct cctacccctg tgagctccag ccccacggcc tggtgaactg | 240 |
| caactggctg ttcctgaagt ctgtgcccca cttctccatg cagcaccccc gtggcaatgt | 300 |
| caccagcctt tccttgtcct ccaaccgcat ccaccacctc catgattctg actttgccca | 360 |
| cctgcccagc ctgcggcatc tcaacctcaa gtggaactgc cgccggttg gcctcagccc | 420 |
| catgcacttc ccctgccaca tgaccatcga gcccagcacc ttcttggctg tgcccaccct | 480 |
| ggaagagcta aacctgagct acaacaacat catgactgtg cctgcgctgc ccaaatccct | 540 |
| catatccctg tccctcagcc ataccaacat cctgatgcta gactctgcca gcctcgccgg | 600 |
| cctgcatgcc ctgcgcttcc tattcatgga cggcaactgt tattacaaga acccctgcag | 660 |
| gcaggcactg gaggtggccc gggtgcccct ccttggcctg gcaacctca cccacctgtc | 720 |
| actcaagtac aacaacctca ctgtggtgcc ccgcaacctg ccttccagcc tggagtatct | 780 |
| gctgttgtcc tacaaccgca tcgtcaaact ggcgcctgag gacctggcca atctgaccgc | 840 |
| cctgcgtgtg ctcgatgtgg gcggaaattg ccgccgctgc gaccacgctc caaccctg | 900 |
| catggagtgc cctcgtcact ccccccagct acatcccgat accttcagcc acctgagccg | 960 |
| tcttgaaggc ctggtgttga aggacagttc tctctcctgg ctgaatgcca gttggttccg | 1020 |
| tgggctggga aacctccgag tgctggacct gagtgagaac ttcctctaca aatgcatcac | 1080 |
| taaaaccaag gccttccagg gcctaacaca gctgcgcaag cttaacctgt ccttcaatta | 1140 |
| ccaaaagagg gtgtccttg cccacctgtc tctggcccct tccttcggga gcctggtcgc | 1200 |
| cctgaaggag ctggacatgc acggcatctt cttccgctca ctcgatgaga ccacgctccg | 1260 |
| gccactggcc cgcctgccca tgctccagac tctgcgtctg cagatgaact tcatcaacca | 1320 |
| ggcccagctc ggcatcttca gggccttccc tggcctgcgc tacgtggacc tgtcggacaa | 1380 |
| ccgcatcagc ggagcttcgg agctgacagc caccatgggg gaggcagatg gaggggagaa | 1440 |
| ggtctggctg cagcctgggg accttgctcc ggccccagtg gacactccca gctctgaaga | 1500 |
| cttcaggccc aactgcagca ccctcaactt caccttggat ctgtcacgga caacctggt | 1560 |
| gaccgtgcag ccggagatgt ttgcccagct ctcgcacctg cagtgcctgc gcctgagcca | 1620 |
| caactgcatc tcgcaggcag tcaatggctc ccagttcctg ccgctgaccg tctgcaggt | 1680 |
| gctagacctg tcccacaata gctggacct ctaccacgag cactcattca cggagctacc | 1740 |
| acgactggag gccctggacc tcagctacaa cagccagccc tttggcatgc agggcgtggg | 1800 |
| ccacaacttc agcttcgtgg ctcacctgcg caccctgcgc cacctcagcc tggcccacaa | 1860 |
| caacatccac agccaagtgt cccagcagct ctgcagtacg tcgctgcggg ccctggactt | 1920 |
| cagcggcaat gcactgggcc atatgtgggc cgagggagac ctctatctgc acttcttcca | 1980 |
| aggcctgagc ggtttgatct ggctggactt gtcccagaac cgcctgcaca ccctcctgcc | 2040 |

```
ccaaaccctg cgcaacctcc ccaagagcct acaggtgctg cgtctccgtg acaattacct    2100
ggccttcttt aagtggtgga gcctccactt cctgcccaaa ctggaagtcc tcgacctggc    2160
aggaaaccag ctgaaggccc tgaccaatgg cagcctgcct gctggcaccc ggctccggag    2220
gctggatgtc agctgcaaca gcatcagctt cgtggccccc ggcttctttt ccaaggccaa    2280
ggagctgcga gagctcaacc ttagcgccaa cgccctcaag acagtggacc actcctggtt    2340
tgggcccctg cgcagtgccc tgcaaatact agatgtaagc gccaaccctc tgcactgcgc    2400
ctgtggggcg gcctttatgg acttcctgct ggaggtgcag gctgccgtgc ccggtctgcc    2460
cagccgggtg aagtgtggca gtccgggcca gctccagggc ctcagcatct ttgcacagga    2520
cctgcgcctc tgcctggatg aggccctctc ctgggactgt ttcgccctct cgctgctggc    2580
tgtggctctg ggcctgggtg tgcccatgct gcatcacctc tgtggctggg acctctggta    2640
ctgcttccac ctgtgcctgg cctggcttcc ctggcggggg cggcaaagtg ggcgagatga    2700
ggatgccctg ccctacgatg ccttcgtggt cttcgacaaa acgcagagcg cagtggcaga    2760
ctgggtgtac aacgagcttc gggggcagct ggaggagtgc cgtgggcgct gggcactccg    2820
cctgtgcctg gaggaacgcg actggctgcc tggcaaaacc ctctttgaga acctgtgggc    2880
ctcggtctat ggcagccgca agacgctgtt tgtgctggcc cacacggacc gggtcagtgg    2940
tctcttgcgc gccagcttcc tgctggccca gcagcgcctg ctggaggacc gcaaggacgt    3000
cgtggtgctg gtgatcctga gccctgacgg ccgccgctcc cgctacgtgc ggctgcgcca    3060
gcgcctctgc cgccagagtg tcctcctctg gccccaccag cccagtggtc agcgcagctt    3120
ctgggcccag ctgggcatgg ccctgaccag ggacaaccac cacttctata accggaactt    3180
ctgccaggga cccacggccg aatagccgtg agccggaatc ctgcacggtg ccacctccac    3240
actcacctca cctctgc                                                   3257
```

<210> SEQ ID NO 36
<211> LENGTH: 1055
<212> TYPE: PRT
<213> ORGANISM: Homo sapiens

<400> SEQUENCE: 36

```
Met Pro Met Lys Trp Ser Gly Trp Arg Trp Ser Trp Gly Pro Ala Thr
1               5                   10                  15

His Thr Ala Leu Pro Pro Pro Gln Gly Phe Cys Arg Ser Ala Leu His
            20                  25                  30

Pro Leu Ser Leu Val Gln Ala Ile Met Leu Ala Met Thr Leu Ala
        35                  40                  45

Leu Gly Thr Leu Pro Ala Phe Leu Pro Cys Glu Leu Gln Pro His Gly
    50                  55                  60

Leu Val Asn Cys Asn Trp Leu Phe Leu Lys Ser Val Pro His Phe Ser
65                  70                  75                  80

Met Ala Ala Pro Arg Gly Asn Val Thr Ser Leu Ser Leu Ser Ser Asn
                85                  90                  95

Arg Ile His His Leu His Asp Ser Asp Phe Ala His Leu Pro Ser Leu
            100                 105                 110

Arg His Leu Asn Leu Lys Trp Asn Cys Pro Pro Val Gly Leu Ser Pro
        115                 120                 125

Met His Phe Pro Cys His Met Thr Ile Glu Pro Ser Thr Phe Leu Ala
    130                 135                 140

Val Pro Thr Leu Glu Glu Leu Asn Leu Ser Tyr Asn Asn Ile Met Thr
```

```
            145                 150                 155                 160
Val Pro Ala Leu Pro Lys Ser Leu Ile Ser Leu Ser Leu Ser His Thr
                165                 170                 175
Asn Ile Leu Met Leu Asp Ser Ala Ser Leu Ala Gly Leu His Ala Leu
                180                 185                 190
Arg Phe Leu Phe Met Asp Gly Asn Cys Tyr Tyr Lys Asn Pro Cys Arg
                195                 200                 205
Gln Ala Leu Glu Val Ala Pro Gly Ala Leu Leu Gly Leu Gly Asn Leu
                210                 215                 220
Thr His Leu Ser Leu Lys Tyr Asn Asn Leu Thr Val Val Pro Arg Asn
225                 230                 235                 240
Leu Pro Ser Ser Leu Glu Tyr Leu Leu Leu Ser Tyr Asn Arg Ile Val
                245                 250                 255
Lys Leu Ala Pro Glu Asp Leu Ala Asn Leu Thr Ala Leu Arg Val Leu
                260                 265                 270
Asp Val Gly Gly Asn Cys Arg Arg Cys Asp His Ala Pro Asn Pro Cys
                275                 280                 285
Met Glu Cys Pro Arg His Phe Pro Gln Leu His Pro Asp Thr Phe Ser
                290                 295                 300
His Leu Ser Arg Leu Glu Gly Leu Val Leu Lys Asp Ser Ser Leu Ser
305                 310                 315                 320
Trp Leu Asn Ala Ser Trp Phe Arg Gly Leu Gly Asn Leu Arg Val Leu
                325                 330                 335
Asp Leu Ser Glu Asn Phe Leu Tyr Lys Cys Ile Thr Lys Thr Lys Ala
                340                 345                 350
Phe Gln Gly Leu Thr Gln Leu Arg Lys Leu Asn Leu Ser Phe Asn Tyr
                355                 360                 365
Gln Lys Arg Val Ser Phe Ala His Leu Ser Leu Ala Pro Ser Phe Gly
                370                 375                 380
Ser Leu Val Ala Leu Lys Glu Leu Asp Met His Gly Ile Phe Phe Arg
385                 390                 395                 400
Ser Leu Asp Glu Thr Thr Leu Arg Pro Leu Ala Arg Leu Pro Met Leu
                405                 410                 415
Gln Thr Leu Arg Leu Gln Met Asn Phe Ile Asn Gln Ala Gln Leu Gly
                420                 425                 430
Ile Phe Arg Ala Phe Pro Gly Leu Arg Tyr Val Asp Leu Ser Asp Asn
                435                 440                 445
Arg Ile Ser Gly Ala Ser Glu Leu Thr Ala Thr Met Gly Glu Ala Asp
                450                 455                 460
Gly Gly Glu Lys Val Trp Leu Gln Pro Gly Asp Leu Ala Pro Ala Pro
465                 470                 475                 480
Val Asp Thr Pro Ser Ser Glu Asp Phe Arg Pro Asn Cys Ser Thr Leu
                485                 490                 495
Asn Phe Thr Leu Asp Leu Ser Arg Asn Asn Leu Val Thr Val Gln Pro
                500                 505                 510
Glu Met Phe Ala Gln Leu Ser His Leu Gln Cys Leu Arg Leu Ser His
                515                 520                 525
Asn Cys Ile Ser Gln Ala Val Asn Gly Ser Gln Phe Leu Pro Leu Thr
                530                 535                 540
Gly Leu Gln Val Leu Asp Leu Ser His Asn Lys Leu Asp Leu Tyr His
545                 550                 555                 560
Glu His Ser Phe Thr Glu Leu Pro Arg Leu Glu Ala Leu Asp Leu Ser
                565                 570                 575
```

```
Tyr Asn Ser Gln Pro Phe Gly Met Gln Gly Val Gly His Asn Phe Ser
            580                 585                 590

Phe Val Ala His Leu Arg Thr Leu Arg His Leu Ser Leu Ala His Asn
        595                 600                 605

Asn Ile His Ser Gln Val Ser Gln Gln Leu Cys Ser Thr Ser Leu Arg
610                 615                 620

Ala Leu Asp Phe Ser Gly Asn Ala Leu Gly His Met Trp Ala Glu Gly
625                 630                 635                 640

Asp Leu Tyr Leu His Phe Phe Gln Gly Leu Ser Gly Leu Ile Trp Leu
            645                 650                 655

Asp Leu Ser Gln Asn Arg Leu His Thr Leu Leu Pro Gln Thr Leu Arg
            660                 665                 670

Asn Leu Pro Lys Ser Leu Gln Val Leu Arg Leu Arg Asp Asn Tyr Leu
            675                 680                 685

Ala Phe Phe Lys Trp Trp Ser Leu His Phe Leu Pro Lys Leu Glu Val
            690                 695                 700

Leu Asp Leu Ala Gly Asn Gln Leu Lys Ala Leu Thr Asn Gly Ser Leu
705                 710                 715                 720

Pro Ala Gly Thr Arg Leu Arg Arg Leu Asp Val Ser Cys Asn Ser Ile
            725                 730                 735

Ser Phe Val Ala Pro Gly Phe Phe Ser Lys Ala Lys Glu Leu Arg Glu
            740                 745                 750

Leu Asn Leu Ser Ala Asn Ala Leu Lys Thr Val Asp His Ser Trp Phe
            755                 760                 765

Gly Pro Leu Ala Ser Ala Leu Gln Ile Leu Asp Val Ser Ala Asn Pro
770                 775                 780

Leu His Cys Ala Cys Gly Ala Ala Phe Met Asp Phe Leu Leu Glu Val
785                 790                 795                 800

Gln Ala Ala Val Pro Gly Leu Pro Ser Arg Val Lys Cys Gly Ser Pro
            805                 810                 815

Gly Gln Leu Gln Gly Leu Ser Ile Phe Ala Gln Asp Leu Arg Leu Cys
            820                 825                 830

Leu Asp Glu Ala Leu Ser Trp Asp Cys Phe Ala Leu Ser Leu Leu Ala
            835                 840                 845

Val Ala Leu Gly Leu Gly Val Pro Met Leu His His Leu Cys Gly Trp
850                 855                 860

Asp Leu Trp Tyr Cys Phe His Leu Cys Leu Ala Trp Leu Pro Trp Arg
865                 870                 875                 880

Gly Arg Gln Ser Gly Arg Asp Glu Asp Ala Leu Pro Tyr Asp Ala Phe
            885                 890                 895

Val Val Phe Asp Lys Thr Gln Ser Ala Val Ala Asp Trp Val Tyr Asn
            900                 905                 910

Glu Leu Arg Gly Gln Leu Glu Glu Cys Arg Gly Arg Trp Ala Leu Arg
            915                 920                 925

Leu Cys Leu Glu Glu Arg Asp Trp Leu Pro Gly Lys Thr Leu Phe Glu
            930                 935                 940

Asn Leu Trp Ala Ser Val Tyr Gly Ser Arg Lys Thr Leu Phe Val Leu
945                 950                 955                 960

Ala His Thr Asp Arg Val Ser Gly Leu Leu Arg Ala Ser Phe Leu Leu
            965                 970                 975

Ala Gln Gln Arg Leu Leu Glu Asp Arg Lys Asp Val Val Val Leu Val
            980                 985                 990
```

```
Ile Leu Ser Pro Asp Gly Arg Arg   Ser Arg Tyr Val Arg   Leu Arg Gln
    995                 1000                  1005

Arg Leu Cys Arg Gln Ser Val Leu   Leu Trp Pro His   Gln Pro Ser
    1010                1015                1020

Gly Gln Arg Ser Phe Trp Ala   Gln Leu Gly Met Ala   Leu Thr Arg
    1025                1030                1035

Asp Asn His His Phe Tyr Asn   Arg Asn Phe Cys   Gln Gly Pro Thr
    1040                1045                1050

Ala Glu
    1055

<210> SEQ ID NO 37
<211> LENGTH: 3165
<212> TYPE: DNA
<213> ORGANISM: Homo sapiens

<400> SEQUENCE: 37
```

| | | | | | |
|---|---|---|---|---|---|
| atgcccatga | agtggagtgg | gtggaggtgg | agctgggggc | cggccactca | cacagccctc | 60 |
| ccaccccac | agggtttctg | ccgcagcgcc | ctgcacccgc | tgtctctcct | ggtgcaggcc | 120 |
| atcatgctgg | ccatgaccct | ggccctgggt | accttgcctg | ccttcctacc | ctgtgagctc | 180 |
| cagccccacg | gcctggtgaa | ctgcaactgg | ctgttcctga | agtctgtgcc | ccacttctcc | 240 |
| atggcagcac | cccgtggcaa | tgtcaccagc | cttccttgt | cctccaaccg | catccaccac | 300 |
| ctccatgatt | ctgactttgc | ccacctgccc | agcctgcggc | atctcaacct | caagtggaac | 360 |
| tgcccgccgg | ttggcctcag | ccccatgcac | ttcccctgcc | acatgaccat | cgagcccagc | 420 |
| accttcttgg | ctgtgcccac | cctggaagag | ctaaacctga | gctacaacaa | catcatgact | 480 |
| gtgcctgcgc | tgcccaaatc | cctcatatcc | ctgtccctca | gccataccaa | catcctgatg | 540 |
| ctagactctg | ccagcctcgc | cggcctgcat | gccctgcgct | tcctattcat | ggacggcaac | 600 |
| tgttattaca | agaaccccctg | caggcaggca | ctggaggtgg | ccccgggtgc | cctccttggc | 660 |
| ctgggcaacc | tcacccacct | gtcactcaag | tacaacaacc | tcactgtggt | gccccgcaac | 720 |
| ctgccttcca | gcctggagta | tctgctgttg | tcctacaacc | gcatcgtcaa | actggcgcct | 780 |
| gaggacctgg | ccaatctgac | cgccctgcgt | gtgctcgatg | tgggcggaaa | ttgccgccgc | 840 |
| tgcgaccacg | ctcccaaccc | ctgcatggag | tgccctcgtc | acttccccca | gctacatccc | 900 |
| gataccttca | gccacctgag | ccgtcttgaa | ggcctggtgt | tgaaggacag | ttctctctcc | 960 |
| tggctgaatg | ccagttggtt | ccgtgggctg | ggaaacctcc | gagtgctgga | cctgagtgag | 1020 |
| aacttcctct | acaaatgcat | cactaaaacc | aaggccttcc | agggcctaac | acagctgcgc | 1080 |
| aagcttaacc | tgtccttcaa | ttaccaaaag | agggtgtcct | tgcccacct | gtctctggcc | 1140 |
| ccttccttcg | ggagcctggt | cgccctgaag | gagctggaca | tgcacggcat | cttcttccgc | 1200 |
| tcactcgatg | agaccacgct | ccggccactg | gcccgcctgc | catgctccca | gactctgcgt | 1260 |
| ctgcagatga | acttcatcaa | ccaggcccag | ctcggcatct | tcagggcctt | ccctggcctg | 1320 |
| cgctacgtgg | acctgtcgga | caaccgcatc | agcggagctt | cggagctgac | agccaccatg | 1380 |
| ggggaggcag | atgagggga | gaaggtctgg | ctgcagcctg | ggaccttgc | tccggcccca | 1440 |
| gtggacactc | ccagctctga | agacttcagg | cccaactgca | gcaccctcaa | cttcaccttg | 1500 |
| gatctgtcac | ggaacaacct | ggtgaccgtg | cagccggaga | tgtttgccca | gctctcgcac | 1560 |
| ctgcagtgcc | tgcgcctgag | ccacaactgc | atccgcagg | cagtcaatgg | ctcccagttc | 1620 |
| ctgccgctga | ccggtctgca | ggtgctagac | ctgtcccaca | ataagctgga | cctctaccac | 1680 |

| | |
|---|---|
| gagcactcat tcacggagct accacgactg gaggccctgg acctcagcta acagccag | 1740 |
| cccctttggca tgcagggcgt gggccacaac ttcagcttcg tggctcacct gcgcaccctg | 1800 |
| cgccacctca gcctggccca acaacatc cacagccaag tgtcccagca gctctgcagt | 1860 |
| acgtcgctgc gggccctgga cttcagcggc aatgcactgg ccatatgtg gccgaggga | 1920 |
| gacctctatc tgcacttctt ccaaggcctg agcggtttga tctggctgga cttgtcccag | 1980 |
| aaccgcctgc acaccctcct gccccaaacc ctgcgcaacc tccccaagag cctacaggtg | 2040 |
| ctgcgtctcc gtgacaatta cctggccttc tttaagtggt ggagcctcca cttcctgccc | 2100 |
| aaactggaag tcctcgacct ggcaggaaac cagctgaagg ccctgaccaa tggcagcctg | 2160 |
| cctgctggca cccggctccg gaggctggat gtcagctgca acagcatcag cttcgtggcc | 2220 |
| cccggcttct tttccaaggc caaggagctg cgagagctca accttagcgc caacgccctc | 2280 |
| aagacagtgg accactcctg gtttgggccc ctggcgagtg ccctgcaaat actagatgta | 2340 |
| agcgccaacc tctgcactg cgcctgtggg gcggcctta tggacttcct gctggaggtg | 2400 |
| caggctgccg tgcccggtct gcccagccgg gtgaagtgtg gcagtccggg ccagctccag | 2460 |
| ggcctcagca tctttgcaca ggacctgcgc ctctgcctgg atgaggccct ctcctgggac | 2520 |
| tgtttcgccc tctcgctgct ggctgtggct ctgggcctgg gtgtgcccat gctgcatcac | 2580 |
| ctctgtggct gggacctctg gtactgcttc cacctgtgcc tggcctggct ccctggcgg | 2640 |
| gggcggcaaa gtgggcgaga tgaggatgcc ctgcccctacg atgccttcgt ggtcttcgac | 2700 |
| aaaacgcaga gcgcagtggc agactgggtg tacaacgagc ttcgggggca gctggaggag | 2760 |
| tgccgtgggc gctgggcact ccgcctgtgc ctggaggaac gcgactggct gcctggcaaa | 2820 |
| accctctttg agaacctgtg ggcctcggtc tatggcagcc gcaagacgct gtttgtgctg | 2880 |
| gcccacacgg accgggtcag tggtctcttg cgcgccagct tcctgctggc ccagcagcgc | 2940 |
| ctgctggagg accgcaagga cgtcgtggtg ctggtgatcc tgagccctga cggccgccgc | 3000 |
| tcccgctatg tgcggctgcg ccagcgcctc tgccgccaga gtgtcctcct ctggcccac | 3060 |
| cagcccagtg gtcagcgcag cttctgggcc cagctgggca tggccctgac cagggacaac | 3120 |
| caccacttct ataaccggaa cttctgccag ggacccacgg ccgaa | 3165 |

<210> SEQ ID NO 38
<211> LENGTH: 1032
<212> TYPE: PRT
<213> ORGANISM: Mus musculus

<400> SEQUENCE: 38

```
Met Val Leu Arg Arg Arg Thr Leu His Pro Leu Ser Leu Leu Val Gln
1               5                   10                  15

Ala Ala Val Leu Ala Glu Thr Leu Ala Leu Gly Thr Leu Pro Ala Phe
            20                  25                  30

Leu Pro Cys Glu Leu Lys Pro His Gly Leu Val Asp Cys Asn Trp Leu
        35                  40                  45

Phe Leu Lys Ser Val Pro Arg Phe Ser Ala Ala Ser Cys Ser Asn
    50                  55                  60

Ile Thr Arg Leu Ser Leu Ile Ser Asn Arg Ile His His Leu His Asn
65                  70                  75                  80

Ser Asp Phe Val His Leu Ser Asn Leu Arg Gln Leu Asn Leu Lys Trp
                85                  90                  95

Asn Cys Pro Pro Thr Gly Leu Ser Pro Leu His Phe Ser Cys His Met
            100                 105                 110
```

```
Thr Ile Glu Pro Arg Thr Phe Leu Ala Met Arg Thr Leu Glu Glu Leu
            115                 120                 125

Asn Leu Ser Tyr Asn Gly Ile Thr Thr Val Pro Arg Leu Pro Ser Ser
        130                 135                 140

Leu Val Asn Leu Ser Leu Ser His Thr Asn Ile Leu Val Leu Asp Ala
145                 150                 155                 160

Asn Ser Leu Ala Gly Leu Tyr Ser Leu Arg Val Leu Phe Met Asp Gly
                165                 170                 175

Asn Cys Tyr Tyr Lys Asn Pro Cys Thr Gly Ala Val Lys Val Thr Pro
            180                 185                 190

Gly Ala Leu Leu Gly Leu Ser Asn Leu Thr His Leu Ser Leu Lys Tyr
        195                 200                 205

Asn Asn Leu Thr Lys Val Pro Arg Gln Leu Pro Pro Ser Leu Glu Tyr
210                 215                 220

Leu Leu Val Ser Tyr Asn Leu Ile Val Lys Leu Gly Pro Glu Asp Leu
225                 230                 235                 240

Ala Asn Leu Thr Ser Leu Arg Val Leu Asp Val Gly Gly Asn Cys Arg
                245                 250                 255

Arg Cys Asp His Ala Pro Asn Pro Cys Ile Glu Cys Gly Gln Lys Ser
            260                 265                 270

Leu His Leu His Pro Glu Thr Phe His His Leu Ser His Leu Glu Gly
        275                 280                 285

Leu Val Leu Lys Asp Ser Ser Leu His Thr Leu Asn Ser Ser Trp Phe
        290                 295                 300

Gln Gly Leu Val Asn Leu Ser Val Leu Asp Leu Ser Glu Asn Phe Leu
305                 310                 315                 320

Tyr Glu Ser Ile Asn His Thr Asn Ala Phe Gln Asn Leu Thr Arg Leu
                325                 330                 335

Arg Lys Leu Asn Leu Ser Phe Asn Tyr Arg Lys Lys Val Ser Phe Ala
            340                 345                 350

Arg Leu His Leu Ala Ser Ser Phe Lys Asn Leu Val Ser Leu Gln Glu
        355                 360                 365

Leu Asn Met Asn Gly Ile Phe Phe Arg Ser Leu Asn Lys Tyr Thr Leu
370                 375                 380

Arg Trp Leu Ala Asp Leu Pro Lys Leu His Thr Leu His Leu Gln Met
385                 390                 395                 400

Asn Phe Ile Asn Gln Ala Gln Leu Ser Ile Phe Gly Thr Phe Arg Ala
                405                 410                 415

Leu Arg Phe Val Asp Leu Ser Asp Asn Arg Ile Ser Gly Pro Ser Thr
            420                 425                 430

Leu Ser Glu Ala Thr Pro Glu Glu Ala Asp Asp Ala Glu Gln Glu Glu
        435                 440                 445

Leu Leu Ser Ala Asp Pro His Pro Ala Pro Leu Ser Thr Pro Ala Ser
450                 455                 460

Lys Asn Phe Met Asp Arg Cys Lys Asn Phe Lys Phe Thr Met Asp Leu
465                 470                 475                 480

Ser Arg Asn Asn Leu Val Thr Ile Lys Pro Glu Met Phe Val Asn Leu
                485                 490                 495

Ser Arg Leu Gln Cys Leu Ser Leu Ser His Asn Ser Ile Ala Gln Ala
            500                 505                 510

Val Asn Gly Ser Gln Phe Leu Pro Leu Thr Asn Leu Gln Val Leu Asp
        515                 520                 525

Leu Ser His Asn Lys Leu Asp Leu Tyr His Trp Lys Ser Phe Ser Glu
```

```
                530             535             540
Leu Pro Gln Leu Gln Ala Leu Asp Leu Ser Tyr Asn Ser Gln Pro Phe
545                 550             555                 560

Ser Met Lys Gly Ile Gly His Asn Phe Ser Phe Val Ala His Leu Ser
                565             570             575

Met Leu His Ser Leu Ser Leu Ala His Asn Asp Ile His Thr Arg Val
                580             585             590

Ser Ser His Leu Asn Ser Asn Ser Val Arg Phe Leu Asp Phe Ser Gly
            595             600             605

Asn Gly Met Gly Arg Met Trp Asp Glu Gly Gly Leu Tyr Leu His Phe
            610             615             620

Phe Gln Gly Leu Ser Gly Leu Leu Lys Leu Asp Leu Ser Gln Asn Asn
625                 630             635                 640

Leu His Ile Leu Arg Pro Gln Asn Leu Asp Asn Leu Pro Lys Ser Leu
                645             650             655

Lys Leu Leu Ser Leu Arg Asp Asn Tyr Leu Ser Phe Phe Asn Trp Thr
                660             665             670

Ser Leu Ser Phe Leu Pro Asn Leu Glu Val Leu Asp Leu Ala Gly Asn
            675             680             685

Gln Leu Lys Ala Leu Thr Asn Gly Thr Leu Pro Asn Gly Thr Leu Leu
            690             695             700

Gln Lys Leu Asp Val Ser Ser Asn Ser Ile Val Ser Val Val Pro Ala
705                 710             715                 720

Phe Phe Ala Leu Ala Val Glu Leu Lys Glu Val Asn Leu Ser His Asn
                725             730             735

Ile Leu Lys Thr Val Asp Arg Ser Trp Phe Gly Pro Ile Val Met Asn
                740             745             750

Leu Thr Val Leu Asp Val Arg Ser Asn Pro Leu His Cys Ala Cys Gly
            755             760             765

Ala Ala Phe Val Asp Leu Leu Leu Glu Val Gln Thr Lys Val Pro Gly
            770             775             780

Leu Ala Asn Gly Val Lys Cys Gly Ser Pro Gly Gln Leu Gln Gly Arg
785                 790             795                 800

Ser Ile Phe Ala Gln Asp Leu Arg Leu Cys Leu Asp Glu Val Leu Ser
                805             810             815

Trp Asp Cys Phe Gly Leu Ser Leu Leu Ala Val Ala Val Gly Met Val
                820             825             830

Val Pro Ile Leu His His Leu Cys Gly Trp Asp Val Trp Tyr Cys Phe
            835             840             845

His Leu Cys Leu Ala Trp Leu Pro Leu Leu Ala Arg Ser Arg Arg Ser
850                 855             860

Ala Gln Ala Leu Pro Tyr Asp Ala Phe Val Val Phe Asp Lys Ala Gln
865                 870             875                 880

Ser Ala Val Ala Asp Trp Val Tyr Asn Glu Leu Arg Val Arg Leu Glu
                885             890             895

Glu Arg Arg Gly Arg Arg Ala Leu Arg Leu Cys Leu Glu Asp Arg Asp
            900             905             910

Trp Leu Pro Gly Gln Thr Leu Phe Glu Asn Leu Trp Ala Ser Ile Tyr
            915             920             925

Gly Ser Arg Lys Thr Leu Phe Val Leu Ala His Thr Asp Arg Val Ser
            930             935             940

Gly Leu Leu Arg Thr Ser Phe Leu Leu Ala Gln Gln Arg Leu Leu Glu
945                 950             955                 960
```

Asp Arg Lys Asp Val Val Leu Val Ile Leu Arg Pro Asp Ala His
            965                 970                 975

Arg Ser Arg Tyr Val Arg Leu Arg Gln Arg Leu Cys Arg Gln Ser Val
        980                 985                 990

Leu Phe Trp Pro Gln Gln Pro Asn Gly Gln Gly Gly Phe Trp Ala Gln
    995                 1000                1005

Leu Ser Thr Ala Leu Thr Arg Asp Asn Arg His Phe Tyr Asn Gln
    1010                1015                1020

Asn Phe Cys Arg Gly Pro Thr Ala Glu
    1025                1030

<210> SEQ ID NO 39
<211> LENGTH: 3200
<212> TYPE: DNA
<213> ORGANISM: Mus musculus

<400> SEQUENCE: 39

| | | | | | |
|---|---|---|---|---|---|
| tgtcagaggg | agcctcggga | gaatcctcca | tctcccaaca | tggttctccg | tcgaaggact | 60 |
| ctgcacccct | tgtccctcct | ggtacaggct | gcagtgctgg | ctgagactct | ggccctgggt | 120 |
| accctgcctg | ccttcctacc | ctgtgagctg | aagcctcatg | gcctggtgga | ctgcaattgg | 180 |
| ctgttcctga | agtctgtacc | ccgtttctct | gcggcagcat | cctgctccaa | catcacccgc | 240 |
| ctctccttga | tctccaaccg | tatccaccac | ctgcacaact | ccgacttcgt | ccacctgtcc | 300 |
| aacctgcggc | agctgaacct | caagtggaac | tgtccaccca | ctggccttag | cccctgcac | 360 |
| ttctcttgcc | acatgaccat | tgagcccaga | accttcctgg | ctatgcgtac | actggaggag | 420 |
| ctgaacctga | gctataatgg | tatcaccact | gtgccccgac | tgcccagctc | cctggtgaat | 480 |
| ctgagcctga | gccacaccaa | catcctggtt | ctagatgcta | acagcctcgc | cggcctatac | 540 |
| agcctgcgcg | ttctcttcat | ggacgggaac | tgctactaca | agaaccctg | cacaggagcg | 600 |
| gtgaaggtga | ccccaggcgc | cctcctgggc | ctgagcaatc | tcacccatct | gtctctgaag | 660 |
| tataacaacc | tcacaaaggt | gccccgccaa | ctgccccca | gcctggagta | cctcctggtg | 720 |
| tcctataacc | tcattgtcaa | gctggggcct | gaagacctgg | ccaatctgac | ctcccttcga | 780 |
| gtacttgatg | tgggtgggaa | ttgccgtcgc | tgcgaccatg | cccccaatcc | ctgtatagaa | 840 |
| tgtggccaaa | agtccctcca | cctgcaccct | gagaccttcc | atcacctgag | ccatctggaa | 900 |
| ggcctggtgc | tgaaggacag | ctctctccat | acactgaact | cttcctggtt | ccaaggtctg | 960 |
| gtcaacctct | cggtgctgga | cctaagcgag | aactttctct | atgaaagcat | caaccacacc | 1020 |
| aatgcctttc | agaacctaac | ccgcctgcgc | aagctcaacc | tgtccttcaa | ttaccgcaag | 1080 |
| aaggtatcct | ttgcccgcct | ccacctggca | agttccttca | agaacctggt | gtcactgcag | 1140 |
| gagctgaaca | tgaacggcat | cttcttccgc | tcgctcaaca | agtacacgct | cagatggctg | 1200 |
| gccgatctgc | ccaaactcca | cactctgcat | cttcaaatga | acttcatcaa | ccaggcacag | 1260 |
| ctcagcatct | ttggtacctt | ccgagccctt | cgctttgtgg | acttgtcaga | caatcgcatc | 1320 |
| agtgggcctt | caacgctgtc | agaagccacc | cctgaagagg | cagatgatgc | agagcaggag | 1380 |
| gagctgttgt | ctgcggatcc | tcacccagct | ccactgagca | cccctgcttc | taagaacttc | 1440 |
| atggacaggt | gtaagaactt | caagttcacc | atggacctgt | ctcggaacaa | cctggtgact | 1500 |
| atcaagccag | agatgtttgt | caatctctca | cgcctccagt | gtcttagcct | gagccacaac | 1560 |
| tccattgcac | aggctgtcaa | tggctctcag | ttcctgccgc | tgactaatct | gcaggtgctg | 1620 |
| gacctgtccc | ataacaaact | ggacttgtac | cactggaaat | cgttcagtga | gctaccacag | 1680 |

```
ttgcaggccc tggacctgag ctacaacagc cagcccttta gcatgaaggg tataggccac   1740
aatttcagtt ttgtggccca tctgtccatg ctacacagcc ttagcctggc acacaatgac   1800
attcataccc gtgtgtcctc acatctcaac agcaactcag tgaggtttct tgacttcagc   1860
ggcaacggta tgggccgcat gtgggatgag gggggccttt atctccattt cttccaaggc   1920
ctgagtggcc tgctgaagct ggacctgtct caaaataacc tgcatatcct ccggccccag   1980
aaccttgaca acctccccaa gagcctgaag ctgctgagcc tccgagacaa ctacctatct   2040
ttctttaact ggaccagtct gtccttcctg cccaacctgg aagtcctaga cctggcaggc   2100
aaccagctaa aggccctgac caatggcacc ctgcctaatg gcaccctcct ccagaaactg   2160
gatgtcagca gcaacagtat cgtctctgtg gtcccagcct tcttcgctct ggcggtcgag   2220
ctgaaagagg tcaacctcag ccacaacatt ctcaagacgg tggatcgctc ctggtttggg   2280
cccattgtga tgaacctgac agttctagac gtgagaagca accctctgca ctgtgcctgt   2340
ggggcagcct tcgtagactt actgttggag gtgcagacca aggtgcctgg cctggctaat   2400
ggtgtgaagt gtggcagccc cggccagctg cagggccgta gcatcttcgc acaggacctg   2460
cggctgtgcc tggatgaggt cctctcttgg gactgctttg gcctttcact cttggctgtg   2520
gccgtgggca tggtggtgcc tatactgcac catctctgcg gctgggacgt ctggtactgt   2580
tttcatctgt gcctggcatg gctacctttg ctggcccgca gccgacgcag cgcccaagct   2640
ctcccctatg atgccttcgt ggtgttcgat aaggcacaga gcgcagttgc ggactgggtg   2700
tataacgagc tgcgggtgcg gctggaggag cggcgcggtc gccgagccct acgcttgtgt   2760
ctggaggacc gagattggct gcctggccag acgctcttcg agaacctctg ggcttccatc   2820
tatgggagcc gcaagactct atttgtgctg gcccacacgg accgcgtcag tggcctcctg   2880
cgcaccagct tcctgctggc tcagcagcgc ctgttggaag accgcaagga cgtggtggtg   2940
ttggtgatcc tgcgtccgga tgcccaccgc tcccgctatg tgcgactgcg ccagcgtctc   3000
tgccgccaga gtgtgctctt ctggccccag cagcccaacg ggcaggggg cttctgggcc   3060
cagctgagta cagccctgac tagggacaac cgccacttct ataaccagaa cttctgccgg   3120
ggacctacag cagaatagct cagagcaaca gctggaaaca gctgcatctt catgcctggt   3180
tcccgagttg ctctgcctgc                                              3200
```

IMMUNOSTIMULATORY G, U-CONTAINING OLIGORIBONUCLEOTIDES

RELATED APPLICATIONS

This application is a continuation and claims the benefit under 35 U.S.C. §120 of U.S. application Ser. No. 11/368,333, now U.S. Pat. No. 8,658,607, issued Feb. 25, 2014, entitled "IMMUNOSTIMULATORY G, U-CONTAINING OLIGORIBONUCLEOTIDES" filed on Mar. 3, 2006, which is a continuation and claims the benefit under 35 U.S.C. §120 of U.S. application Ser. No. 10/407,952, now U.S. Pat. No. 8,153,141, issued Apr. 10, 2012, entitled "IMMUNOSTIMULATORY G, U-CONTAINING OLIGO-RIBONUCLEOTIDES" filed on Apr. 4, 2003, which claims priority under 35 U.S.C. §119(e) to U.S. Provisional Application Ser. No. 60/421,966, entitled "IMMUNOSTIMULATORY G, U-CONTAINING OLIGORIBONUCLE-OTIDES" filed on Oct. 29, 2002, and U.S. Provisional Application Ser. No. 60/370,515, entitled "NATURAL LIGANDS OF TLR7 AND TLR8" filed on Apr. 4, 2002, which are herein incorporated by reference in their entirety.

FIELD OF THE INVENTION

The present invention relates generally to the field of immunology and immune stimulation. More particularly, the present invention relates to immunostimulatory ribonucleic acids, homologs of said immunostimulatory ribonucleic acids, and methods of use of said immunostimulatory ribonucleic acids and homologs. Compositions and methods of the invention are believed to be useful for inducing signaling through Toll-like receptor 7 (TLR7) and Toll-like receptor 8 (TLR8).

BACKGROUND OF THE INVENTION

The immune response is conceptually divided into innate immunity and adaptive immunity. Innate immunity is believed to involve recognition of pathogen-associated molecular patterns (PAMPs) shared in common by certain classes of molecules expressed by infectious microorganisms or foreign macromolecules. PAMPs are believed to be recognized by pattern recognition receptors (PRRs) on certain immune cells.

Toll-like receptors (TLRs) are a family of highly conserved polypeptides that play a critical role in innate immunity in mammals. Currently ten family members, designated TLR1-TLR10, have been identified. The cytoplasmic domains of the various TLRs are characterized by a Toll-interleukin 1 (IL-1) receptor (TIR) domain. Medzhitov R et al. (1998) *Mol Cell* 2:253-8. Recognition of microbial invasion by TLRs triggers activation of a signaling cascade that is evolutionarily conserved in *Drosophila* and mammals. The TIR domain-containing adapter protein MyD88 has been reported to associate with TLRs and to recruit IL-1 receptor-associated kinase (IRAK) and tumor necrosis factor (TNF) receptor-associated factor 6 (TRAF6) to the TLRs. The MyD88-dependent signaling pathway is believed to lead to activation of NF-kB transcription factors and c-Jun $NH_2$ terminal kinase (Jnk) mitogen-activated protein kinases (MAPKs), critical steps in immune activation and production of inflammatory cytokines. For a review, see Aderem A et al. (2000) *Nature* 406:782-87.

While a number of specific TLR ligands have been reported, ligands for some TLRs remain to be identified. Ligands for TLR2 include peptidoglycan and lipopeptides. Yoshimura A et al. (1999) *J Immunol* 163:1-5; Yoshimura A et al. (1999) *J Immunol* 163:1-5; Aliprantis A O et al. (1999) *Science* 285:736-9. Viral-derived double-stranded RNA (dsRNA) and poly I:C, a synthetic analog of dsRNA, have been reported to be ligands of TLR3. Alexopoulou L et al. (2001) *Nature* 413:732-8. Lipopolysaccharide (LPS) is a ligand for TLR4. Poltorak A et al. (1998) *Science* 282:2085-8; Hoshino K et al. (1999) *J Immunol* 162:3749-52. Bacterial flagellin is a ligand for TLR5. Hayashi F et al. (2001) *Nature* 410:1099-1103. Peptidoglycan has been reported to be a ligand not only for TLR2 but also for TLR6. Ozinsky A et al. (2000) *Proc Natl Acad Sci USA* 97:13766-71; Takeuchi O et al. (2001) *Int Immunol* 13:933-40. Bacterial DNA (CpG DNA) has been reported to be a TLR9 ligand. Hemmi H et al. (2000) *Nature* 408:740-5; Bauer S et al. (2001) *Proc Natl Acad Sci USA* 98, 9237-42. The TLR ligands listed above all include natural ligands, i.e., TLR ligands found in nature as molecules expressed by infectious microorganisms.

The natural ligands for TLR1, TLR7, TLR8 and TLR10 are not known, although recently certain low molecular weight synthetic compounds, the imidazoquinolones imiquimod (R-837) and resiquimod (R-848), were reported to be ligands of TLR7. Hemmi H et al. (2002) *Nat Immunol* 3:196-200.

SUMMARY OF THE INVENTION

The present invention is based in part on the novel discovery by the inventors of certain immunostimulatory RNA and RNA-like (hereinafter, simply "RNA") molecules. The immunostimulatory RNA molecules of the invention are believed by the inventors to require a base sequence that includes at least one guanine (G) and at least one uracil (U), wherein optionally the at least one G can be a variant or homolog of G and/or the at least one U can independently be a variant or homolog of U. Surprisingly, the immunostimulatory RNA molecules of the invention can be either single-stranded or at least partially double-stranded. Also surprisingly, the immunostimulatory RNA molecules of the invention do not require a CpG motif in order to exert their immunostimulatory effect. Without meaning to be bound by any particular theory or mechanism, it is the belief of the inventors that the immunostimulatory RNA molecules of the invention signal through an MyD88-dependent pathway, probably through a TLR. Also without meaning to be bound by any particular theory or mechanism, it is the belief of the inventors that the immunostimulatory RNA molecules of the invention interact with and signal through TLR8, TLR7, or some other TLR yet to be identified.

The immunostimulatory RNA molecules of the invention are also believed by the inventors to be representative of a class of RNA molecules, found in nature, which can induce an immune response. Without meaning to be bound by any particular theory or mechanism, it is the belief of the inventors that the corresponding class of RNA molecules found in nature is believed to be present in ribosomal RNA (rRNA), transfer RNA (tRNA), messenger RNA (mRNA), and viral RNA (vRNA). It is to be noted in this regard that the immunostimulatory RNA molecules of the present invention can be as small as 5-40 nucleotides long. Such short RNA molecules fall outside the range of full length messenger RNAs described to be useful in transfecting dendritic cells in order to induce an immune response to cancer antigens. See, e.g., Boczkowski D et al. (1996) *J Exp Med* 184:465-72; Mitchell D A et al. (2000) *Curr Opin Mol Ther* 2:176-81.

It has also been discovered according to the present invention that the immunostimulatory RNA molecules of the invention can be advantageously combined with certain agents which promote stabilization of the RNA, local clustering of the RNA molecules, and/or trafficking of the RNA molecules into the endosomal compartment of cells. In particular, it has been discovered according to the present invention that certain lipids and/or liposomes are useful in this regard. For example, certain cationic lipids, including in particular N-[1-(2,3 dioleoyloxy)-propyl]-N,N,N-trimethylammonium methyl-sulfate (DOTAP), appear to be especially advantageous when combined with the immunostimulatory RNA molecules of the invention. As another example, covalent conjugation of a cholesteryl moiety to the RNA, for example to the 3' end of the RNA, promotes the immunostimulatory effect of the RNA, even in the absence of cationic lipid.

The invention provides compositions of matter and methods related to the immunostimulatory RNA molecules of the invention. The compositions and methods are useful, inter alia, for activating immune cells in vivo, in vitro, and ex vivo; treating infection; treating cancer; preparing a pharmaceutical composition; identifying a target receptor for the immunostimulatory RNA; and screening for and characterizing additional immunostimulatory compounds. Furthermore, the compositions of matter and methods related to the immunostimulatory RNA molecules of the instant invention can advantageously be combined with other immunostimulatory compositions of matter and methods related to such other immunostimulatory compositions of matter.

In one aspect the invention provides an immunostimulatory composition. The immunostimulatory composition according to this aspect of the invention includes an isolated RNA oligomer 5-40 nucleotides long having a base sequence having at least one guanine (G) and at least one uracil (U), and optionally a cationic lipid. The RNA oligomer can be of natural or non-natural origin. An RNA oligomer of natural origin can in one embodiment be derived from prokaryotic RNA and in another embodiment can be derived from eukaryotic RNA. In addition, the RNA oligomer of natural origin can include a portion of a ribosomal RNA. An RNA oligomer of non-natural origin can include an RNA molecule synthesized outside of a cell, e.g., using chemical techniques known by those of skill in the art. In one embodiment an RNA oligomer can include a derivative of an RNA oligomer of natural origin.

In one embodiment the isolated RNA oligomer is a G,U-rich RNA as defined below.

In one embodiment the G,U-containing immunostimulatory RNA is an isolated RNA molecule at least 5 nucleotides long which includes a base sequence as provided by 5'-RURGY-3', wherein R represents purine, U represents uracil, G represents guanine, and Y represents pyrimidine. In one embodiment the G,U-containing immunostimulatory RNA is an isolated RNA molecule at least 5 nucleotides long which includes a base sequence as provided by 5'-GUAGU-3', wherein A represents adenine. In one embodiment the G,U-containing immunostimulatory RNA is an isolated RNA molecule which includes a base sequence as provided by 5'-GUAGUGU-3'.

In one embodiment the G,U-containing immunostimulatory RNA is an isolated RNA molecule at least 5 nucleotides long which includes a base sequence as provided by 5'-GUUGB-3', wherein B represents U, G, or C.

In one embodiment the G,U-containing immunostimulatory RNA is an isolated RNA molecule at least 5 nucleotides long which includes a base sequence as provided by 5'-GUGUG-3'.

In other embodiments the isolated RNA molecule can contain multiples of any of the foregoing sequences, combinations of any of the foregoing sequences, or combinations of any of the foregoing sequences including multiples of any of the foregoing sequences. The multiples and combinations can be linked directly or they can be linked indirectly, i.e, through an intervening nucleoside or sequence. In one embodiment the intervening linking nucleoside is G; in one embodiment the intervening linking nucleoside is U.

In one embodiment the base sequence includes 5'-GUGUUUAC-3'. In one embodiment the base sequence is 5'-GUGUUUAC-3'.

In another embodiment the base sequence includes 5'-GUAGGCAC-3'. In one embodiment the base sequence is 5'-GUAGGCAC-3'.

In yet another embodiment the base sequence includes 5'-CUAGGCAC-3'. In one embodiment the base sequence is 5'-CUAGGCAC-3'.

In still another embodiment the base sequence includes 5'-CUCGGCAC-3'. In one embodiment the base sequence is 5'-CUCGGCAC-3'.

In one embodiment the oligomer is 5-12 nucleotides long. In one embodiment the oligomer is 8-12 nucleotides long.

Also according to this aspect of the invention, in one embodiment the base sequence is free of CpG dinucleotide. Thus in this embodiment the immunostimulatory RNA is not a CpG nucleic acid.

In certain embodiments according to this aspect of the invention, the base sequence of the RNA oligomer is at least partially self-complementary. In one embodiment the extent of self-complementarity is at least 50 percent. The extent of self-complementarity can extend to and include 100 percent. Thus for example the base sequence of the at least partially self-complementary RNA oligomer in various embodiments can be at least 50 percent, at least 60 percent, at least 70 percent, at least 80 percent, at least 90 percent, or 100 percent self-complementary. Complementary base pairs include guanine-cytosine (G-C), adenine-uracil (A-U), adenine-thymine (A-T), and guanine-uracil (G-U). G-U "wobble" basepairing, which is fairly common in ribosomal RNA and in RNA retroviruses, is somewhat weaker than traditional Watson-Crick basepairing between G-C, A-T, or A-U. A partially self-complementary sequence can include one or more portions of self-complementary sequence. In an embodiment which involves a partially self-complementary sequence, the RNA oligomer can include a self-complementary portion positioned at and encompassing each end of the oligomer.

In one embodiment according to this aspect of the invention, the oligomer is a plurality of oligomers, i.e., a plurality of RNA oligomers each 6-40 nucleotides long having a base sequence comprising at least one guanine (G) and at least one uracil (U). The plurality of oligomers can, but need not, include sequences which are at least partially complementary to one another. In one embodiment the plurality of oligomers includes an oligomer having a first base sequence and an oligomer having a second base sequence, wherein the first base sequence and the second base sequence are at least 50 percent complementary. Thus for example the at least partially complementary base sequences in various embodiments can be at least 50 percent, at least 60 percent, at least 70 percent, at least 80 percent, at least 90 percent, or 100 percent complementary. As described above, complementary base pairs include guanine-cytosine (G-C), adenine-uracil (A-U), adenine-thymine (A-T), and guanine-uracil (G-U). Partially complementary sequences can include one or more portions of complementary sequence. In an embodiment which involves partially complementary sequences, the RNA oligomers can include a complementary portion positioned at and encompassing at least one end of the oligomers.

In one embodiment the oligomer is a plurality of oligomers which includes an oligomer having a base sequence including 5'-GUGUUUAC-3' and an oligomer having a base sequence including 5'-GUAGGCAC-3'. In one embodiment the oligomer is a plurality of oligomers which includes an oligomer having a base sequence 5'-GUGUUUAC-3' and an oligomer having a base sequence 5'-GUAGGCAC-3'.

Further according to this aspect of the invention, in various embodiments the oligomer includes a non-natural backbone linkage, a modified base, a modified sugar, or any combination of the foregoing. The non-natural backbone linkage can be a stabilized linkage, i.e., a linkage which is relatively resistant against RNAse or nuclease degradation, compared with phosphodiester linkage. In one embodiment the non-natural backbone linkage is a phosphorothioate linkage. The oligomer can include one non-natural backbone linkage or a plurality of non-natural backbone linkages, each selected independently of the rest. The modified base can be a modified G, U, A, or C, including the at least one G and the at least one U of the base sequence according to this aspect of the invention. In some embodiments the modified base can be selected from 7-deazaguanosine, 8-azaguanosine, 5-methyluracil, and pseudouracil. The oligomer can include one modified base or a plurality of modified bases, each selected independently of the rest. The modified sugar can be a methylated sugar, arabinose. The oligomer can include one modified sugar or a plurality of modified sugars, each selected independently of the rest.

In one embodiment the cationic lipid is N-[1-(2,3-dioleoyloxy)propyl]-N,N,N-trimethylammonium methyl-sulfate (DOTAP). DOTAP is believed to transport RNA oligomer into cells and specifically traffic to the endosomal compartment, where it can release the RNA oligomer in a pH-dependent fashion. Once in the endosomal compartment, the RNA can interact with certain intracellular Toll-like receptor molecules (TLRs), triggering TLR-mediated signal transduction pathways involved in generating an immune response. Other agents with similar properties including trafficking to the endosomal compartment can be used in place of or in addition to DOTAP.

In one embodiment the immunostimulatory composition further includes an antigen. In one embodiment the antigen is an allergen. In one embodiment the antigen is a cancer antigen. In one embodiment the antigen is a microbial antigen.

Also according to this aspect of the invention, in another embodiment the invention is a pharmaceutical composition. The pharmaceutical composition includes an immunostimulatory composition of the invention and a pharmaceutically acceptable carrier. Methods for preparing the pharmaceutical composition are also provided. Such methods entail placing an immunostimulatory composition of the invention in contact with a pharmaceutically acceptable carrier. The pharmaceutical composition can be formulated in a unit dosage for convenience.

In another aspect the invention provides a method of activating an immune cell. The method involves contacting an immune cell with an immunostimulatory composition of the invention, described above, in an effective amount to induce activation of the immune cell. In one embodiment the activation of the immune cell involves secretion of a cytokine by the immune cell. The cytokine in one embodiment is selected from the group consisting of interleukin 6 (IL-6), interleukin 12 (IL-12), an interferon (IFN), and tumor necrosis factor (TNF). In one embodiment the activation of the immune cell includes secretion of a chemokine. In one embodiment the secreted chemokine is interferon-gamma-induced protein 10 (IP-10). In one embodiment the activation of the immune cell includes expression of a costimulatory/accessory molecule by the immune cell. In one embodiment the costimulatory/accessory molecule is selected from the group consisting of intercellular adhesion molecules (ICAMs, e.g., CD54), leukocyte function-associated antigens (LFAs, e.g., CD58), B7s (CD80, CD86), and CD40.

Also according to this aspect of the invention, in one embodiment the activation of the immune cell involves activation of a MyD88-dependent signal transduction pathway. MyD88 is believed to be an adapter molecule that interacts with the Toll/interleukin-1 receptor (TIR) domain of various Toll-like receptor (TLR) molecules and participates in signal transduction pathways that ultimately result in activation of nuclear factor kappa B (NF-κB). Thus in one embodiment the MyD88-dependent signal transduction pathway is associated with a TLR. More particularly, in one embodiment the TLR is TLR8. In another embodiment the TLR is TLR7.

Also according to this aspect of the invention in one embodiment the immune cell is a human immune cell. The immune cell in one embodiment is a myeloid dendritic cell.

In one embodiment of this aspect of the invention the contacting occurs in vitro. In another embodiment the contacting occurs in vivo.

The invention in another aspect provides a method of inducing an immune response in a subject. The method according to this aspect of the invention involves administering to a subject an immunostimulatory composition of the invention in an effective amount to induce an immune response in the subject. It is to be noted that the method according to this aspect of the invention does not involve administration of an antigen to the subject. In one embodiment the subject is a human. In one embodiment the subject has or is at risk of having a cancer. In one embodiment the subject has or is at risk of having an infection with an agent selected from the group consisting of viruses, bacteria, fungi, and parasites. In a particular embodiment the subject has or is at risk of having a viral infection. It is also to be noted that the method according to this aspect of the invention can be used to treat a subject with a suppressed capacity to mount an effective or desirable immune response. For example the subject can have a suppressed immune system due to an infection, a cancer, an acute or chronic disease such as kidney or liver insufficiency, surgery, and an exposure to an immunosuppressive agent such as chemotherapy, radiation, certain drugs, or the like. In one embodiment the subject has or is at risk of having an allergy or asthma. Such a subject can be exposed to or at risk of exposure to an allergen that is associated with an allergic response or asthma in the subject.

In yet another aspect the invention provides a method of inducing an immune response in a subject. The method according to this aspect of the invention involves administering an antigen to a subject, and administering to the subject an immunostimulatory composition of the invention in an effective amount to induce an immune response to the antigen. It is to be noted that the antigen can be administered before, after, or concurrently with the immunostimulatory composition of the invention. In addition, both the antigen and the immunostimulatory compound can be administered to the subject more than once.

In one embodiment according to this aspect of the invention the antigen is an allergen. In one embodiment according to this aspect of the invention the antigen is a cancer antigen. The cancer antigen in one embodiment can be a cancer antigen isolated from the subject. In another embodiment the antigen is a microbial antigen. The microbial antigen can be an antigen of a virus, a bacterium, a fungus, or a parasite.

The invention further provides, in yet another aspect, a method of inducing an immune response in a subject. The method according to this aspect of the invention involves isolating dendritic cells of a subject, contacting the dendritic cells ex vivo with an immunostimulatory composition of the invention, contacting the dendritic cells ex vivo with an antigen, and administering the contacted dendritic cells to the subject.

In one embodiment according to this aspect of the invention the antigen is an allergen. In one embodiment according to this aspect of the invention the antigen is a cancer antigen. The cancer antigen in one embodiment can be a cancer antigen isolated from the subject. In another embodiment the antigen is a microbial antigen. The microbial antigen can be an antigen of a virus, a bacterium, a fungus, or a parasite.

An immune response arising from stimulation of one TLR can be modified, enhanced or amplified by stimulation of another TLR, and the combined immunostimulatory effect may be synergistic. For example, TLR9 is reported to respond to bacterial DNA and, more generally, CpG DNA. An immune response arising from TLR9 contacting its natural ligand (or any TLR9 ligand) may be modified, enhanced or amplified by also selectively contacting TLR7 with a TLR7 ligand, or by also selectively contacting TLR8 with a TLR8 ligand, or both. Likewise, an immune response arising from TLR7 contacting a TLR7 ligand may be modified, enhanced or amplified by also selectively contacting TLR8 with a TLR8 ligand, or by also selectively contacting TLR9 with CpG DNA (or any suitable TLR9 ligand), or both. As yet another example, an immune response arising from TLR8 contacting a TLR8 ligand may be modified, enhanced or amplified by also selectively contacting TLR7 with a TLR7 ligand, or by also selectively contacting TLR9 with CpG DNA (or any suitable TLR9 ligand), or both.

The present invention is based in part on the novel discovery by the inventors of what are believed to be natural ligands for TLR7 and TLR8. While naturally occurring ligands derived from microbes have been described for certain TLRs, natural ligands for TLR7 and TLR8 have not previously been described. Certain synthetic small molecules, imidazoquinoline compounds, have been described as ligands for TLR7, but such compounds are to be distinguished from the natural ligands of the present invention. Hemmi H et al. (2002) *Nat Immunol* 3:196-200.

Isolated natural ligands of TLR7 and TLR8 are useful as compositions that can induce, enhance, and complement an immune response. The natural ligands of TLR7 and TLR8 are useful for preparation of novel compositions that can induce, enhance, and complement an immune response. In addition, the natural ligands of TLR7 and TLR8 are useful for selectively inducing TLR7- and TLR8-mediated signaling and for selectively inducing TLR7- and TLR8-mediated immune responses. Furthermore, the natural ligands of TLR7 and TLR8 are useful in designing and performing screening assays for identification and selection of immunostimulatory compounds.

The present invention is also based in part on the novel discovery according to the invention that human neutrophils strongly express TLR8. This observation is important because neutrophils are very often the first cells to engage infectious pathogens and thus to initiate responses. It is believed that activated neutrophils secrete chemokines and cytokines, which in turn are instrumental in recruiting dendritic cells. TLR9-expressing dendritic cells drawn to the site of the activated neutrophils there become activated, thereby amplifying the immune response.

The present invention is also based in part on the appreciation of the differential expression of various TLRs, including TLR7, TLR8, and TLR9, on various cells of the immune system. This segregation may be of particular significance in humans with respect to TLR7, TLR8, and TLR9. The immune response arising from stimulation of any one of these TLRs may be enhanced or amplified by stimulation of another TLR, and the combined immunostimulatory effect may be synergistic. For example, TLR9 is reported to respond to bacterial DNA and, more generally, CpG DNA. An immune response arising from TLR9 contacting its natural ligand (or any TLR9 ligand) may be enhanced or amplified by also selectively contacting TLR7 with its natural ligand (or any suitable TLR7 ligand), or by also selectively contacting TLR8 with its natural ligand (or any suitable TLR8 ligand), or both. Likewise, an immune response arising from TLR7 contacting its natural ligand (or any TLR7 ligand) may be enhanced or amplified by also selectively contacting TLR8 with its natural ligand (or any suitable TLR8 ligand), or by also selectively contacting TLR9 with CpG DNA (or any suitable TLR9 ligand), or both. As yet another example, an immune response arising from TLR8 contacting its natural ligand (or any TLR8 ligand) may be enhanced or amplified by also selectively contacting TLR7 with its natural ligand (or any suitable TLR7 ligand), or by also selectively contacting TLR9 with CpG DNA (or any suitable TLR9 ligand), or both.

In a further aspect the invention provides a composition including an effective amount of a ligand for TLR8 to induce TLR8 signaling and an effective amount of a ligand for a second TLR selected from the group consisting of: TLR1, TLR2, TLR3, TLR4, TLR5, TLR6, TLR7, TLR9 and TLR10 to induce signaling by the second TLR. In one embodiment the second TLR is TLR3. In one embodiment the second TLR is TLR7. In one embodiment the second TLR is TLR9. In one embodiment the ligand for TLR8 and the ligand for the second TLR are linked. In yet another embodiment the composition further includes a pharmaceutically acceptable carrier.

In another aspect the invention provides a composition including an effective amount of a ligand for TLR7 to induce TLR7 signaling and an effective amount of a ligand for a second TLR selected from the group consisting of: TLR1, TLR2, TLR3, TLR4, TLR5, TLR6, TLR8, TLR9, and TLR10 to induce signaling by the second TLR. In one embodiment the second TLR is TLR3. In one embodiment the second TLR is TLR8. In one embodiment the second TLR is TLR9. In one embodiment the ligand for TLR7 and the ligand for the second TLR are linked. In yet another embodiment the composition further includes a pharmaceutically acceptable carrier.

In a further aspect the invention provides a composition including a DNA:RNA conjugate, wherein DNA of the conjugate includes an immunostimulatory motif effective for stimulating TLR9 signaling and wherein RNA of the conjugate includes RNA effective for stimulating signaling by TLR3, TLR7, TLR8, or any combination thereof. In one embodiment the immunostimulatory motif effective for stimulating TLR9 signaling is a CpG motif. In another embodiment the immunostimulatory motif effective for stimulating TLR9 signaling is poly-dT. In yet another embodiment the immunostimulatory motif effective for stimulating TLR9 signaling is poly-dG. In one embodiment the conjugate includes a chimeric DNA:RNA backbone. In one embodiment the chimeric backbone includes a cleavage site between the DNA and the RNA. In one embodiment the conjugate includes a double-stranded DNA:RNA heteroduplex. In yet another embodiment the composition further includes a pharmaceutically acceptable carrier.

In another aspect the invention provides a method for stimulating TLR8 signaling. The method involves contacting TLR8 with an isolated RNA in an effective amount to stimulate TLR8 signaling. In one embodiment the RNA is double-stranded RNA. In one embodiment the RNA is ribosomal RNA. In one embodiment the RNA is transfer RNA. In one embodiment the RNA is messenger RNA. In one embodiment the RNA is viral RNA. In one embodiment the RNA is G,U-rich RNA. In one embodiment the RNA consists essentially of G and U.

In yet another aspect the invention provides a method for stimulating TLR8 signaling. The method according to this aspect involves contacting TLR8 with a mixture of nucleosides consisting essentially of G and U in a ratio between 1G:50U and 10G:1U, in an amount effective to stimulate TLR8 signaling. In one embodiment the nucleosides are ribonucleosides. In one embodiment the nucleosides comprise a mixture of ribonucleosides and deoxyribonucleosides. In one embodiment the G is a guanosine derivative selected from the group consisting of: 8-bromoguanosine, 8-oxoguanosine, 8-mercaptoguanosine, 7-allyl-8-oxoguanosine, guanosine ribonucleoside vanadyl complex, inosine, and nebularine.

A further aspect of the invention provides a method for stimulating TLR8 signaling. The method according to this aspect involves contacting TLR8 with a mixture of ribonucleoside vanadyl complexes. In one embodiment the mixture comprises guanosine ribonucleoside vanadyl complexes.

In another aspect the invention provides a method for stimulating TLR8 signaling. The method according to this aspect involves contacting TLR8 with an isolated G,U-rich oligonucleotide comprising a sequence selected from the group consisting of: UUGUGG, UGGUUG, GUGUGU, and GGGUUU, in an amount effective to stimulate TLR8 signaling. In one embodiment the oligonucleotide is an oligoribonucleotide. In one embodiment the oligonucleotide is 7-50 bases long. In one embodiment the oligonucleotide is 12-24 bases long. In one embodiment the oligonucleotide has a sequence 5'-GUUGUGGUUGUGGUUGUG-3' (SEQ ID NO:1).

The invention provides in another aspect a method for stimulating TLR8 signaling. The method according to this aspect involves contacting TLR8 with an at least partially double-stranded nucleic acid molecule comprising at least one G-U base pair, in an amount effective to stimulate TLR8 signaling.

In yet another aspect the invention provides a method for supplementing a TLR8-mediated immune response. The method involves contacting TLR8 with an effective amount of a TLR8 ligand to induce a TLR8-mediated immune response, and contacting a TLR other than TLR8 with an effective amount of a ligand for the TLR other than TLR8 to induce an immune response mediated by the TLR other than TLR8.

In a further aspect the invention provides a method for supplementing a TLR8-mediated immune response in a subject. The method according to this aspect involves administering to a subject in need of an immune response an effective amount of a TLR8 ligand to induce a TLR8-mediated immune response, and administering to the subject an effective amount of a ligand for a TLR other than TLR8 to induce an immune response mediated by the TLR other than TLR8. In one embodiment the TLR other than TLR8 is TLR9. In one embodiment the ligand for TLR9 is a CpG nucleic acid. In one embodiment the CpG nucleic acid has a stabilized backbone. In one embodiment the ligand for TLR8 and the ligand for TLR9 are a conjugate. In one embodiment the conjugate comprises a double-stranded DNA:RNA heteroduplex. In one embodiment the conjugate comprises a chimeric DNA:RNA backbone. In one embodiment the chimeric backbone comprises a cleavage site between the DNA and the RNA.

The invention in a further aspect provides a method for stimulating TLR7 signaling. The method according to this aspect involves contacting TLR7 with an isolated guanosine ribonucleoside in an effective amount to stimulate TLR7 signaling. In one embodiment the guanosine ribonucleoside is a guanosine ribonucleoside derivative selected from the group consisting of: 8-bromoguanosine, 8-oxoguanosine, 8-mercaptoguanosine, 7-allyl-8-oxoguanosine, guanosine ribonucleoside vanadyl complex, inosine, and nebularine. In one embodiment the guanosine ribonucleoside derivative is 8-oxoguanosine. In one embodiment the guanosine nucleoside is a ribonucleoside. In one embodiment the guanosine nucleoside comprises a mixture of ribonucleosides and deoxyribonucleosides.

In another aspect the invention further provides a method for stimulating TLR7 signaling. The method according to this aspect involves contacting TLR7 with an isolated nucleic acid comprising a terminal oxidized or halogenized guanosine in an effective amount to stimulate TLR7 signaling. In one embodiment the oxidized or halogenized guanosine is 8-oxoguanosine.

In another aspect the invention provides a method for stimulating TLR7 signaling. The method according to this aspect involves contacting TLR7 with an isolated RNA in an effective amount to stimulate TLR7 signaling. In one embodiment the RNA is double-stranded RNA. In one embodiment the RNA is ribosomal RNA. In one embodiment the RNA is transfer RNA. In one embodiment the RNA is messenger RNA. In one embodiment the RNA is viral RNA. In one embodiment the RNA is G-rich RNA. In one embodiment the RNA is part of a DNA:RNA heteroduplex. In one embodiment the RNA consists essentially of guanosine ribonucleoside.

The invention in yet another aspect provides a method for stimulating TLR7 signaling. The method according to this aspect involves contacting TLR7 with a mixture of nucleosides consisting essentially of G and U in a ratio between 1G:50U and 10G:1U, in an amount effective to stimulate TLR7 signaling.

Provided in yet another aspect of the invention is a method for stimulating TLR7 signaling. The method according to this aspect involves contacting TLR7 with a mixture of ribonucleoside vanadyl complexes. In one embodiment the mixture comprises guanosine ribonucleoside vanadyl complexes.

In a further aspect the invention provides a method for supplementing a TLR7-mediated immune response. The method according to this aspect involves contacting TLR7 with an effective amount of a TLR7 ligand to induce a TLR7-mediated immune response, and contacting a TLR other than TLR7 with an effective amount of a ligand for the TLR other than TLR7 to induce an immune response mediated by the TLR other than TLR7.

In yet another aspect the invention provides a method for supplementing a TLR7-mediated immune response in a subject. The method involves administering to a subject in need of an immune response an effective amount of a TLR7 ligand to induce a TLR7-mediated immune response, and administering to the subject an effective amount of a ligand for a TLR other than TLR7 to induce an immune response mediated by the TLR other than TLR7. In one embodiment the TLR other than TLR7 is TLR9. In one embodiment the ligand for TLR9 is a CpG nucleic acid. In one embodiment the CpG nucleic acid has a stabilized backbone. In one embodiment the ligand for TLR7 and the ligand for TLR9 are a conjugate. In one embodiment the conjugate comprises a double-stranded DNA:RNA heteroduplex. In one embodiment the conjugate comprises a chimeric DNA:RNA backbone. In one embodiment the chimeric backbone comprises a cleavage site between the DNA and the RNA.

The invention in another aspect provides a method for screening candidate immunostimulatory compounds. The method according to this aspect involves measuring a TLR8-mediated reference signal in response to an RNA reference, measuring a TLR8-mediated test signal in response to a candidate immunostimulatory compound, and comparing the TLR8-mediated test signal to the TLR8-mediated reference signal.

In yet another aspect the invention provides a method for screening candidate immunostimulatory compounds, comprising measuring a TLR8-mediated reference signal in response to an imidazoquinoline reference, measuring a TLR8-mediated test signal in response to a candidate immunostimulatory compound, and comparing the TLR8-mediated test signal to the TLR8-mediated reference signal.

Also provided according to yet another aspect of the invention is a method for screening candidate immunostimulatory compounds. The method involves measuring a TLR7-mediated reference signal in response to an imidazoquinoline reference, measuring a TLR7-mediated test signal in response to a candidate immunostimulatory compound, and comparing the TLR7-mediated test signal to the TLR7-mediated reference signal.

In some embodiments the imidazoquinoline is resiquimod (R-848).

In some embodiments the imidazoquinoline is imiquimod (R-837).

In a further aspect the invention also provides a method for screening candidate immunostimulatory compounds. The method according to this aspect involves measuring a TLR7-mediated reference signal in response to a 7-allyl-8-oxoguanosine reference, measuring a TLR7-mediated test signal in response to a candidate immunostimulatory compound, and comparing the TLR7-mediated test signal to the TLR7-mediated reference signal.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE FIGURES

FIG. 9 depicts nucleic acid binding domains in TLR7, TLR8, and TLR9.

DETAILED DESCRIPTION OF THE INVENTION

Figure 1:
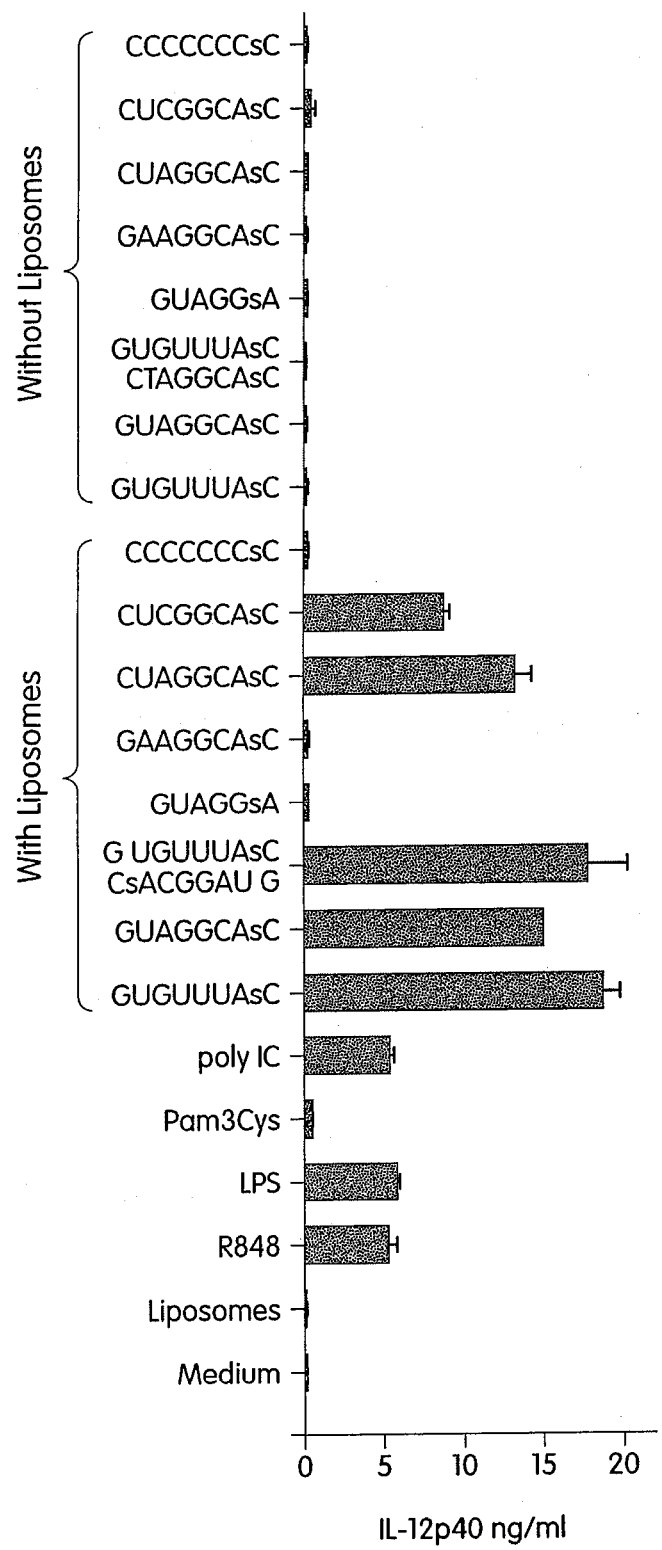
FIG. 1 is a bar graph depicting IL-12 p40 secretion by human peripheral blood mononuclear cells (PBMCs) in response to certain stimuli including selected G,U-containing RNA oligonucleotides with or without DOTAP ("with Liposomes" and "without Liposomes", respectively), as measured by specific enzyme-linked immunosorbent assay (ELISA). The lower case letter "s" appearing in the base sequences signifies phosphorothioate linkage.

The invention relates in part to the discovery by the inventors of a number of RNA and RNA-related molecules that are effective as immunostimulatory compounds. Identification of the immunostimulatory compounds arose through a systematic effort aimed at identifying naturally occurring ligands for TLR7 and TLR8. As a result of this effort, it has now been discovered that RNA and RNA-like molecules containing guanine (G) and uracil (U), including specific sequences containing G and U, are immunostimulatory and appear to act through an MyD88-dependent pathway, implicating TLR involvement. Significantly, some of the RNA sequences occur in highly conserved structural features of 5' untranslated regions of viral RNA that are important to viral replication. The identified immunostimulatory RNA sequences also correspond to or very nearly correspond to other RNAs, including tRNAs derived from bacteria and yeast, as well as rRNA derived from bacteria and possibly some eukaryotes. Importantly, the immunostimulatory RNA of the invention includes single-stranded RNA, in addition to partially or wholly double-stranded RNA, and its effect can be abrogated by RNase treatment. Where the RNA is at least partially double-stranded, it can in one embodiment include a stem-loop structure. As described in greater detail below, it has been discovered according to the invention that single-stranded G,U-rich RNAs as short as 5 nucleotides long can stimulate immune cells to produce large amounts of a number of cytokines and chemokines, including TNF-α, IL-6, IL-12, type 1 interferon (e.g., IFN-α), and IP-10.

It has now been surprisingly discovered by the inventors that certain G,U-containing RNA molecules and their analogs, but not their DNA counterparts, are immunostimulatory. Significantly, the G,U-containing oligoribonucleotides of the invention can be substantially smaller than the messenger RNAs previously described to be useful in preparing dendritic cell vaccines. See, e.g., Boczkowski D et al. (1996) *J Exp Med* 184:465-72; Mitchell D A et al. (2000) *Curr Opin Mol Ther* 2:176-81. Although the G,U-containing RNA molecules of the invention can be surrogates for ribosomal RNA and/or viral RNA as found in nature, they can be as small as 5-40 nucleotides long. As described further herein, the G,U-containing oligoribonucleotides of the invention include at least one G and at least one U. Surprisingly, elimination of either G or U from the G,U-containing oligoribonucleotides of the invention essentially abrogates their immunostimulatory effect. The at least one G and at least U can be adjacent to one another, or they can be separated by intervening nucleosides or sequence. Also significantly, the immunostimulatory G,U-containing RNA molecules of the invention do not require a CpG dinucleotide.

In one aspect the invention provides an immunostimulatory composition. The immunostimulatory composition according to this aspect of the invention includes an isolated RNA oligomer 5-40 nucleotides long having a base sequence having at least one guanine (G) and at least one uracil (U). As will be described in greater detail further below, the immunostimulatory RNA oligomer 5-40 nucleotides long having a base sequence having at least one guanine (G) and at least one uracil (U) is advantageously formulated such that the RNA oligomer is stabilized against degradation, concentrated in or on a particle such as a liposome, and/or targeted for delivery to the endosomal compartment of cells. In one formulation, described in the examples below, the RNA oligomer is advantageously combined with the cationic lipid DOTAP, which is believed to assist in trafficking the G,U-containing oligoribonucleotides into the endosomal compartment. Thus, in one aspect the invention is an immunostimulatory composition which includes an RNA oligomer 5-40 nucleotides long having a base sequence having at least one G and at least one U and optionally a cationic lipid.

The RNA oligomer of the invention can be of natural or non-natural origin. RNA as it occurs in nature is a type of nucleic acid that generally refers to a linear polymer of certain ribonucleoside units, each ribonucleoside unit made up of a purine or pyrimidine base and a ribose sugar, linked by internucleoside phosphodiester bonds. In this regard "linear" is meant to describe the primary structure of RNA. RNA in general can be single-stranded or double-stranded, including partially double-stranded.

As used herein, "nucleoside" refers to a single sugar moiety (e.g., ribose or deoxyribose) linked to an exchangeable organic base, which is either a substituted pyrimidine (e.g., cytosine (C), thymidine (T) or uracil (U)) or a substituted purine (e.g., adenine (A) or guanine (G)). As described herein, the nucleoside may be a naturally occurring nucleoside, a modified nucleoside, or a synthetic (artificial) nucleoside.

The terms "nucleic acid" and "oligonucleotide" are used interchangeably to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymidine (T) or uracil (U)) or a substituted purine (e.g., adenine (A) or guanine (G)). As used herein, the terms refer to oligoribonucleotides as well as oligodeoxyribonucleotides. The terms shall also include polynucleosides (i.e., a polynucleotide minus the phosphate) and any other organic base-containing polymer. Nucleic acid molecules can be obtained from existing nucleic acid sources (e.g., genomic or cDNA), but are preferably synthetic (e.g., produced by nucleic acid synthesis).

The terms nucleic acid and oligonucleotide also encompass nucleic acids or oligonucleotides with substitutions or modifications, such as in the bases and/or sugars. For example, they include nucleic acids having backbone sugars which are covalently attached to low molecular weight organic groups other than a hydroxyl group at the 3' position and other than a phosphate group at the 5' position. Thus modified nucleic acids may include a 2'-O-alkylated ribose group. In addition, modified nucleic acids may include sugars such as arabinose instead of ribose. Thus the nucleic acids may be heterogeneous in backbone composition thereby containing any possible combination of polymer units linked together such as peptide nucleic acids (which have amino acid backbone with nucleic acid bases). In some embodiments, the nucleic acids are homogeneous in backbone composition. Nucleic acids also include substituted purines and pyrimidines such as C-5 propyne modified bases. Wagner R W et al. (1996) *Nat Biotechnol* 14:840-4. Purines and pyrimidines include but are not limited to adenine, cytosine, guanine, thymidine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art.

A natural nucleoside base can be replaced by a modified nucleoside base, wherein the modified nucleoside base is for example selected from hypoxanthine; dihydrouracil; pseudouracil; 2-thiouracil; 4-thiouracil; 5-aminouracil; 5-($C_1$-$C_6$)-alkyluracil; 5-($C_2$-$C_6$)-alkenyluracil; 5-($C_2$-$C_6$)-alkynyluracil; 5-(hydroxymethyl)uracil; 5-chlorouracil; 5-fluorouracil; 5-bromouracil; 5-hydroxycytosine; 5-($C_1$-$C_6$)-alkylcytosine; 5-($C_2$-$C_6$)-alkenylcytosine; 5-($C_2$-$C_6$)-alkynylcytosine; 5-chlorocytosine; 5-fluorocytosine; 5-bromocytosine; $N^2$-dimethylguanine; 2,4-diamino-purine; 8-azapurine (including, in particular, 8-azaguanine); a substituted 7-deazapurine (including, in particular, 7-deazaguanine), including 7-deaza-7-substituted and/or 7-deaza-8-substituted purine; or other modifications of a natural nucleoside bases. This list is meant to be exemplary and is not to be interpreted to be limiting.

In particular, the at least one guanine base of the immunostimulatory G,U-containing oligoribonucleotide can be a substituted or modified guanine such as 7-deazaguanine; 8-azaguanine; 7-deaza-7-substituted guanine (such as 7-deaza-7-(C2-C6)alkynylguanine); 7-deaza-8-substituted guanine; hypoxanthine; 2,6-diaminopurine; 2-aminopurine; purine; 8-substituted guanine such as 8-hydroxyguanine; and 6-thioguanine. This list is meant to be exemplary and is not to be interpreted to be limiting.

Also in particular, the at least one uracil base of the G,U-containing oligoribonucleotide can be a substituted or modified uracil such as pseudouracil and 5-methyluracil.

For use in the instant invention, the nucleic acids of the invention can be synthesized de novo using any of a number of procedures well known in the art. For example, the β-cyanoethyl phosphoramidite method (Beaucage S L et al. (1981) *Tetrahedron Lett* 22:1859); nucleoside H-phosphonate method (Garegg et al. (1986) *Tetrahedron Lett* 27:4051-4; Froehler et al. (1986) *Nucl Acid Res* 14:5399-407; Garegg et al. (1986) *Tetrahedron Lett* 27:4055-8; Gaffney et al. (1988) *Tetrahedron Lett* 29:2619-22). These chemistries can be performed by a variety of automated nucleic acid synthesizers available in the market. These nucleic acids are referred to as synthetic nucleic acids. Alternatively, T-rich and/or TG dinucleotides can be produced on a large scale in plasmids, (see Sambrook T et al., "Molecular Cloning: A Laboratory Manual", Cold Spring Harbor laboratory Press, New York, 1989) and separated into smaller pieces or administered whole. Nucleic acids can be prepared from existing nucleic acid sequences (e.g., genomic or cDNA) using known techniques, such as those employing restriction enzymes, exonucleases or endonucleases. Nucleic acids prepared in this manner are referred to as isolated nucleic acid. An isolated nucleic acid generally refers to a nucleic acid which is separated from components which it is normally associated with in nature. As an example, an isolated nucleic acid may be one which is separated from a cell, from a nucleus, from mitochondria or from chromatin. The term "nucleic acid" encompasses both synthetic and isolated nucleic acid.

For use in vivo, the nucleic acids may optionally be relatively resistant to degradation (e.g., are stabilized). In some embodiments only specific portions of the nucleic acids may optionally be stabilized. A "stabilized nucleic acid molecule" shall mean a nucleic acid molecule that is relatively resistant to in vivo degradation (e.g., via an exo- or endo-nuclease). Stabilization can be a function of length or secondary structure. Nucleic acids that are tens to hundreds of kbs long are relatively resistant to in vivo degradation. For shorter nucleic acids, secondary structure can stabilize and increase their effect. For example, if the 3' end of an nucleic acid has self-complementarity to an upstream region, so that it can fold back and form a sort of stem loop structure, then the nucleic acid becomes stabilized and therefore exhibits more activity.

In certain embodiments according to this aspect of the invention, the base sequence of the RNA oligomer is at least partially self-complementary. A self-complementary sequence as used herein refers to a base sequence which, upon suitable alignment, may form intramolecular or, more typically, intermolecular basepairing between G-C, A-U, and/or G-U wobble pairs. In one embodiment the extent of self-complementarity is at least 50 percent. For example an 8-mer that is at least 50 percent self-complementary may have a sequence capable of forming 4, 5, 6, 7, or 8 G-C, A-U, and/or G-U wobble basepairs. Such basepairs may but need not necessarily involve bases located at either end of the self-complementary RNA oligomer. Where nucleic acid stabilization may be important to the RNA oligomers, it may be advantageous to "clamp" together one or both ends of a double-stranded nucleic acid, either by basepairing or by any other suitable means. The degree of self-complementarity may depend on the alignment between oligomers, and such alignment may or may not include single- or multiple-nucleoside overhangs. In other embodiments, the degree of self-complementarity is at least 60 percent, at least 70 percent, at least 80 percent, at least 90 percent, or even 100 percent. The foregoing notwithstanding, it should be noted that double-strandedness is not a requirement of the RNA oligomers of the invention.

Similar considerations apply to intermolecular basepairing between RNA oligonucleotides of different base sequence. Thus where a plurality of RNA oligomers are used together, the plurality of oligomers may, but need not, include sequences which are at least partially complementary to one another. In one embodiment the plurality of oligomers includes an oligomer having a first base sequence and an oligomer having a second base sequence, wherein the first base sequence and the second base sequence are at least 50 percent complementary. For example, as between two 8-mers that are at least 50 percent complementary, they may form 4, 5, 6, 7, or 8 G-C, A-U, and/or G-U wobble basepairs. Such basepairs may but need not necessarily involve bases located at either end of the complementary RNA oligomers. The degree of complementarity may depend on the alignment between oligomers, and such alignment may or may not include single- or multiple-nucleoside overhangs. In other embodiments, the degree of complementarity is at least 60 percent, at least 70 percent, at least 80 percent, at least 90 percent, or even 100 percent.

Alternatively, nucleic acid stabilization can be accomplished via phosphate backbone modifications. Preferred stabilized nucleic acids of the instant invention have a modified backbone. It has been demonstrated that modification of the nucleic acid backbone provides enhanced activity of the nucleic acids when administered in vivo. One type of modified backbone is a phosphate backbone modification. Inclusion in immunostimulatory nucleic acids of at least two phosphorothioate linkages at the 5' end of the oligonucleotide and multiple (preferably five) phosphorothioate linkages at the 3' end, can in some circumstances provide maximal activity and protect the nucleic acid from degradation by intracellular exo- and endonucleases. Other modified nucleic acids include phosphodiester-modified nucleic acids, combinations of phosphodiester and phosphorothioate nucleic acids, alkylphosphonate and arylphosphonate, alkylphosphorothioate and arylphosphorothioate, methylphosphonate, methylphosphorothioate, phosphorodithioate, p-ethoxy, morpholino, and combinations thereof. Nucleic acids having phosphorothioate linkages provide maximal activity and protect the nucleic acid from degradation by intracellular exo- and endo-nucleases. and combinations thereof. Each of these combinations and their particular effects on immune cells is discussed in more detail with respect to CpG nucleic acids in issued U.S. Pat. Nos. 6,207,646 and 6,239,116, the entire contents of which are hereby incorporated by reference. It is believed that these modified nucleic acids may show more stimulatory activity due to enhanced nuclease resistance, increased cellular uptake, increased protein binding, and/or altered intracellular localization.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Pat. No. 092,574) can be prepared by automated solid phase synthesis using commercially available reagents. Methods for making other DNA backbone modifications and substitutions have been described. Uhlmann E et al. (1990) *Chem Rev* 90:544; Goodchild J (1990) *Bioconjugate Chem* 1:165.

Other stabilized nucleic acids include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

Another class of backbone modifications include 2'-O-methylribonucleosides (2'-OMe). These types of substitutions are described extensively in the prior art and in particular with respect to their immunostimulating properties in Zhao et al. (1999) *Bioorg Med Chem Lett* 9:24:3453-8. Zhao et al. describes methods of preparing 2'-OMe modifications to nucleic acids.

The immunostimulatory G,U-containing RNA oligomers of the invention are typically about 5 to about 40 nucleotides long. Thus in certain distinct embodiments, the G,U-containing RNA oligomer can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides long. In one embodiment the G,U-containing RNA oligomer can be 5, 6, 7, 8, 9, 10, 11, 12, 13, 14, 15, 16, 17, 18, 19, or 20 nucleotides long. In one embodiment the G,U-containing RNA oligomer can be 5, 6, 7, 8, 9, 10, 11, or 12 nucleotides long. In one embodiment the G,U-containing RNA oligomer can be 8, 9, 10, 11, or 12 nucleotides long.

For example, RNA oligomers with the following base sequences have been discovered to be useful in the compositions and practice of the invention: 5'-GUGUUUAC-3'; 5'-GUAGGCAC-3'; 5'-CUAGGCAC-3'; 5'-CUCGGCAC-3'; and 5'-GUGUUUAC-3' in combination with 5'-GUAGGCAC-3'.

Because the immunostimulatory effects of the G,U-containing RNA oligomers of the invention have been discovered to be MyD88-dependent, it is the belief of the inventors that the immunostimulatory G,U-containing RNA oligomers of the invention may interact with at least one TLR as a step in exerting their immunostimulatory effect. The immunostimulatory G,U-containing RNA oligomers of the invention may thus represent or mimic at least portions of natural ligands for the at least one TLR. Such natural ligands may include ribosomal RNA, either prokaryotic or eukaryotic, as well as certain viral RNAs. The TLR or TLRs may be TLR8, TLR7, or some yet-to-be defined TLR. Natural ligands for TLR1, TLR7, TLR8, and TLR10 have not previously been described.

The immunostimulatory RNA molecules of the invention have been discovered to occur in nature in all types of RNA, usually in association with highly conserved sequence or key structural feature. In one example, immunostimulatory RNA has been discovered to occur in the context of an internal ribosome entry site (IRES).

An IRES is a minimal cis-acting RNA element contained within a complex structural feature in the 5' untranslated region (5' UTR) of viral RNA and other mRNAs that regulates the initiation of translation of the viral genome in a cap-independent manner. Hellen C U et al. (2001) *Genes Dev* 15:1593-1612. Cap-independent initiation of viral RNA translation was first observed in picornaviruses. Jackson R J et al. (1990) *Trends Biochem Sci* 15:477-83; Jackson R J et al. (1995) *RNA* 1:985-1000.

In most eukaryotic cells, mRNA translation initiation commences with recruitment of the cap binding complex eukaryotic initiation factor (eIF)4F, composed of eIF4E (cap binding protein), eIF4A, and eIF4G, to the 5' capped end of the mRNA. The 40S ribosomal subunit, carrying eIF3, and the ternary initiator complex tRNA-eIF2-GTP are then recruited to the 5' end of the mRNA through interaction between eIF3 and eIF4G. The 40S subunit then scans the mRNA in a 5' to 3' direction until it encounters an appropriate start codon, whereupon the anticodon of initiator methionine-tRNA is engaged, the 60S subunit joins to form an 80S ribosome, and translation commences.

Thus the significance of an IRES, at least in the context of a virus, is believed to be the ability of the IRES to confer a selective advantage to the virus over usual cap-dependent translation in the cell.

The following viruses have been reported to have IRES elements in their genome: all picornaviruses; bovine viral diarrhea virus; classic swine fever virus; cricket paralysis virus; encephalomyocarditis virus; foot-and-mouth disease virus; Friend murine leukemia virus gag mRNA; HCV; human immunodeficiency virus env mRNA; Kaposi's sarcoma-associated herpesvirus; Moloney murine leukemia virus gag mRNA; *Plautia stali* intestine virus; poliovirus; rhinovirus; *Rhopalosiphum padi* virus; and Rous sarcoma virus. Hellen C U et al. (2001) *Genes Dev* 15:1593-1612. This list is not intended to be limiting.

The viral proteins of hepatitis C virus (HCV) are translated from a 9.5 kb single-stranded positive sense RNA which is flanked by 5' and 3' UTRs. The highly conserved 5' UTR includes an IRES present in nt 40-370. Reynolds J E et al. (1996) *RNA* 2:867-78. The HCV 5' UTR is believed to have four major structural domains (1-IV), of which domains II and III have subdomains. Subdomain IIId includes a 27 nt stem-loop (nt 253-279) that on the basis of in vivo mutational studies has been reported to be critical in HCV IRES-mediated translation. Kieft J S et al. (1999) *J Mol Biol* 292:513-29; Klinck R et al. (2000) *RNA* 6:1423-31. The sequence of the IIId 27-mer is provided by 5'-GCCGA GUAGUGUUGGGUCGCGAAAGGC-3' (SEQ ID NO:4), wherein the UUGGGU forms the terminal loop. The stem-loop structure is reported to include a number of non-Watson-Crick base pairs, typical of other RNAs, including wobble U∘G, U∘A, G∘A, and A∘A base pairs.

As another example, the immunostimulatory RNA sequences of the invention have been discovered to occur in G,U-rich sequence near the 5' end of the viral RNA of human immunodeficiency virus type 1 (HIV-1) that is crucial to efficient viral RNA packaging. Russell R S et al. (2002) *Virology* 303:152-63. Specifically, two key G,U-rich sequences within U5, namely 5'-GUAGUGUGUG-3' (SEQ ID NO:2) and 5'-GUCUGUUGUGUG-3' (SEQ ID NO:3), corresponding to nt 99-108 and 112-123 of strain BH10, respectively, have been found according to the present invention to be highly immunostimulatory (see Example 11 below). It will be noted that SEQ ID NO:2 includes both GUAGU and GUGUG, and SEQ ID NO:3 includes GUGUG.

As yet another example, the immunostimulatory RNA sequences of the invention have been found to occur in 5S ribosomal RNA loop E of a large number of species of bacteria.

Figure 8:
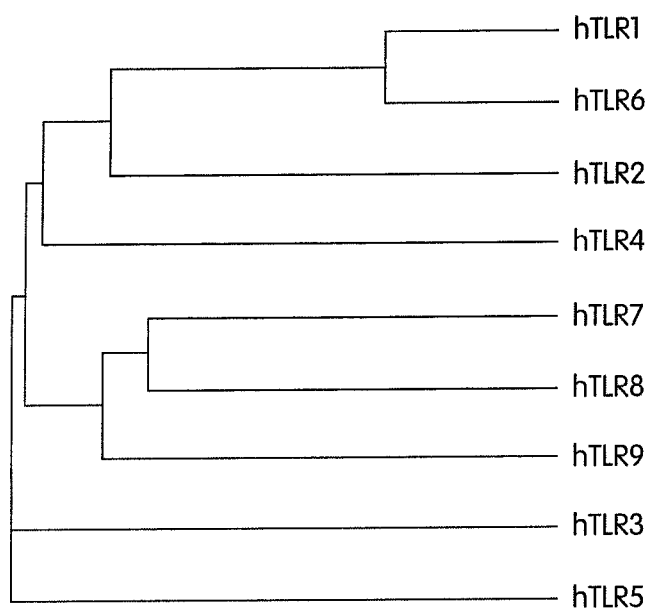
FIG. 8 is a graph depicting apparent relatedness among TLRs.

TLR8 and TLR7 show high sequence homology to TLR9 (FIG. 8). TLR9 is the CpG-DNA receptor and transduces immunostimulatory signals. Two DNA binding motifs have been described in TLR9 (U.S. patent application Ser. No. 09/954,987) that are also present in TLR8 and TLR7 with some modifications (FIG. 9). Despite this similarity, however, TLR7 and TLR8 do not bind CpG-DNA.

It has been discovered according to the present invention that guanosine, particularly guanosine in combination with uracil, and certain guanosine-containing nucleic acids and derivatives thereof, are natural ligands of TLR8. It has been discovered according to the present invention that RNA, oxidized RNA, G,U-rich nucleic acids, and at least partially double-stranded nucleic acid molecules having at least one G-U base pair are TLR8 ligands. In certain preferred embodiments involving guanosine, guanosine derivatives, and G,U-rich nucleic acids, guanosine is the ribonucleoside. Nucleic acid molecules containing GUU, GUG, GGU, GGG, UGG, UGU, UUG, UUU, multiples and any combinations thereof are believed to be TLR8 ligands. In some embodiments the TLR8 ligand is a G,U-rich oligonucleotide that includes a hexamer sequence $(UUGUGG)_n$, $(UGGUUG)_n$, $(GUGUGU)_n$, or $(GGGUUU)_n$ where n is an integer from 1 to 8, and preferably n is at least 3. In addition, it has also been discovered according to the present invention that mixtures of ribonucleoside vanadyl complexes (i.e., mixtures of adenine, cytosine, guanosine, and uracil ribonucleoside vanadyl complexes), and guanosine ribonucleoside vanadyl complexes alone, are TLR8 ligands. In addition, it has been discovered according the present invention that certain imidazoquinolines, including resiquimod and imiquimod, are TLR8 ligands.

It has also been discovered according to the present invention that guanosine, and certain guanosine-containing nucleic acids and derivatives thereof, are natural ligands of TLR7. It has been discovered according to the present invention that RNA, oxidized RNA, G-rich nucleic acids, and at least partially double-stranded nucleic acid molecules that are rich in G content are TLR7 ligands. In certain preferred embodiments involving guanosine, guanosine derivatives, and G-rich nucleic acids, guanosine is the ribonucleoside. In addition, it has also been discovered according to the present invention that mixtures of ribonucleoside vanadyl complexes (i.e., mixtures of adenine, cytosine, guanosine, and uracil ribonucleoside vanadyl complexes), and guanosine ribonucleoside vanadyl complexes alone, are TLR7 ligands. In addition, it has been discovered according the present invention that 7-allyl-8-oxoguanosine (loxoribine) is a TLR7 ligand.

In addition to having diverse ligands, the various TLRs are believed to be differentially expressed in various tissues and on various types of immune cells. For example, human TLR7 has been reported to be expressed in placenta, lung, spleen, lymph nodes, tonsil and on plasmacytoid precursor dendritic cells (pDCs). Chuang T-H et al. (2000) *Eur Cytokine Netw* 11:372-8; Kadowaki N et al. (2001) *J Exp Med* 194:863-9. Human TLR8 has been reported to be expressed in lung, peripheral blood leukocytes (PBL), placenta, spleen, lymph nodes, and on monocytes. Kadowaki N et al. (2001) *J Exp Med* 194:863-9; Chuang T-H et al. (2000) *Eur Cytokine Netw* 11:372-8. Human TLR9 is reportedly expressed in spleen, lymph nodes, bone marrow, PBL, and on pDCs, B cells, and CD123+DCs. Kadowaki N et al. (2001) *J Exp Med* 194:863-9; Bauer S et al. (2001) *Proc Natl Acad Sci USA* 98:9237-42; Chuang T-H et al. (2000) *Eur Cytokine Netw* 11:372-8.

Guanosine derivatives have previously been described as B-cell and NK cell activators, but their receptors and mechanism of action were not understood. Goodman M G et al. (1994) *J Pharm Exp Ther* 274:1552-57; Reitz A B et al. (1994) *J Med Chem* 37:3561-78. Such guanosine derivatives include, but are not limited to, 8-bromoguanosine, 8-oxoguanosine, 8-mercaptoguanosine, and 7-allyl-8-oxoguanosine (loxoribine).

Imidazoquinolines are synthetic small molecule immune response modifiers thought to induce expression of several cytokines including interferons (e.g., IFN-α and IFN-γ), tumor necrosis factor alpha (TNF-α) and some interleukins (e.g., IL-1, IL-6 and IL-12). Imidazoquinolines are capable of stimulating a Th1 immune response, as evidenced in part by their ability to induce increases in IgG2a levels. Imidazoquinoline agents reportedly are also capable of inhibiting production of Th2 cytokines such as IL-4, IL-5, and IL-13. Some of the cytokines induced by imidazoquinolines are produced by macrophages and dendritic cells. Some species of imidazoquinolines have been reported to increase NK cell lytic activity and to stimulate B-cell proliferation and differentiation, thereby inducing antibody production and secretion.

As used herein, an imidazoquinoline agent includes imidazoquinoline amines, imidazopyridine amines, 6,7-fused cycloalkylimidazopyridine amines, and 1,2 bridged imidazoquinoline amines. These compounds have been described in U.S. Pat. Nos. 4,689,338, 4,929,624, 5,238,944, 5,266,575, 5,268,376, 5,346,905, 5,352,784, 5,389,640, 5,395,937, 5,494,916, 5,482,936, 5,525,612, 6,039,969 and 6,110,929. Particular species of imidazoquinoline agents include 4-amino-α,α-dimethyl-2-ethoxymethyl-1H-imidazo[4,5-c]quinoline-1-ethanol (resiquimod or R-848 or S-28463; PCT/US01/28764, WO 02/22125); and 1-(2-methylpropyl)-1H-imidazo[4,5-c]quinoline-4-amine (imiquimod or R-837 or S-26308). Imiquimod is currently used in the topical treatment of warts such as genital and anal warts and has also been tested in the topical treatment of basal cell carcinoma.

Nucleotide and amino acid sequences of human and murine TLR3 are known. See, for example, GenBank Accession Nos. U88879, NM_003265, NM_126166, AF355152; and AAC34134, NP_003256, NP_569054, AAK26117. Human TLR3 is reported to be 904 amino acids long and to have a sequence provided in SEQ ID NO:20. A corresponding nucleotide sequence is provided as SEQ ID NO:21. Murine TLR3 is reported to be 905 amino acids long and to have a sequence as provided in SEQ ID NO:22. A corresponding nucleotide sequence is provided as SEQ ID NO:23. TLR3 polypeptide includes an extracellular domain having leucine-rich repeat region, a transmembrane domain, and an intracellular domain that includes a TIR domain.

As used herein a "TLR3 polypeptide" refers to a polypeptide including a full-length TLR3 according to one of the sequences above, orthologs, allelic variants, SNPs, variants incorporating conservative amino acid substitutions, TLR3 fusion proteins, and functional fragments of any of the foregoing. Preferred embodiments include human TLR3 polypeptides having at least 65 percent sequence identity, more preferably at least 80 percent sequence identity, even more preferably with at least 90 percent sequence identity, and most preferably with at least 95 percent sequence identity with the human TLR3 amino acid sequence of SEQ ID NO:20. Preferred embodiments also include murine TLR3 polypeptides having at least 65 percent sequence identity, more preferably at least 80 percent sequence identity, even more preferably with at least 90 percent sequence identity, and most preferably with at least 95 percent sequence identity with the murine TLR3 amino acid sequence of SEQ ID NO:22.

As used herein "TLR3 signaling" refers to an ability of a TLR3 polypeptide to activate the TLR/IL-1R (TIR) signaling pathway, also referred to herein as the TLR signal transduction pathway. Changes in TLR3 activity can be measured by assays such as those disclosed herein, including expression of genes under control of κB-sensitive promoters and enhancers. Such naturally occurring genes include the genes encoding IL-1β, IL-6, IL-8, the p40 subunit of interleukin 12 (IL-12 p40), and the costimulatory molecules CD80 and CD86. Other genes can be placed under the control of such regulatory elements (see below) and thus serve to report the level of TLR3 signaling. Additional nucleotide sequence can be added to SEQ ID NO:21 or SEQ ID NO:23, preferably to the 5' or the 3' end of the open reading frame of SEQ ID NO:21, to yield a nucleotide sequence encoding a chimeric polypeptide that includes a detectable or reporter moiety, e.g., FLAG, luciferase (luc), green fluorescent protein (GFP), and others known by those skilled in the art.

```
                                                                SEQ ID NO: 20
Human TLR3 amino acid
MRQTLPCIYF WGGLLPFGML CASSTTKCTV SHEVADCSHL KLTQVPDDLP TNITVLNLTH  60

NQLRRLPAAN FTRYSQLTSL DVGFNTISKL EPELCQKLPM LKVLNLQHNE LSQLSDKTFA 120

FCTNLTELHL MSNSIQKIKN NPFVKQKNLI TLDLSHNGLS STKLGTQVQL ENLQELLLSN 180

NKIQALKSEE LDIFANSSLK KLELSSNQIK EFSPGCFHAI GRLFGLFLNN VQLGPSLTEK 240

LCLELANTSI RNLSLSNSQL STTSNTTFLG LKWTNLTMLD LSYNNLNVVG NDSFAWLPQL 300

EYFFLEYNNI QHLFSHSLHG LFNVRYLNLK RSFTKQSISL ASLPKIDDFS FQWLKCLEHL 360

NMEDNDIPGI KSNMFTGLIN LKYLSLSNSF TSLRTLTNET FVSLAHSPLH ILNLTKNKIS 420

KIESDAFSWL GHLEVLDLGL NEIGQELTGQ EWRGLENIFE IYLSYNKYLQ LTRNSFALVP 480

SLQRLMLRRV ALKNVDSSPS PFQPLRNLTI LDLSNNNIAN INDDMLEGLE KLEILDLQHN 540

NLARLWKHAN PGGPIYFLKG LSHLHILNLE SNGFDEIPVE VFKDLFELKI IDLGLNNLNT 600

LPASVFNNQV SLKSLNLQKN LITSVEKKVF GPAFRNLTEL DMRFNPFDCT CESIAWFVNW 660

INETHTNIPE LSSHYLCNTP PHYHGFPVRL FDTSSCKDSA PFELFFMINT SILLIFIFIV 720

LLIHFEGWRI SFYWNVSVHR VLGFKEIDRQ TEQFEYAAYI IHAYKDKDWV WEHFSSMEKE 780

DQSLKFCLEE RDFEAGVFEL EAIVNSIKRS RKIIFVITHH LLKDPLCKRF KVHHAVQQAI 840

EQNLDSIILV FLEEIPDYKL NHALCLRRGM FKSHCILNWP VQKERIGAFR HKLQVALGSK 900

NSVH                                                              904

SEQ ID NO: 21
Human TLR3 nucleotide
cactttcgag agtgccgtct atttgccaca cacttccctg atgaaatgtc tggatttgga  60
ctaaagaaaa aaggaaaggc tagcagtcat ccaacagaat catgagacag actttgcctt 120
gtatctactt ttgggggggc cttttgccct tgggatgct gtgtgcatcc tccaccacca 180
agtgcactgt tagccatgaa gttgctgact gcagccacct gaagttgact caggtacccg 240
atgatctacc cacaaacata acagtgttga accttaccca taatcaactc agaagattac 300
cagccgccaa cttcacaagg tatagccagc taactagctt ggatgtagga tttaacacca 360
tctcaaaact ggagccagaa ttgtgccaga aacttcccat gttaaaagtt ttgaacctcc 420
agcacaatga gctatctcaa cttctgata aaaccttgc cttctgcacg aatttgactg 480
aactccatct catgtccaac tcaatccaga aaattaaaaa taatcccttt gtcaagcaga 540
agaatttaat cacattagat ctgtctcata atggcttgtc atctacaaaa ttaggaactc 600
```

-continued

```
aggttcagct ggaaaatctc caagagcttc tattatcaaa caataaaatt caagcgctaa  660
aaagtgaaga actggatatc tttgccaatt catctttaaa aaaattagag ttgtcatcga  720
atcaaattaa agagtttct ccagggtgtt ttcacgcaat tggaagatta tttggcctct  780
ttctgaacaa tgtccagctg ggtcccagcc ttacagagaa gctatgtttg gaattagcaa  840
acacaagcat tcggaatctg tctctgagta acagccagct gtccaccacc agcaatacaa  900
ctttcttggg actaaagtgg acaaatctca ctatgctcga tctttcctac aacaacttaa  960
atgtggttgg taacgattcc tttgcttggc ttccacaact agaatatttc ttcctagagt 1020
ataataatat acagcatttg ttttctcact ctttgcacgg gcttttcaat gtgaggtacc 1080
tgaatttgaa acggtctttt actaaacaaa gtatttccct tgcctcactc cccaagattg 1140 atgattttc ttttcagtgg ctaaaatgtt tggagcacct taacatggaa gataatgata 1200
ttccaggcat aaaaagcaat atgttcacag gattgataaa cctgaaatac ttaagtctat 1260
ccaactcctt tacaagtttg cgaactttga caaatgaaac atttgtatca cttgctcatt 1320
ctcccttaca catactcaac ctaaccaaga ataaaatctc aaaaatagag agtgatgctt 1380
tctcttggtt gggccaccta gaagtacttg acctgggcct taatgaaatt gggcaagaac 1440
tcacaggcca ggaatggaga ggtctagaaa atattttcga aatctatctt tcctacaaca 1500
agtacctgca gctgactagg aactcctttg ccttggtccc aagccttcaa cgactgatgc 1560
tccgaagggt ggcccttaaa aatgtggata gctctccttc accattccag cctcttcgta 1620
acttgaccat tctggatcta agcaacaaca acatagccaa cataaatgat gacatgttgg 1680
agggtcttga gaaactagaa attctcgatt tgcagcataa caacttagca cggctctgga 1740
aacacgcaaa ccctggtggt cccatttatt tcctaaaggg tctgtctcac ctccacatcc 1800
ttaacttgga gtccaacggc tttgacgaga tcccagttga ggtcttcaag gatttatttg 1860
aactaaagat catcgattta ggattgaata atttaaacac acttccagca tctgtctttta 1920 ataatcaggt gtctctaaag tcattgaacc ttcagaagaa tctcataaca tccgttgaga 1980
agaaggtttt cgggccagct ttcaggaacc tgactgagtt agatatgcgc tttaatccct 2040
ttgattgcac gtgtgaaagt attgcctggt ttgttaattg gattaacgag acccatacca 2100
acatccctga gctgtcaagc cactaccttt gcaacactcc acctcactat catgggttcc 2160
cagtgagact ttttgataca tcatcttgca aagacagtgc cccctttgaa ctcttttca 2220 tgatcaatac cagtatcctg ttgatttta tctttattgt acttctcatc cactttgagg 2280
gctggaggat atcttttttat tggaatgttt cagtacatcg agttcttggt ttcaaagaaa 2340
tagacagaca gacagaacag tttgaatatg cagcatatat aattcatgcc tataaagata 2400
aggattgggt ctgggaacat ttctcttcaa tggaaaagga agaccaatct ctcaaatttt 2460
gtctggaaga aagggacttt gaggcgggtg ttttttgaact agaagcaatt gttaacagca 2520
tcaaaagaag cagaaaaatt attttttgtta taacacacca tctattaaaa gacccattat 2580
gcaaaagatt caaggtacat catgcagttc aacaagctat tgaacaaaat ctggattcca 2640
ttatattggt tttccttgag gagattccag attataaact gaaccatgca ctctgtttgc 2700
gaagaggaat gtttaaatct cactgcatct tgaactggcc agttcagaaa gaacggatag 2760 gtgccttttcg tcataaattg caagtagcac ttggatccaa aaactctgta cattaaattt 2820
atttaaatat tcaattagca aaggagaaac tttctcaatt taaaaagttc tatggcaaat 2880
ttaagttttc cataaaggtg ttataatttg tttattcata tttgtaaatg attatattct 2940
atcacaatta catctcttct aggaaaatgt gtctccttat ttcaggccta tttttgacaa 3000
```

-continued

```
ttgacttaat tttacccaaa ataaaacata taagcacgta aaaaaaaaaa aaaaaaa    3057
```

SEQ ID NO: 22
Murine TLR3 amino acid

```
MKGCSSYLMY SFGGLLSLWI LLVSSTNQCT VRYNVADCSH LKLTHIPDDL PSNITVLNLT   60
HNQLRRLPPT NFTRYSQLAI LDAGFNSISK LEPELCQILP LLKVLNLQHN ELSQISDQTF  120
VFCTNLTELD LMSNSIHKIK SNPFKNQKNL IKLDLSHNGL SSTKLGTGVQ LENLQELLLA  180
KNKILALRSE ELEFLGNSSL RKLDLSSNPL KEFSPGCFQT IGKLFALLLN NAQLNPHLTE  240
KLCWELSNTS IQNLSLANNQ LLATSESTFS GLKWTNLTQL DLSYNNLHDV GNGSFSYLPS  300
LRYLSLEYNN IQRLSPRSFY GLSNLRYLSL KRAFTKQSVS LASHPNIDDF SFQWLKYLEY  360
LNMDDNNIPS TKSNTFTGLV SLKYLSLSKT FTSLQTLTNE TFVSLAHSPL LTLNLTKNHI  420
SKIANGTFSW LGQLRILDLG LNEIEQKLSG QEWRGLRNIF EIYLSYNKYL QLSTSSFALV  480
PSLQRLMLRR VALKNVDISP SPFRPLRNLT ILDLSNNNIA NINEDLLEGL ENLEILDFQH  540
NNLARLWKRA NPGGPVNFLK GLSHLHILNL ESNGLDEIPV GVFKNLFELK SINLGLNNLN  600
KLEPFIFDDQ TSLRSLNLQK NLITSVEKDV FGPPFQNLNS LDMRFNPFDC TCESISWFVN  660
WINQTHTNIF ELSTHYLCNT PHHYYGFPLK LFDTSSCKDS APFELLFIIS TSMLLVFILV  720
VLLIHIEGWR ISFYWNVSVH RILGFKEIDT QAEQFEYTAY IIHAHKDRDW VWEHFSPMEE  780
QDQSLKFCLE ERDFEAGVLG LEAIVNSIKR SRKIIFVITH HLLKDPLCRR FKVHHAVQQA  840
IEQNLDSIIL IFLQNIPDYK LNHALCLRRG MFKSHCILNW PVQKERINAF HHKLQVALGS  900
RNSAH                                                             904
```

SEQ ID NO: 23
Murine TLR3 nucleotide

```
tagaatatga tacagggatt gcacccataa tctgggctga atcatgaaag ggtgttcctc   60
ttatctaatg tactcctttg ggggactttt gtccctatgg attcttctgg tgtcttccac  120
aaaccaatgc actgtgagat acaacgtagc tgactgcagc catttgaagc taacacacat  180
acctgatgat cttccctcta acataacagt gttgaatctt actcacaacc aactcagaag  240
attaccacct accaactttta caagatacag ccaacttgct atcttggatg caggatttaa  300
ctccatttca aaactggagc cagaactgtg ccaaatactc cctttgttga agtattgaa  360
cctgcaacat aatgagctct ctcagatttc tgatcaaacc tttgtcttct gcacgaacct  420
gacagaactc gatctaatgt ctaactcaat cacaaaaatt aaaagcaacc ctttcaaaaa  480
ccagaagaat ctaatcaaat tagatttgtc tcataatggt ttatcatcta caaagttggg  540
aacgggggtc caactggaga acctccaaga actgctctta gcaaaaaata aaatccttgc  600
gttgcgaagt gaagaacttg agtttcttgg caattcttct ttacgaaagt tggacttgtc  660
atcaaatcca cttaaagagt tctccccggg gtgtttccag acaattggca agttattcgc  720
cctcctcttg aacaacgccc aactgaaccc ccacctcaca gagaagcttt gctgggaact  780
ttcaaacaca agcatccaga atctctctct ggctaacaac cagctgctgg ccaccagcga  840
gagcactttc tctgggctga agtggacaaa tctcacccag ctcgatcttt cctacaacaa  900
cctccatgat gtcggcaacg gttccttctc ctatctccca agcctgaggt atctgtctct  960
ggagtacaac aatatacagc gtctgtcccc tcgctctttt tatggactct ccaacctgag 1020
gtacctgagt ttgaagcgag catttactaa gcaaagtgtt tcacttgctt cacatcccaa 1080
cattgacgat ttttccttc aatggttaaa atatttggaa tatctcaaca tggatgacaa 1140
taatattcca gtaccaaaaa gcaataccttt cacgggattg gtgagtctga agtacctaag 1200
tctttccaaa actttcacaa gtttgcaaac tttaacaaat gaaacatttg tgtcacttgc 1260
tcattctccc ttgctcactc tcaacttaac gaaaaatcac atctcaaaaa tagcaaatgg 1320
```

-continued

```
tactttctct tggttaggcc aactcaggat acttgatctc ggccttaatg aaattgaaca 1380
aaaactcagc ggccaggaat ggagaggtct gagaaatata tttgagatct acctatccta 1440
taacaaatac ctccaactgt ctaccagttc ctttgcattg gtccccagcc ttcaaagact 1500
gatgctcagg agggtggccc ttaaaaatgt ggatatctcc ccttcacctt tccgccctct 1560
tcgtaacttg accattctgg acttaagcaa caacaacata gccaacataa atgaggactt 1620
gctggagggt cttgagaatc tagaaatcct ggattttcag cacaataact tagccaggct 1680
ctggaaacgc gcaaaccccg gtggtcccgt taatttcctg aagggctgt ctcacctcca 1740
catcttgaat ttagagtcca acggcttaga tgaaatccca gtcggggttt tcaagaactt 1800
attcgaacta aagagcatca atctaggact gaataactta aacaaacttg aaccattcat 1860
ttttgatgac cagacatctc taaggtcact gaacctccag aagaacctca taacatctgt 1920
tgagaaggat gttttcgggc cgccttttca aaacctgaac agtttagata tgcgcttcaa 1980
tccgttcgac tgcacgtgtg aaagtatttc ctggtttgtt aactggatca accagaccca 2040
cactaatatc tttgagctgt ccactcacta cctctgtaac actccacatc attattatgg 2100
cttcccctg aagcttttcg atacatcatc ctgtaaagac agcgcccct ttgaactcct 2160
cttcataatc agcaccagta tgctcctggt ttttatactt gtggtactgc tcattcacat 2220
cgagggctgg aggatctctt tttactggaa tgtttcagtg catcggattc ttggtttcaa 2280
ggaaatagac acacaggctg agcagtttga atatacagcc tacataattc atgcccataa 2340
agacagagac tgggtctggg aacatttctc cccaatggaa gaacaagacc aatctctcaa 2400
attttgccta gaagaaaggg acttgaagc aggcgtcctt ggacttgaag caattgttaa 2460
tagcatcaaa agaagccgaa aaatcatttt cgttatcaca caccatttat taaaagaccc 2520
tctgtgcaga agattcaagg tacatcacgc agttcagcaa gctattgagc aaaatctgga 2580
ttcaattata ctgatttttc tccagaatat tccagattat aaactaaacc atgcactctg 2640
tttgcgaaga ggaatgttta atctcattg catcttgaac tggccagttc agaaagaacg 2700
gataaatgcc tttcatcata aattgcaagt agcacttgga tctcggaatt cagcacatta 2760
aactcatttg aagatttgga gtcggtaaag ggatagatcc aatttataaa ggtccatcat 2820
gaatctaagt tttacttgaa agttttgtat atttatttat atgtatagat gatgatatta 2880
catcacaatc caatctcagt tttgaaatat ttcggcttat ttcattgaca tctggtttat 2940
tcactccaaa taaacacatg ggcagttaaa aacatcctct attaatagat tacccattaa 3000
ttcttgaggt gtatcacagc tttaaagggt tttaaatatt tttatataaa taagactgag 3060
agttttataa atgtaatttt ttaaaactcg agtcttactg tgtagctcag aaaggcctgg 3120
aaattaatat attagagagt catgtcttga acttatttat ctctgcctcc ctctgtctcc 3180
agagtgttgc ttttaagggc atgtagcacc acacccagct atgtacgtgt gggattttat 3240
aatgctcatt tttgagacgt ttatagaata aagataatt gcttttatgg tataaggcta 3300
cttgaggtaa                                                        3310
```

Nucleotide and amino acid sequences of human and murine TLR7 are known. See, for example, GenBank Accession Nos. AF240467, AF245702, NM_016562, AF334942, NM_133211; and AAF60188, AAF78035, NP_057646, AAL73191, AAL73192. Human TLR7 is reported to be 1049 amino acids long and to have a sequence provided in SEQ ID NO:24. A corresponding nucleotide sequence is provided as SEQ ID NO:25. Murine TLR7 is reported to be 1050 amino acids long and to have a sequence as provided in SEQ ID NO:26. A corresponding nucleotide sequence is provided as SEQ ID NO:27. TLR7 polypeptide includes an extracellular domain having leucine-rich repeat region, a transmembrane domain, and an intracellular domain that includes a TIR domain.

As used herein a "TLR7 polypeptide" refers to a polypeptide including a full-length TLR7 according to one of the sequences above, orthologs, allelic variants, SNPs, variants incorporating conservative amino acid substitutions, TLR7 fusion proteins, and functional fragments of any of the foregoing. Preferred embodiments include human TLR7 polypeptides having at least 65 percent sequence identity, more preferably at least 80 percent sequence identity, even more preferably with at least 90 percent sequence identity, and most preferably with at least 95 percent sequence identity with the human TLR7 amino acid sequence of SEQ ID NO:24. Preferred embodiments also include murine TLR7 polypeptides having at least 65 percent sequence identity, more preferably at least 80 percent sequence identity, even more preferably with at least 90 percent sequence identity, and most preferably with at least 95 percent sequence identity with the murine TLR7 amino acid sequence of SEQ ID NO:26.

As used herein "TLR7 signaling" refers to an ability of a TLR7 polypeptide to activate the TLR/IL-1R (TIR) signaling pathway, also referred to herein as the TLR signal transduction pathway. Changes in TLR7 activity can be measured by assays such as those disclosed herein, including expression of genes under control of κB-sensitive promoters and enhancers. Such naturally occurring genes include the genes encoding IL-1β, IL-6, IL-8, the p40 subunit of interleukin 12 (IL-12 p40), and the costimulatory molecules CD80 and CD86. Other genes can be placed under the control of such regulatory elements (see below) and thus serve to report the level of TLR7 signaling. Additional nucleotide sequence can be added to SEQ ID NO:25 or SEQ ID NO:27, preferably to the 5' or the 3' end of the open reading frame of SEQ ID NO:25, to yield a nucleotide sequence encoding a chimeric polypeptide that includes a detectable or reporter moiety, e.g., FLAG, luciferase (luc), green fluorescent protein (GFP), and others known by those skilled in the art.

```
                                                              SEQ ID NO: 24
Human TLR7 amino acid
MVFPMWTLKR  QILILFNIIL  ISKLLGARWF  PKTLPCDVTL  DVPKNHVIVD  CTDKHLTEIP    60

GGIPTNTTNL  TLTINHIPDI  SPASFHRLDH  LVEIDFRCNC  VPIPLGSKNN  MCIKRLQIKP   120

RSFSGLTYLK  SLYLDGNQLL  EIPQGLPPSL  QLLSLEANNI  FSIRKENLTE  LANIEILYLG   180

QNCYYRNPCY  VSYSIEKDAF  LNLTKLKVLS  LKDNNVTAVP  TVLPSTLTEL  YLYNNMIAKI   240

QEDDFNNLNQ  LQILDLSGNC  PRCYNAPFPC  APCKNNSPLQ  IPVNAFDALT  ELKVLRLHSN   300

SLQHVPPRWF  KNINKLQELD  LSQNFLAKEI  GDAKFLHFLP  SLIQLDLSFN  FELQVYRASM   360

NLSQAFSSLK  SLKILRIRGY  VFKELKSFNL  SPLHNLQNLE  VLDLGTNFIK  IANLSMFKQF   420

KRLKVIDLSV  NKISPSGDSS  EVGFCSNART  SVESYEPQVL  EQLHYFRYDK  YARSCRFKNK   480

EASFMSVNES  CYKYGQTLDL  SKNSIFFVKS  SDFQHLSFLK  CLNLSGNLIS  QTLNGSEFQP   540

LAELRYLDFS  NNRLDLLHST  AFEELHKLEV  LDISSNSHYF  QSEGITHMLN  FTKNLKVLQK   600

LMMNDNDISS  STSRTMESES  LRTLEFRGNH  LDVLWREGDN  RYLQLFKNLL  KLEELDISKN   660

SLSFLPSGVF  DGMPPNLKNL  SLAKNGLKSF  SWKKLQCLKN  LETLDLSHNQ  LTTVPERLSN   720

CSRSLKNLIL  KNNQIRSLTK  YFLQDAFQLR  YLDLSSNKIQ  MIQKTSFPEN  VLNNLKMLLL   780

HHNRFLCTCD  AVWFVWWVNH  TEVTIPYLAT  DVTCVGPGAH  KGQSVISLDL  YTCELDLTNL   840

ILFSLSISVS  LFLMVMMTAS  HLYFWDVWYI  YHFCKAKIKG  YQRLISPDCC  YDAFIVYDTK   900

DPAVTEWVLA  ELVAKLEDPR  EKHFNLCLEE  RDWLPGQPVL  ENLSQSIQLS  KKTVFVMTDK   960

YAKTENFKIA  FYLSHQRLMD  EKVDVIILIF  LEKPFQKSKF  LQLRKRLCGS  SVLEWPTNPQ  1020

AHPYFWQCLK  NALATDNHVA  YSQVFKETV                                      1049

SEQ ID NO: 25
Human TLR7 nucleotide
actccagata  taggatcact  ccatgccatc  aagaaagttg  atgctattgg  gcccatctca    60
agctgatctt  ggcacctctc  atgctctgct  ctcttcaacc  agacctctac  attccatttt   120
ggaagaagac  taaaaatggt  gtttccaatg  tggacactga  agagacaaat  tcttatcctt   180
tttaacataa  tcctaatttc  caaactcctt  ggggctagat  ggtttcctaa  aactctgccc   240
tgtgatgtca  ctctggatgt  tccaaagaac  catgtgatcg  tggactgcac  agacaagcat   300
ttgacagaaa  ttcctggagg  tattcccacg  aacaccacga  acctcaccct  caccattaac   360
cacataccag  acatctcccc  agcgtccttt  cacagactgg  accatctggt  agagatcgat   420
ttcagatgca  actgtgtacc  tattccactg  gggtcaaaaa  acaacatgtg  catcaagagg   480
ctgcagatta  aacccagaag  ctttagtgga  ctcacttatt  aaaatccct   ttacctggat   540 ggaaaccagc  tactagagat  accgcagggc  ctcccgccta  gcttacagct  tctcagcctt   600
```

-continued

```
gaggccaaca acatctttc catcagaaaa gagaatctaa cagaactggc caacatagaa  660
atactctacc tgggccaaaa ctgttattat cgaaatcctt gttatgtttc atattcaata  720
gagaaagatg ccttcctaaa cttgacaaag ttaaaagtgc tctccctgaa agataacaat  780
gtcacagccg tccctactgt tttgccatct actttaacag aactatatct ctacaacaac  840
atgattgcaa aaatccaaga agatgatttt aataacctca accaattaca aattcttgac  900
ctaagtggaa attgccctcg ttgttataat gccccatttc cttgtgcgcc gtgtaaaaat  960
aattctcccc tacagatccc tgtaaatgct tttgatgcgc tgacagaatt aaaagtttta 1020
cgtctacaca gtaactctct tcagcatgtg cccccaagat ggtttaagaa catcaacaaa 1080
ctccaggaac tggatctgtc ccaaaacttc ttggccaaag aaattgggga tgctaaattt 1140
ctgcattttc tccccagcct catccaattg gatctgtctt caattttga acttcaggtc 1200 tatcgtgcat ctatgaatct atcacaagca ttttcttcac tgaaaagcct gaaaattctg 1260
cggatcagag gatatgtctt taagagttg aaaagcttta acctctcgcc attacataat 1320
cttcaaaatc ttgaagttct tgatcttggc actaacttta taaaaattgc taacctcagc 1380
atgtttaaac aatttaaaag actgaaagtc atagatcttt cagtgaataa aatatcacct 1440
tcaggagatt caagtgaagt tggcttctgc tcaaatgcca gaacttctgt agaaagttat 1500 gaacccccagg tcctggaaca attacattat ttcagatatg ataagtatgc aaggagttgc 1560
agattcaaaa acaagaggc ttctttcatg tctgttaatg aaagctgcta caagtatggg 1620
cagaccttgg atctaagtaa aaatagtata ttttttgtca gtcctctga ttttcagcat 1680 cttctttcc tcaaatgcct gaatctgtca ggaaatctca ttagccaaac tcttaatggc 1740
agtgaattcc aacctttagc agagctgaga tatttggact ctccaacaa ccggcttgat 1800 ttactccatt caacagcatt tgaagagctt cacaaactgg aagttctgga tataagcagt 1860
aatagccatt attttcaatc agaaggaatt actcatatgc taaactttac caagaaccta 1920
aaggttctgc agaaactgat gatgaacgac aatgacatct cttcctccac cagcaggacc 1980
atggagagtg agtctcttag aactctggaa ttcagaggaa atcacttaga tgttttatgg 2040
agagaaggtg ataacagata cttacaatta ttcaagaatc tgctaaaatt agaggaatta 2100
gacatctcta aaaattccct aagtttcttg ccttctggag ttttgatgg tatgcctcca 2160 aatctaaaga atctctcttt ggccaaaaat gggctcaaat ctttcagttg gaagaaactc 2220
cagtgtctaa agaacctgga aactttggac ctcagccaca accaactgac cactgtccct 2280
gagagattat ccaactgttc cagaagcctc aagaatctga ttcttaagaa taatcaaatc 2340
aggagtctga cgaagtattt tctacaagat gccttccagt tgcgatatct ggatctcagc 2400
tcaaataaaa tccagatgat ccaaaagacc agcttcccag aaaatgtcct caacaatctg 2460
aagatgttgc ttttgcatca taatcggttt ctgtgcacct gtgatgctgt gtggtttgtc 2520
tggtgggtta ccatacgga ggtgactatt ccttacctgg ccacagatgt gacttgtgtg 2580
gggccaggag cacacaaggg ccaaagtgtg atctccctgg atctgtacac ctgtgagtta 2640
gatctgacta acctgattct gttctcactt tccatatctg tatctctctt tctcatggtg 2700
atgatgacag caagtcacct ctatttctgg gatgtgtggt atatttacca tttctgtaag 2760
gccaagataa aggggtatca gcgtctaata tcaccagact gttgctatga tgctttatt 2820 gtgtatgaca ctaaagaccc agctgtgacc gagtgggttt ggctgagct ggtggccaaa 2880 ctggaagacc caagagagaa acattttaat ttatgtctcg aggaaaggga ctggttacca 2940
gggcagccat ttctgaaaaa cctttcccag agcatacagc ttagcaaaaa gacagtgttt 3000
gtgatgacag acaagtatgc aaagactgaa aattttaaga tagcatttta cttgtcccat 3060
```

```
cagaggctca tggatgaaaa agttgatgtg attatcttga tatttcttga gaagcccttt 3120
cagaagtcca agttcctcca gctccggaaa aggctctgtg ggagttctgt ccttgagtgg 3180
ccaacaaacc cgcaagctca cccatacttc tggcagtgtc taaagaacgc cctggccaca 3240
gacaatcatg tggcctatag tcaggtgttc aaggaaacgg tctagccctt ctttgcaaaa 3300
cacaactgcc tagtttacca aggagaggcc tggctgttta aattgttttc atatatatca 3360
caccaaaagc gtgttttgaa attcttcaag aaatgagatt gcccatattt caggggagcc 3420
accaacgtct gtcacaggag ttggaaagat ggggtttata taatgcatca agtcttcttt 3480
cttatctctc tgtgtctcta tttgcacttg agtctctcac ctcagctcct gtaaaagagt 3540
ggcaagtaaa aaacatgggg ctctgattct cctgtaattg tgataattaa atatacacac 3600
aatcatgaca ttgagaagaa ctgcatttct acccttaaaa agtactggta tatacagaaa 3660
tagggttaaa aaaaactcaa gctctctcta tatgagacca aaatgtacta gagttagttt 3720
agtgaaataa aaaaccagtc agctggccgg gcatggtggc tcatgcttgt aatcccagca 3780
ctttgggagg ccgaggcagg tggatcacga ggtcaggagt ttgagaccag tctggccaac 3840
atggtgaaac cccgtctcta ctaaaaatac aaaaattagc tgggcgtggt ggtgggtgcc 3900
tgtaatccca gctacttggg aggctgaggc aggagaatcg cttgaacccg ggaggtggag 3960
gtggcagtga gccgagatca cgccactgca atgcagcccg gcaacagag ctagactgtc 4020 tcaaaagaac aaaaaaaaaa aaacacaaaa aaactcagtc agcttcttaa ccaattgctt 4080
ccgtgtcatc cagggcccca ttctgtgcag attgagtgtg gcaccacac aggtggttgc 4140 tgcttcagtg cttcctgctc ttttttccttg ggcctgcttc tgggttccat agggaaacag 4200
taagaaagaa agacacatcc ttaccataaa tgcatatggt ccacctacaa atagaaaaat 4260
atttaaatga tctgccttta tacaaagtga tattctctac ctttgataat ttacctgctt 4320
aaatgttttt atctgcactg caaagtactg tatccaaagt aaaatttcct catccaatat 4380
ctttcaaact gttttgttaa ctaatgccat atatttgtaa gtatctgcac acttgataca 4440
gcaacgttag atggttttga tggtaaaccc taaaggagga ctccaagagt gtgtatttat 4500
ttatagtttt atcagagatg acaattattt gaatgccaat tatatggatt cctttcattt 4560
tttgctggag gatgggagaa gaaaccaaag tttatagacc ttcacattga gaaagcttca 4620
gttttgaact tcagctatca gattcaaaaa caacagaaag aaccaagaca ttcttaagat 4680
gcctgtactt tcagctgggt ataaattcat gagttcaaag attgaaacct gaccaatttg 4740 cttatttca tggaagaagt gatctacaaa ggtgtttgtg ccatttggaa aacagcgtgc 4800
atgtgttcaa gccttagatt ggcgatgtcg tattttcctc acgtgtggca atgccaaagg 4860
ctttacttta cctgtgagta cacactatat gaattatttc caacgtacat ttaatcaata 4920
agggtcacaa attcccaaat caatctctgg aataaataga gaggtaatta aattgctgga 4980
gccaactatt tcacaacttc tgtaagc               5007
                                                                      SEQ ID NO: 26
Murine TLR7 amino acid
MVFSMWTRKR QILIFLNMLL VSRVFGFRWF PKTLPCEVKV NIPEAHVIVD CTDKHLTEIP  60

EGIPTNTTNL TLTINHIPSI SPDSFRRLNH LEEIDLRCNC VPVLLGSKAN VCTKRLQIRP 120

GSFSGLSDLK ALYLDGNQLL EIPQDLPSSL HLLSLEANNI FSITKENLTE LVNIETLYLG 180

QNCYYRNPCN VSYSIEKDAF LVMRNLKVLS LKDNNVTAVP TTLPPNLLEL YLYNNIIKKI 240

QENDFNNLNE LQVLDLSGNC PRCYNVPYPC TPCENNSPLQ IHDNAFNSLT ELKVLRLHSN 300

SLQHVPPTWF KNMRNLQELD LSQNYLAREI EEAKFLHFLP NLVELDFSFN YELQVYHASI 360
```

-continued

```
TLPHSLSSLE NLKILRVKGY VFKELKNSSL SVLHKLPRLE VLDLGTNFIK IADLNIFKHF  420

ENLKLIDLSV NKISPSEESR EVGFCPNAQT SVDRHGPQVL EALHYFRYDE YARSCRFKNK  480

EPPSFLPLNA DCHIYGQTLD LSRNNIFFIK PSDFQHLSFL KCLNLSGNTI GQTLNGSELW  540

PLRELRYLDF SNNRLDLLYS TAFEELQSLE VLDLSSNSHY FQAEGITHML NFTKKLRLLD  600

KLMMNDNDIS TSASRTMESD SLRILEFRGN HLDVLWRAGD NRYLDFFKNL FNLEVLDISR  660

NSLNSLPPEV FEGMPPNLKN LSLAKNGLKS FFWDRLQLLK HLEILDLSHN QLTKVPERLA  720

NCSKSLTTLI LKHNQIRQLT KYFLEDALQL RYLDISSNKI QVIQKTSFPE NVLNNLEMLV  780

LHHNRFLCNC DAVWFVWWVN HTDVTIPYLA TDVTCVGPGA HKGQSVISLD LYTCELDLTN  840

LILFSVSISS VLFLMVVMTT SHLFFWDMWY IYYFWKAKIK GYQHLQSMES CYDAFIVYDT  900

KNSAVTEWVL QELVAKLEDP REKHFNLCLE ERDWLPGQPV LENLSQSIQL SKKTVFVMTQ  960

KYAKTESFKM AFYLSHQRLL DEKVDVIILI FLEKPLQKSK FLQLRKRLCR SSVLEWPANP 1020

QAHPYFWQCL KNALTTDNHV AYSQMFKETV                                 1050
```

SEQ ID NO: 27
Murine TLR7 nucleotide

```
attctcctcc accagacctc ttgattccat tttgaaagaa aactgaaaat ggtgttttcg   60
atgtggacac ggaagagaca aattttgatc tttttaaata tgctcttagt ttctagagtc  120
tttgggtttc gatggtttcc taaaactcta ccttgtgaag ttaaagtaaa tatcccagag  180
gcccatgtga tcgtggactg cacagacaag catttgacag aaatccctga ggcattccc   240
actaacacca ccaatcttac ccttaccatc aaccacatac aagcatctc tccagattcc   300
ttccgtaggc tgaaccatct ggaagaaatc gatttaagat gcaattgtgt acctgttcta  360
ctggggtcca aagccaatgt gtgtaccaag aggctgcaga ttagacctgg aagctttagt  420
ggactctctg acttaaaagc cctttacctg atggaaaacc aacttctgga ataccacag   480
gatctgccat ccagcttaca tcttctgagc cttgaggcta acaacatctt ctccatcacg  540
aaggagaatc taacagaact ggtcaacatt gaaacactct acctgggtca aaactgttat  600
tatcgaaatc cttgcaatgt ttcctattct attgaaaaag atgctttcct agttatgaga  660
aatttgaagg ttctctcact aaaagataac aatgtcacag ctgtccccac cactttgcca  720
cctaatttac tagagctcta tctttataac aatatcatta agaaaatcca agaaaatgat  780
tttaataacc tcaatgagtt gcaagttctt gacctaagtg gaaattgccc tcgatgttat  840
aatgtcccat atccgtgtac accgtgtgaa ataattccc cttacagat ccatgacaat   900
gctttcaatt cattgacaga attaaaagtt ttacgtttac acagtaattc tcttcagcat  960
gtgccccaa catggtttaa aaacatgaga aacctccagg aactagacct ctcccaaaac 1020
tacttggcca gagaaattga ggaggccaaa tttttgcatt tcttcccaa ccttgttgag  1080
ttggattttt ctttcaatta tgagctgcag gtctaccatg catctataac tttaccacat 1140
tcactctctt cattggaaaa cttgaaaatt ctgcgtgtca aggggtatgt ctttaaagag 1200
ctgaaaaact ccagtctttc tgtattgcac aagcttccca ggctggaagt tcttgacctt 1260
ggcactaact tcataaaaat tgctgacctc aacatattca acattttga aaacctcaaa 1320
ctcatagacc tttcagtgaa taagatatct ccttcagaag agtcaagaga agttggcttt 1380
tgtcctaatg ctcaaacttc tgtagaccgt catgggcccc aggtccttga ggccttacac 1440
tatttccgat acgatgaata tgcacggagc tgcaggttca aaaacaaaga gccaccttct 1500
ttcttgcctt tgaatgcaga ctgccacata tatgggcaga ccttagactt aagtagaaat 1560
aacatatttt ttattaaacc ttctgatttt cagcatcttt cattcctcaa atgcctcaac 1620
ttatcaggaa acaccattgg ccaaactctt aatggcagtg aactctggcc gttgagagag 1680
```

```
ttgcggtact tagacttctc caacaaccgg cttgatttac tctactcaac agcctttgaa 1740
gagctccaga gtcttgaagt tctggatcta agtagtaaca gccactattt tcaagcagaa 1800
ggaattactc acatgctaaa ctttaccaag aaattacggc ttctggacaa actcatgatg 1860
aatgataatg acatctctac ttcggccagc aggaccatgg aaagtgactc tcttcgaatt 1920
ctggagttca gaggcaacca tttagatgtt ctatggagag ccggtgataa cagatacttg 1980
gacttcttca agaatttgtt caatttagag gtattagata tctccagaaa ttccctgaat 2040
tccttgcctc ctgaggtttt tgagggtatg ccgccaaatc taaagaatct ctccttggcc 2100
aaaaatgggc tcaaatcttt cttttgggac agactccagt tactgaagca tttggaaatt 2160
ttggacctca gccataacca gctgacaaaa gtacctgaga gattggccaa ctgttccaaa 2220
agtctcacaa cactgattct taagcataat caaatcaggc aattgacaaa atattttcta 2280
gaagatgctt tgcaattgcg ctatctagac atcagttcaa ataaaatcca ggtcattcag 2340
aagactagct tcccagaaaa tgtcctcaac aatctggaga tgttggtttt acatcacaat 2400
cgctttcttt gcaactgtga tgctgtgtgg tttgtctggt gggttaacca tacagatgtt 2460
actattccat acctggccac tgatgtgact tgtgtaggtc caggagcaca caaaggtcaa 2520
agtgtcatat cccttgatct gtatacgtgt gagttagatc tcacaaacct gattctgttc 2580
tcagtttcca tatcatcagt cctctttctt atggtagtta tgacaacaag tcacctcttt 2640
ttctgggata tgtggtacat ttattatttt tggaaagcaa agataaaggg gtatcagcat 2700
ctgcaatcca tggagtcttg ttatgatgct tttattgtgt atgacactaa aaactcagct 2760
gtgacagaat gggttttgca ggagctggtg gcaaaattgg aagatccaag agaaaaacac 2820
ttcaatttgt gtctagaaga aagagactgg ctaccaggac agccagttct agaaaacctt 2880
tcccagagca tacagctcag caaaaagaca gtgtttgtga tgacacagaa atatgctaag 2940
actgagagtt ttaagatggc attttatttg tctcatcaga ggctcctgga tgaaaaagtg 3000
gatgtgatta tcttgatatt cttggaaaag cctcttcaga agtctaagtt tcttcagctc 3060
aggaagagac tctgcaggag ctctgtcctt gagtggcctg caaatccaca ggctcaccca 3120
tacttctggc agtgcctgaa aaatgccctg accacagaca atcatgtggc ttatagtcaa 3180
atgttcaagg aaacagtcta gctctctgaa gaatgtcacc acctaggaca tgccttgaat 3240
cga                                                            3243
```

Nucleotide and amino acid sequences of human and murine TLR8 are known. See, for example, GenBank Accession Nos. AF246971, AF245703, NM_016610, XM045706, AY035890, NM_133212; and AAF64061, AAF78036, NP_057694, XP_045706, AAK62677, NP_573475. Human TLR8 is reported to exist in at least two isoforms, one 1041 amino acids long having a sequence provided in SEQ ID NO:28, and the other 1059 amino acids long having a sequence as provided in SEQ ID NO:30. Corresponding nucleotide sequences are provided as SEQ ID NO:29 and SEQ ID NO:31, respectively. The shorter of these two isoforms is believed to be more important. Murine TLR8 is 1032 amino acids long and has a sequence as provided in SEQ ID NO:32. The corresponding nucleotide sequence is provided as SEQ ID NO:33. TLR8 polypeptide includes an extracellular domain having leucine-rich repeat region, a transmembrane domain, and an intracellular domain that includes a TIR domain.

As used herein a "TLR8 polypeptide" refers to a polypeptide including a full-length TLR8 according to one of the sequences above, orthologs, allelic variants, SNPs, variants incorporating conservative amino acid substitutions, TLR8 fusion proteins, and functional fragments of any of the foregoing. Preferred embodiments include human TLR8 polypeptides having at least 65 percent sequence identity, more preferably at least 80 percent sequence identity, even more preferably with at least 90 percent sequence identity, and most preferably with at least 95 percent sequence identity with the human TLR8 amino acid sequence of SEQ ID NO:28. Preferred embodiments also include murine TLR8 polypeptides having at least 65 percent sequence identity, more preferably at least 80 percent sequence identity, even more preferably with at least 90 percent sequence identity, and most preferably with at least 95 percent sequence identity with the murine TLR8 amino acid sequence of SEQ ID NO:32.

As used herein "TLR8 signaling" refers to an ability of a TLR8 polypeptide to activate the TLR/IL-1R (TIR) signaling pathway, also referred to herein as the TLR signal transduction pathway. Changes in TLR8 activity can be measured by assays such as those disclosed herein, including expression of genes under control of κB-sensitive promoters and enhancers. Such naturally occurring genes include the genes encoding IL-1β, IL-6, IL-8, the p40 subunit of interleukin 12 (IL-12 p40), and the costimulatory molecules CD80 and CD86. Other genes can be placed under the control of such regulatory elements (see below) and thus serve to report the level of TLR8 signaling. Additional nucleotide sequence can be added to SEQ ID NO:29 or SEQ ID NO:33, preferably to the 5' or the 3' end of the open reading frame of SEQ ID NO:29, to yield a nucleotide sequence encoding a chimeric polypeptide that includes a detectable or reporter moiety, e.g., FLAG, luciferase (luc), green fluorescent protein (GFP), and others known by those skilled in the art.

```
                                                            SEQ ID NO: 28
Human TLR8 amino acid (1041)
MENMFLQSSM  LTCIFLLISG  SCELCAEENF  SRSYPCDEKK  QNDSVIAECS  NRRLQEVPQT   60

VGKYVTELDL  SDNFITHITN  ESFQGLQNLT  KINLNHNPNV  QHQNGNPGIQ  SNGLNITDGA  120

FLNLKNLREL  LLEDNQLPQI  PSGLPESLTE  LSLIQNNIYN  ITKEGISRLI  NLKNLYLAWN  180

CYFNKVCEKT  NIEDGVFETL  TNLELLSLSF  NSLSHVPPKL  PSSLRKLFLS  NTQIKYISEE  240

DFKGLINLTL  LDLSGNCPRC  FNAPFPCVPC  DGGASINIDR  FAFQNLTQLR  YLNLSSTSLR  300

KINAAWFKNM  PHLKVLDLEF  NYLVGEIASG  AFLTMLPRLE  ILDLSFNYIK  GSYPQHINIS  360

RNFSKLLSLR  ALHLRGYVFQ  ELREDDFQPL  MQLPNLSTIN  LGINFIKQID  FKLFQNFSNL  420

EIIYLSENRI  SPLVKDTRQS  YANSSSFQRH  IRKRRSTDFE  FDPHSNFYHF  TRPLIKPQCA  480

AYGKALDLSL  NSIFFIGPNQ  FENLPDIACL  NLSANSNAQV  LSGTEFSAIP  HVKYLDLTNN  540

RLDFDNASAL  TELSDLEVLD  LSYNSHYFRI  AGVTHHLEFI  QNFTNLKVLN  LSHNNIYTLT  600

DKYNLESKSL  VELVFSGNRL  DILWNDDDNR  YISIFKGLKN  LTRLDLSLNR  LKHIPNEAFL  660

NLPASLTELH  INDNMLKFFN  WTLLQQFPRL  ELLDLRGNKL  LFLTDSLSDF  TSSLRTLLLS  720

HNRISHLPSG  FLSEVSSLKH  LDLSSNLLKT  INKSALETKT  TTKLSMLELH  GNPFECTCDI  780

GDFRRWMDEH  LNVKIPRLVD  VICASPGDQR  GKSIVSLELT  TCVSDVTAVI  LFFFTFFITT  840

MVMLAALAHH  LFYWDVWFIY  NVCLAKVKGY  RSLSTSQTFY  DAYISYDTKD  ASVTDWVINE  900

LRYHLEESRD  KNVLLCLEER  DWDPGLAIID  NLMQSINQSK  KTVFVLTKKY  AKSWNFKTAF  960

YLALQRLMDE  NMDVIIFILL  EPVLQHSQYL  RLRQRICKSS  ILQWPDNPKA  EGLFWQTLRN 1020

VVLTENDSRY  NNMYVDSIKQ  Y                                             1041
                                                            SEQ ID NO: 29
Human TLR8 nucleotide
ttctgcgctg  ctgcaagtta  cggaatgaaa  aattagaaca  acagaaacat  ggaaaacatg   60
ttccttcagt  cgtcaatgct  gacctgcatt  ttcctgctaa  tatctggttc  ctgtgagtta  120
tgcgccgaag  aaaattttc   tagaagctat  ccttgtgatg  agaaaaagca  aaatgactca  180
gttattgcag  agtgcagcaa  tcgtcgacta  caggaagttc  cccaaacggt  gggcaaatat  240
gtgacagaac  tagacctgtc  tgataatttc  atcacacaca  taacgaatga  atcatttcaa  300
gggctgcaaa  atctcactaa  aataaatcta  aaccacaacc  ccaatgtaca  gcaccagaac  360
ggaaatcccg  gtatacaatc  aaatggcttg  aatatcacag  acggggcatt  cctcaaccta  420
aaaaacctaa  gggagttact  gcttgaagac  aaccagttac  cccaaatacc  ctctggtttg  480
ccagagtctt  tgacagaact  tagtctaatt  caaaacaata  tatacaacat  aactaaagag  540
ggcatttcaa  gacttataaa  cttgaaaaat  ctctatttgg  cctggaactg  ctattttaac  600
aaagtttgcg  agaaaactaa  catagaagat  ggagtatttg  aaacgctgac  aaatttggag  660
ttgctatcac  tatctttcaa  ttctctttca  cacgtgccac  ccaaactgcc  aagctcccta  720
cgcaaacttt  ttctgagcaa  cacccagatc  aaatacatta  gtgaagaaga  tttcaaggga  780
ttgataaatt  taacattact  agatttaagc  gggaactgtc  cgaggtgctt  caatgcccca  840
tttccatgcg  tgccttgtga  tggtggtgct  tcaattaata  tagatcgttt  tgcttttcaa  900
aacttgaccc  aacttcgata  cctaaacctc  tctagcactt  ccctcaggaa  gattaatgct  960
```

-continued

```
gcctggttta aaaatatgcc tcatctgaag gtgctggatc ttgaattcaa ctatttagtg 1020
ggagaaatag cctctggggc attttttaacg atgctgcccc gcttagaaat acttgacttg 1080
tcttttaact atataaaggg gagttatcca cagcatatta atatttccag aaacttctct 1140
aaacttttgt ctctacgggc attgcattta agaggttatg tgttccagga actcagagaa 1200
gatgatttcc agcccctgat gcagcttcca aacttatcga ctatcaactt gggtattaat 1260
tttattaagc aaatcgattt caaacttttc caaaatttct ccaatctgga aattatttac 1320
ttgtcagaaa acagaatatc accgttggta aaagataccc ggcagagtta tgcaaatagt 1380 tcctctttc aacgtcatat ccggaaacga cgctcaacag attttgagtt tgacccacat 1440
tcgaactttt atcatttcac ccgtcccttta ataaagccac aatgtgctgc ttatggaaaa 1500
gccttagatt taagcctcaa cagtattttc ttcattgggc caaaccaatt tgaaaatctt 1560
cctgacattg cctgtttaaa tctgtctgca aatagcaatg ctcaagtgtt aagtggaact 1620
gaattttcag ccattcctca tgtcaaatat ttggattttga caaacaatag actagacttt 1680
gataatgcta gtgctcttac tgaattgtcc gacttggaag ttctagatct cagctataat 1740
tcacactatt tcagaatagc aggcgtaaca catcatctag aatttattca aaatttcaca 1800
aatctaaaag ttttaaactt gagccacaac aacatttata ctttaacaga taagtataac 1860
ctggaaagca agtccctggt agaattagtt ttcagtggca atcgccttga cattttgtgg 1920
aatgatgatg acaacaggta tatctccatt ttcaaaggtc tcaagaatct gacacgtctg 1980
gatttatccc ttaataggct gaagcacatc ccaaatgaag cattccttaa tttgccagcg 2040
agtctcactg aactacatat aaatgataat atgttaaagt tttttaactg gacattactc 2100
cagcagttcc ctcgtctcga gttgcttgac ttacgtggaa acaaactact cttttttaact 2160 gatagcctat ctgactttac atcttcccctt cggacactgc tgctgagtca taacaggatt 2220
tcccacctac cctctggctt tcttttctgaa gtcagtagtc tgaagcacct cgatttaagt 2280
tccaatctgc taaaaacaat caacaaatcc gcacttgaaa ctaagaccac caccaaatta 2340
tctatgttgg aactacacgg aaaccccttt gaatgcacct gtgacattgg agatttccga 2400
agatggatgg atgaacatct gaatgtcaaa attcccagac tggtagatgt catttgtgcc 2460
agtcctgggg atcaaagagg gaagagtatt gtgagtctgg agctgacaac ttgtgtttca 2520
gatgtcactg cagtgatatt attttttcttc acgttctttta tcaccaccat ggttatgttg 2580
gctgccctgg ctcaccattt gttttactgg gatgtttggt ttatatataa tgtgtgttta 2640
gctaaggtaa aaggctacag gtctctttcc acatcccaaa ctttctatga tgcttacatt 2700
tcttatgaca ccaaagatgc ctctgttact gactgggtga taaatgagct gcgctaccac 2760
cttgaagaga gccgagacaa aaacgttctc ctttgtctag aggagaggga ttgggacccg 2820
ggattggcca tcatcgacaa cctcatgcag agcatcaacc aaagcaagaa aacagtattt 2880
gttttaacca aaaatatgc aaaaagctgg aactttaaaa cagcttttta cttggctttg 2940
cagaggctaa tggatgagaa catggatgtg attatattta tcctgctgga gccagtgtta 3000
cagcattctc agtatttgag gctacggcag cggatctgta agagctccat cctccagtgg 3060
cctgacaacc cgaaggcaga aggcttgttt tggcaaactc tgagaaatgt ggtcttgact 3120
gaaaatgatt cacggtataa caatatgtat gtcgattcca ttaagcaata ctaactgacg 3180
ttaagtcatg atttcgcgcc ataataaaga tgcaaaggaa tgacatttct gtattagtta 3240
tctattgcta tgtaacaaat tatcccaaaa cttagtggtt taaaacaaca catttgctgg 3300 cccacagtttt                                                      3311
```

SEQ ID NO: 30

Human TLR8 amino acid (1059)
```
MKESSLQNSS CSLGKETKKE NMFLQSSMLT CIFLLISGSC ELCAEENFSR SYPCDEKKQN   60
DSVIAECSNR RLQEVPQTVG KYVTELDLSD NFITHITNES FQGLQNLTKI NLNHNPNVQH  120
QNGNPGIQSN GLNITDGAFL NLKNLRELLL EDNQLPQIPS GLPESLTELS LIQNNIYNIT  180
KEGISRLINL KNLYLAWNCY FNKVCEKTNI EDGVFETLTN LELLSLSFNS LSHVSPKLPS  240
SLRKLFLSNT QIKYISEEDF KGLINLTLLD LSGNCPRCFN APFPCVPCDG GASINIDRFA  300
FQNLTQLRYL NLSSTSLRKI NAAWFKNMPH LKVLDLEFNY LVGEIASGAF LTMLPRLEIL  360
DLSFNYIKGS YPQHINISRN FSKPLSLRAL HLRGYVFQEL REDDFQPLMQ LPNLSTINLG  420
INFIKQIDFK LFQNFSNLEI IYLSENRISP LVKDTRQSYA NSSSFQRHIR KRRSTDFEFD  480
PHSNFYHFTR PLIKPQCAAY GKALDLSLNS IFFIGPNQFE NLPDIACLNL SANSNAQVLS  540
GTEFSAIPHV KYLDLTNNRL DFDNASALTE LSDLEVLDLS YNSHYFRIAG VTHHLEFIQN  600
FTNLKVLNLS HNNIYTLTDK YNLESKSLVE LVFSGNRLDI LWNDDDNRYI SIFKGLKNLT  660
RLDLSLNRLK HIPNEAFLNL PASLTELHIN DNMLKFFNWT LLQQFPRLEL LDLRGNKLLF  720
LTDSLSDFTS SLRTLLLSHN RISHLPSGFL SEVSSLKHLD LSSNLLKTIN KSALETKTTT  780
KLSMLELHGN PFECTCDIGD FRRWMDEHLN VKIPRLVDVI CASPGDQRGK SIVSLELTTC  840
VSDVTAVILF FFTFFITTMV MLAALAHHLF YWDVWFIYNV CLAKIKGYRS LSTSQTFYDA  900
YISYDTKDAS VTDWVINELR YHLEESRDKN VLLCLEERDW DPGLAIIDNL MQSINQSKKT  960
VFVLTKKYAK SWNFKTAFYL ALQRLMDENM DVIIFILLEP VLQHSQYLRL RQRICKSSIL 1020
QWPDNPKAEG LFWQTLRNVV LTENDSRYNN MYVDSIKQY                       1059
```

SEQ ID NO: 31

Human TLR8 nucleotide
```
ctcctgcata gagggtacca ttctgcgctg ctgcaagtta cggaatgaaa aattagaaca   60
acagaaacgt ggttctcttg acacttcagt gttagggaac atcagcaaga cccatcccag  120
gagaccttga aggaagcctt tgaaagggag aatgaaggag tcatctttgc aaaatagctc  180
ctgcagcctg ggaaggagaa ctaaaaagga aacatgttcc ttcagtcgtc aatgctgacc  240
tgcatttttc ctgctaatat ctggttcctg tgagttatgc gccgaagaaa attttttctag  300
aagctatcct tgtgatgaga aaaagcaaaa tgactcagtt attgcagagt gcagcaatcg  360
tcgactacag gaagttcccc aaacggtggg caaatatgtg acagaactag acctgtctga  420
taatttcatc acacacataa cgaatgaatc atttcaaggg ctgcaaaatc tcactaaaat  480
aaatctaaac cacaaccca atgtacagca ccagaacgga atcccggta caatcaaa    540
tggcttgaat atcacagacg gggcattcct caacctaaaa aacctaaggg agttactgct  600
tgaagacaac cagttacccc aaatacccctc tggtttgcca gagtctttga cagaacttag  660
tctaattcaa aacaatatat acaacataac taaagagggc atttcaagac ttataaactt  720
gaaaaatctc tatttggcct ggaactgcta ttttaacaaa gtttgcgaga aaactaacat  780
agaagatgga gtatttgaaa cgctgacaaa tttggagttg ctatcactat ctttcaattc  840
tctttcacac gtgtcaccca aactgccaag ctccctacgc aaactttttc tgagcaacac  900
ccagatcaaa tacattagtg aagaagattt caagggattg ataaatttaa cattactaga  960
tttaagcggg aactgtccga ggtgcttcaa tgccccattt ccatgcgtgc cttgtgatgg 1020
tggtgcttca attaatatag atcgttttgc ttttcaaaac ttgacccaac ttcgataccct 1080
aaacctctct agcacttccc tcaggaagat taatgctgcc tggtttaaaa atatgcctca 1140
tctgaaggtg ctggatcttg aattcaacta tttagtggga gaaatagcct ctggggcatt 1200
```

-continued

```
tttaacgatg ctgccccgct tagaaatact tgacttgtct tttaactata taaaggggag  1260
ttatccacag catattaata tttccagaaa cttctctaaa cctttgtctc tacgggcatt  1320
gcatttaaga ggttatgtgt tccaggaact cagagaagat gatttccagc ccctgatgca  1380
gcttccaaac ttatcgacta tcaacttggg tattaatttt attaagcaaa tcgatttcaa  1440
acttttccaa aatttctcca atctggaaat tatttacttg tcagaaaaca gaatatcacc  1500
gttggtaaaa gatacccggc agagttatgc aaatagttcc tcttttcaac gtcatatccg  1560
gaaacgacgc tcaacagatt ttgagtttga cccacattcg aacttttatc atttcacccg  1620
tcctttaata aagccacaat gtgctgctta tggaaaagcc ttagatttaa gcctcaacag  1680
tattttcttc attgggccaa accaatttga aaatcttcct gacattgcct gtttaaatct  1740
gtctgcaaat agcaatgctc aagtgttaag tggaactgaa ttttcagcca ttcctcatgt  1800
caaatatttg gatttgacaa acaatagact agactttgat aatgctagtg ctcttactga  1860
attgtccgac ttggaagttc tagatctcag ctataattca cactatttca gaatagcagg  1920
cgtaacacat catctagaat ttattcaaaa tttcacaaat ctaaaagttt taaacttgag  1980
ccacaacaac atttatactt taacagataa gtataacctg gaaagcaagt ccctggtaga  2040
attagttttc agtggcaatc gccttgacat tttgtggaat gatgatgaca acaggtatat  2100
ctccattttc aaaggtctca agaatctgac acgtctggat ttatccctta ataggctgaa  2160
gcacatccca aatgaagcat tccttaattt gccagcgagt ctcactgaac tacatataaa  2220
tgataatatg ttaaagtttt ttaactggac attactccag cagtttcctc gtctcgagtt  2280
gcttgactta cgtggaaaca aactactctt tttaactgat agcctatctg actttacatc  2340
ttcccttcgg acactgctgc tgagtcataa caggatttcc cacctaccct ctggctttct  2400
ttctgaagtc agtagtctga agcacctcga tttaagttcc aatctgctaa aaacaatcaa  2460
caaatccgca cttgaaacta agaccaccac caaattatct atgttggaac tacacggaaa  2520
cccctttgaa tgcacctgtg acattggaga tttccgaaga tggatggatg aacatctgaa  2580
tgtcaaaatt cccagactgg tagatgtcat ttgtgccagt cctggggatc aaagagggaa  2640
gagtattgtg agtctggagc taacaacttg tgtttcagat gtcactgcag tgatattatt  2700
tttcttcacg ttctttatca ccaccatggt tatgttggct gccctggctc accatttgtt  2760
ttactgggat gtttggttta tatataatgt gtgtttagct aagataaaag gctacaggtc  2820
tctttccaca tcccaaactt tctatgatgc ttacattttct tatgacacca aagatgcctc  2880
tgttactgac tgggtgataa atgagctgcg ctaccacctt gaagagagcc gagacaaaaa  2940
cgttctcctt tgtctagagg agagggattg ggacccggga ttggccatca tcgacaacct  3000
catgcagagc atcaaccaaa gcaagaaaac agtatttgtt ttaaccaaaa aatatgcaaa  3060
aagctggaac tttaaaacag cttttttactt ggctttgcag aggctaatgg atgagaacat  3120
ggatgtgatt atatttatcc tgctggagcc agtgttacag cattctcagt atttgaggct  3180
acggcagcgg atcgtaaga gctccatcct ccagtggcct gacaacccga aggcagaagg  3240
cttgttttgg caaactctga gaaatgtggt cttgactgaa atgattcac ggtataacaa  3300 tatgtatgtc gattccatta agcaatacta actgacgtta agtcatgatt tcgcgccata  3360
ataaaga                                                           3367
```

SEQ ID NO: 32

Murine TLR8 amino acid

```
MENMPPQSWI LTCFCLLSSG TSAIFHKANY SRSYPCDEIR HNSLVIAECN HRQLHEVPQT   60

IGKYVTNIDL SDNAITHITK ESFQKLQNLT KIDLNHNAKQ QHPNENKNGM NITEGALLSL  120

RNLTVLLLED NQLYTIPAGL PESLKELSLI QNNIFQVTKN NTFGLRNLER LYLGWNCYFK  180
```

-continued

```
CNQTFKVEDG AFKNLIHLKV LSLSFNNLFY VPPKLPSSLR KLFLSNAKIM NITQEDFKGL   240
ENLTLLDLSG NCPRCYNAPF PCTPCKENSS IHIHPLAFQS LTQLLYLNLS STSLRTIPST   300
WFENLSNLKE LHLEFNYLVQ EIASGAFLTK LPSLQILDLS FNFQYKEYLQ FINISSNFSK   360
LRSLKKLHLR GYVFRELKKK HFEHLQSLPN LATINLGINF IEKIDFKAFQ NFSKLDVIYL   420
SGNRIASVLD GTDYSSWRNR LRKPLSTDDD EFDPHVNFYH STKPLIKPQC TAYGKALDLS   480
LNNIFIIGKS QFEGFQDIAC LNLSFNANTQ VFNGTEFSSM PHIKYLDLTN NRLDFDDNNA   540
FSDLHDLEVL DLSHNAHYFS IAGVTHRLGF IQNLINLRVL NLSHNGIYTL TEESELKSIS   600
LKELVFSGNR LDHLWNANDG KYWSIFKSLQ NLIRLDLSYN NLQQIPNGAF LNLPQSLQEL   660
LISGNKLRFF NWTLLQYFPH LHLLDLSRNE LYFLPNCLSK FAHSLETLLL SHNHFSHLPS   720
GFLSEARNLV HLDLSFNTIK MINKSSLQTK MKTNLSILEL HGNYFDCTCD ISDFRSWLDE   780
NLNITIPKLV NVICSNPGDQ KSKSIMSLDL TTCVSDTTAA VLFFLTFLTT SMVMLAALVH   840
HLFYWDVWFI YHMCSAKLKG YRTSSTSQTF YDAYISYDTK DASVTDWVIN ELRYHLEESE   900
DKSVLLCLEE RDWDPGLPII DNLMQSINQS KKTIFVLTKK YAKSWNFKTA FYLALQRLMD   960
ENMDVIIFIL LEPVLQYSQY LRLRQRICKS SILQWPNNPK AENLFWQSLK NVVLTENDSR  1020
YDDLYIDSIR QY                                                    1032
                                                  SEQ ID NO: 33
Murine TLR8 nucleotide
attcagagtt ggatgttaag agagaaacaa acgttttacc ttcctttgtc tatagaacat    60
ggaaaacatg cccctcagt catggattct gacgtgcttt tgtctgctgt cctctggaac   120
cagtgccatc ttccataaag cgaactattc cagaagctat ccttgtgacg agataaggca   180
caactccctt gtgattgcag aatgcaacca tcgtcaactg catgaagttc cccaaactat   240
aggcaagtat gtgacaaaca tagacttgtc agacaatgcc attacacata taacgaaaga   300
gtcctttcaa aagctgcaaa acctcactaa aatcgatctg aaccacaatg ccaaacaaca   360
gcacccaaat gaaaataaaa atggtatgaa tattacagaa ggggcacttc tcagcctaag   420
aaatctaaca gttttactgc tggaagacaa ccagttatat actatacctg ctgggttgcc   480
tgagtctttg aaagaactta gcctaattca aacaatatat tttcaggtaa ctaaaaacaa   540
cacttttggg cttaggaact tggaaagact ctatttgggc tggaactgct attttaaatg   600
taatcaaacc tttaaggtag aagatggggc atttaaaaat cttatacact tgaaggtact   660
ctcattatct ttcaataacc ttttctatgt gccccccaaa ctaccaagtt ctctaaggaa   720
actttttctg agtaatgcca aaatcatgaa catcactcag gaagacttca aaggactgga   780
aaatttaaca ttactagatc tgagtggaaa ctgtccaagg tgttacaatg ctccatttcc   840
ttgcacacct tgcaaggaaa actcatccat ccacatatac cctctggctt tcaaagtct    900
cacccaactt ctctatctaa accttccag cacttccctc aggacgattc cttctacctg    960
gtttgaaaat ctgtcaaatc tgaaggaact ccatcttgaa ttcaactatt tagttcaaga  1020
aattgcctcg ggggcatttt taacaaaact acccagttta caaatccttg atttgtcctt  1080
caactttcaa tataaggaat atttacaatt tattaatatt tcctcaaatt tctctaagct  1140
tcgttctctc aagaagttgc acttaagagg ctatgtgttc cgagaactta aaagaagca   1200
tttcgagcat ctccagagtc ttccaaactt ggcaaccatc aacttgggca ttaacttat   1260
tgagaaaatt gatttcaaag cttttcagaa ttttccaaa ctcgacgtta tctatttatc   1320
aggaaatcgc atagcatctg tattagatgg tacagattat tcctcttggc gaaatcgtct  1380
tcggaaacct ctctcaacag acgatgatga gtttgatcca cacgtgaatt tttaccatag  1440
```

```
-continued
caccaaacct ttaataaagc cacagtgtac tgcttatggc aaggccttgg atttaagttt 1500
gaacaatatt ttcattattg ggaaaagcca atttgaaggt tttcaggata tcgcctgctt 1560
aaatctgtcc ttcaatgcca atactcaagt gtttaatggc acagaattct cctccatgcc 1620
ccacattaaa tatttggatt taaccaacaa cagactagac tttgatgata acaatgcttt 1680
cagtgatctt cacgatctag aagtgctgga cctgagccac aatgcacact atttcagtat 1740
agcaggggta acgcaccgtc taggatttat ccagaactta ataaacctca gggtgttaaa 1800
cctgagccac aatggcattt acaccctcac agaggaaagt gagctgaaaa gcatctcact 1860
gaaagaattg gttttcagtg gaaatcgtct tgaccatttg tggaatgcaa atgatggcaa 1920
atactggtcc atttttaaaa gtctccagaa tttgatacgc ctggacttat catacaataa 1980
ccttcaacaa atcccaaatg gagcattcct caatttgcct cagagcctcc aagagttact 2040
tatcagtggt aacaaattac gtttctttaa ttggacatta ctccagtatt ttcctcacct 2100
tcacttgctg gatttatcga gaatgagct gtattttcta cccaattgcc tatctaagtt 2160
tgcacattcc ctggagacac tgctactgag ccataatcat ttctctcacc taccctctgg 2220
cttcctctcc gaagccagga atctggtgca cctggatcta agtttcaaca caataaagat 2280
gatcaataaa tcctccctgc aaaccaagat gaaaacgaac ttgtctattc tggagctaca 2340
tgggaactat tttgactgca cgtgtgacat aagtgatttt cgaagctggc tagatgaaaa 2400
tctgaatatc acaattccta aattggtaaa tgttatatgt tccaatcctg gggatcaaaa 2460
atcaaagagt atcatgagcc tagatctcac gacttgtgta tcggatacca ctgcagctgt 2520
cctgtttttc ctcacattcc ttaccacctc catggttatg ttggctgctc tggttcacca 2580
cctgttttac tgggatgttt ggtttatcta tcacatgtgc tctgctaagt taaaaggcta 2640
caggacttca tccacatccc aaactttcta tgatgcttat atttcttatg acaccaaaga 2700
tgcatctgtt actgactggg taatcaatga actgcgctac caccttgaag agagtgaaga 2760
caaaagtgtc ctcctttgtt tagaggagag ggattgggat ccaggattac ccatcattga 2820
taacctcatg cagagcataa accagagcaa gaaaacaatc tttgttttaa ccaagaaata 2880
tgccaagagc tggaacttta aaacagcttt ctacttggcc ttgcagaggc taatggatga 2940
gaacatggat gtgattattt tcatcctcct ggaaccagtg ttacagtact cacagtacct 3000
gaggcttcgg cagaggatct gtaagagctc catcctccag tggcccaaca atcccaaagc 3060
agaaaacttg ttttggcaaa gtctgaaaaa tgtggtcttg actgaaaatg attcacggta 3120
tgacgatttg tacattgatt ccattaggca atactagtga tgggaagtca cgactctgcc 3180
atcataaaaa cacacagctt ctccttacaa tgaaccgaat                   3220
```

Nucleotide and amino acid sequences of human and murine TLR9 are known. See, for example, GenBank Accession Nos. NM_017442, AF259262, AB045180, AF245704, AB045181, AF348140, AF314224, NM_031178; and NP_059138, AAF 72189, BAB19259, AAF78037, BAB 19260, AAK29625, AAK28488, NP_112455. Human TLR9 is reported to exist in at least two isoforms, one 1032 amino acids long having a sequence provided in SEQ ID NO:34, and the other 1055 amino acids long having a sequence as provided in SEQ ID NO:36. Corresponding nucleotide sequences are provided as SEQ ID NO:35 and SEQ ID NO:37, respectively. The shorter of these two isoforms is believed to be more important. Murine TLR9 is 1032 amino acids long and has a sequence as provided in SEQ ID NO:38. A corresponding nucleotide sequence is provided as SEQ ID NO:39. TLR9 polypeptide includes an extracellular domain having leucine-rich repeat region, a transmembrane domain, and an intracellular domain that includes a TIR domain.

As used herein a "TLR9 polypeptide" refers to a polypeptide including a full-length TLR9 according to one of the sequences above, orthologs, allelic variants, SNPs, variants incorporating conservative amino acid substitutions, TLR9 fusion proteins, and functional fragments of any of the foregoing. Preferred embodiments include human TLR9 polypeptides having at least 65 percent sequence identity, more preferably at least 80 percent sequence identity, even more preferably with at least 90 percent sequence identity, and most preferably with at least 95 percent sequence identity with the human TLR9 amino acid sequence of SEQ ID NO:34. Preferred embodiments also include murine TLR9 polypeptides having at least 65 percent sequence identity, more preferably at least 80 percent sequence identity, even more preferably with at least 90 percent sequence identity, and most preferably with at least 95 percent sequence identity with the murine TLR9 amino acid sequence of SEQ ID NO:38.

As used herein "TLR9 signaling" refers to an ability of a TLR9 polypeptide to activate the TLR/IL-1R (TIR) signaling pathway, also referred to herein as the TLR signal transduction pathway. Without meaning to be held to any particular theory, it is believed that the TLR/IL-1R signaling pathway involves signaling via the molecules myeloid differentiation marker 88 (MyD88) and tumor necrosis factor (TNF) receptor-associated factor 6 (TRAF6), leading to activation of kinases of the IκB kinase complex and the c-jun NH$_2$-terminal kinases (e.g., Jnk 1/2). Häcker H et al. (2000) *J Exp Med* 192:595-600. Changes in TLR9 activity can be measured by assays such as those disclosed herein, including expression of genes under control of κB-sensitive promoters and enhancers. Such naturally occurring genes include the genes encoding IL-1β, IL-6, IL-8, the p40 subunit of interleukin 12 (IL-12 p40), and the costimulatory molecules CD80 and CD86. Other genes can be placed under the control of such regulatory elements (see below) and thus serve to report the level of TLR9 signaling. Additional nucleotide sequence can be added to SEQ ID NO:35 or SEQ ID NO:39, preferably to the 5' or the 3' end of the open reading frame of SEQ ID NO:35, to yield a nucleotide sequence encoding a chimeric polypeptide that includes a detectable or reporter moiety, e.g., FLAG, luciferase (luc), green fluorescent protein (GFP), and others known by those skilled in the art.

```
                                                              SEQ ID NO: 34
Human TLR9 amino acid (1032)
MGFCRSALHP  LSLLVQAIML  AMTLALGTLP  AFLPCELQPH  GLVNCNWLFL  KSVPHFSMAA    60

PRGNVTSLSL  SSNRIHHLHD  SDFAHLPSLR  HLNLKWNCPP  VGLSPMHFPC  HMTIEPSTFL   120

AVPTLEELNL  SYNNIMTVPA  LPKSLISLSL  SHTNILMLDS  ASLAGLHALR  FLFMDGNCYY   180

KNPCRQALEV  APGALLGLGN  LTHLSLKYNN  LTVVPRNLPS  SLEYLLLSYN  RIVKLAPEDL   240

ANLTALRVLD  VGGNCRRCDH  APNPCMECPR  HFPQLHPDTF  SHLSRLEGLV  LKDSSLSWLN   300

ASWFRGLGNL  RVLDLSENFL  YKCITKTKAF  QGLTQLRKLN  LSFNYQKRVS  FAHLSLAPSF   360

GSLVALKELD  MHGIFFRSLD  ETTLRPLARL  PMLQTLRLQM  NFINQAQLGI  FRAFPGLRYV   420

DLSDNRISGA  SELTATMGEA  DGGEKVWLQP  GDLAPAPVDT  PSSEDFRPNC  STLNFTLDLS   480

RNNLVTVQPE  MFAQLSHLQC  LRLSHNCISQ  AVNGSQFLPL  TGLQVLDLSH  NKLDLYHEHS   540

FTELPRLEAL  DLSYNSQPFG  MQGVGHNFSF  VAHLRTLRHL  SLAHNNIHSQ  VSQQLCSTSL   600

RALDFSGNAL  GHMWAEGDLY  LHFFQGLSGL  IWLDLSQNRL  HTLLPQTLRN  LPKSLQVLRL   660

RDNYLAFFKW  WSLHFLPKLE  VLDLAGNQLK  ALTNGSLPAG  TRLRRLDVSC  NSISFVAPGF   720

FSKAKELREL  NLSANALKTV  DHSWFGPLAS  ALQILDVSAN  PLHCACGAAF  MDFLLEVQAA   780

VPGLPSRVKC  GSPGQLQGLS  IFAQDLRLCL  DEALSWDCFA  LSLLAVALGL  GVPMLHHLCG   840

WDLWYCFHLC  LAWLPWRGRQ  SGRDEDALPY  DAFVVFDKTQ  SAVADWVYNE  LRGQLEECRG   900

RWALRLCLEE  RDWLPGKTLF  ENLWASVYGS  RKTLFVLAHT  DRVSGLLRAS  FLLAQQRLLE   960

DRKDVVVLVI  LSPDGRRSRY  VRLRQRLCRQ  SVLLWPHQPS  GQRSFWAQLG  MALTRDNHHF  1020

YNRNFCQGPT  AE                                                         1032

SEQ ID NO: 35
Human TLR9 nucleotide
ccgctgctgc  ccctgtggga  agggacctcg  agtgtgaagc  atccttccct  gtagctgctg    60
tccagtctgc  ccgccagacc  ctctggagaa  gcccctgccc  cccagcacgg  gtttctgccg   120
cagcgccctg  cacccgctgt  ctctcctggt  gcaggccatc  atgctggcca  tgaccctggc   180
cctgggtacc  ttgcctgcct  tcctaccctg  tgagctccag  ccccacggcc  tggtgaactg   240
caactggctg  ttcctgaagt  ctgtgcccca  cttctccatg  gcagcacccc  gtggcaatgt   300
caccagcctt  tccttgtcct  ccaaccgcat  ccaccccctc  catgattctg  actttgccca   360
cctgcccagc  ctgcggcatc  tcaacctcaa  gtggaactgc  cgccggttg   gcctcagccc   420 catgcacttc  ccctgccaca  tgaccatcga  gcccagcacc  ttcttggctg  tgcccaccct   480
ggaagagcta  aacctgagct  acaacaacat  catgactgtg  cctgcgctgc  ccaaatccct   540
catatccctg  tccctcagcc  ataccaacat  cctgatgcta  gactctgcca  gcctcgccgg   600
cctgcatgcc  ctgcgcttcc  tattcatgga  cggcaactgt  tattacaaga  accctgcag    660 gcaggcactg  gaggtggccc  cgggtgccct  ccttggcctg  ggcaacctca  cccacctgtc   720
```

-continued

```
actcaagtac aacaacctca ctgtggtgcc ccgcaacctg ccttccagcc tggagtatct  780
gctgttgtcc tacaaccgca tcgtcaaact ggcgcctgag gacctggcca atctgaccgc  840
cctgcgtgtg ctcgatgtgg gcggaaattg ccgccgctgc gaccacgctc ccaacccctg  900
catggagtgc cctcgtcact tcccccagct acatcccgat accttcagcc acctgagccg  960
tcttgaaggc ctggtgttga aggacagttc tctctcctgg ctgaatgcca gttggttccg 1020
tgggctggga aacctccgag tgctggacct gagtgagaac ttcctctaca aatgcatcac 1080
taaaaccaag gccttccagg gcctaacaca gctgcgcaag cttaacctgt ccttcaatta 1140
ccaaaagagg gtgtcctttg cccacctgtc tctggcccct ccttcggga gcctggtcgc 1200
cctgaaggag ctggacatgc acggcatctt cttccgctca ctcgatgaga ccacgctccg 1260
gccactggcc cgcctgccca tgctccagac tctgcgtctg cagatgaact tcatcaacca 1320
ggcccagctc ggcatcttca gggccttccc tggcctgcgc tacgtggacc tgtcggacaa 1380
ccgcatcagc ggagcttcgg agctgacagc caccatgggg gaggcagatg gagggagaa 1440
ggtctggctg cagcctgggg accttgctcc ggccccagtg gacactccca gctctgaaga 1500
cttcaggccc aactgcagca ccctcaactt caccttggat ctgtcacgga caacctggt 1560
gaccgtgcag ccggagatgt ttgcccagct ctcgcacctg cagtgcctgc gcctgagcca 1620
caactgcatc tcgcaggcag tcaatggctc ccagttcctg ccgctgaccg gtctgcaggt 1680
gctagacctg tcccacaata agctggacct ctaccacgag cactcattca cggagctacc 1740
acgactggag gccctggacc tcagctacaa cagccagccc tttggcatgc agggcgtggg 1800
ccacaacttc agcttcgtgg ctcacctgcg caccctgcgc cacctcagcc tggcccacaa 1860
caacatccac agccaagtgt cccagcagct ctgcagtacg tcgctgcggg ccctggactt 1920
cagcggcaat gcactgggcc atatgtgggc cgagggagac ctctatctgc acttcttcca 1980
aggcctgagc ggtttgatct ggctggactt gtcccagaac cgcctgcaca ccctcctgcc 2040
ccaaaccctg cgcaacctcc caagagcct acaggtgctg cgtctccgtg acaattacct 2100
ggccttcttt aagtggtgga gcctccactt cctgcccaaa ctggaagtcc tcgacctggc 2160
aggaaaccag ctgaaggccc tgaccaatgg cagcctgcct gctggcaccc ggctccggag 2220
gctggatgtc agctgcaaca gcatcagctt cgtggccccc ggcttctttt ccaaggccaa 2280
ggagctgcga gagctcaacc ttagcgccaa cgccctcaag acagtggacc actcctggtt 2340
tgggcccctg gcgagtgccc tgcaaatact agatgtaagc gccaaccctc tgcactgcgc 2400
ctgtggggcg gcctttatgg acttcctgct ggaggtgcag gctgccgtgc ccggtctgcc 2460
cagccgggtg aagtgtggca gtccgggcca gctccagggc ctcagcatct ttgcacagga 2520
cctgcgcctc tgcctggatg aggccctctc ctgggactgt ttcgccctct cgctgctggc 2580
tgtggctctg ggcctgggtg tgcccatgct gcatcacctc tgtggctggg acctctggta 2640
ctgcttccac ctgtgcctgg cctggcttcc ctggcggggg cggcaaagtg ggcgagatga 2700
ggatgccctg ccctacgatg ccttcgtggt cttcgacaaa acgcagagcg cagtggcaga 2760
ctgggtgtac aacagcttc gggggcagct ggaggagtgc cgtgggcgct ggcactccg 2820
cctgtgcctg gaggaacgcg actggctgcc tggcaaaacc ctctttgaga acctgtgggc 2880
ctcggtctat ggcagccgca agacgctgtt tgtgctggcc cacacggacc gggtcagtgg 2940
tctcttgcgc ccagcttcc tgctggccca gcagcgcctg ctgaggacc gcaaggacgt 3000
cgtggtgctg gtgatcctga gccctgacgg ccgccgctcc cgctacgtgc ggctgcgcca 3060
gcgcctctgc cgccagagtg tcctcctctg gccccaccag cccagtggtc agcgcagctt 3120
ctgggcccag ctgggcatgg ccctgaccag ggacaaccac cacttctata accggaactt 3180
```

```
ctgccaggga cccacggccg aatagccgtg agccggaatc ctgcacggtg ccacctccac 3240
actcacctca cctctgc                                                 3258
                                                      SEQ ID NO: 36
Human TLR9 amino acid (1055)
MPMKWSGWRW SWGPATHTAL PPPQGFCRSA LHPLSLLVQA IMLAMTLALG TLPAFLPCEL   60

QPHGLVNCNW LFLKSVPHFS MAAPRGNVTS LSLSSNRIHH LHDSDFAHLP SLRHLNLKWN  120

CPPVGLSPMH FPCHMTIEPS TFLAVPTLEE LNLSYNNIMT VPALPKSLIS LSLSHTNILM  180

LDSASLAGLH ALRFLFMDGN CYYKNPCRQA LEVAPGALLG LGNLTHLSLK YNNLTVVPRN  240

LPSSLEYLLL SYNRIVKLAP EDLANLTALR VLDVGGNCRR CDHAPNPCME CPRHFPQLHP  300

DTFSHLSRLE GLVLKDSSLS WLNASWFRGL GNLRVLDLSE NFLYKCITKT KAFQGLTQLR  360

KLNLSFNYQK RVSFAHLSLA PSFGSLVALK ELDMHGIFFR SLDETTLRPL ARLPMLQTLR  420

LQMNFINQAQ LGIFRAFPGL RYVDLSDNRI SGASELTATM GEADGGEKVW LQPGDLAPAP  480

VDTPSSEDFR PNCSTLNFTL DLSRNNLVTV QPEMFAQLSH LQCLRLSHNC ISQAVNGSQF  540

LPLTGLQVLD LSHNKLDLYH EHSFTELPRL EALDLSYNSQ PFGMQGVGHN FSFVAHLRTL  600

RHLSLAHNNI HSQVSQQLCS TSLRALDFSG NALGHMWAEG DLYLHFFQGL SGLIWLDLSQ  660

NRLHTLLPQT LRNLPKSLQV LRLRDNYLAF FKWWSLHFLP KLEVLDLAGN QLKALTNGSL  720

PAGTRLRRLD VSCNSISFVA PGFFSKAKEL RELNLSANAL KTVDHSWFGP LASALQILDV  780

SANPLHCACG AAFMDFLLEV QAAVPGLPSR VKCGSPGQLQ GLSIFAQDLR LCLDEALSWD  840

CFALSLLAVA LGLGVPMLHH LCGWDLWYCF HLCLAWLPWR GRQSGRDEDA LPYDAFVVFD  900

KTQSAVADWV YNELRGQLEE CRGRWALRLC LEERDWLPGK TLFENLWASV YGSRKTLFVL  960

AHTDRVSGLL RASFLLAQQR LLEDRKDVVV LVILSPDGRR SRYVRLRQRL CRQSVLLWPH 1020

QPSGQRSFWA QLGMALTRDN HHFYNRNFCQ GPTAE                            1055
                                                      SEQ ID NO: 37
Human TLR9 nucleotide
atgcccatga agtggagtgg gtggaggtgg agctgggggc cggccactca cacagccctc   60 ccaccccac  agggtttctg ccgcagcgcc ctgcacccgc tgtctctcct ggtgcaggcc  120
atcatgctgg ccatgaccct ggccctgggt accttgcctg ccttcctacc ctgtgagctc  180
cagccccacg gcctggtgaa ctgcaactgg ctgttcctga gtctgtgcc  ccacttctcc  240 atggcagcac cccgtggcaa tgtcaccagc ctttccttgt cctccaaccg catccaccac  300
ctccatgatt ctgactttgc ccacctgccc agcctgcggc atctcaacct caagtggaac  360
tgccccgcgg ttggcctcag ccccatgcac ttccctgcc  acatgaccat cgagcccagc  420
accttcttgg ctgtgcccac cctggaagag ctaaacctga gctacaacaa catcatgact  480
gtgcctgcgc tgcccaaatc cctcatatcc ctgtccctca gccataccaa catcctgatg  540
ctagactctg ccagcctcgc cggcctgcat gccctgcgct tcctattcat ggacggcaac  600
tgttattaca agaaccctg  caggcaggca ctggaggtgg ccccgggtgc cctccttggc  660
ctgggcaacc tcacccacct gtcactcaag tacaacaacc tcactgtggt gccccgcaac  720
ctgccttcca gcctggagta tctgctgttg tcctacaacc gcatcgtcaa actggcgcct  780
gaggacctgg ccaatctgac cgccctgcgt gtgctcgatg tgggcggaaa ttgccgccgc  840
tgcgaccacg ctcccaaccc ctgcatggag tgcctcgtc  acttccccca gctacatccc  900
gataccttca gccacctgag ccgtcttgaa ggcctggtgt tgaaggacag ttctctctcc  960
tggctgaatg ccagttggtt ccgtgggctg ggaaacctcc gagtgctgga cctgagtgag 1020
aacttcctct acaaatgcat cactaaaacc aaggccttac agggcctaac acagctgcgc 1080
```

```
-continued
aagcttaacc tgtccttcaa ttaccaaaag agggtgtcct ttgcccacct gtctctggcc 1140
ccttccttcg ggagcctggt cgccctgaag gagctggaca tgcacggcat cttcttccgc 1200
tcactcgatg agaccacgct ccggccactg gcccgcctgc ccatgctcca gactctgcgt 1260
ctgcagatga acttcatcaa ccaggcccag ctcggcatct tcagggcctt ccctggcctg 1320
cgctacgtgg acctgtcgga caaccgcatc agcggagctt cggagctgac agccaccatg 1380
ggggaggcag atggagggga gaaggtctgg ctgcagcctg ggaccttgc tccggcccca 1440 gtggacactc ccagctctga agacttcagg cccaactgca gcaccctcaa cttcaccttg 1500
gatctgtcac ggaacaacct ggtgaccgtg cagccggaga tgtttgccca gctctcgcac 1560
ctgcagtgcc tgcgcctgag ccacaactgc atctcgcagg cagtcaatgg ctcccagttc 1620
ctgccgctga ccgtctgca ggtgctagac ctgtcccaca ataagctgga cctctaccac 1680
gagcactcat tcacggagct accacgactg gaggccctgg acctcagcta acagccag 1720 cccttttggca tgcagggcgt gggccacaac ttcagcttcg tggctcacct gcgcaccctg 1800
cgccacctca gcctggccca acaacatc acagccaag tgcccagca gctctgcagt 1860 acgtcgctgc gggccctgga cttcagcggc aatgcactgg ccatatgtg gccgaggga 1920 gacctctatc tgcacttctt ccaaggcctg agcggtttga tctggctgga cttgtcccag 1980
aaccgcctgc acaccctcct gccccaaacc ctgcgcaacc tccccaagag cctacaggtg 2040
ctgcgtctcc gtgacaatta cctggccttc tttaagtggt ggagcctcca cttcctgccc 2100
aaactggaag tcctcgacct ggcaggaaac cagctgaagg ccctgaccaa tggcagcctg 2160
cctgctggca cccggctccg gaggctggat gtcagctgca cagcatcag cttcgtggcc 2220 cccggcttct tttccaaggc caaggagctg cgagagctca accttagcgc caacgccctc 2280
aagacagtgg accactcctg gtttgggccc ctggcgagtg ccctgcaaat actagatgta 2340
agcgccaacc tctgcactg cgcctgtggg gcggcttta tggacttcct gctggaggtg 2400
caggctgccg tgcccggtct gcccagccgg gtgaagtgtg cagtccggg ccagctccag 2460 ggcctcagca tctttgcaca ggacctgcgc ctctgcctgg atgaggccct ctcctgggac 2520
tgtttcgccc tctcgctgct ggctgtggct ctgggcctgg gtgtgcccat gctgcatcac 2580
ctctgtggct gggacctctg gtactgcttc cacctgtgcc tggcctggct tccctggcgg 2640
gggcggcaaa gtgggcgaga tgaggatgcc ctgccctacg atgccttcgt ggtcttcgac 2700
aaaacgcaga gcgcagtggc agactgggtg tacaacgagc ttcgggggca gctggaggag 2760
tgccgtgggc gctgggcact ccgcctgtgc ctggaggaac gcgactggct gcctggcaaa 2820
accctctttg agaacctgtg ggcctcggtc tatggcagcc gcaagacgct gtttgtgctg 2880
gcccacacgg accgggtcag tggtctcttg cgcgccagct tcctgctggc ccagcagcgc 2940
ctgctggagg accgcaagga cgtcgtgtg ctggtgatcc tgagccctga cggccgccgc 3000
tcccgctatg tgcggctgcg ccagcgcctc tgccgccaga gtgtcctcct ctggccccac 3060
cagcccagtg gtcagcgcag cttctgggcc cagctgggca tggccctgac cagggacaac 3120
caccacttct ataaccggaa cttctgccag ggacccacgg ccgaa 3165
                                                       SEQ ID NO: 38
Murine TLR9 amino acid
MVLRRRTLHP LSLLVQAAVL AETLALGTLP AFLPCELKPH GLVDCNWLFL KSVPRFSAAA    60

SCSNITRLSL ISNRIHHLHN SDFVHLSNLR QLNLKWNCPP TGLSPLHFSC HMTIEPRTFL   120

AMRTLEELNL SYNGITTVPR LPSSLVNLSL SHTNILVLDA NSLAGLYSLR VLFMDGNCYY   180

KNPCTGAVKV TPGALLGLSN LTHLSLKYNN LTKVPRQLPP SLEYLLVSYN LIVKLGPEDL   240

ANLTSLRVLD VGGNCRRCDH APNPCIECGQ KSLHLHPETF HHLSHLEGLV LKDSSLHTLN   300
```

-continued

```
SSWFQGLVNL SVLDLSENFL YESINHTNAF QNLTRLRKLN LSFNYRKKVS FARLHLASSF  360

KNLVSLQELN MNGIFFRSLN KYTLRWLADL PKLHTLHLQM NFINQAQLSI FGTFRALRFV  420

DLSDNRISGP STLSEATPEE ADDAEQEELL SADPHPAPLS TPASKNFMDR CKNFKFTMDL  480

SRNNLVTIKP EMFVNLSRLQ CLSLSHNSIA QAVNGSQFLP LTNLQVLDLS HNKLDLYHWK  540

SFSELPQLQA LDLSYNSQPF SMKGIGHNFS FVAHLSMLHS LSLAHNDIHT RVSSHLNSNS  600

VRFLDFSGNG MGRMWDEGGL YLHFFQGLSG LLKLDLSQNN LHILRPQNLD NLPKSLKLLS  660

LRDNYLSFFN WTSLSFLPNL EVLDLAGNQL KALTNGTLPN GTLLQKLDVS SNSIVSVVPA  720

FFALAVELKE VNLSHNILKT VDRSWFGPIV MNLTVLDVRS NPLHCACGAA FVDLLLEVQT  780

KVPGLANGVK CGSPGQLQGR SIFAQDLRLC LDEVLSWDCF GLSLLAVAVG MVVPILHHLC  840

GWDVWYCFHL CLAWLPLLAR SRRSAQALPY DAFVVFDKAQ SAVADWVYNE LRVRLEERRG  900

RRALRLCLED RDWLPGQTLF ENLWASIYGS RKTLFVLAHT DRVSGLLRTS FLLAQQRLLE  960

DRKDVVVLVI LRPDAHRSRY VRLRQRLCRQ SVLFWPQQPN GQGGFWAQLS TALTRDNRHF 1020

YNQNFCRGPT AE                                                    1032
```

SEQ ID NO: 39
Murine TLR9 nucleotide

```
tgtcagaggg agcctcggga gaatcctcca tctcccaaca tggttctccg tcgaaggact   60
ctgcacccct tgtccctcct ggtacaggct gcagtgctgg ctgagactct ggccctgggt  120
accctgcctg ccttcctacc ctgtgagctg aagcctcatg gctggtgga ctgcaattgg  180 ctgttcctga gtctgtacc ccgtttctct gcggcagcat cctgctccaa catcacccgc  240
ctctccttga tctccaaccg tatccaccac ctgcacaact ccgacttcgt ccacctgtcc  300
aacctgcggc agctgaacct caagtggaac tgtccaccca ctggccttag ccccctgcac  360
ttctcttgcc acatgaccat tgagcccaga accttcctgg ctatgcgtac actggaggag  420
ctgaacctga gctataatgg tatcaccact gtgccccgac tgcccagctc cctggtgaat  480
ctgagcctga gccacaccaa catcctggtt ctagatgcta acagcctcgc cggcctatac  540
agcctgcgcg ttctcttcat ggacgggaac tgctactaca agaaccctg cacaggagcg  600 gtgaaggtga ccccaggcgc cctcctgggc ctgagcaatc tcacccatct gtctctgaag  660
tataacaacc tcacaaaggt gccccgccaa ctgcccccca gcctggagta cctcctggtg  720
tcctataacc tcattgtcaa gctggggcct gaagacctgg ccaatctgac ctcccttcga  780
gtacttgatg tgggtgggaa ttgccgtcgc tgcgaccatg cccccaatcc ctgtatagaa  840
tgtggccaaa agtccctcca cctgcaccct gagaccttcc atcacctgag ccatctggaa  900
ggcctggtgc tgaaggacag ctctctccat acactgaact cttcctggtt ccaaggtctg  960
gtcaacctct cggtgctgga cctaagcgag aactttctct atgaaagcat caaccacacc 1020
aatgcctttc agaacctaac ccgcctgcgc aagctcaacc tgtccttcaa ttaccgcaag 1080
aaggtatcct ttgcccgcct ccacctggca agttccttca agaacctggt gtcactgcag 1140
gagctgaaca tgaacggcat cttcttccgc tcgctcaaca gtacacgct cagatggctg 1200 gccgatctgc ccaaactcca cactctgcat cttcaaatga acttcatcaa ccaggcacag 1260
ctcagcatct ttggtaccctt ccgagccctt cgctttgtgg acttgtcaga caatcgcatc 1320
agtgggcctt caacgctgtc agaagccacc cctgaagagg cagatgatgc agagcaggag 1380
gagctgttgt ctgcggatcc tcacccagct ccactgagca cccctgcttc taagaacttc 1440
atggacaggt gtaagaactt caagttcacc atggacctgt ctcggaacaa cctggtgact 1500
atcaagccag agatgtttgt caatctctca cgcctccagt gtcttagcct gagccacaac 1560
```

```
                                              -continued
tccattgcac aggctgtcaa tggctctcag ttcctgccgc tgactaatct gcaggtgctg 1620
gacctgtccc ataacaaact ggacttgtac cactggaaat cgttcagtga gctaccacag 1680
ttgcaggccc tggacctgag ctacaacagc cagcccttta gcatgaaggg tataggccac 1740
aatttcagtt ttgtggccca tctgtccatg ctacacagcc ttagcctggc acacaatgac 1800 attcatacc gtgtgtcctc acatctcaac agcaactcag tgaggtttct tgacttcagc 1860
ggcaacggta tgggccgcat gtgggatgag ggggccttt atctccattt cttccaaggc 1920
ctgagtggcc tgctgaagct ggacctgtct caaaataacc tgcatatcct ccggcccag 1980 aaccttgaca acctcccaa gagcctgaag ctgctgagcc tccgagacaa ctacctatct 2040
ttctttaact ggaccagtct gtccttcctg cccaacctgg aagtcctaga cctggcaggc 2100
aaccagctaa aggccctgac caatggcacc ctgcctaatg gcaccctcct ccagaaactg 2160
gatgtcagca gcaacagtat cgtctctgtg gtcccagcct tcttcgctct ggcggtcgag 2220
ctgaaagagg tcaacctcag ccacaacatt ctcaagacgg tggatcgctc ctggtttggg 2280
cccattgtga tgaacctgac agttctagac gtgagaagca accctctgca ctgtgcctgt 2340
ggggcagcct tcgtagactt actgttggag gtgcagacca aggtgcctgg cctggctaat 2400
ggtgtgaagt gtggcagccc cggccagctg cagggccgta gcatcttcgc acaggacctg 2460
cggctgtgcc tggatgaggt cctctcttgg gactgctttg gcctttcact cttggctgtg 2520
gccgtgggca tggtggtgcc tatactgcac catctctgcg gctgggacgt ctggtactgt 2580
tttcatctgt gcctggcatg gctacctttg ctggcccgca gccgacgcag cgcccaagct 2640
ctcccctatg atgccttcgt ggtgttcgat aaggcacaga gcgcagttgc ggactgggtg 2700
tataacgagc tgcgggtgcg gctggaggag cggcgcggtc gccgagccct acgcttgtgt 2760
ctggaggacc gagattggct gcctggccag acgctcttcg agaacctctg ggcttccatc 2820
tatgggagcc gcaagactct atttgtgctg gcccacacgg accgcgtcag tggcctcctg 2880
cgcaccagct tcctgctggc tcagcagcgc ctgttggaag accgcaagga cgtggtggtg 2940
ttggtgatcc tgcgtccgga tgcccaccgc tcccgctatg tgcgactgcg ccagcgtctc 3000
tgccgccaga gtgtgctctt ctggccccag cagcccaacg ggcagggggg cttctgggcc 3060
cagctgagta cagccctgac tagggacaac cgccacttct ataaccagaa cttctgccgg 3120
ggacctacag cagaatagct cagagcaaca gctggaaaca gctgcatctt catgcctggt 3180
tcccgagttg ctctgcctgc                                           3200
```

Ribonucleoside vanadyl complexes (i.e., mixtures of adenine, cytosine, guanosine, and uracil ribonucleoside vanadyl complexes), are well known by those of skill in the art as RNAse inhibitors. Berger S L et al. (1979) *Biochemistry* 18:5143; Puskas R S et al. (1982) *Biochemistry* 21:4602. Ribonucleoside vanadyl complexes are commercially available from suppliers including Sigma-Aldrich, Inc.

In one embodiment, the immunostimulatory G,U-containing RNA oligomer of the invention does not contain a CpG dinucleotide and is not a CpG immunostimulatory nucleic acid. In some embodiments, a CpG immunostimulatory nucleic acid is used in the methods of the invention.

A CpG immunostimulatory nucleic acid is a nucleic acid which contains a CG dinucleotide, the C residue of which is unmethylated. CpG immunostimulatory nucleic acids are known to stimulate Th1-type immune responses. CpG sequences, while relatively rare in human DNA are commonly found in the DNA of infectious organisms such as bacteria. The human immune system has apparently evolved to recognize CpG sequences as an early warning sign of infection and to initiate an immediate and powerful immune response against invading pathogens without causing adverse reactions frequently seen with other immune stimulatory agents. Thus CpG containing nucleic acids, relying on this innate immune defense mechanism can utilize a unique and natural pathway for immune therapy. The effects of CpG nucleic acids on immune modulation have been described extensively in U.S. patents such as U.S. Pat. Nos. 6,194,388 B1, 6,207,646 B1, 6,239,116 B1 and No. 6,218,371 B1, and published patent applications, such as PCT/US98/03678, PCT/US98/10408, PCT/US98/04703, and PCT/US99/09863. The entire contents of each of these patents and patent applications is hereby incorporated by reference.

A CpG nucleic acid is a nucleic acid which includes at least one unmethylated CpG dinucleotide. A nucleic acid containing at least one unmethylated CpG dinucleotide is a nucleic acid molecule which contains an unmethylated cytosine in a cytosine-guanine dinucleotide sequence (i.e., "CpG DNA" or DNA containing a 5' cytosine followed by 3' guanosine and linked by a phosphate bond) and activates the immune system. The CpG nucleic acids can be double-stranded or single-stranded. Generally, double-stranded molecules are more stable in vivo, while single-stranded molecules have increased immune activity. Thus in some aspects of the invention it is preferred that the nucleic acid be single stranded and in other aspects it is preferred that the nucleic acid be double stranded. In certain embodiments, while the nucleic acid is single stranded, it is capable of forming secondary and tertiary structures (e.g., by folding back on itself, or by hybridizing with itself either throughout its entirety or at select segments along its length). Accordingly, while the primary structure of such a nucleic acid may be single stranded, its higher order structures may be double or triple stranded. The terms CpG nucleic acid or CpG oligonucleotide as used herein refer to an immunostimulatory CpG nucleic acid unless otherwise indicated. The entire immunostimulatory nucleic acid can be unmethylated or portions may be unmethylated but at least the C of the 5' CG 3' must be unmethylated.

In one aspect the invention provides a method of activating an immune cell. The method involves contacting an immune cell with an immunostimulatory composition of the invention, described above, in an effective amount to induce activation of the immune cell. As used herein, an "immune cell" is cell that belongs to the immune system. Immune cells participate in the regulation and execution of inflammatory and immune responses. They include, without limitation, B lymphocytes (B cells), T lymphocytes (T cells), natural killer (NK) cells, dendritic cells, other tissue-specific antigen-presenting cells (e.g., Langerhans cells), macrophages, monocytes, granulocytes (neutrophils, eosinophils, basophils), and mast cells. Splenocytes, thymocytes, and peripheral blood mononuclear cells (PBMCs) include immune cells. Immune cells can be isolated from the blood, spleen, marrow, lymph nodes, thymus, and other tissues using methods well known to those of skill in the art. Immune cells can also include certain cell lines as well as primary cultures maintained in vitro or ex vivo.

In one embodiment the activation of the immune cell involves secretion of a cytokine by the immune cell. In one embodiment the activation of the immune cell involves secretion of a chemokine by the immune cell. In one embodiment the activation of the immune cell involves expression of a costimulatory/accessory molecule by the immune cell. In one embodiment the costimulatory/accessory molecule is selected from the group consisting of intercellular adhesion molecules (ICAMs, e.g., CD54), leukocyte function-associated antigens (LFAs, e.g., CD58), B7s (CD80, CD86), and CD40.

"Activation of an immune cell" shall refer to a transition of an immune cell from a resting or quiescent state to a state of heightened metabolic activity and phenotype associated with immune cell function. Such immune cell function can include, for example, secretion of soluble products such as immunoglobulins, cytokines, and chemokines; cell surface expression of costimulatory/accessory molecules and MHC antigens; immune cell migration; phagocytosis and cytotoxic activity toward target cells; and immune cell maturation. In some instances immune activation can refer to Th1 immune activation; in other instances immune activation can refer to Th2 immune activation.

"Th1 immune activation" as used herein refers to the activation of immune cells to express Th1-like secreted products, including certain cytokines, chemokines, and subclasses of immunoglobulin; and activation of certain immune cells. Th1-like secreted products include, for example, the cytokines IFN-γ, IL-2, IL-12, IL-18, TNF-α, and the chemokine IP-10 (CXCL10). In the mouse, Th1 immune activation stimulates secretion of IgG2a. Th1 immune activation also may include activation of NK cells and dendritic cells, i.e., cells involved in cellular immunity. Th1 immune activation is believed to counter-regulate Th2 immune activation.

"Th2 immune activation" as used herein refers to the activation of immune cells to express Th2-like secreted products, including certain cytokines and subclasses of immunoglobulin. Th2-like secreted products include, for example, the cytokines IL-4 and IL-10. In the mouse, Th2 immune activation stimulates secretion of IgG1 and IgE. Th2 immune activation is believed to counter-regulate Th1 immune activation.

In another aspect, the invention provides a method of inducing an immune response in a subject. The method entails administering to a subject a composition of the invention in an effective amount to induce an immune response in the subject. Thus the compositions of the invention may be used to treat a subject in need of immune activation. A subject in need of immune activation may include a subject in need of Th1-like immune activation.

The compositions and methods of the invention can be used, alone or in conjunction with other agents, to treat a subject in need of Th1-like immune activation. A "subject in need of Th1-like immune activation" is a subject that has or is at risk of developing a disease, disorder, or condition that would benefit from an immune response skewed toward Th1. Such a subject may have or be at risk of having a Th2-mediated disorder that is susceptible to Th1-mediated cross-regulation or suppression. Such disorders include, for example, certain organ-specific autoimmune diseases. Alternatively, such a subject may have or be at risk of having a Th1-deficient state. Such disorders include, for example, tumors, infections with intracellular pathogens, and AIDS.

As used herein, "G,U-rich RNA" shall mean RNA at least 5 nucleotides long that by base composition is at least 60 percent, more preferably at least 80 percent, and most preferably at least 90 percent guanine (G) and uracil (U). Such base composition is measured over the full length of the RNA if it is no more than 10 bases long, and over a stretch of at least 10 contiguous bases if the RNA is more than 10 bases long.

As used herein, "G-rich RNA" shall mean RNA that by base composition is at least 70 percent, more preferably at least 80 percent, even more preferably at least 90 percent, and most preferably at least 95 percent guanine (G). Such base composition is measured over the full length of the RNA if it is no more than 10 bases long, and over a stretch of at least 10 contiguous bases if the RNA is more than 10 bases long.

In some embodiments the compositions of the present invention include a DNA:RNA conjugate. A DNA:RNA conjugate shall mean a molecule or complex that includes at least one deoxyribonucleoside linked to at least one ribonucleoside. The deoxyribonucleoside and ribonucleoside components may be linked by base pair interaction. Alternatively, the deoxyribonucleoside and ribonucleoside components may be linked by covalent linkage between the sugar moieties of the at least one deoxyribonucleoside and the at least one ribonucleoside. The covalent linkage between the sugar moieties may be direct or indirect, for example through a linker. Base pair interactions typically are, but are not limited to, non-covalent Watson-Crick type base pair interactions. Other base pair interactions, including non-covalent (e.g., Hoogstein base pairing) and covalent interactions are contemplated by the invention. Base pair interactions also typically will involve duplex formation involving two strands, but higher order interactions are also contemplated by the invention.

A DNA:RNA conjugate involving a covalent linkage between the sugar moieties of the at least one deoxyribonucleoside and the at least one ribonucleoside is referred to herein as having a chimeric DNA:RNA backbone. The DNA:RNA conjugate having a chimeric DNA:RNA backbone will have primary structure defined by its base sequence, and it may further have a secondary or higher order structure. A secondary or higher order structure will include at least one intramolecular base pair interaction, e.g., a stem-loop structure, or intermolecular base pair interaction.

Heteroduplex base pairing shall refer to intramolecular or intermolecular base pair interaction between DNA and RNA. For example, heteroduplex base pairing may occur between individual complementary single-stranded DNA and RNA molecules. Alternatively, as in the case of suitable DNA:RNA chimeric backbone nucleic acid molecules, heteroduplex base pairing may occur between complementary DNA and RNA regions within the same molecule.

In some embodiments the compositions of the present invention include a chimeric DNA:RNA backbone having a cleavage site between the DNA and RNA. A cleavage site refers to a structural element along the chimeric backbone that is susceptible to cleavage by any suitable means. The cleavage site may be a phosphodiester bond that is relatively susceptible to cleavage by endonuclease. In this instance the DNA and RNA each may include internucleotide linkages that are stabilized, such that the chimeric backbone is most susceptible to endonuclease cleavage at the phosphodiester junction between the stabilized DNA and the stabilized RNA. The cleavage site may be designed so that it is susceptible to cleavage under certain pH conditions, e.g., relatively more stable at higher pH than at lower pH, or vice versa. Such pH sensitivity may be accomplished, for example, by preparation of the chimeric DNA:RNA composition in liposomes. The cleavage site may involve a disulfide linkage. Such disulfide linkage may be relatively more stable under oxidizing conditions than under reducing conditions, e.g., the latter conditions present within an endosome. The cleavage site may also involve a linker that is susceptible to cleavage by an enzyme, pH, redox condition, or the like. In some embodiments the composition may include more than one cleavage site.

Conjugates of the invention permit selection of fixed molar ratios of the components of the conjugates. In the case of DNA:RNA conjugates it may be advantageous or convenient to have a 1:1 ratio of DNA and RNA. Conjugates that are heteroduplex DNA:RNA will commonly have a 1:1 ratio of DNA and RNA. Conjugates that have a chimeric DNA:RNA backbone may also commonly have a 1:1 ratio of DNA and RNA. Conjugates having other DNA:RNA ratios are contemplated by the invention, including, but not limited to, 1:2, 1:3, 1:4, 2:1, 3:1, 4:1, and so on. The conjugation may stabilize one or more components in comparison to the stability of the same component or components alone. Conjugatation may also facilitate delivery of the components into cells at the selected ratio.

Cleavage sites may serve any of several purposes useful in the present invention. Once delivered to a cell of interest, the components joined via the cleavage site (or sites) may be liberated to become independently or optimally active within the cell or in the vicinity of the cell. In some embodiments the cleavage sites may be important to pharmacokinetics of at least one of the components of the conjugate. For instance, the cleavage sites may be designed and selected to confer an extended time release of one of the components.

The invention generally provides efficient methods of identifying immunostimulatory compounds and the compounds and agents so identified. Generally, the screening methods involve assaying for compounds which inhibit or enhance signaling through a particular TLR. The methods employ a TLR, a suitable reference ligand for the TLR, and a candidate immunostimulatory compound. The selected TLR is contacted with a suitable reference compound (TLR ligand) and a TLR-mediated reference signal is measured. The selected TLR is also contacted with a candidate immunostimulatory compound and a TLR-mediated test signal is measured. The test signal and the reference signal are then compared. A favorable candidate immunostimulatory compound may subsequently be used as a reference compound in the assay. Such methods are adaptable to automated, high throughput screening of candidate compounds. Examples of such high throughput screening methods are described in U.S. Pat. Nos. 6,103,479; 6,051,380; 6,051,373; 5,998,152; 5,876,946; 5,708,158; 5,443,791; 5,429,921; and 5,143,854.

The assay mixture comprises a candidate immunostimulatory compound. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate immunostimulatory compounds encompass numerous chemical classes, although typically they are organic compounds. Preferably, the candidate immunostimulatory compounds are small organic compounds, i.e., those having a molecular weight of more than 50 yet less than about 2500. Polymeric candidate immunostimulatory compounds can have higher molecular weights, e.g., oligonucleotides in the range of about 2500 to about 12,500. Candidate immunostimulatory compounds comprise functional chemical groups necessary for structural interactions with polypeptides, and may include at least an amine, carbonyl, hydroxyl or carboxyl group, preferably at least two of the functional chemical groups and more preferably at least three of the functional chemical groups. The candidate immunostimulatory compounds can comprise cyclic carbon or heterocyclic structure and/or aromatic or polyaromatic structures substituted with one or more of the above-identified functional groups. Candidate immunostimulatory compounds also can be biomolecules such as nucleic acids, peptides, saccharides, fatty acids, sterols, isoprenoids, purines, pyrimidines, derivatives or structural analogs of the above, or combinations thereof and the like. Where the candidate immunostimulatory compound is a nucleic acid, the candidate immunostimulatory compound typically is a DNA or RNA molecule, although modified nucleic acids having non-natural bonds or subunits are also contemplated.

Candidate immunostimulatory compounds are obtained from a wide variety of sources, including libraries of natural, synthetic, or semisynthetic compounds, or any combination thereof. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc., to produce structural analogs of the candidate immunostimulatory compounds.

Therefore, a source of candidate immunostimulatory compounds are libraries of molecules based on known TLR ligands, e.g., CpG oligonucleotides known to interact with TLR9, in which the structure of the ligand is changed at one or more positions of the molecule to contain more or fewer chemical moieties or different chemical moieties. The structural changes made to the molecules in creating the libraries of analog inhibitors can be directed, random, or a combination of both directed and random substitutions and/or additions. One of ordinary skill in the art in the preparation of combinatorial libraries can readily prepare such libraries based on existing TLR9 ligands.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 1 minute and 10 hours.

After incubation, the level of TLR signaling is detected by any convenient method available to the user. For cell-free binding type assays, a separation step is often used to separate bound from unbound components. The separation step may be accomplished in a variety of ways. For example, separation can be accomplished in solution, or, conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal-to-noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as measurement of an induced polypeptide within, on the surface of, or secreted by the cell. Examples of detection methods useful in cell-based assays include fluorescence-activated cell sorting (FACS) analysis, bioluminescence, fluorescence, enzyme-linked immunosorbent assay (ELISA), reverse transcriptase-polymerase chain reaction (RT-PCR), and the like. Examples of detection methods useful in cell-free assays include bioluminescence, fluorescence, enzyme-linked immunosorbent assay (ELISA), reverse transcriptase-polymerase chain reaction (RT-PCR), and the like.

A subject shall mean a human or animal including but not limited to a dog, cat, horse, cow, pig, sheep, goat, chicken, rodent, e.g., rats and mice, primate, e.g., monkey, and fish or aquaculture species such as fin fish (e.g., salmon) and shellfish (e.g., shrimp and scallops). Subjects suitable for therapeutic or prophylactic methods include vertebrate and invertebrate species. Subjects can be house pets (e.g., dogs, cats, fish, etc.), agricultural stock animals (e.g., cows, horses, pigs, chickens, etc.), laboratory animals (e.g., mice, rats, rabbits, etc.), zoo animals (e.g., lions, giraffes, etc.), but are not so limited. Although many of the embodiments described herein relate to human disorders, the invention is also useful for treating other nonhuman vertebrates.

As used herein, the term "treat", when used with respect to one of the disorders described herein, refers both to a prophylactic treatment which decreases the likelihood that a subject will develop the disorder as well as to treatment of an established disorder, e.g., to reduce or eliminate the disorder or symptoms of the disorder, or to prevent the disorder or symptoms of the disorder from becoming worse.

A subject that has a disorder refers to a subject that has an objectively measureable manifestation of the disorder. Thus for example a subject that has a cancer is a subject that has detectable cancerous cells. A subject that has an infection is a subject that has been exposed to an infectious organism and has acute or chronic detectable levels of the organism in the body. The infection may be latent (dormant) or active.

A subject at risk of having a disorder is defined as a subject that has a higher than normal risk of developing the disorder. The normal risk is generally the risk of a population of normal individuals that do not have the disorder and that are not identifiably predisposed, e.g., either genetically or environmentally, to developing the disorder. Thus a subject at risk of having a disorder may include, without limitation, a subject that is genetically predisposed to developing the disorder, as well as a subject that is or will be exposed to an environmental agent known or believed to cause the disorder. Environmental agents specifically include, but are not limited to, infectious agents such as viruses, bacteria, fungi, and parasites. Other environmental agents may include, for example, tobacco smoke, certain organic chemicals, asbestos, and the like.

The term "effective amount" of a nucleic acid or other therapeutic agent refers to the amount necessary or sufficient to realize a desired biologic effect. In general, an effective amount is that amount necessary to cause activation of the immune system, resulting potentially in the development of an antigen-specific immune response. In some embodiments, the nucleic acid or other therapeutic agent are administered in an effective amount to stimulate or induce a Th1 immune response or a general immune response. An effective amount to stimulate a Th1 immune response may be defined as that amount which stimulates the production of one or more Th1-type cytokines, such as IL-2, IL-12, TNF-α, and IFN-γ, and/or production of one or more Th1-type antibodies.

In yet another aspect the invention provides a method of inducing an immune response in a subject. The method according to this aspect of the invention involves administering to a subject an antigen, and administering to the subject an immunostimulatory composition of the invention in an effective amount to induce an immune response to the antigen. It is to be noted that the antigen may be administered before, after, or concurrently with the immunostimulatory composition of the invention. In addition, both the antigen and the immunostimulatory compound can be administered to the subject more than once.

The invention further provides, in yet another aspect, a method of inducing an immune response in a subject. The method according to this aspect of the invention involves isolating dendritic cells of a subject, contacting the dendritic cells ex vivo with an immunostimulatory composition of the invention, contacting the dendritic cells ex vivo with an antigen, and administering the contacted dendritic cells to the subject.

The term "antigen" refers to a molecule capable of provoking an immune response. The term antigen broadly includes any type of molecule that is recognized by a host system as being foreign. Antigens include but are not limited to microbial antigens, cancer antigens, and allergens. Antigens include, but are not limited to, cells, cell extracts, proteins, polypeptides, peptides, polysaccharides, polysaccharide conjugates, peptide and non-peptide mimics of polysaccharides and other molecules, small molecules, lipids, glycolipids, and carbohydrates. Many antigens are protein or polypeptide in nature, as proteins and polypeptides are generally more antigenic than carbohydrates or fats.

The antigen may be an antigen that is encoded by a nucleic acid vector or it may not be encoded in a nucleic acid vector. In the former case the nucleic acid vector is administered to the subject and the antigen is expressed in vivo. In the latter case the antigen may be administered directly to the subject. An antigen not encoded in a nucleic acid vector as used herein refers to any type of antigen that is not a nucleic acid. For instance, in some aspects of the invention the antigen not encoded in a nucleic acid vector is a peptide or a polypeptide. Minor modifications of the primary amino acid sequences of peptide or polypeptide antigens may also result in a polypeptide which has substantially equivalent antigenic activity as compared to the unmodified counterpart polypeptide. Such modifications may be deliberate, as by site-directed mutagenesis, or may be spontaneous. All of the polypeptides produced by these modifications are included herein as long as antigenicity still exists. The peptide or polypeptide may be, for example, virally derived. The antigens useful in the invention may be any length, ranging from small peptide fragments of a full length protein or polypeptide to the full length form. For example, the antigen may be less than 5, less than 8, less than 10, less than 15, less than 20, less than 30, less than 50, less than 70, less than 100, or more amino acid residues in length, provided it stimulates a specific immune response.

The nucleic acid encoding the antigen is operatively linked to a gene expression sequence which directs the expression of the antigen nucleic acid within a eukaryotic cell. The gene expression sequence is any regulatory nucleotide sequence, such as a promoter sequence or promoter-enhancer combination, which facilitates the efficient transcription and translation of the antigen nucleic acid to which it is operatively linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, β-actin promoter and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, the long terminal repeats (LTR) of Moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined antigen nucleic acid. The gene expression sequences optionally include enhancer sequences or upstream activator sequences as desired.

The antigen nucleic acid is operatively linked to the gene expression sequence. As used herein, the antigen nucleic acid sequence and the gene expression sequence are said to be operably linked when they are covalently linked in such a way as to place the expression or transcription and/or translation of the antigen coding sequence under the influence or control of the gene expression sequence. Two DNA sequences are said to be operably linked if induction of a promoter in the 5' gene expression sequence results in the transcription of the antigen sequence and if the nature of the linkage between the two DNA sequences does not (1) result in the introduction of a frame-shift mutation, (2) interfere with the ability of the promoter region to direct the transcription of the antigen sequence, or (3) interfere with the ability of the corresponding RNA transcript to be translated into a protein. Thus, a gene expression sequence would be operably linked to an antigen nucleic acid sequence if the gene expression sequence were capable of effecting transcription of that antigen nucleic acid sequence such that the resulting transcript is translated into the desired protein or polypeptide.

The antigen nucleic acid of the invention may be delivered to the immune system alone or in association with a vector. In its broadest sense, a vector is any vehicle capable of facilitating the transfer of the antigen nucleic acid to the cells of the immune system so that the antigen can be expressed and presented on the surface of the immune cell. The vector generally transports the nucleic acid to the immune cells with reduced degradation relative to the extent of degradation that would result in the absence of the vector. The vector optionally includes the above-described gene expression sequence to enhance expression of the antigen nucleic acid in immune cells. In general, the vectors useful in the invention include, but are not limited to, plasmids, phagemids, viruses, other vehicles derived from viral or bacterial sources that have been manipulated by the insertion or incorporation of the antigen nucleic acid sequences. Viral vectors are a preferred type of vector and include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murray, E. J. Methods in Molecular Biology, vol. 7, Humana Press, Inc., Cliffton, N.J. (1991).

A preferred virus for certain applications is the adeno-associated virus, a double-stranded DNA virus. The adeno-associated virus can be engineered to be replication-deficient and is capable of infecting a wide range of cell types and species. It further has advantages, such as heat and lipid solvent stability; high transduction frequencies in cells of diverse lineages, including hemopoietic cells; and lack of superinfection inhibition thus allowing multiple series of transductions. Reportedly, wild-type adeno-associated virus manifest some preference for integration sites into human cellular DNA, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion. Recombinant adeno-associated viruses that lack the replicase protein apparently lack this integration sequence specificity.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC19, pRc/CMV, SV40, and pBlueScript. Other plasmids are well-known to those of ordinary skill in the art. Additionally, plasmids may be custom designed using restriction enzymes and ligation reactions to remove and add specific fragments of DNA.

It has recently been discovered that gene-carrying plasmids can be delivered to the immune system using bacteria. Modified forms of bacteria such as *Salmonella* can be transfected with the plasmid and used as delivery vehicles. The bacterial delivery vehicles can be administered to a host subject orally or by other administration means. The bacteria deliver the plasmid to immune cells, e.g., B cells, dendritic cells, likely by passing through the gut barrier. High levels of immune protection have been established using this methodology. Such methods of delivery are useful for the aspects of the invention utilizing systemic delivery of antigen, nucleic acids, and/or other therapeutic agent.

In some aspects of the invention, the nucleic acids are administered along with therapeutic agents such as disorder-specific medicaments. As used herein, a disorder-specific medicament is a therapy or agent that is used predominately in the treatment or prevention of a disorder.

In one aspect, the combination of nucleic acid and disorder-specific medicaments allows for the administration of higher doses of disorder-specific medicaments without as many side effects as are ordinarily experienced at those high doses. In another aspect, the combination of nucleic acid and disorder-specific medicaments allows for the administration of lower, sub-therapeutic doses of either compound, but with higher efficacy than would otherwise be achieved using such low doses. As one example, by administering a combination of an immunostimulatory nucleic acid and a medicament, it is possible to achieve an effective response even though the medicament is administered at a dose which alone would not provide a therapeutic benefit (i.e., a sub-therapeutic dose). As another example, the combined administration achieves a response even though the nucleic acid is administered at a dose which alone would not provide a therapeutic benefit.

The nucleic acids and/or other therapeutic agents can also be administered on fixed schedules or in different temporal relationships to one another. The various combinations have many advantages over the prior art methods of modulating immune responses or preventing or treating disorders, particularly with regard to decreased non-specific toxicity to normal tissues.

Cancer is a disease which involves the uncontrolled growth (i.e., division) of cells. Some of the known mechanisms which contribute to the uncontrolled proliferation of cancer cells include growth factor independence, failure to detect genomic mutation, and inappropriate cell signaling. The ability of cancer cells to ignore normal growth controls may result in an increased rate of proliferation. Although the causes of cancer have not been firmly established, there are some factors known to contribute, or at least predispose a subject, to cancer. Such factors include particular genetic mutations (e.g., BRCA gene mutation for breast cancer, APC for colon cancer), exposure to suspected cancer-causing agents, or carcinogens (e.g., asbestos, UV radiation) and familial disposition for particular cancers such as breast cancer.

The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g., small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

A "subject having a cancer" is a subject that has detectable cancerous cells.

A "subject at risk of developing a cancer" is one who has a higher than normal probability of developing cancer. These subjects include, for instance, subjects having a genetic abnormality that has been demonstrated to be associated with a higher likelihood of developing a cancer, subjects having a familial disposition to cancer, subjects exposed to cancer-causing agents (i.e., carcinogens) such as tobacco, asbestos, or other chemical toxins, and subjects previously treated for cancer and in apparent remission.

A "cancer antigen" as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen P A et al. (1994) Cancer Res 54:1055-8, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

The terms "cancer antigen" and "tumor antigen" are used interchangeably and refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Examples of tumor antigens include MAGE, MART-1/Melan-A, gp100, Dipeptidyl peptidase IV (DPPIV), adenosine deaminase-binding protein (ADAbp), cyclophilin b, Colorectal associated antigen (CRC)—0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, HA, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2.

Cancers or tumors and tumor antigens associated with such tumors (but not exclusively), include acute lymphoblastic leukemia (etv6; aml1; cyclophilin b), B cell lymphoma (Ig-idiotype), glioma (E-cadherin; α-catenin; β-catenin; γ-catenin; p120ctn), bladder cancer (p21ras), biliary cancer (p21ras), breast cancer (MUC family; HER2/neu; c-erbB-2), cervical carcinoma (p53; p21ras), colon carcinoma (p21ras; HER2/neu; c-erbB-2; MUC family), colorectal cancer (Colorectal associated antigen (CRC)—0017-1A/GA733; APC), choriocarcinoma (CEA), epithelial cell cancer (cyclophilin b), gastric cancer (HER2/neu; c-erbB-2; ga733 glycoprotein), hepatocellular cancer (α-fetoprotein), Hodgkins lymphoma (lmp-1; EBNA-1), lung cancer (CEA; MAGE-3; NY-ESO-1), lymphoid cell-derived leukemia (cyclophilin b), melanoma (p15 protein, gp75, oncofetal antigen, GM2 and GD2 gangliosides), myeloma (MUC family; p21ras), non-small cell lung carcinoma (HER2/neu; c-erbB-2), nasopharyngeal cancer (lmp-1; EBNA-1), ovarian cancer (MUC family; HER2/neu; c-erbB-2), prostate cancer (Prostate Specific Antigen (PSA) and its immunogenic epitopes PSA-1, PSA-2, and PSA-3; PSMA; HER2/neu; c-erbB-2), pancreatic cancer (p21ras; MUC family; HER2/neu; c-erbB-2; ga733 glycoprotein), renal cancer (HER2/neu; c-erbB-2), squamous cell cancers of cervix and esophagus (viral products such as human papilloma virus proteins), testicular cancer (NY-ESO-1), T-cell leukemia (HTLV-1 epitopes), and melanoma (Melan-A/MART-1; cdc27; MAGE-3; p21ras; gp100$^{Pmel117}$).

For examples of tumor antigens which bind to either or both MHC class I and MHC class II molecules, see the following references: Coulie, Stem Cells 13:393-403, 1995; Traversari et al. J Exp Med 176:1453-1457, 1992; Chaux et al. J Immunol 163:2928-2936, 1999; Fujie et al. Int J Cancer 80:169-172, 1999; Tanzarella et al. Cancer Res 59:2668-2674, 1999; van der Bruggen et al. Eur J Immunol 24:2134-2140, 1994; Chaux et al. J Exp Med 189:767-778, 1999; Kawashima et al. Hum Immunol 59:1-14, 1998; Tahara et al. Clin Cancer Res 5:2236-2241, 1999; Gaugler et al. J Exp Med 179:921-930, 1994; van der Bruggen et al. Eur J Immunol 24:3038-3043, 1994; Tanaka et al. Cancer Res 57:4465-4468, 1997; Oiso et al. Int J Cancer 81:387-394, 1999; Herman et al. Immunogenetics 43:377-383, 1996; Manici et al. J Exp Med 189:871-876, 1999; Duffour et al. Eur J Immunol 29:3329-3337, 1999; Zorn et al. Eur J Immunol 29:602-607, 1999; Huang et al. J Immunol 162:6849-6854, 1999; Boel et al. Immunity 2:167-175, 1995; Van den Eynde et al. J Exp Med 182:689-698, 1995; De Backer et al. Cancer Res 59:3157-3165, 1999; Jäger et al. J Exp Med 187:265-270, 1998; Wang et al. J Immunol 161:3596-3606, 1998; Aarnoudse et al. Int J Cancer 82:442-448, 1999; Guilloux et al. J Exp Med 183:1173-1183, 1996; Lupetti et al. J Exp Med 188:1005-1016, 1998; Wölfel et al. Eur J Immunol 24:759-764, 1994; Skipper et al. J Exp Med 183:527-534, 1996; Kang et al. J Immunol 155:1343-1348, 1995; Morel et al. Int J Cancer 83:755-759, 1999; Brichard et al. Eur J Immunol 26:224-230, 1996; Kittlesen et al. J Immunol 160:2099-2106, 1998; Kawakami et al. J Immunol 161:6985-6992, 1998; Topalian et al. J Exp Med 183:1965-1971, 1996; Kobayashi et al. Cancer Research 58:296-301, 1998; Kawakami et al. J Immunol 154:3961-3968, 1995; Tsai et al. J Immunol 158:1796-1802, 1997; Cox et al.

Science 264:716-719, 1994; Kawakami et al. *Proc Natl Acad Sci USA* 91:6458-6462, 1994; Skipper et al. *J Immunol* 157:5027-5033, 1996; Robbins et al. *J Immunol* 159:303-308, 1997; Castelli et al. *J Immunol* 162:1739-1748, 1999; Kawakami et al. *Exp Med* 180:347-352, 1994; Castelli et al. *J Exp Med* 181:363-368, 1995; Schneider et al. *Int J Cancer* 75:451-458, 1998; Wang et al. *J Exp Med* 183:1131-1140, 1996; Wang et al. *J Exp Med* 184:2207-2216, 1996; Parkhurst et al. *Cancer Research* 58:4895-4901, 1998; Tsang et al. *J Natl Cancer Inst* 87:982-990, 1995; Correale et al. *J Natl Cancer Inst* 89:293-300, 1997; Coulie et al. *Proc Natl Acad Sci USA* 92:7976-7980, 1995; Wölfel et al. *Science* 269:1281-1284, 1995; Robbins et al. *J Exp Med* 183:1185-1192, 1996; Brändle et al. *J Exp Med* 183:2501-2508, 1996; ten Bosch et al. *Blood* 88:3522-3527, 1996; Mandruzzato et al. *J Exp Med* 186:785-793, 1997; Guéguen et al. *J Immunol* 160:6188-6194, 1998; Gjertsen et al. *Int J Cancer* 72:784-790, 1997; Gaudin et al. *J Immunol* 162:1730-1738, 1999; Chiari et al. *Cancer Res* 59:5785-5792, 1999; Hogan et al. *Cancer Res* 58:5144-5150, 1998; Pieper et al. *J Exp Med* 189:757-765, 1999; Wang et al. *Science* 284:1351-1354, 1999; Fisk et al. *J Exp Med* 181:2109-2117, 1995; Brossart et al. *Cancer Res* 58:732-736, 1998; Röpke et al. *Proc Natl Acad Sci USA* 93:14704-14707, 1996; Ikeda et al. *Immunity* 6:199-208, 1997; Ronsin et al. *J Immunol* 163:483-490, 1999; Vonderheide et al. *Immunity* 10:673-679, 1999. These antigens as well as others are disclosed in PCT Application PCT/US98/18601

The compositions and methods of the invention can be used alone or in conjunction with other agents and methods useful for the treatment of cancer. Cancer is currently treated using a variety of modalities including surgery, radiation therapy and chemotherapy. The choice of treatment modality will depend upon the type, location and dissemination of the cancer. For example, surgery and radiation therapy may be more appropriate in the case of solid, well-defined tumor masses and less practical in the case of non-solid tumor cancers such as leukemia and lymphoma. One of the advantages of surgery and radiation therapy is the ability to control to some extent the impact of the therapy, and thus to limit the toxicity to normal tissues in the body. However, surgery and radiation therapy are often followed by chemotherapy to guard against any remaining or radio-resistant cancer cells. Chemotherapy is also the most appropriate treatment for disseminated cancers such as leukemia and lymphoma as well as metastases.

Chemotherapy refers to therapy using chemical and/or biological agents to attack cancer cells. Unlike localized surgery or radiation, chemotherapy is generally administered in a systemic fashion and thus toxicity to normal tissues is a major concern. Because many chemotherapy agents target cancer cells based on their proliferative profiles, tissues such as the gastrointestinal tract and the bone marrow which are normally proliferative are also susceptible to the effects of the chemotherapy. One of the major side effects of chemotherapy is myelosuppression (including anemia, neutropenia and thrombocytopenia) which results from the death of normal hemopoietic precursors.

Many chemotherapeutic agents have been developed for the treatment of cancer. Not all tumors, however, respond to chemotherapeutic agents and others although initially responsive to chemotherapeutic agents may develop resistance. As a result, the search for effective anti-cancer drugs has intensified in an effort to find even more effective agents with less non-specific toxicity.

Cancer medicaments function in a variety of ways. Some cancer medicaments work by targeting physiological mechanisms that are specific to tumor cells. Examples include the targeting of specific genes and their gene products (i.e., proteins primarily) which are mutated in cancers. Such genes include but are not limited to oncogenes (e.g., Ras, Her2, bcl-2), tumor suppressor genes (e.g., EGF, p53, Rb), and cell cycle targets (e.g., CDK4, p21, telomerase). Cancer medicaments can alternately target signal transduction pathways and molecular mechanisms which are altered in cancer cells. Targeting of cancer cells via the epitopes expressed on their cell surface is accomplished through the use of monoclonal antibodies. This latter type of cancer medicament is generally referred to herein as immunotherapy.

Other cancer medicaments target cells other than cancer cells. For example, some medicaments prime the immune system to attack tumor cells (i.e., cancer vaccines). Still other medicaments, called angiogenesis inhibitors, function by attacking the blood supply of solid tumors. Since the most malignant cancers are able to metastasize (i.e., exit the primary tumor site and seed a another site, thereby forming a secondary tumor), medicaments that impede this metastasis are also useful in the treatment of cancer. Angiogenic mediators include basic FGF, VEGF, angiopoietins, angiostatin, endostatin, TNF-$\alpha$, TNP-470, thrombospondin-1, platelet factor 4, CAI, and certain members of the integrin family of proteins. One category of this type of medicament is a metalloproteinase inhibitor, which inhibits the enzymes used by the cancer cells to exist the primary tumor site and extravasate into another tissue.

Some cancer cells are antigenic and thus can be targeted by the immune system. In one aspect, the combined administration of nucleic acid and cancer medicaments, particularly those which are classified as cancer immunotherapies, is useful for stimulating a specific immune response against a cancer antigen.

The theory of immune surveillance is that a prime function of the immune system is to detect and eliminate neoplastic cells before a tumor forms. A basic principle of this theory is that cancer cells are antigenically different from normal cells and thus elicit immune reactions that are similar to those that cause rejection of immunologically incompatible allografts. Studies have confirmed that tumor cells differ, either qualitatively or quantitatively, in their expression of antigens. For example, "tumor-specific antigens" are antigens that are specifically associated with tumor cells but not normal cells. Examples of tumor specific antigens are viral antigens in tumors induced by DNA or RNA viruses. "Tumor-associated" antigens are present in both tumor cells and normal cells but are present in a different quantity or a different form in tumor cells. Examples of such antigens are oncofetal antigens (e.g., carcinoembryonic antigen), differentiation antigens (e.g., T and Tn antigens), and oncogene products (e.g., HER/neu).

Different types of cells that can kill tumor targets in vitro and in vivo have been identified: natural killer (NK) cells, cytolytic T lymphocytes (CTLs), lymphokine-activated killer cells (LAKs), and activated macrophages. NK cells can kill tumor cells without having been previously sensitized to specific antigens, and the activity does not require the presence of class I antigens encoded by the major histocompatibility complex (MHC) on target cells. NK cells are thought to participate in the control of nascent tumors and in the control of metastatic growth. In contrast to NK cells, CTLs can kill tumor cells only after they have been sensitized to tumor antigens and when the target antigen is expressed on the tumor cells that also express MHC class I. CTLs are thought to be effector cells in the rejection of transplanted tumors and of tumors caused by DNA viruses.

LAK cells are a subset of null lymphocytes distinct from the NK and CTL populations. Activated macrophages can kill tumor cells in a manner that is neither antigen-dependent nor MHC-restricted once activated. Activated macrophages are through to decrease the growth rate of the tumors they infiltrate. In vitro assays have identified other immune mechanisms such as antibody-dependent, cell-mediated cytotoxic reactions and lysis by antibody plus complement. However, these immune effector mechanisms are thought to be less important in vivo than the function of NK, CTLs, LAK, and macrophages in vivo (for review see Piessens W F et al. "Tumor Immunology", In: *Scientific American Medicine*, Vol. 2, Scientific American Books, N.Y., pp. 1-13, 1996).

The goal of immunotherapy is to augment a patient's immune response to an established tumor. One method of immunotherapy includes the use of adjuvants. Adjuvant substances derived from microorganisms, such as *bacillus* Calmette-Guérin, heighten the immune response and enhance resistance to tumors in animals.

Immunotherapeutic agents are medicaments which derive from antibodies or antibody fragments which specifically bind or recognize a cancer antigen. Antibody-based immunotherapies may function by binding to the cell surface of a cancer cell and thereby stimulate the endogenous immune system to attack the cancer cell. Another way in which antibody-based therapy functions is as a delivery system for the specific targeting of toxic substances to cancer cells. Antibodies are usually conjugated to toxins such as ricin (e.g., from castor beans), calicheamicin and maytansinoids, to radioactive isotopes such as Iodine-131 and Yttrium-90, to chemotherapeutic agents (as described herein), or to biological response modifiers. In this way, the toxic substances can be concentrated in the region of the cancer and non-specific toxicity to normal cells can be minimized. In addition to the use of antibodies which are specific for cancer antigens, antibodies which bind to vasculature, such as those which bind to endothelial cells, are also useful in the invention. This is because solid tumors generally are dependent upon newly formed blood vessels to survive, and thus most tumors are capable of recruiting and stimulating the growth of new blood vessels. As a result, one strategy of many cancer medicaments is to attack the blood vessels feeding a tumor and/or the connective tissues (or stroma) supporting such blood vessels.

Cancer vaccines are medicaments which are intended to stimulate an endogenous immune response against cancer cells. Currently produced vaccines predominantly activate the humoral immune system (i.e., the antibody-dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells.

Although cancer vaccines may take one of several forms, as discussed infra, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. One form of cancer vaccine is a whole cell vaccine which is a preparation of cancer cells which have been removed from a subject, treated ex vivo and then reintroduced as whole cells in the subject. Lysates of tumor cells can also be used as cancer vaccines to elicit an immune response. Another form cancer vaccine is a peptide vaccine which uses cancer-specific or cancer-associated small proteins to activate T cells. Cancer-associated proteins are proteins which are not exclusively expressed by cancer cells (i.e., other normal cells may still express these antigens). However, the expression of cancer-associated antigens is generally consistently upregulated with cancers of a particular type. Other cancer vaccines include ganglioside vaccines, heat-shock protein vaccines, viral and bacterial vaccines, and nucleic acid vaccines.

Yet another form of cancer vaccine is a dendritic cell vaccine which includes whole dendritic cells which have been exposed to a cancer antigen or a cancer-associated antigen in vitro. Lysates or membrane fractions of dendritic cells may also be used as cancer vaccines. Dendritic cell vaccines are able to activate APCs directly. A dendritic cell is a professional APC. Dendritic cells form the link between the innate and the acquired immune system by presenting antigens and through their expression of pattern recognition receptors which detect microbial molecules like LPS in their local environment. Dendritic cells efficiently internalize, process, and present soluble specific antigen to which it is exposed. The process of internalizing and presenting antigen causes rapid upregulation of the expression of major histocompatibility complex (MHC) and costimulatory molecules, the production of cytokines, and migration toward lymphatic organs where they are believed to be involved in the activation of T cells.

As used herein, chemotherapeutic agents embrace all other forms of cancer medicaments which do not fall into the categories of immunotherapeutic agents or cancer vaccines. Chemotherapeutic agents as used herein encompass both chemical and biological agents. These agents function to inhibit a cellular activity which the cancer cell is dependent upon for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation.

An "infectious disease" or, equivalently, an "infection" as used herein, refers to a disorder arising from the invasion of a host, superficially, locally, or systemically, by an infectious organism. Infectious organisms include bacteria, viruses, fungi, and parasites. Accordingly, "infectious disease" includes bacterial infections, viral infections, fungal infections and parasitic infections.

A subject having an infectious disease is a subject that has been exposed to an infectious organism and has acute or chronic detectable levels of the organism in the body. Exposure to the infectious organism generally occurs with the external surface of the subject, e.g., skin or mucosal membranes and/or refers to the penetration of the external surface of the subject by the infectious organism.

A subject at risk of developing an infectious disease is a subject who has a higher than normal risk of exposure to an infection causing pathogen. For instance, a subject at risk may be a subject who is planning to travel to an area where a particular type of infectious agent is found or it may be a subject who through lifestyle or medical procedures is exposed to bodily fluids which may contain infectious organisms or directly to the organism or a subject living in an area where an infectious organism has been identified. Subjects at risk of developing an infectious disease also include general populations to which a medical agency recommends vaccination against a particular infectious organism.

A subject at risk of developing an infectious disease includes those subjects that have a general risk of exposure to a microorganism, e.g., influenza, but that do not have the active disease during the treatment of the invention, as well as subjects that are considered to be at specific risk of developing an infectious disease because of medical or environmental factors that expose the subject to a particular microorganism.

Bacteria are unicellular organisms which multiply asexually by binary fission. They are classified and named based on their morphology, staining reactions, nutrition and metabolic requirements, antigenic structure, chemical composition, and genetic homology. Bacteria can be classified into three groups based on their morphological forms, spherical (*coccus*), straight-rod (*bacillus*) and curved or spiral rod (vibrio, campylobacter, spirillum, and spirochaete). Bacteria are also more commonly characterized based on their staining reactions into two classes of organisms, gram-positive and gram-negative. Gram refers to the method of staining which is commonly performed in microbiology labs. Gram-positive organisms retain the stain following the staining procedure and appear a deep violet color. Gram-negative organisms do not retain the stain but take up the counterstain and thus appear pink.

Infectious bacteria include, but are not limited to, gram negative and gram positive bacteria. Gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris, Borrelia burgdorferi, Legionella pneumophilia, Mycobacteria* sps (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic species), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira, Rickettsia*, and *Actinomyces israelli*.

Viruses are small infectious agents which generally contain a nucleic acid core and a protein coat, but are not independently living organisms. Viruses can also take the form of infectious nucleic acids lacking a protein. A virus cannot survive in the absence of a living cell within which it can replicate. Viruses enter specific living cells either by endocytosis or direct injection of DNA (phage) and multiply, causing disease. The multiplied virus can then be released and infect additional cells. Some viruses are DNA-containing viruses and others are RNA-containing viruses. In some aspects, the invention also intends to treat diseases in which prions are implicated in disease progression such as for example bovine spongiform encephalopathy (i.e., mad cow disease, BSE) or scrapie infection in animals, or Creutzfeldt-Jakob disease in humans.

Viruses include, but are not limited to, enteroviruses (including, but not limited to, viruses that the family picornaviridae, such as polio virus, coxsackie virus, echo virus), rotaviruses, adenovirus, hepatitis virus. Specific examples of viruses that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxyiridae (variola viruses, vaccinia viruses, pox viruses); Iridoviridae (e.g., African swine fever virus); and unclassified viruses (e.g., the etiological agents of spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Fungi are eukaryotic organisms, only a few of which cause infection in vertebrate mammals. Because fungi are eukaryotic organisms, they differ significantly from prokaryotic bacteria in size, structural organization, life cycle and mechanism of multiplication. Fungi are classified generally based on morphological features, modes of reproduction and culture characteristics. Although fungi can cause different types of disease in subjects, such as respiratory allergies following inhalation of fungal antigens, fungal intoxication due to ingestion of toxic substances, such as *Amanita phalloides* toxin and phallotoxin produced by poisonous mushrooms and aflatoxins, produced by *aspergillus* species, not all fungi cause infectious disease.

Infectious fungi can cause systemic or superficial infections. Primary systemic infection can occur in normal healthy subjects, and opportunistic infections are most frequently found in immunocompromised subjects. The most common fungal agents causing primary systemic infection include *Blastomyces, Coccidioides*, and *Htoplasma*. Common fungi causing opportunistic infection in immunocompromised or immunosuppressed subjects include, but are not limited to, *Candida albicans, Cryptococcus neoformans*, and various *Aspergillus* species. Systemic fungal infections are invasive infections of the internal organs. The organism usually enters the body through the lungs, gastrointestinal tract, or intravenous catheters. These types of infections can be caused by primary pathogenic fungi or opportunistic fungi.

Superficial fungal infections involve growth of fungi on an external surface without invasion of internal tissues. Typical superficial fungal infections include cutaneous fungal infections involving skin, hair, or nails.

Diseases associated with fungal infection include aspergillosis, blastomycosis, candidiasis, chromoblastomycosis, coccidioidomycosis, cryptococcosis, fungal eye infections, fungal hair, nail, and skin infections, histoplasmosis, lobomycosis, mycetoma, otomycosis, paracoccidioidomycosis, disseminated *Penicillium marneffei*, phaeohyphomycosis, rhinosporidioisis, sporotrichosis, and zygomycosis.

Parasites are organisms which depend upon other organisms in order to survive and thus must enter, or infect, another organism to continue their life cycle. The infected organism, i.e., the host, provides both nutrition and habitat to the parasite. Although in its broadest sense the term parasite can include all infectious agents (i.e., bacteria, viruses, fungi, protozoa and helminths), generally speaking, the term is used to refer solely to protozoa, helminths, and ectoparasitic arthropods (e.g., ticks, mites, etc.). Protozoa are single-celled organisms which can replicate both intracellularly and extracellularly, particularly in the blood, intestinal tract or the extracellular matrix of tissues. Helminths are multicellular organisms which almost always are extracellular (an exception being *Trichinella* spp.). Helminths normally require exit from a primary host and transmission into a secondary host in order to replicate. In contrast to these aforementioned classes, ectoparasitic arthropods form a parasitic relationship with the external surface of the host body.

Parasites include intracellular parasites and obligate intracellular parasites. Examples of parasites include but are not limited to *Plasmodium falciparum, Plasmodium ovale, Plasmodium malariae, Plasmdodium vivax, Plasmodium knowlesi, Babesia micron, Babesia divergens, Trypanosoma cruzi, Toxoplasma gondii, Trichinella spiralis, Leishmania major, Leishmania donovani, Leishmania braziliensis, Leishmania tropica, Trypanosoma gambiense, Trypanosoma rhodesiense* and *Schistosoma mansoni*.

Other medically relevant microorganisms have been described extensively in the literature, e.g., see C. G. A Thomas, *Medical Microbiology*, Bailliere Tindall, Great Britain 1983, the entire contents of which is hereby incorporated by reference. Each of the foregoing lists is illustrative and is not intended to be limiting.

The compositions and methods of the invention can be used alone or in conjunction with other agents and methods useful for the treatment of infection. Infection medicaments include but are not limited to anti-bacterial agents, anti-viral agents, anti-fungal agents and anti-parasitic agents. Phrases such as "anti-infective agent", "antibiotic", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites. Many antibiotics are low molecular weight molecules which are produced as secondary metabolites by cells, such as microorganisms. In general, antibiotics interfere with one or more functions or structures which are specific for the microorganism and which are not present in host cells.

One of the problems with anti-infective therapies is the side effects occurring in the host that is treated with the anti-infective agent. For instance, many anti-infectious agents can kill or inhibit a broad spectrum of microorganisms and are not specific for a particular type of species. Treatment with these types of anti-infectious agents results in the killing of the normal microbial flora living in the host, as well as the infectious microorganism. The loss of the microbial flora can lead to disease complications and predispose the host to infection by other pathogens, since the microbial flora compete with and function as barriers to infectious pathogens. Other side effects may arise as a result of specific or non-specific effects of these chemical entities on non-microbial cells or tissues of the host.

Another problem with widespread use of anti-infectants is the development of antibiotic-resistant strains of microorganisms. Already, vancomycin-resistant *enterococci*, penicillin-resistant *pneumococci*, multi-resistant *S. aureus*, and multi-resistant *tuberculosis* strains have developed and are becoming major clinical problems. Widespread use of anti-infectants will likely produce many antibiotic-resistant strains of bacteria. As a result, new anti-infective strategies will be required to combat these microorganisms.

Antibacterial antibiotics which are effective for killing or inhibiting a wide range of bacteria are referred to as broad-spectrum antibiotics. Other types of antibacterial antibiotics are predominantly effective against the bacteria of the class gram-positive or gram-negative. These types of antibiotics are referred to as narrow-spectrum antibiotics. Other antibiotics which are effective against a single organism or disease and not against other types of bacteria, are referred to as limited-spectrum antibiotics.

Anti-bacterial agents are sometimes classified based on their primary mode of action. In general, anti-bacterial agents are cell wall synthesis inhibitors, cell membrane inhibitors, protein synthesis inhibitors, nucleic acid synthesis or functional inhibitors, and competitive inhibitors. Cell wall synthesis inhibitors inhibit a step in the process of cell wall synthesis, and in general in the synthesis of bacterial peptidoglycan. Cell wall synthesis inhibitors include β-lactam antibiotics, natural penicillins, semi-synthetic penicillins, ampicillin, clavulanic acid, cephalolsporins, and bacitracin.

The β-lactams are antibiotics containing a four-membered β-lactam ring which inhibits the last step of peptidoglycan synthesis. β-lactam antibiotics can be synthesized or natural. The β-lactam antibiotics produced by *penicillium* are the natural penicillins, such as penicillin G or penicillin V. These are produced by fermentation of *Penicillium chrysogenum*. The natural penicillins have a narrow spectrum of activity and are generally effective against *Streptococcus, Gonococcus,* and *Staphylococcus*. Other types of natural penicillins, which are also effective against gram-positive bacteria, include penicillins F, X, K, and O.

Semi-synthetic penicillins are generally modifications of the molecule 6-aminopenicillanic acid produced by a mold. The 6-aminopenicillanic acid can be modified by addition of side chains which produce penicillins having broader spectrums of activity than natural penicillins or various other advantageous properties. Some types of semi-synthetic penicillins have broad spectrums against gram-positive and gram-negative bacteria, but are inactivated by penicillinase. These semi-synthetic penicillins include ampicillin, carbenicillin, oxacillin, azlocillin, mezlocillin, and piperacillin. Other types of semi-synthetic penicillins have narrower activities against gram-positive bacteria, but have developed properties such that they are not inactivated by penicillinase. These include, for instance, methicillin, dicloxacillin, and nafcillin. Some of the broad spectrum semi-synthetic penicillins can be used in combination with β-lactamase inhibitors, such as clavulanic acids and sulbactam. The β-lactamase inhibitors do not have anti-microbial action but they function to inhibit penicillinase, thus protecting the semi-synthetic penicillin from degradation.

One of the serious side effects associated with penicillins, both natural and semi-synthetic, is penicillin allergy. Penicillin allergies are very serious and can cause death rapidly. In a subject that is allergic to penicillin, the β-lactam molecule will attach to a serum protein which initiates an IgE-mediated inflammatory response. The inflammatory response leads to anaphylaxis and possibly death.

Another type of β-lactam antibiotic is the cephalolsporins. They are sensitive to degradation by bacterial β-lactamases, and thus, are not always effective alone. Cephalolsporins, however, are resistant to penicillinase. They are effective against a variety of gram-positive and gram-negative bacteria. Cephalolsporins include, but are not limited to, cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, and moxalactam.

Bacitracin is another class of antibiotics which inhibit cell wall synthesis, by inhibiting the release of muropeptide subunits or peptidoglycan from the molecule that delivers the subunit to the outside of the membrane. Although bacitracin is effective against gram-positive bacteria, its use is limited in general to topical administration because of its high toxicity.

Carbapenems are another broad-spectrum β-lactam antibiotic, which is capable of inhibiting cell wall synthesis. Examples of carbapenems include, but are not limited to, imipenems. Monobactams are also broad-spectrum β-lactam antibiotics, and include, eurtreonam. An antibiotic produced by *Streptomyces*, vancomycin, is also effective against gram-positive bacteria by inhibiting cell membrane synthesis.

Another class of anti-bacterial agents is the anti-bacterial agents that are cell membrane inhibitors. These compounds disorganize the structure or inhibit the function of bacterial membranes. One problem with anti-bacterial agents that are cell membrane inhibitors is that they can produce effects in eukaryotic cells as well as bacteria because of the similarities in phospholipids in bacterial and eukaryotic membranes. Thus these compounds are rarely specific enough to permit these compounds to be used systemically and prevent the use of high doses for local administration.

One clinically useful cell membrane inhibitor is Polymyxin. Polymyxins interfere with membrane function by binding to membrane phospholipids. Polymyxin is effective mainly against Gram-negative bacteria and is generally used in severe *Pseudomonas* infections or *Pseudomonas* infections that are resistant to less toxic antibiotics. The severe side effects associated with systemic administration of this compound include damage to the kidney and other organs.

Other cell membrane inhibitors include Amphotericin B and Nystatin which are anti-fungal agents used predominantly in the treatment of systemic fungal infections and *Candida* yeast infections. Imidazoles are another class of antibiotic that is a cell membrane inhibitor. Imidazoles are used as anti-bacterial agents as well as anti-fungal agents, e.g., used for treatment of yeast infections, dermatophytic infections, and systemic fungal infections. Imidazoles include but are not limited to clotrimazole, miconazole, ketoconazole, itraconazole, and fluconazole.

Many anti-bacterial agents are protein synthesis inhibitors. These compounds prevent bacteria from synthesizing structural proteins and enzymes and thus cause inhibition of bacterial cell growth or function or cell death. In general these compounds interfere with the processes of transcription or translation. Anti-bacterial agents that block transcription include but are not limited to Rifampins and Ethambutol. Rifampins, which inhibit the enzyme RNA polymerase, have a broad spectrum activity and are effective against gram-positive and gram-negative bacteria as well as *Mycobacterium tuberculosis*. Ethambutol is effective against *Mycobacterium tuberculosis*.

Anti-bacterial agents which block translation interfere with bacterial ribosomes to prevent mRNA from being translated into proteins. In general this class of compounds includes but is not limited to tetracyclines, chloramphenicol, the macrolides (e.g., erythromycin) and the aminoglycosides (e.g., streptomycin).

The aminoglycosides are a class of antibiotics which are produced by the bacterium *Streptomyces*, such as, for instance streptomycin, kanamycin, tobramycin, amikacin, and gentamicin Aminoglycosides have been used against a wide variety of bacterial infections caused by Gram-positive and Gram-negative bacteria. Streptomycin has been used extensively as a primary drug in the treatment of tuberculosis. Gentamicin is used against many strains of Gram-positive and Gram-negative bacteria, including *Pseudomonas* infections, especially in combination with Tobramycin. Kanamycin is used against many Gram-positive bacteria, including penicillin-resistant *Staphylococci*. One side effect of aminoglycosides that has limited their use clinically is that at dosages which are essential for efficacy, prolonged use has been shown to impair kidney function and cause damage to the auditory nerves leading to deafness.

Another type of translation inhibitor anti-bacterial agent is the tetracyclines. The tetracyclines are a class of antibiotics that are broad-spectrum and are effective against a variety of gram-positive and gram-negative bacteria. Examples of tetracyclines include tetracycline, minocycline, doxycycline, and chlortetracycline. They are important for the treatment of many types of bacteria but are particularly important in the treatment of Lyme disease. As a result of their low toxicity and minimal direct side effects, the tetracyclines have been overused and misused by the medical community, leading to problems. For instance, their overuse has led to widespread development of resistance.

Anti-bacterial agents such as the macrolides bind reversibly to the 50 S ribosomal subunit and inhibit elongation of the protein by peptidyl transferase or prevent the release of uncharged tRNA from the bacterial ribosome or both. These compounds include erythromycin, roxithromycin, clarithromycin, oleandomycin, and azithromycin. Erythromycin is active against most Gram-positive bacteria, *Neisseria, Legionella* and *Haemophilus*, but not against the *Enterobacteriaceae*. Lincomycin and clindamycin, which block peptide bond formation during protein synthesis, are used against gram-positive bacteria.

Another type of translation inhibitor is chloramphenicol. Chloramphenicol binds the 70 S ribosome inhibiting the bacterial enzyme peptidyl transferase thereby preventing the growth of the polypeptide chain during protein synthesis. One serious side effect associated with chloramphenicol is aplastic anemia. Aplastic anemia develops at doses of chloramphenicol which are effective for treating bacteria in a small proportion (1/50,000) of patients. Chloramphenicol which was once a highly prescribed antibiotic is now seldom uses as a result of the deaths from anemia. Because of its effectiveness it is still used in life-threatening situations (e.g., typhoid fever).

Some anti-bacterial agents disrupt nucleic acid synthesis or function, e.g., bind to DNA or RNA so that their messages cannot be read. These include but are not limited to quinolones and co-trimoxazole, both synthetic chemicals and rifamycins, a natural or semi-synthetic chemical. The quinolones block bacterial DNA replication by inhibiting the DNA gyrase, the enzyme needed by bacteria to produce their circular DNA. They are broad spectrum and examples include norfloxacin, ciprofloxacin, enoxacin, nalidixic acid and temafloxacin. Nalidixic acid is a bactericidal agent that binds to the DNA gyrase enzyme (topoisomerase) which is essential for DNA replication and allows supercoils to be relaxed and reformed, inhibiting DNA gyrase activity. The main use of nalidixic acid is in treatment of lower urinary tract infections (UTI) because it is effective against several types of Gram-negative bacteria such as *E. coli, Enterobacter aerogenes, K. pneumoniae* and *Proteus* species which are common causes of UTI. Co-trimoxazole is a combination of sulfamethoxazole and trimethoprim, which blocks the bacterial synthesis of folic acid needed to make DNA nucleotides. Rifampicin is a derivative of rifamycin that is active against Gram-positive bacteria (including *Mycobacterium tuberculosis* and meningitis caused by *Neisseria meningitidis*) and some Gram-negative bacteria. Rifampicin binds to the beta subunit of the polymerase and blocks the addition of the first nucleotide which is necessary to activate the polymerase, thereby blocking mRNA synthesis.

Another class of anti-bacterial agents is compounds that function as competitive inhibitors of bacterial enzymes. The competitive inhibitors are mostly all structurally similar to a bacterial growth factor and compete for binding but do not perform the metabolic function in the cell. These compounds include sulfonamides and chemically modified forms of sulfanilamide which have even higher and broader antibacterial activity. The sulfonamides (e.g., gantrisin and trimethoprim) are useful for the treatment of *Streptococcus pneumoniae*, beta-hemolytic *streptococci* and *E. coli*, and have been used in the treatment of uncomplicated UTI caused by *E. coli*, and in the treatment of meningococcal meningitis.

Anti-viral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleoside analogues), maturation of new virus proteins (e.g. protease inhibitors), and budding and release of the virus.

Another category of anti-viral agents are nucleoside analogues. Nucleoside analogues are synthetic compounds which are similar to nucleosides, but which have an incomplete or abnormal deoxyribose or ribose group. Once the nucleoside analogues are in the cell, they are phosphorylated, producing the triphosphate form which competes with normal nucleotides for incorporation into the viral DNA or RNA. Once the triphosphate form of the nucleoside analogue is incorporated into the growing nucleic acid chain, it causes irreversible association with the viral polymerase and thus chain termination. Nucleoside analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncytial virus), dideoxyinosine, dideoxycytidine, and zidovudine (azidothymidine).

Another class of anti-viral agents includes cytokines such as interferons. The interferons are cytokines which are secreted by virus-infected cells as well as immune cells. The interferons function by binding to specific receptors on cells adjacent to the infected cells, causing the change in the cell which protects it from infection by the virus. $\alpha$ and $\beta$-interferon also induce the expression of Class I and Class II MHC molecules on the surface of infected cells, resulting in increased antigen presentation for host immune cell recognition. $\alpha$ and $\beta$-interferons are available as recombinant forms and have been used for the treatment of chronic hepatitis B and C infection. At the dosages which are effective for anti-viral therapy, interferons have severe side effects such as fever, malaise and weight loss.

Immunoglobulin therapy is used for the prevention of viral infection. Immunoglobulin therapy for viral infections is different from bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immune globulin therapy and hyper-immune globulin therapy. Normal immune globulin therapy utilizes a antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Examples of hyper-immune globulins include zoster immune globulin (useful for the prevention of varicella in immunocompromised children and neonates), human rabies immune globulin (useful in the post-exposure prophylaxis of a subject bitten by a rabid animal), hepatitis B immune globulin (useful in the prevention of hepatitis B virus, especially in a subject exposed to the virus), and RSV immune globulin (useful in the treatment of respiratory syncitial virus infections).

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, imidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g., chitinase) or immunosuppression (501 cream).

Parasiticides are agents that kill parasites directly. Such compounds are known in the art and are generally commercially available. Examples of parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide.

The compositions and methods of the invention may also find use in the treatment of allergy and asthma.

An "allergy" refers to acquired hypersensitivity to a substance (allergen). Allergic conditions include but are not limited to eczema, allergic rhinitis or coryza, hay fever, allergic conjunctivitis, bronchial asthma, urticaria (hives) and food allergies, other atopic conditions including atopic dermatitis; anaphylaxis; drug allergy; and angioedema. Allergic diseases include but are not limited to rhinitis (hay fever), asthma, urticaria, and atopic dermatitis.

Allergy is a disease associated with the production of antibodies from a particular class of immunoglobulin, IgE, against allergens. The development of an IgE-mediated response to common aeroallergens is also a factor which indicates predisposition towards the development of asthma. If an allergen encounters a specific IgE which is bound to an IgE Fc receptor (FcεR) on the surface of a basophil (circulating in the blood) or mast cell (dispersed throughout solid tissue), the cell becomes activated, resulting in the production and release of mediators such as histamine, serotonin, and lipid mediators.

A subject having an allergy is a subject that is currently experiencing or has previously experienced an allergic reaction in response to an allergen.

A subject at risk of developing an allergy or asthma is a subject that has been identified as having an allergy or asthma in the past but who is not currently experiencing the active disease, as well as a subject that is considered to be at risk of developing asthma or allergy because of genetic or environmental factors. A subject at risk of developing allergy or asthma can also include a subject who has any risk of exposure to an allergen or a risk of developing asthma, i.e., someone who has suffered from an asthmatic attack previously or has a predisposition to asthmatic attacks. For instance, a subject at risk may be a subject who is planning to travel to an area where a particular type of allergen or asthmatic initiator is found or it may even be any subject living in an area where an allergen has been identified. If the subject develops allergic responses to a particular antigen and the subject may be exposed to the antigen, i.e., during pollen season, then that subject is at risk of exposure to the antigen.

The generic name for molecules that cause an allergic reaction is allergen. An "allergen" as used herein is a molecule capable of provoking an immune response characterized by production of IgE. An allergen is a substance that can induce an allergic or asthmatic response in a susceptible subject. Thus, in the context of this invention, the term allergen means a specific type of antigen which can trigger an allergic response which is mediated by IgE antibody. The method and preparations of this invention extend to a broad class of such allergens and fragments of allergens or haptens acting as allergens. The list of allergens is enormous and can include pollens, insect venoms, animal dander, dust, fungal spores, and drugs (e.g., penicillin).

There are numerous species of allergens. The allergic reaction occurs when tissue-sensitizing immunoglobulin of the IgE type reacts with foreign allergen. The IgE antibody is bound to mast cells and/or basophils, and these specialized cells release chemical mediators (vasoactive amines) of the allergic reaction when stimulated to do so by allergens bridging the ends of the antibody molecule. Htamine, platelet activating factor, arachidonic acid metabolites, and serotonin are among the best known mediators of allergic reactions in man. Htamine and the other vasoactive amines are normally stored in mast cells and basophil leukocytes. The mast cells are dispersed throughout animal tissue and the basophils circulate within the vascular system. These cells manufacture and store histamine within the cell unless the specialized sequence of events involving IgE binding occurs to trigger its release.

The symptoms of the allergic reaction vary, depending on the location within the body where the IgE reacts with the antigen. If the reaction occurs along the respiratory epithelium, the symptoms are sneezing, coughing and asthmatic reactions. If the interaction occurs in the digestive tract, as in the case of food allergies, abdominal pain and diarrhea are common. Systemic reactions, for example following a bee sting, can be severe and often life-threatening.

Delayed-type hypersensitivity, also known as type IV allergy reaction, is an allergic reaction characterized by a delay period of at least 12 hours from invasion of the antigen into the allergic subject until appearance of the inflammatory or immune reaction. The T lymphocytes (sensitized T lymphocytes) of individuals in an allergic condition react with the antigen, triggering the T lymphocytes to release lymphokines (macrophage migration inhibitory factor (MIF), macrophage activating factor (MAF), mitogenic factor (MF), skin-reactive factor (SRF), chemotactic factor, neo-vascularization-accelerating factor, etc.), which function as inflammation mediators, and the biological activity of these lymphokines, together with the direct and indirect effects of locally appearing lymphocytes and other inflammatory immune cells, give rise to the type IV allergy reaction. Delayed allergy reactions include tuberculin type reaction, homograft rejection reaction, cell-dependent type protective reaction, contact dermatitis hypersensitivity reaction, and the like, which are known to be most strongly suppressed by steroidal agents. Consequently, steroidal agents are effective against diseases which are caused by delayed allergy reactions. Long-term use of steroidal agents at concentrations currently being used can, however, lead to the serious side-effect known as steroid dependence. The methods of the invention solve some of these problems, by providing for lower and fewer doses to be administered.

Immediate hypersensitivity (or anaphylactic response) is a form of allergic reaction which develops very quickly, i.e., within seconds or minutes of exposure of the patient to the causative allergen, and it is mediated by IgE antibodies made by B lymphocytes. In nonallergic patients, there is no IgE antibody of clinical relevance; but, in a person suffering with allergic diseases, IgE antibody mediates immediate hypersensitivity by sensitizing mast cells which are abundant in the skin, lymphoid organs, in the membranes of the eye, nose and mouth, and in the respiratory tract and intestines.

Mast cells have surface receptors for IgE, and the IgE antibodies in allergy-suffering patients become bound to them. As discussed briefly above, when the bound IgE is subsequently contacted by the appropriate allergen, the mast cell is caused to degranulate and to release various substances called bioactive mediators, such as histamine, into the surrounding tissue. It is the biologic activity of these substances which is responsible for the clinical symptoms typical of immediate hypersensitivity; namely, contraction of smooth muscle in the airways or the intestine, the dilation of small blood vessels and the increase in their permeability to water and plasma proteins, the secretion of thick sticky mucus, and in the skin, redness, swelling and the stimulation of nerve endings that results in itching or pain.

"Asthma" as used herein refers to a disorder of the respiratory system characterized by inflammation, narrowing of the airways, and increased reactivity of the airways to inhaled agents. Asthma is frequently, although not exclusively, associated with an atopic or allergic condition. Symptoms of asthma include recurrent episodes of wheezing, breathlessness, and chest tightness, and coughing, resulting from airflow obstruction. Airway inflammation associated with asthma can be detected through observation of a number of physiological changes, such as, denudation of airway epithelium, collagen deposition beneath basement membrane, edema, mast cell activation, inflammatory cell infiltration, including neutrophils, inosineophils, and lymphocytes. As a result of the airway inflammation, asthma patients often experience airway hyper-responsiveness, airflow limitation, respiratory symptoms, and disease chronicity. Airflow limitations include acute bronchoconstriction, airway edema, mucous plug formation, and airway remodeling, features which often lead to bronchial obstruction. In some cases of asthma, sub-basement membrane fibrosis may occur, leading to persistent abnormalities in lung function.

Research over the past several years has revealed that asthma likely results from complex interactions among inflammatory cells, mediators, and other cells and tissues resident in the airway. Mast cells, inosineophils, epithelial cells, macrophage, and activated T-cells all play an important role in the inflammatory process associated with asthma. Djukanovic R et al. (1990) *Am Rev Respir Dis* 142:434-457. It is believed that these cells can influence airway function through secretion of preformed and newly synthesized mediators which can act directly or indirectly on the local tissue. It has also been recognized that subpopulations of T-lymphocytes (Th2) play an important role in regulating allergic inflammation in the airway by releasing selective cytokines and establishing disease chronicity. Robinson D S et al. (1992) *N Engl J Med* 326:298-304.

Asthma is a complex disorder which arises at different stages in development and can be classified based on the degree of symptoms as acute, subacute or chronic. An acute inflammatory response is associated with an early recruitment of cells into the airway. The subacute inflammatory response involves the recruitment of cells as well as the activation of resident cells causing a more persistent pattern of inflammation. Chronic inflammatory response is characterized by a persistent level of cell damage and an ongoing repair process, which may result in permanent abnormalities in the airway.

A "subject having asthma" is a subject that has a disorder of the respiratory system characterized by inflammation, narrowing of the airways and increased reactivity of the airways to inhaled agents. Asthma is frequently, although not exclusively, associated with atopic or allergic symptoms. An "initiator" as used herein refers to a composition or environmental condition which triggers asthma. Initiators include, but are not limited to, allergens, cold temperatures, exercise, viral infections, $SO_2$.

The compositions and methods of the invention can be used alone or in conjucnction with other agents and methods useful in the treatment of asthma. An "asthma/allergy medicament" as used herein is a composition of matter which reduces the symptoms of, prevents the development of, or inhibits an asthmatic or allergic reaction. Various types of medicaments for the treatment of asthma and allergy are described in the Guidelines For The Diagnosis and Management of Asthma, Expert Panel Report 2, NIH Publication No. 97/4051, Jul. 19, 1997, the entire contents of which are incorporated herein by reference. The summary of the medicaments as described in the NIH publication is presented below. In most embodiments the asthma/allergy medicament is useful to some degree for treating both asthma and allergy.

Medications for the treatment of asthma are generally separated into two categories, quick-relief medications and long-term control medications. Asthma patients take the long-term control medications on a daily basis to achieve and maintain control of persistent asthma. Long-term control medications include anti-inflammatory agents such as corticosteroids, chromolyn sodium and nedocromil; long-acting bronchodilators, such as long-acting $\beta_2$-agonists and methylxanthines; and leukotriene modifiers. The quick-relief medications include short-acting $\beta_2$ agonists, anti-cholinergics, and systemic corticosteroids. There are many side effects associated with each of these drugs and none of the drugs alone or in combination is capable of preventing or completely treating asthma.

Asthma medicaments include, but are not limited, PDE-4 inhibitors, bronchodilator/beta-2 agonists, K+ channel openers, VLA-4 antagonists, neurokin antagonists, thromboxane A2 (TXA2) synthesis inhibitors, xanthines, arachidonic acid antagonists, 5 lipoxygenase inhibitors, TXA2 receptor antagonists, TXA2 antagonists, inhibitor of 5-lipox activation proteins, and protease inhibitors.

Bronchodilator/$\beta_2$ agonists are a class of compounds which cause bronchodilation or smooth muscle relaxation. Bronchodilator/$\beta_2$ agonists include, but are not limited to, salmeterol, salbutamol, albuterol, terbutaline, D2522/formoterol, fenoterol, bitolterol, pirbuerol methylxanthines and orciprenaline. Long-acting $\beta_2$ agonists and bronchodilators are compounds which are used for long-term prevention of symptoms in addition to the anti-inflammatory therapies. Long-acting $\beta_2$ agonists include, but are not limited to, salmeterol and albuterol. These compounds are usually used in combination with corticosteroids and generally are not used without any inflammatory therapy. They have been associated with side effects such as tachycardia, skeletal muscle tremor, hypokalemia, and prolongation of QTc interval in overdose.

Methylxanthines, including for instance theophylline, have been used for long-term control and prevention of symptoms. These compounds cause bronchodilation resulting from phosphodiesterase inhibition and likely adenosine antagonism. Dose-related acute toxicities are a particular problem with these types of compounds. As a result, routine serum concentration must be monitored in order to account for the toxicity and narrow therapeutic range arising from individual differences in metabolic clearance. Side effects include tachycardia, tachyarrhythmias, nausea and vomiting, central nervous system stimulation, headache, seizures, hematemesis, hyperglycemia and hypokalemia. Short-acting $\beta_2$ agonists include, but are not limited to, albuterol, bitolterol, pirbuterol, and terbutaline. Some of the adverse effects associated with the administration of short-acting $\beta_2$ agonists include tachycardia, skeletal muscle tremor, hypokalemia, increased lactic acid, headache, and hyperglycemia.

Conventional methods for treating or preventing allergy have involved the use of anti-histamines or desensitization therapies. Anti-histamines and other drugs which block the effects of chemical mediators of the allergic reaction help to regulate the severity of the allergic symptoms but do not prevent the allergic reaction and have no effect on subsequent allergic responses. Desensitization therapies are performed by giving small doses of an allergen, usually by injection under the skin, in order to induce an IgG-type response against the allergen. The presence of IgG antibody helps to neutralize the production of mediators resulting from the induction of IgE antibodies, it is believed. Initially, the subject is treated with a very low dose of the allergen to avoid inducing a severe reaction and the dose is slowly increased. This type of therapy is dangerous because the subject is actually administered the compounds which cause the allergic response and severe allergic reactions can result.

Allergy medicaments include, but are not limited to, anti-histamines, steroids, and prostaglandin inducers. Antihistamines are compounds which counteract histamine released by mast cells or basophils. These compounds are well known in the art and commonly used for the treatment of allergy. Anti-histamines include, but are not limited to, astemizole, azelastine, betatastine, buclizine, ceterizine, cetirizine analogues, CS 560, desloratadine, ebastine, epinastine, fexofenadine, HSR 609, levocabastine, loratidine, mizolastine, norastemizole, terfenadine, and tranilast.

Prostaglandin inducers are compounds which induce prostaglandin activity. Prostaglandins function by regulating smooth muscle relaxation. Prostaglandin inducers include, but are not limited to, S-5751.

The asthma/allergy medicaments also include steroids and immunomodulators. The steroids include, but are not limited to, beclomethasone, fluticasone, triamcinolone, budesonide, corticosteroids and budesonide.

Corticosteroids include, but are not limited to, beclomethasome dipropionate, budesonide, flunisolide, fluticaosone propionate, and triamcinolone acetonide. Although dexamethasone is a corticosteroid having anti-inflammatory action, it is not regularly used for the treatment of asthma/allergy in an inhaled form because it is highly absorbed and it has long-term suppressive side effects at an effective dose. Dexamethasone, however, can be used according to the invention for the treating of asthma/allergy because when administered in combination with nucleic acids of the invention it can be administered at a low dose to reduce the side effects. Some of the side effects associated with corticosteroid include cough, dysphonia, oral thrush (candidiasis), and in higher doses, systemic effects, such as adrenal suppression, osteoporosis, growth suppression, skin thinning and easy bruising. Barnes & Peterson (1993) *Am Rev Respir Dis* 148:S1-S26; and Kamada A K et al. (1996) *Am J Respir Crit. Care Med* 153:1739-48.

Systemic corticosteroids include, but are not limited to, methylprednisolone, prednisolone and prednisone. Cortosteroids are associated with reversible abnormalities in glucose metabolism, increased appetite, fluid retention, weight gain, mood alteration, hypertension, peptic ulcer, and aseptic necrosis of bone. These compounds are useful for short-term (3-10 days) prevention of the inflammatory reaction in inadequately controlled persistent asthma. They also function in a long-term prevention of symptoms in severe persistent asthma to suppress and control and actually reverse inflammation. Some side effects associated with longer term use include adrenal axis suppression, growth suppression, dermal thinning, hypertension, diabetes, Cushing's syndrome, cataracts, muscle weakness, and in rare instances, impaired immune function. It is recommended that these types of compounds be used at their lowest effective dose (guidelines for the diagnosis and management of asthma; expert panel report to; NIH Publication No. 97-4051; July 1997).

The immunomodulators include, but are not limited to, the group consisting of anti-inflammatory agents, leukotriene antagonists, IL-4 muteins, soluble IL-4 receptors, immunosuppressants (such as tolerizing peptide vaccine), anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, and downregulators of IgE.

Leukotriene modifiers are often used for long-term control and prevention of symptoms in mild persistent asthma. Leukotriene modifiers function as leukotriene receptor antagonists by selectively competing for LTD-4 and LTE-4 receptors. These compounds include, but are not limited to, zafirlukast tablets and zileuton tablets. Zileuton tablets function as 5-lipoxygenase inhibitors. These drugs have been associated with the elevation of liver enzymes and some cases of reversible hepatitis and hyperbilirubinemia. Leukotrienes are biochemical mediators that are released from mast cells, inosineophils, and basophils that cause contraction of airway smooth muscle and increase vascular permeability, mucous secretions and activate inflammatory cells in the airways of patients with asthma.

Other immunomodulators include neuropeptides that have been shown to have immunomodulating properties. Functional studies have shown that substance P, for instance, can influence lymphocyte function by specific receptor-mediated mechanisms. Substance P also has been shown to modulate distinct immediate hypersensitivity responses by stimulating the generation of arachidonic acid-derived mediators from mucosal mast cells. McGillies J et al. (1987) *Fed Proc* 46:196-9 (1987). Substance P is a neuropeptide first identified in 1931. Von Euler and Gaddum *J Physiol* (*London*) 72:74-87 (1931). Its amino acid sequence was reported by Chang et al. in 1971. Chang M M et al. (1971) *Nature New Biol* 232:86-87. The immunoregulatory activity of fragments of substance P has been studied by Siemion I Z et al. (1990) *Molec Immunol* 27:887-890 (1990).

Another class of compounds is the down-regulators of IgE. These compounds include peptides or other molecules with the ability to bind to the IgE receptor and thereby prevent binding of antigen-specific IgE. Another type of downregulator of IgE is a monoclonal antibody directed against the IgE receptor-binding region of the human IgE molecule. Thus, one type of downregulator of IgE is an anti-IgE antibody or antibody fragment. Anti-IgE is being developed by Genentech. One of skill in the art could prepare functionally active antibody fragments of binding peptides which have the same function. Other types of IgE downregulators are polypeptides capable of blocking the binding of the IgE antibody to the Fc receptors on the cell surfaces and displacing IgE from binding sites upon which IgE is already bound.

One problem associated with downregulators of IgE is that many molecules do not have a binding strength to the receptor corresponding to the very strong interaction between the native IgE molecule and its receptor. The molecules having this strength tend to bind irreversibly to the receptor. However, such substances are relatively toxic since they can bind covalently and block other structurally similar molecules in the body. Of interest in this context is that the α chain of the IgE receptor belongs to a larger gene family where, e.g., several of the different IgG Fc receptors are contained. These receptors are absolutely essential for the defense of the body against, e.g., bacterial infections. Molecules activated for covalent binding are, furthermore, often relatively unstable and therefore they probably have to be administered several times a day and then in relatively high concentrations in order to make it possible to block completely the continuously renewing pool of IgE receptors on mast cells and basophilic leukocytes.

Chromolyn sodium and nedocromil are used as long-term control medications for preventing primarily asthma symptoms arising from exercise or allergic symptoms arising from allergens. These compounds are believed to block early and late reactions to allergens by interfering with chloride channel function. They also stabilize mast cell membranes and inhibit activation and release of mediators from inosineophils and epithelial cells. A four to six week period of administration is generally required to achieve a maximum benefit.

Anticholinergics are generally used for the relief of acute bronchospasm. These compounds are believed to function by competitive inhibition of muscarinic cholinergic receptors. Anticholinergics include, but are not limited to, ipratropium bromide. These compounds reverse only cholinerigically-mediated bronchospasm and do not modify any reaction to antigen. Side effects include drying of the mouth and respiratory secretions, increased wheezing in some individuals, and blurred vision if sprayed in the eyes.

In addition to standard asthma/allergy medicaments, other methods for treating asthma/allergy have been used either alone or in combination with established medicaments. One preferred, but frequently impossible, method of relieving allergies is allergen or initiator avoidance. Another method currently used for treating allergic disease involves the injection of increasing doses of allergen to induce tolerance to the allergen and to prevent further allergic reactions.

Allergen injection therapy (allergen immunotherapy) is known to reduce the severity of allergic rhinitis. This treatment has been theorized to involve the production of a different form of antibody, a protective antibody which is termed a "blocking antibody". Cooke R A et al. (1935) Serologic Evidence of Immunity with Coexisting Sensitization in a Type of Human Allergy, *Exp Med* 62:733. Other attempts to treat allergy involve modifying the allergen chemically so that its ability to cause an immune response in the patient is unchanged, while its ability to cause an allergic reaction is substantially altered. These methods, however, can take several years to be effective and are associated with the risk of side effects such as anaphylactic shock.

The compositions and methods of the invention can be used to modulate an immune response. The ability to modulate an immune response allows for the prevention and/or treatment of particular disorders that can be affected via immune system modulation.

Treatment after a disorder has started aims to reduce, ameliorate, or altogether eliminate the disorder, and/or its associated symptoms, or prevent it from becoming worse. Treatment of subjects before a disorder has started (i.e., prophylactic treatment) aims to reduce the risk of developing the disorder. As used herein, the term "prevent" refers to the prophylactic treatment of patients who are at risk of developing a disorder (resulting in a decrease in the probability that the subject will develop the disorder), and to the inhibition of further development of an already established disorder.

Different doses may be necessary for treatment of a subject, depending on activity of the compound, manner of administration, purpose of the immunization (i.e., prophylactic or therapeutic), nature and severity of the disorder, age and body weight of the subject. The administration of a given dose can be carried out both by single administration in the form of an individual dose unit or else several smaller dose units. Multiple administration of doses at specific intervals of weeks or months apart is usual for boosting antigen-specific immune responses.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic agent being administered (e.g., in the case of an immunostimulatory nucleic acid, the type of nucleic acid, i.e., a CpG nucleic acid, the number of unmethylated CpG motifs or their location in the nucleic acid, the degree of modification of the backbone to the oligonucleotide, etc.), the size of the subject, or the severity of the disease or condition. One of ordinary skill in the art can empirically determine the effective amount of a particular nucleic acid and/or other therapeutic agent without necessitating undue experimentation.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 0.1 µg to 20 mg/kg/day, more typically from about 1 to 10 mg/kg/day, and most typically from about 1 to 5 mg/kg/day.

The pharmaceutical compositions containing nucleic acids and/or other compounds can be administered by any suitable route for administering medications. A variety of administration routes are available. The particular mode selected will depend, of course, upon the particular agent or agents selected, the particular condition being treated, and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed herein. For use in therapy, an effective amount of the nucleic acid and/or other therapeutic agent can be administered to a subject by any mode that delivers the agent to the desired surface, e.g., mucosal, systemic.

Administering the pharmaceutical composition of the present invention may be accomplished by any means known to the skilled artisan. Routes of administration include but are not limited to oral, parenteral, intravenous, intramuscular, intranasal, sublingual, intratracheal, inhalation, subcutaneous, ocular, vaginal, and rectal. For the treatment or prevention of asthma or allergy, such compounds are preferably inhaled, ingested or administered by systemic routes. Systemic routes include oral and parenteral. Inhaled medications are preferred in some embodiments because of the direct delivery to the lung, the site of inflammation, primarily in asthmatic patients. Several types of devices are regularly used for administration by inhalation. These types of devices include metered dose inhalers (MDI), breath-actuated MDI, dry powder inhaler (DPI), spacer/holding chambers in combination with MDI, and nebulizers.

The therapeutic agents of the invention may be delivered to a particular tissue, cell type, or to the immune system, or both, with the aid of a vector. In its broadest sense, a "vector" is any vehicle capable of facilitating the transfer of the compositions to the target cells. The vector generally transports the immunostimulatory nucleic acid, antibody, antigen, and/or disorder-specific medicament to the target cells with reduced degradation relative to the extent of degradation that would result in the absence of the vector.

In general, the vectors useful in the invention are divided into two classes: biological vectors and chemical/physical vectors. Biological vectors and chemical/physical vectors are useful in the delivery and/or uptake of therapeutic agents of the invention.

Most biological vectors are used for delivery of nucleic acids and this would be most appropriate in the delivery of therapeutic agents that are or that include immunostimulatory nucleic acids.

In addition to the biological vectors discussed herein, chemical/physical vectors may be used to deliver therapeutic agents including immunostimulatory nucleic acids, antibodies, antigens, and disorder-specific medicaments. As used herein, a "chemical/physical vector" refers to a natural or synthetic molecule, other than those derived from bacteriological or viral sources, capable of delivering the nucleic acid and/or other medicament.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vesicles (LUVs), which range in size from 0.2-4.0 µm can encapsulate large macromolecules. RNA, DNA and intact virions can be encapsulated within the aqueous interior and be delivered to cells in a biologically active form. Fraley et al. (1981) *Trends Biochem Sci* 6:77.

Liposomes may be targeted to a particular tissue by coupling the liposome to a specific ligand such as a monoclonal antibody, sugar, glycolipid, or protein. Ligands which may be useful for targeting a liposome to an immune cell include, but are not limited to: intact or fragments of molecules which interact with immune cell specific receptors and molecules, such as antibodies, which interact with the cell surface markers of immune cells. Such ligands may easily be identified by binding assays well known to those of skill in the art. In still other embodiments, the liposome may be targeted to the cancer by coupling it to a one of the immunotherapeutic antibodies discussed earlier. Additionally, the vector may be coupled to a nuclear targeting peptide, which will direct the vector to the nucleus of the host cell.

Lipid formulations for transfection are commercially available from QIAGEN, for example, as EFFECTENE™ (a non-liposomal lipid with a special DNA condensing enhancer) and SUPERFECT™ (a novel acting dendrimeric technology).

Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) *Trends Biotechnol* 3:235-241.

In one embodiment, the vehicle is a biocompatible microparticle or implant that is suitable for implantation or administration to the mammalian recipient. Exemplary bioerodible implants that are useful in accordance with this method are described in PCT International application no. PCT/US/03307 (Publication No. WO95/24929, entitled "Polymeric Gene Delivery System". PCT/US/0307 describes a biocompatible, preferably biodegradable polymeric matrix for containing an exogenous gene under the control of an appropriate promoter. The polymeric matrix can be used to achieve sustained release of the therapeutic agent in the subject.

The polymeric matrix preferably is in the form of a microparticle such as a microsphere (wherein the nucleic acid and/or the other therapeutic agent is dispersed throughout a solid polymeric matrix) or a microcapsule (wherein the nucleic acid and/or the other therapeutic agent is stored in the core of a polymeric shell). Other forms of the polymeric matrix for containing the therapeutic agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used, typically injection into a tissue or administration of a suspension by aerosol into the nasal and/or pulmonary areas. Preferably when an aerosol route is used the polymeric matrix and the nucleic acid and/or the other therapeutic agent are encompassed in a surfactant vehicle. The polymeric matrix composition can be selected to have both favorable degradation rates and also to be formed of a material which is bioadhesive, to further increase the effectiveness of transfer when the matrix is administered to a nasal and/or pulmonary surface that has sustained an injury. The matrix composition also can be selected not to degrade, but rather, to release by diffusion over an extended period of time. In some preferred embodiments, the nucleic acid are administered to the subject via an implant while the other therapeutic agent is administered acutely. Biocompatible microspheres that are suitable for delivery, such as oral or mucosal delivery, are disclosed in Chickering et al. (1996) *Biotech Bioeng* 52:96-101 and Mathiowitz E et al. (1997) *Nature* 386:410-414 and PCT Pat. Application WO97/03702.

Both non-biodegradable and biodegradable polymeric matrices can be used to deliver the nucleic acid and/or the other therapeutic agent to the subject. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months is most desirable, particularly for the nucleic acid agents. The polymer optionally is in the form of a hydrogel that can absorb up to about 90% of its weight in water and further, optionally is cross-linked with multi-valent ions or other polymers.

Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate).

If the therapeutic agent is a nucleic acid, the use of compaction agents may also be desirable. Compaction agents also can be used alone, or in combination with, a biological or chemical/physical vector. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver a nucleic acid in a form that is more efficiently taken up by the cell or, more preferably, in combination with one or more of the above-described vectors.

Other exemplary compositions that can be used to facilitate uptake of a nucleic acid include calcium phosphate and other chemical mediators of intracellular transport, microinjection compositions, electroporation and homologous recombination compositions (e.g., for integrating a nucleic acid into a preselected location within the target cell chromosome).

The compounds may be administered alone (e.g., in saline or buffer) or using any delivery vectors known in the art. For instance the following delivery vehicles have been described: cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); liposomes (Childers et al., 1999, Michalek et al., 1989, 1992, de Haan 1995a, 1995b); live bacterial vectors (e.g., *Salmonella, Escherichia coli, Bacillus calmatte-guerin, Shigella, Lactobacillus*) (Hone et al., 1996, Pouwels et al., 1998, Chatfield et al., 1993, Stover et al., 1991, Nugent et al., 1998); live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); microspheres (Gupta et al., 1998, Jones et al., 1996, Maloy et al., 1994, Moore et al., 1995, O'Hagan et al., 1994, Eldridge et al., 1989); nucleic acid vaccines (Fynan et al., 1993, Kuklin et al., 1997, Sasaki et al., 1998, Okada et al., 1997, Ishii et al., 1997); polymers (e.g. carboxymethylcellulose, chitosan) (Hamajima et al., 1998, Jabbal-Gill et al., 1998); polymer rings (Wyatt et al., 1998); proteosomes (Vancott et al., 1998, Lowell et al., 1988, 1996, 1997); sodium fluoride (Hashi et al., 1998); transgenic plants (Tacket et al., 1998, Mason et al., 1998, Haq et al., 1995); virosomes (Gluck et al., 1992, Mengiardi et al., 1995, Cryz et al., 1998); and, virus-like particles (Jiang et al., 1999, Leibl et al., 1998).

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

For oral administration, the compounds (i.e., nucleic acids, antigens, antibodies, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) *Science* 249:1527-1533, which is incorporated herein by reference.

The nucleic acids and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The invention also provides efficient methods of identifying immunostimulatory compounds and optimizing the compounds and agents so identified. Generally, the screening methods involve assaying for compounds which inhibit or enhance signaling through a particular TLR. The methods employ a TLR, a suitable reference ligand for the TLR, and a candidate immunostimulatory compound. The selected TLR is contacted with a suitable reference compound (TLR ligand) and a TLR-mediated reference signal is measured. The selected TLR is also contacted with a candidate immunostimulatory compound and a TLR-mediated test signal is measured. The test signal and the reference signal are then compared. A favorable candidate immunostimulatory compound may subsequently be used as a reference compound in the assay. Such methods are adaptable to automated, high throughput screening of candidate compounds. Examples of such high throughput screening methods are described in U.S. Pat. Nos. 6,103,479; 6,051,380; 6,051,373; 5,998,152; 5,876,946; 5,708,158; 5,443,791; 5,429,921; and 5,143,854.

As used herein "TLR signaling" refers to an ability of a TLR polypeptide to activate the Toll/IL-1R (TIR) signaling pathway, also referred to herein as the TLR signal transduction pathway. Changes in TLR activity can be measured by assays designed to measure expression of genes under control of κB-sensitive promoters and enhancers. Such genes can be naturally occurring genes or they can be genes artificially introduced into a cell. Naturally occurring reporter genes include the genes encoding IL-1β, IL-6, IL-8, the p40 subunit of interleukin 12 (IL-12 p40), and the costimulatory molecules CD80 and CD86. Other genes can be placed under the control of such regulatory elements and thus serve to report the level of TLR signaling.

The assay mixture comprises a candidate immunostimulatory compound. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate immunostimulatory compounds may encompass numerous chemical classes, although typically they are organic compounds. In some embodiments, the candidate immunostimulatory compounds are small RNAs or small organic compounds, i.e., organic compounds having a molecular weight of more than 50 yet less than about 2500 Daltons. Polymeric candidate immunostimulatory compounds can have higher molecular weights, e.g., oligonucleotides in the range of about 2500 to about 12,500. Candidate immunostimulatory compounds also may be biomolecules such as nucleic acids, peptides, saccharides, fatty acids, sterols, isoprenoids, purines, pyrimidines, derivatives or structural analogs of the above, or combinations thereof and the like. Where the candidate immunostimulatory compound is a nucleic acid, the candidate immunostimulatory compound typically is a DNA or RNA molecule, although modified nucleic acids having non-natural bonds or subunits are also contemplated.

Candidate immunostimulatory compounds may be obtained from a wide variety of sources, including libraries of natural, synthetic, or semisynthetic compounds, or any combination thereof. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc., to produce structural analogs of the candidate immunostimulatory compounds.

A variety of other reagents also can be included in the mixture. These include reagents such as salts, buffers, neutral proteins (e.g., albumin), detergents, etc., which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, anti-microbial agents, and the like may also be used.

The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C., more typically about 37° C. Incubation times preferably are minimized to facilitate rapid, high throughput screening, and typically are between 1 minute and 10 hours.

After incubation, the level of TLR signaling is detected by any convenient method available to the user. For cell-free binding type assays, a separation step is often used to separate bound from unbound components. The separation step may be accomplished in a variety of ways. For example, separation can be accomplished in solution, or, conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal-to-noise ratios, primarily to minimize background binding, as well as for ease of separation and cost.

Separation may be effected, for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as measurement of an induced polypeptide within, on the surface of, or secreted by the cell. Examples of detection methods useful in cell-based assays include fluorescence-activated cell sorting (FACS) analysis, bioluminescence, fluorescence, enzyme-linked immunosorbent assay (ELISA), reverse transcriptase-polymerase chain reaction (RT-PCR), and the like. Examples of detection methods useful in cell-free assays include bioluminescence, fluorescence, ELISA, RT-PCR, and the like.

EXAMPLES

Example 1

Responsiveness of Human PBMC to G,U-Containing Oligoribonucleotides

Human peripheral blood mononuclear cells (PBMCs) were isolated from healthy donors, plated at $3\times10^5$ cells/well, stimulated in vitro with various test and control immunostimulatory agents for 16 hours, and then analyzed by enzyme-linked immunosorbent assay (ELISA) using matched antibody pairs from BD-Pharmingen for secreted cytokines IL-12 p40 and TNF-α, performed according to the manufacturer's protocol. Also included were certain negative controls, including medium alone and DOTAP (10 μg/200 μl culture well; "Liposomes") alone. The control immunostimulatory agents included the imidazoquinolone R-848 (2 μg/ml), lipopolysaccharide (LPS; 1 μg/ml), Pam3Cys (5 μg/ml), poly IC (50 μg/ml), and CpG DNA (50 μg/ml). These are reported ligands for TLR7, TLR4, TLR2, TLR3, and TLR9, respectively. Test immunostimulatory agents included the following RNA molecules, each at 50 μg/ml, with and without DOTAP (10 μg total "with Liposomes" and "without Liposomes", respectively): GUGUUUAC alone; GUAGGCAC alone; GUGUUUAC in combination with GUAGGCAC; GUAGGA; GAAGGCAC; CUAGGCAC; CUCGGCAC; and CCCCCCCC. These RNA oligonucleotides each contained a phosphorothioate linkage between the penultimate and 3' terminal nucleoside.

FIG. 1 depicts the responsiveness of human PBMC to the test and control agents listed above, as measured by secreted amounts of IL-12 p40 (pg/ml). As can be seen in FIG. 1, PBMCs were responsive to R-848, LPS, Pam3Cys, and poly IC, while they were unresponsive to DOTAP alone. Significantly, human PBMC secreted large amounts of IL-12 p40 (10-20 ng/ml) in response to G,U-containing RNA oligonucleotides GUGUUUAC alone; GUAGGCAC alone; GUGUUUAC in combination with GUAGGCAC; CUAGGCAC; and CUCGGCAC, each in combination with DOTAP. Also significantly, human PBMC did not secrete significant amounts of IL-12 p40 in response to G,U-free RNA oligonucleotides GAAGGCAC and CCCCCCCC. The immunostimulatory effect of the G,U-containing RNA molecules appeared to be greatly enhanced by the inclusion of DOTAP. In this experiment, the G,U-containing 6-mer RNA GUAGGA appeared to exert little, if any immunostimulatory effect either with or without DOTAP.

Figure 2:
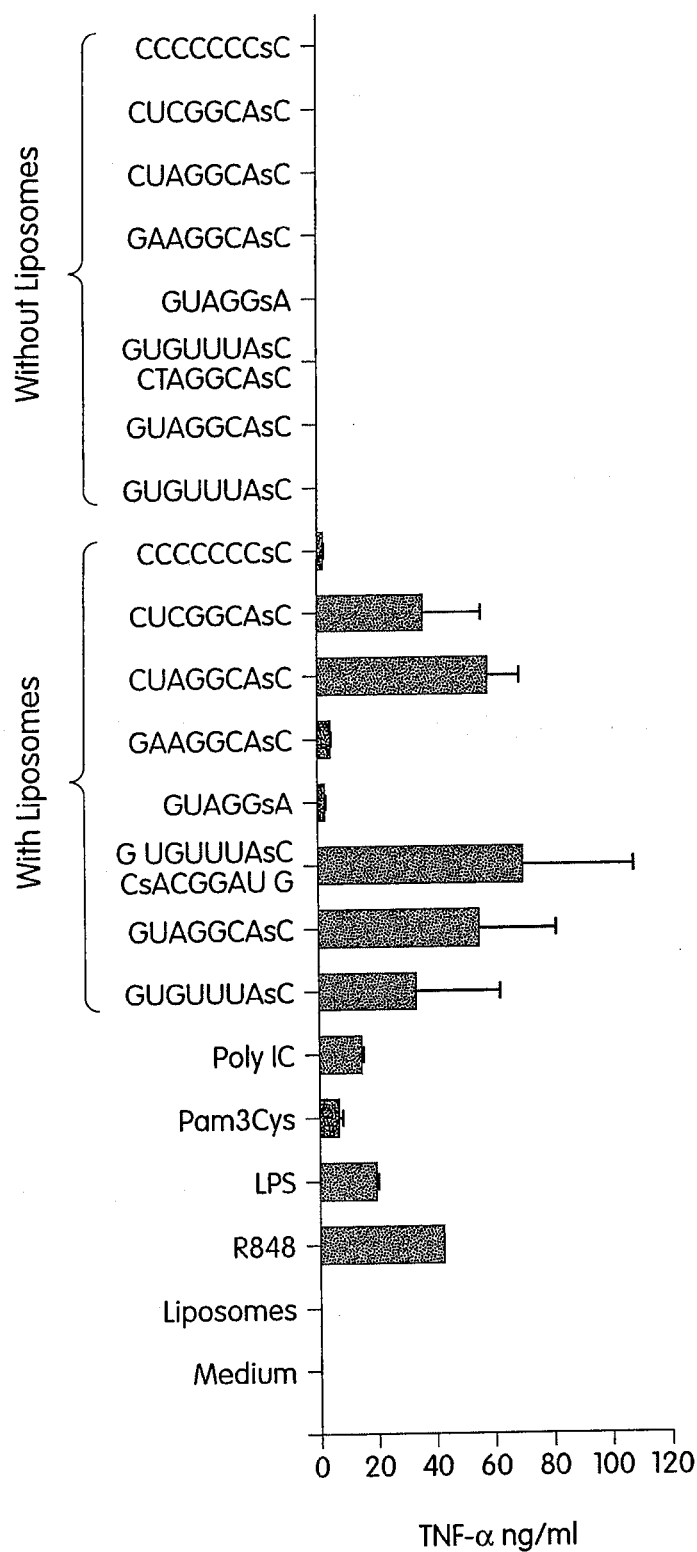
FIG. 2 is a bar graph depicting TNF-α secretion by human PBMCs in response to certain stimuli including selected G,U-containing RNA oligonucleotides with or without DOTAP ("with Liposomes" and "without Liposomes", respectively), as measured by specific ELISA.

FIG. 2 depicts the responsiveness of human PBMC to the test and control agents listed above, as measured by secreted amounts of TNF-α. A similar pattern of results was observed as in FIG. 1, i.e., human PBMC secreted large amounts of TNF-α (40-100 ng/ml) in response to G,U-containing RNA oligonucleotides GUGUUUAC alone; GUAGGCAC alone; GUGUUUAC in combination with GUAGGCAC; CUAGGCAC; and CUCGGCAC, each in combination with DOTAP. Also similar to the results in FIG. 1, human PBMC did not secrete significant amounts of TNF-α in response to G,U-free RNA oligonucleotides GAAGGCAC and CCCCCCCC, or in response to the G,U-containing 6-mer RNA GUAGGA. The immunostimulatory effect of the G,U-containing RNA molecules appeared to be greatly enhanced by the inclusion of DOTAP.

It will be appreciated in this example that the following partial self-complementarity basepairing is possible, where G-U wobble basepairs are shown joined with a dot and G-C and A-U basepairs are shown joined by a line:

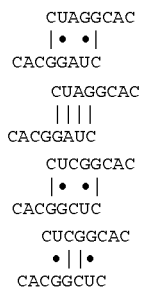

Example 2

Dose-Response Behavior of Human PBMC to G,U-Containing Oligoribonucleotides The experiments described in the preceding example were repeated with varied concentrations of RNA oligonucleotides in order to assess the dose-response behavior of human PBMCs to G,U-containing RNA oligonucleotides of the invention. A total of 10, 3 or 1 µg RNA was added to 10 µg DOTAP and then added to the 200 µl culture wells. After 16 hours IL-12 p40 and TNF-α ELISAs were performed as described in Example 1.

Figure 3:
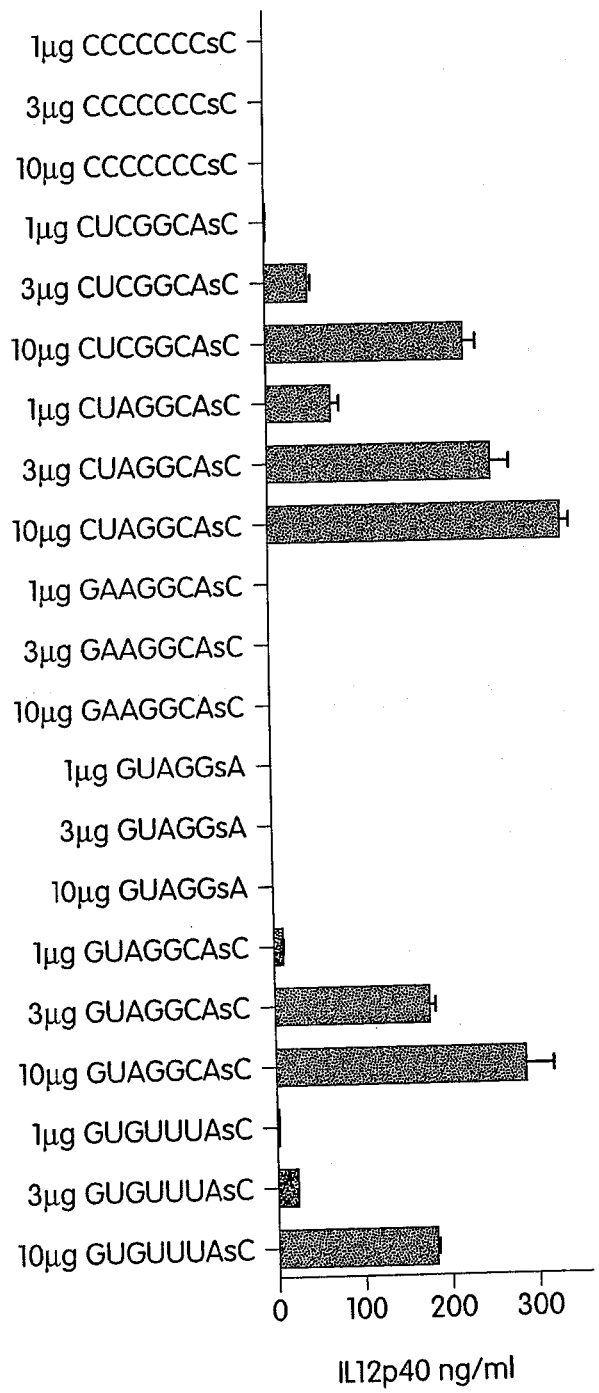
FIG. 3 is a bar graph depicting dose-dependence of IL-12 p40 secretion by human PBMCs in response to various concentrations of selected G,U-containing RNA oligonucleotides (with DOTAP), as measured by specific ELISA.

FIG. 3 depicts the dose-response of human PBMC to the various RNAs as measured by secreted amounts of IL-12 p40 (ng/ml). As can be seen from FIG. 3, human PBMC secreted increasing amounts of IL-12 p40 in response to increasing amounts of G,U-containing RNA oligomers GUGUUUAC; GUAGGCAC; CUAGGCAC; and CUCGGCAC, each in combination with DOTAP. Conversely, FIG. 3 also shows that human PBMC appeared not to secrete IL-12 p40 in response to any of the tested amounts of G,U-free RNA oligomers GAAGGCAC or CCCCCCCC.

Corresponding dose-response of human PBMC to the various RNAs was measured by secreted amounts of TNF-α. A similar pattern of results was observed as in FIG. 3, i.e., human PBMC secreted increasing amounts of TNF-α in response to increasing amounts G,U-containing RNA oligonucleotides GUGUUUAC; GUAGGCAC; CUAGGCAC; and CUCGGCAC, each in combination with DOTAP. Also similar to the results in FIG. 3, human PBMC did not appear to secrete significant amounts of TNF-α in response to any of the tested amounts of G,U-free RNA oligonucleotides GAAGGCAC and CCCCCCCC.

Example 3

Base Sequence Sensitivity of RNA Oligomers

Figure 4:
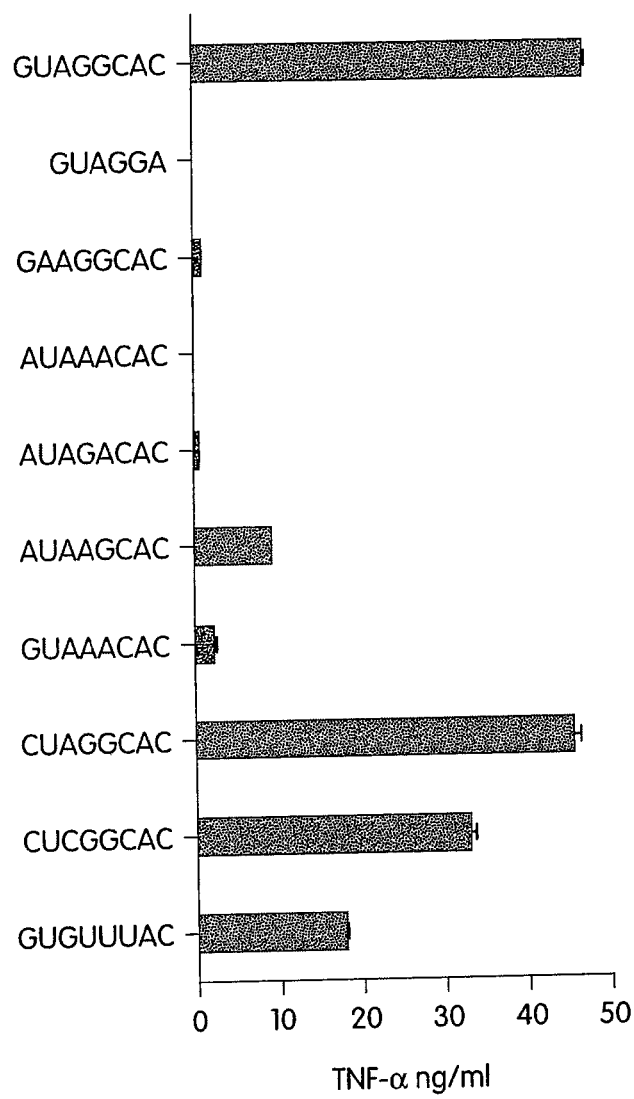
FIG. 4 is a bar graph depicting sequence dependence of TNF-α secretion by human PBMCs in response to various selected RNA oligonucleotides related to the RNA oligonucleotide GUAGGCAC (with DOTAP), as measured by specific ELISA.

Point mutations were made to the RNA oligonucleotide GUAGGCAC by substituting A or C at selected positions. The various oligoribonucleotides included the following: GUAGGCAC; GUAGGA; GAAGGCAC; AUAAACAC; AUAGACAC; AUAAGCAC; GUAAACAC; CUAGGCAC; CUCGGCAC; and GUGUUUAC. The oligonucleotides were titrated onto human PBMC isolated from healthy donors and plated at 3×10⁵ cells/well. A total of 10 µg RNA was added to 10 µg DOTAP and then added to the 200 µl culture wells. Human TNF-α was measured by ELISA using matched antibody pairs from BD-Pharmingen according to the manufacturer's protocol. Results are shown in FIG. 4.

Example 4

Effect of DOTAP on Human PBMC Response to Various Stimuli

In order to characterize further the role of DOTAP in the immunostimulatory effects of the G,U-containing RNA oligomers observed in the previous examples, human PBMCs were isolated from healthy donors, plated at 3×10⁵ cells/well, and stimulated in the presence of known TLR ligands, either with or without DOTAP ("with Liposomes" or "without Liposomes", respectively). The known TLR ligands examined were total RNA prepared from hyphae (hyphae), total RNA prepared from yeast (yeast), total RNA prepared from promyelocytic cell line HL-60 (HL60), in vitro transcribed ribosomal RNA for *E. coli* Sp6, in vitro transcribed ribosomal RNA for *E. coli* T7, LPS, poly IC, Pam3Cys, and R-848. Medium alone and DOTAP alone were used as negative controls. The panel of RNAs from the previous examples, again at 10 µg/ml and without DOTAP, was also included.

Total RNA was isolated from the human promyelocytic cell line HL-60 using Trizol (Sigma). Prior to isolation, cells were treated for 4 hours with 500 µM hydrogen peroxide (H₂O₂), which induces apoptosis in this cell line (HL60 500). Untreated cells served as control (HL60 0).

*Candida albicans* RNA was isolated from yeast or hyphae (induced by 4 h incubation with 10% fetal calf serum). Cells from a 100 ml culture were pelleted, washed and resuspended in 10 ml of Tris/EDTA buffer (10 mM, 1 mM). RNA was isolated by extraction with hot acidic phenol according to methods described in Ausubel F M et al., eds., *Current Protocols in Molecular Biology*, John Wiley & Sons, New York.

The genomic fragment of *E. coli* 16S RNA was amplified with the primers 5'-ATTGAAGAGTTTGATCATGGCTCA-GATTGAACG-3' (SEQ ID NO:5) and 5'-TAAGGAGGT-GATCCAACCGCAGGTTCC-3' (SEQ ID NO:6) from genomic *E. coli* DNA and cloned into the pGEM T easy vector. In vitro transcription was performed using T7 or Sp6 RNA polymerase. Transcribed RNA was further purified by chloroform/phenol extraction, precipitated, and used at 10 µg.

Following 16 hour incubation, ELISAs were performed as before to assess secretion of IL-12 p40 and TNF-α. Representative results are shown in FIG. 5.

Figure 5:
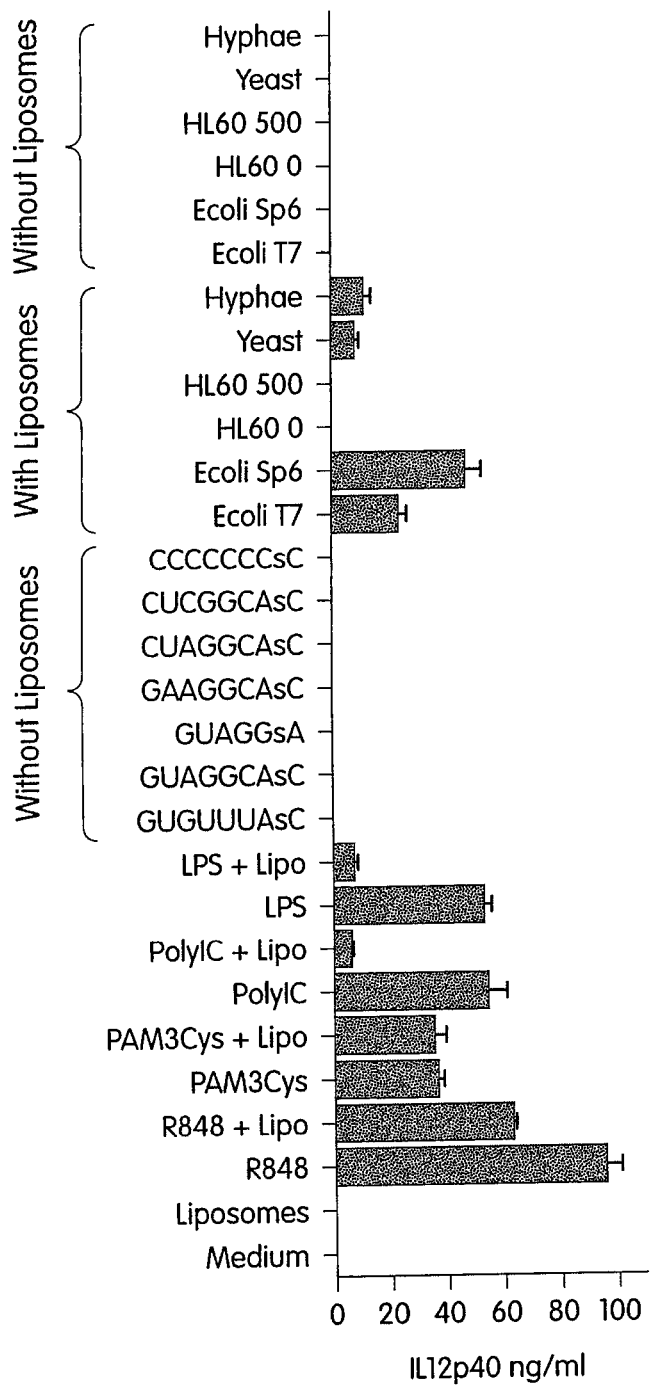
FIG. 5 is a bar graph depicting the effect of DOTAP on IL-12 p40 secretion by human PBMCs in response to various stimuli, as measured by specific ELISA.
Figure 6A:
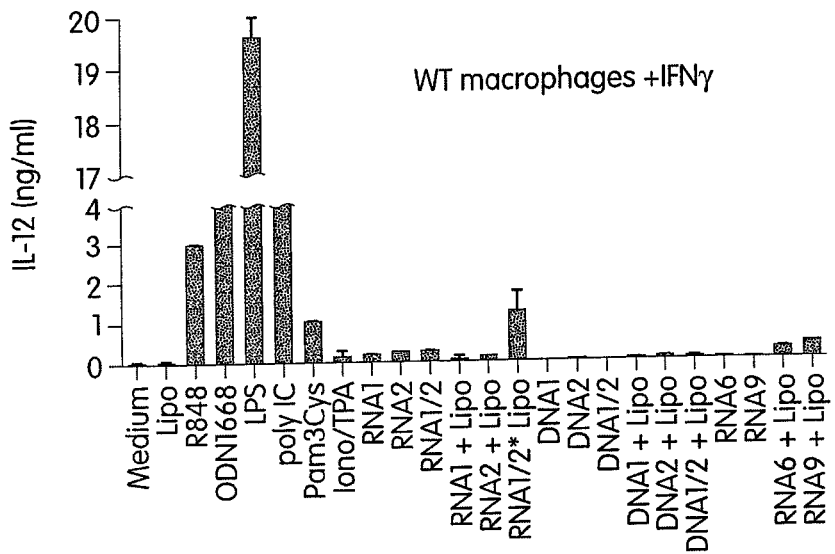
FIG. 6 is a quartet of bar graphs depicting IL-12 p40 secretion by various types of murine macrophage cells in response to a variety of test and control immunostimulatory compounds, as measured by specific ELISA. Panel A, wild type macrophages in the presence of IFN-γ; Panel B, MyD88-deficient macrophages in the presence of IFN-γ; Panel C, J774 macrophage cell line; Panel D, RAW 264.7 macrophage cell line.
Figure 6B:
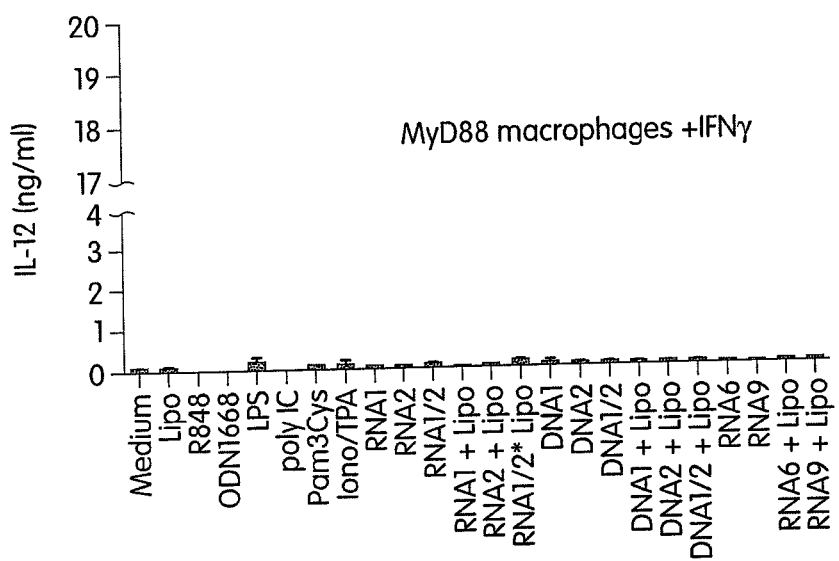
Figure 6C:
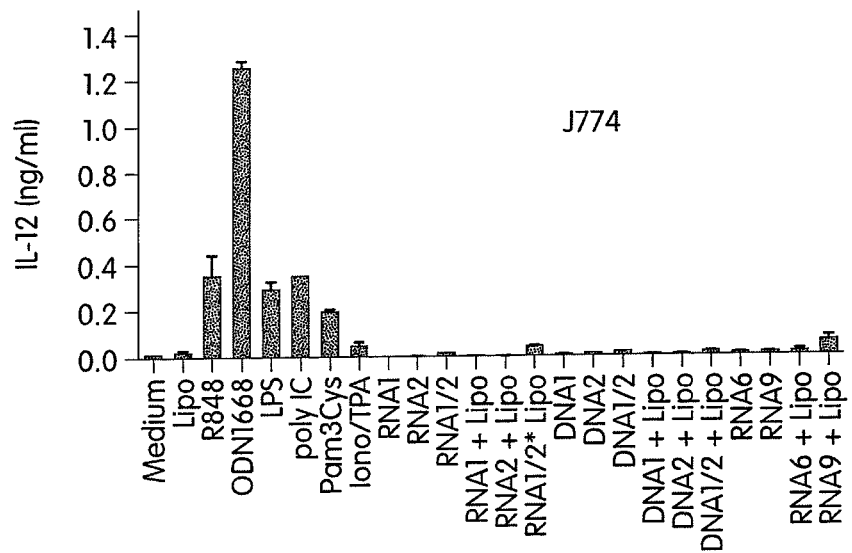
Figure 6D:
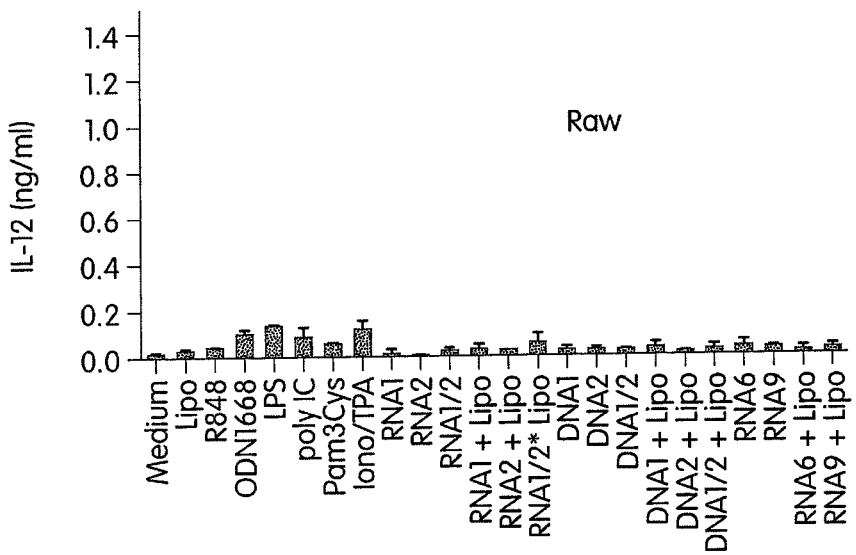

FIG. 5 depicts the effect of DOTAP on the amount of IL-12 p40 secreted by human PBMC following incubation with and without DOTAP. As can be seen from the figure, the following stimuli appeared to exert greater immunostimultory effect in the presence of DOTAP than in its absence: hyphae, yeast, *E. coli* Sp6, and *E. coli* T7. The following stimuli appeared to exert reduced immunostimultory effect in the presence of DOTAP than in its absence: LPS, poly IC. The following stimuli appeared to exert about the same immunostimultory effect in the presence or absence of DOTAP: HL60, Pam3Cys and R-848.

Example 5

Immunostimulatory Effect of G,U-Containing RNA Oligomers is Species- and MyD88-Dependent The following murine cells were isolated and incubated with various RNAs and other known TLR ligands in order to assess species-, cell type-, and signaling pathway-specificity: wild type macrophages in the presence of IFN-γ; MyD88-deficient macrophages in the presence of IFN-γ; J774 (mouse macrophage cell line); and RAW 264.7 (mouse macrophage cell line, e.g., ATCC TIB-71). Murine bone macrophages were generated from wild type or MyD88-deficient C57BL/6 mice by culturing bone marrow cells with 50 ng/ml M-CSF for 5 days. Cells were seeded at 25,000 cells/well and treated with 20 ng/ml IFN-γ for 16 hours. The murine macrophage cell lines RAW and J774 were seeded at 10,000 cells/well.

The following test and control agents were examined: R-848 (2 µg/ml), ODN 1668 (CpG DNA; 5'-TCCAT-GACGTTCCTGATGCT-3'; SEQ ID NO:7); LPS (1 µg/ml); poly IC (50 µg/ml); Pam3Cys (5 µg/ml); Ionomycin/TPA; the following RNA molecules, each with ("+Lipo") and without DOTAP (10 µg/200 µl culture well): GUGUUUAC alone (RNA1); GUAGGCAC alone (RNA2); GUGUUUAC in combination with GUAGGCAC (RNA1/2); UCCG-CAAUGGACGAAAGUCUGACGGA (RNA6; SEQ ID NO:8); GAGAUGGGUGCGAGAGCGUCAGUAUU (RNA9; SEQ ID NO:9); and the following DNA molecules, corresponding to RNA1, RNA2, and RNA1/2: GTGTTTAC alone (DNA1); GTAGGCAC alone (DNA2); and GTGTT-TAC in combination with GTAGGCAC (DNA1/2). These RNA and DNA oligonucleotides each contained a phosphorothioate linkage between the penultimate and 3' terminal nucleoside. RNA6 and RNA9 each contained in addition a phosphorothioate linkage between the penultimate and 5' terminal nucleoside. RNA6 corresponds to a ribosomal RNA stem loop derived from *Listeria monocytogenes*. RNA9 corresponds to a stem loop derived from human immunodeficiency virus (HIV, an RNA retrovirus). The cells were cultured for 12 hours and supernatants were harvested. Murine IL-12 p40, IL-6, and TNF-α were measured by ELISA using matched antibody pairs from BD-Pharmingen according to the manufacturer's protocol. Representative results are shown in FIG. 6.

Panel A of FIG. 6 shows that wild type murine macrophages in the presence of IFN-γ secrete significant amounts of IL-12 p40 in response to R-848; ODN 1668 (CpG DNA); LPS; poly IC; Pam3Cys; and G,U-containing RNA oligomers GUGUUUAC in combination with GUAGGCAC (with DOTAP). In contrast, Panel B of FIG. 6 shows that MyD88-deficient murine macrophages in the presence of IFN-γ secrete little or no IL-12 p40 in response to any of the test and control agents examined, thus demonstrating a dependence on MyD88 for immunostimulatory response to these compounds. Such a result is consistent with participation by a TLR in the immunostimulatory response to any of these compounds, including in particular the G,U-containing RNA oligonucleotides of the invention. Panels C and D of FIG. 6 show generally similar, if somewhat attenuated, response patterns of J774 and RAW 264.7 mouse macrophage cell lines as for wild type murine macrophages in the presence of IFN-γ, as shown in Panel A. Essentially similar results were found in parallel ELISAs measuring IL-6 and TNF-α.

In additional studies involving MyD88 wild-type cells, it was observed that addition of bafilomycin largely or completely abrogated the immunostimulatory effect of the RNA oligomers. Together with the MyD88-dependence, this observation is consistent with involvement of at least one of TLR3, TLR7, TLR8, and TLR9.

Example 6

Use of Cholesteryl Ester in Place of Cationic Lipid

In order to investigate the possibility of using cholesteryl ester-modified RNA oligomer in place of RNA oligomer plus cationic lipid, RNA oligomer GUGUGUGU was prepared with (R 1058) and without (R 1006) a 3' cholesteryl ester modification. These two RNA oligomers with and without DOTAP, were added over a range of concentrations to overnight cultures of human PBMC. Culture supernatants were harvested, and human TNF-α, IL-12 p40, and IFN-α were measured by ELISA using matched antibody pairs from BD-Pharmingen according to the manufacturer's protocol. Representative results for experiments including DOTAP are shown in Table 1.

TABLE 1

| Cholesteryl Ester Modification in Place of DOTAP | | | | | | | |
|---|---|---|---|---|---|---|---|
| | TNF-α + DOTAP | | TNF-α − DOTAP | | IFN-α + DOTAP | | IFN-α − DOTAP |
| ID | EC50 µM | max pg/ml | EC50, µM | max pg/ml | EC50 µM | max pg/ml | EC50 µM | max pg/ml |
| R 1006 | 2.8 | 40000 | 7.8 | 2200 | 4.5 | 5000 | — | — |
| R 1058 | 0.2 | 75000 | 1.0 | 3000 | 0.5 | 3800 | 0.5 | 1500 |

The results indicate that R 1058, with the cholesteryl ester modification, is more potent than R 1006, having the same base sequence but without cholesterol, both with and without DOTAP.

Example 7

Effect of Oligomer Length

RNA oligomers GUGUGUGU, GUGUGUG, GUGUGU, GUGUG, GUGU, GUG, and GU, with and without DOTAP, were added over a range of concentrations to overnight cultures of human PBMC. Culture supernatants were harvested, and human TNF-α, IL-12 p40, and IFN-α were measured by ELISA using matched antibody pairs from BD-Pharmingen according to the manufacturer's protocol. Representative results for experiments including DOTAP are shown in Table 2.

TABLE 2

Effect of RNA Oligomer Length

| ID | SEQ | TNF-α EC50, μM | TNF-α max pg/ml | IL-12 p40 EC50, μM | IL-12 p40 max pg/ml | IFN-α EC50, μM | IFN-α max pg/ml |
|---|---|---|---|---|---|---|---|
| R 1006 | GUGUGUGU | 2.8 | 40000 | 1.6 | 7000 | 4.5 | 5000 |
| R 1048 | GUGUGUG | 2.2 | 30000 | 2.6 | 10000 | 4.6 | 2700 |
| R 1049 | GUGUGU | 6.7 | 30000 | 2.1 | 8000 | 4.8 | 3400 |
| R 1050 | GUGUG | 7.6 | 40000 | 3.9 | 14000 | 6.9 | 400 |
| R 1051 | GUGU | — | — | >20 | 14000 | — | — |
| R 1052 | GUG | — | — | >20 | 6000 | 5.5 | 800 |
| R 1053 | GU | — | — | >20 | 5000 | — | — |

Example 8

Effect of Stabilization of Internucleoside Linkages

GUGUGUGU RNA oligomers were synthesized with specific phosphorothioate and phosphodiester linkages as shown in Table 2, where "*" represents phosphorothioate and "_" represents phosphodiester. RNA oligomers, with and without DOTAP, were added over a range of concentrations to overnight cultures of human PBMC. Culture supernatants were harvested, and human TNF-α, IL-12 p40, and IFN-α were measured by ELISA using matched antibody pairs from BD-Pharmingen according to the manufacturer's protocol. Representative results for experiments including DOTAP are shown in Table 3.

TABLE 3

Effect of Stabilization of Internucleoside Linkages

| ID | SEQ | TNF-α EC50, μM | TNF-α max, pg/ml | IFN-α EC50, μM | IFN-α max, pg/ml |
|---|---|---|---|---|---|
| R 1006 | G*U*G*U*G*U*G*U | 2.8 | 40000 | 4.5 | 5000 |
| R 1054 | G*U_G*U*G*U*G*U | 5.6 | 40000 | 6.7 | 3700 |
| R 1055 | G*U_G*U_G*U*G*U | >20 | 20000 | — | — |
| R 1056 | G*U_G*U_G*U_G*U | >20 | 12000 | — | — |
| R 1057 | G_U_G_U_G_U_G_U | — | — | 0.1 | 6000 |

In like manner, an all-phosphodiester 40-mer capable of forming a stem-loop structure and having a base sequence as provided by 5'-CACACACUGCUUAAGCGCUUGC-CUGCUUAAGUAGUGUGUG-3' (R 1041; SEQ ID NO:10) was synthesized and tested in overnight culture with human PBMC. This RNA oligomer was found to be very potent in its ability to induce IFN-α, with an EC50 of <0.1 μM and a maximum of 5000 pg/ml.

Example 9

DNA:RNA Conjugates

A series of DNA:RNA conjugates, each containing the RNA sequence GUGUGUGU and a poly-dT or a poly-dG sequence, was prepared. The oligomers were as follows, where again "*" represents phosphorothioate and "_" represents phosphodiester:

```
                                    (R 1060; SEQ ID NO: 11)
G*U*G*U*G*U*G*U_dG_dG*dG*dG*dG*dG (R 1061; SEQ ID NO: 12)
dG*dG*dG*dG_dG_G*U*G*U*G*U*G*U (R 1062; SEQ ID NO: 13)
G*U*G*U*G*U*G*U*dT*dT*dT*dT*dT*dT (R 1063; SEQ ID NO: 14)
dT*dT*dT*dT*dT*G*U*G*U*G*U*G*U
```

Human PBMC were cultured overnight in the presence of added DNA:RNA conjugate, with and without DOTAP. Culture supernatants were harvested and human TNF-α, IL-6, IL-12 p40, IP-10, and IFN-α were measured by ELISA using matched antibody pairs from BD-Pharmingen according to the manufacturer's protocol. Representative results for experiments including DOTAP are shown in Table 4.

TABLE 4

Immunostimulatory DNA:RNA Conjugates

| ID | TNF-α EC50, μM | TNF-α max pg/ml | IL-6 EC50, μM | IL-6 max pg/ml | IP-10 EC50, μM | IP-10 max pg/ml |
|---|---|---|---|---|---|---|
| R 1060 | 4.9 | 20000 | — | — | — | — |
| R 1061 | 4.3 | 20000 | >20 | 10000 | 1.1 | 180 |

TABLE 4-continued

Immunostimulatory DNA:RNA Conjugates

| | TNF-α | | IL-6 | | IP-10 | |
|---|---|---|---|---|---|---|
| ID | EC50, µM | max pg/ml | EC50, µM | max pg/ml | EC50, µM | max pg/ml |
| R 1062 | 0.3 | 80000 | 0.4 | 28000 | 0.1 | 400 |
| R 1063 | 0.3 | 60000 | 0.8 | 28000 | 0.1 | 250 |

Example 10

Transfer RNA

Human PBMC were cultured overnight in the presence of various concentrations (1, 3, and 10 µg/ml) of tRNA obtained from wheat germ, bovine, yeast, and *E. coli* sources, added to the culture medium with and without DOTAP. Culture supernatants were harvested and human TNF-α and IL-12 p40 were measured by ELISA using matched antibody pairs from BD-Pharmingen according to the manufacturer's protocol. Yeast and *E. coli* tRNAs, and to a lesser extent bovine tRNA, induced TNF-α and IL-12 p40 when DOTAP was also present. In addition, *E. coli* tRNA at 3 and 10 µg/ml induced minor amounts of both cytokines even without DOTAP.

Example 11

HIV RNA

Figure 7A:
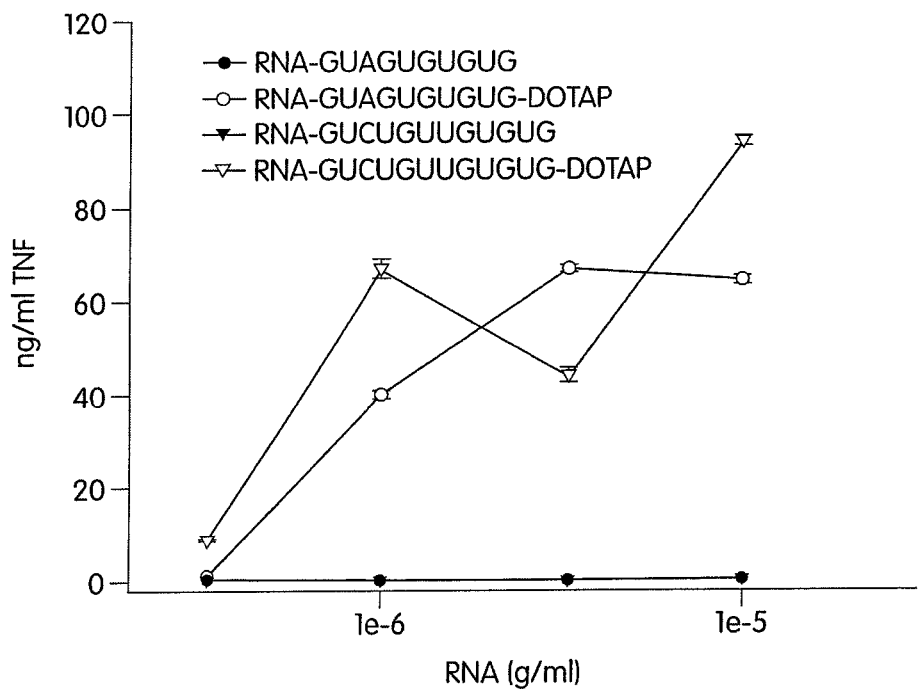
FIG. 7 is a pair of graphs depicting the secretion of (A) TNF-α and (B) IL-12 p40 by human PBMC upon incubation with HIV-1-derived RNA sequences, with and without DOTAP. Circles, 5'-GUAGUGUGUG-3' (SEQ ID NO:2); Triangles, 5'-GUCUGUUGUGUG-3' (SEQ ID NO:3). Open symbols, without DOTAP; closed symbols, with DOTAP.
Figure 7B:
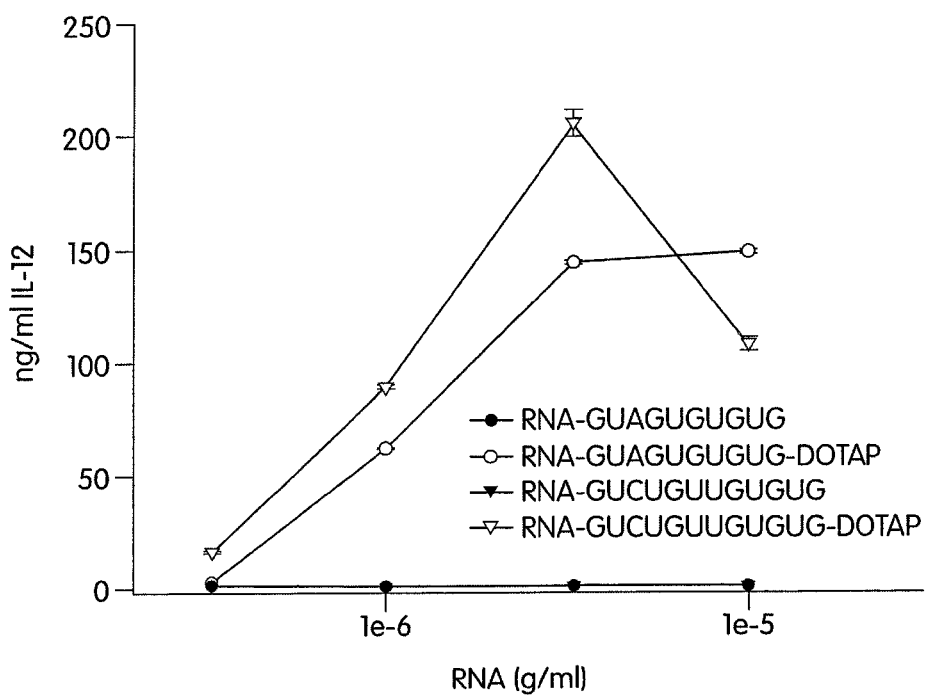

Human PBMC were incubated overnight with either of two key G,U-rich sequences, namely 5'-GUAGUGUGUG-3' (SEQ ID NO:2) and 5'-GUCUGUUGUGUG-3' (SEQ ID NO:3), corresponding to nt 99-108 and 112-123 of HIV-1 strain BH10, respectively, each with and without DOTAP. Culture supernatants were harvested, and human IL-12 p40 and TNF-α were measured by ELISA using matched antibody pairs from BD-Pharmingen according to the manufacturer's protocol. Representative results are shown in FIG. 7. The figure shows that both of these RNA molecules, at micromolar concentrations in the presence of DOTAP, induced 50-100 ng/ml of TNF and 50-200 ng/ml of IL-12 p40.

Example 12

Responsiveness of Human PBMC to Stringent Response Factor

When bacteria are starved they enter into a programmed response termed the stringent response. This involves the production of nucleic acid alarmones and ribosomal loss. Bacteria growing at high rates contain 70,000-80,000 ribosomes accounting for as much as 50% of their dry weight. As growth slows, unneeded ribosomes are hydrolyzed. It was hypothesized that rapidly growing cells in their early stationary phase contain large amounts of oligoribonucleotides that are released into the media when the cells enter a neutral pH environment.

Figure 10:
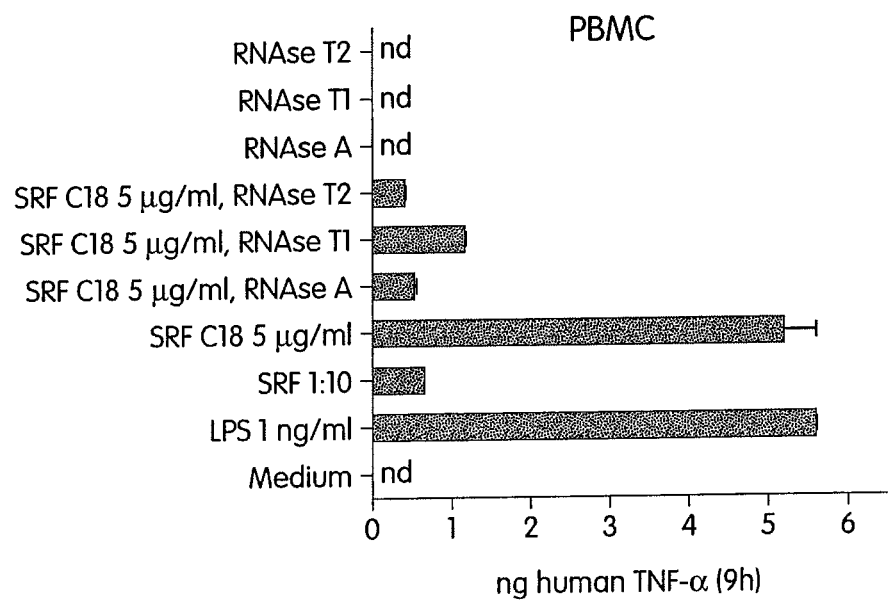
FIG. 10 is a bar graph depicting responsiveness of human PBMC to stringent response factor (SRF).

FIG. 10 depicts the responsiveness of human PBMC to stringent response factor (SRF). SRF is produced by rapidly growing bacteria (in this case *Listeria monocytogenes*) in rich media until their late log phase. The bacteria were pelleted and resuspended in an equal volume of PBS for 24 h. The mixture is centrifuged to remove the bacteria. The supernatant is sterilized by passing it through a 0.2 µm filter. The sterilized solution was passed through a molecular filter with a cutoff of 10 kDa. This fraction was separated on a C18 column and the eluant was tested. At a concentration of 5 µg/ml SRF induced TNF from human PBMC. If SRF was treated with any of three RNAses the activity was destroyed. The activity was not due to substances other than RNA because the RNase-treated SRF had near background stimulatory ability. This implied activity was due to RNA.

Example 13

Responsiveness of Human PBMC to Ribonucleoside Vanadyl Complexes

During studies of SRF it was surprisingly determined that the RNAse inhibitor, ribonucleoside vanadyl complexes (RVCs), could stimulate human PBMC to produce TNF (FIG. 11) and IL-6.

Figure 11:
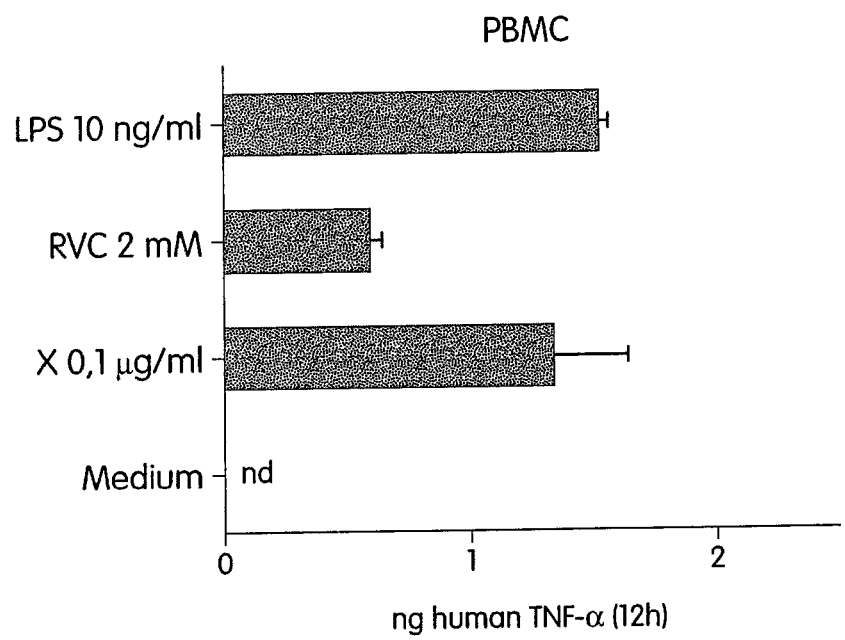
FIG. 11 is a bar graph depicting responsiveness of human PBMC to the ribonucleoside vanadyl complexes (RVCs). X denotes resiquimod.

FIG. 11 depicts the responsiveness of human PBMC to the ribonucleoside vanadyl complexes (RVCs). It was unexpectedly discovered during testing of RNAse inhibitors that RVCs were stimulatory for human PBMC. 2 mM RVC induced the release of substantial TNF. Also tested was the anti-viral imidazoquinoline, resiquimod (R-848) denoted as X and used at 0.1 µg/ml.

Example 14

Responsiveness of Human TLR7 and Human TLR8 to Ribonucleosides

Figure 12:
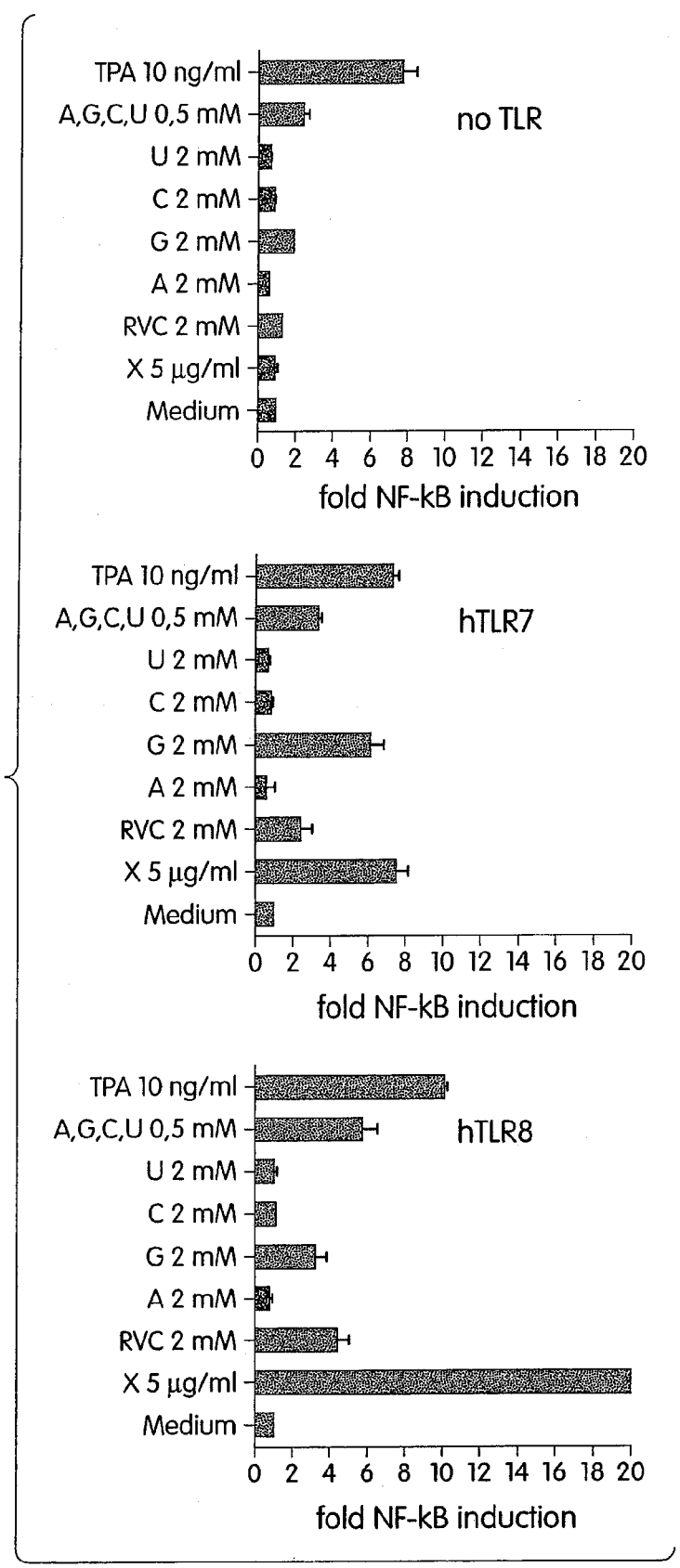
FIG. 12 is a series of three bar graphs depicting responsiveness of human TLR7 and human TLR8 to individual ribonucleosides. X denotes resiquimod.

The observations of Example 13 could be extended to 293 cells genetically reconstituted with TLR7 and TLR8 but not non-transfected 293 cells (FIG. 12). During analysis of individual ribonucleoside vanadyl complexes, it was unexpectedly determined that a mixture of the ribonucleosides A, U, C, and G or the single ribonucleoside G was effective in the absence of vanadate at stimulating PBMC to produce TNF and TLR7 or TLR8 to activate NF-κB (FIG. 12).

FIG. 12 depicts the responsiveness of human TLR7 and human TLR8 to ribonucleosides. It was determined that the response by human PBMC to RNA or RVC was mediated by TLR7 or TLR8 and further that the response could be driven by ribonucleosides only. Human 293 cells were either mock-transfected or transfected with human TLR7 or human TLR8 and monitored for responsiveness to ribonucleosides. The open reading frames of human TLR7 (hTLR7) and human TLR8 (hTLR8) were amplified by PCR from a cDNA library of human PBMC using the following primers pairs: for TLR7, 5'-CACCTCTCATGCTCTGCTCTCTTC-3' (SEQ ID NO:15) and 5'-GCTAGACCGTTTCCTTGAACAC-CTG-3' (SEQ ID NO:16); and for TLR8, 5'-CTGCGCT-GCTGCAAGTTACGGAATG-3' (SEQ ID NO:17) and 5'-GCGCGAAATCATGACTTAACGTCAG-3' (SEQ ID NO:18). The sequence information for primer selection was obtained from Genbank accession numbers AF240467 and AF245703. All full-length TLR fragments were cloned into pGEM-T Easy vector (Promega, Mannheim, Germany), excised with NotI, cloned into the expression vector pcDNA 3.1(−) (Invitrogen, Karlsruhe, Germany) and sequenced. Sequences of the coding region of hTLR7 and hTLR8 correspond to the accession numbers AF240467 (SEQ ID NO:25) and AF245703, respectively (SEQ ID NO:29).

For monitoring transient NF-κB activation, $3 \times 10^6$ 293 HEK cells (ATCC, VA, USA) were electroporated at 200 volt and 960 μF with 1 μg TLR expression plasmid, 20 ng NF-κB luciferase reporter-plasmid and 14 μg of pcDNA3.1 (−) plasmid as carrier in 400 μl RPMI medium supplemented with 25% fetal bovine serum (FCS). Cells were seeded at $10^5$ cells per well and after over night culture stimulated with R-848 (denoted in FIG. 12 as X; commercially synthesized by GLSynthesis Inc., Worcester, Mass., USA), RVCs or ribonucleosides for a further 7 hours. Stimulated cells were lysed using reporter lysis buffer (Promega, Mannheim, Germany), and lysate was assayed for luciferase activity using a Berthold luminometer (Wildbad, Germany).

As depicted in FIG. 12, TLR7 transfectants responded to R-848, RVCs, a mixture of ribonucleosides (A, G, C, U at 0.5 mM) and the ribonucleoside guanosine. Likewise TLR8 showed a similar response pattern.

Example 16

Responsiveness of TLR7 and TLR8 to Mixtures of Two Ribonucleosides

Figure 13:
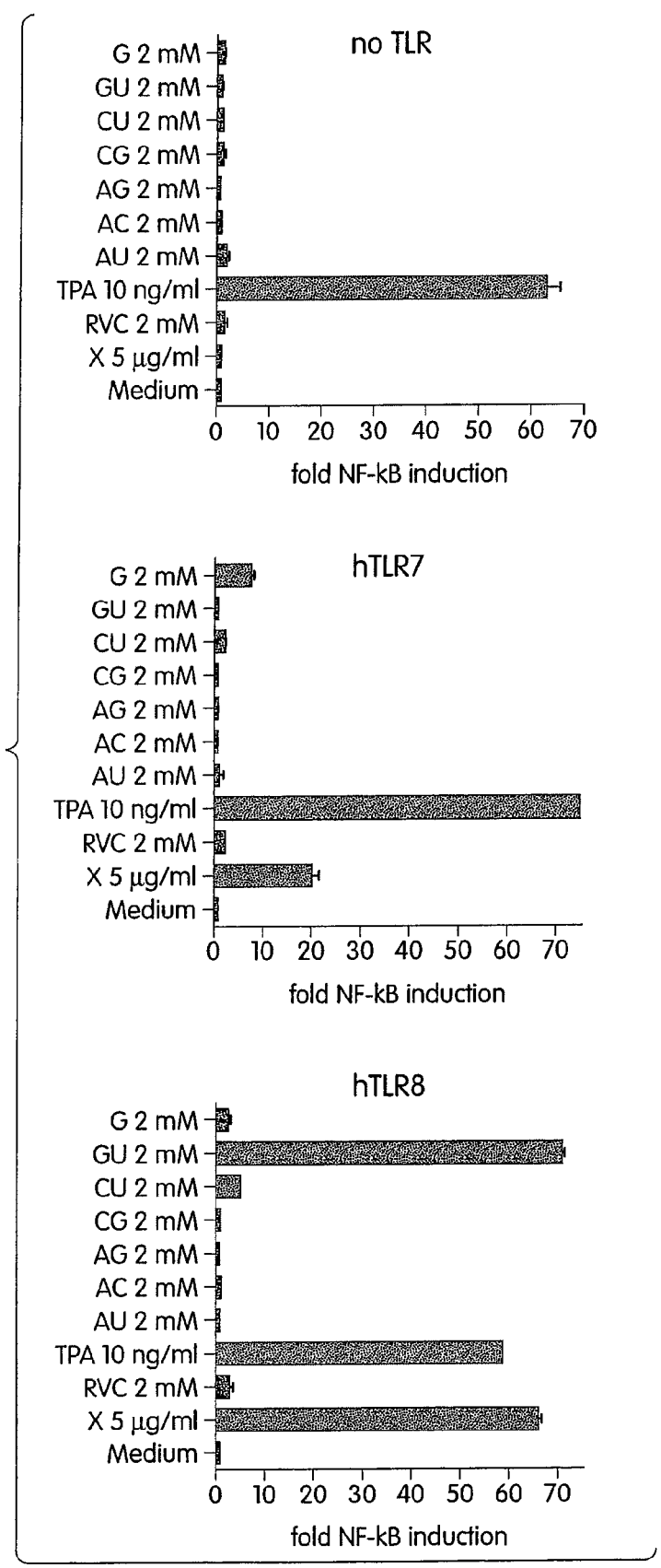
FIG. 13 is a series of three bar graphs depicting responsiveness of TLR7 and TLR8 to mixtures of two ribonucleosides.

FIG. 13 depicts the responsiveness of TLR7 and TLR8 to mixtures of two ribonucleosides. In an experiment conducted as in FIG. 11 it was determined that TLR 8 responded best to a combination of the ribonucleosides G and U, however, TLR7 responded best to G alone. Additionally it can be seen that a minor response was given by a combination of C and U. These data show that ribonucleosides of the proper composition serve as ligands for TLR7 and TLR8. The nonspecific stimulus of TPA served as a control only. X denotes R-848.

Example 17

Human PBMC Respond to a Mixture of the Ribonucleosides G and U

Figure 14:
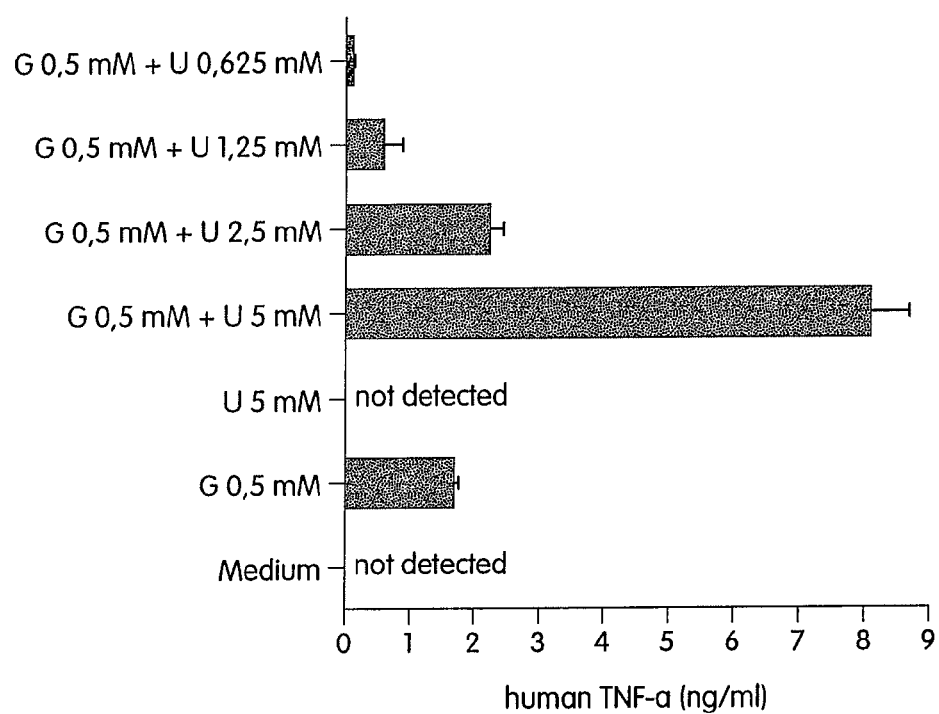
FIG. 14 is a bar graph depicting response of human PBMC to a mixture of the ribonucleosides G and U.

FIG. 14 depicts the response of human PBMC to a mixture of the ribonucleosides G and U. It can be appreciated that the ribonucleosides G and U act synergistically to induce TNF from human PBMC. In this example the ratio of G:U of 1:10 was optimal.

Example 18

Human PBMC Respond to G,U-Rich Oligoribonucleotides

Figure 15:
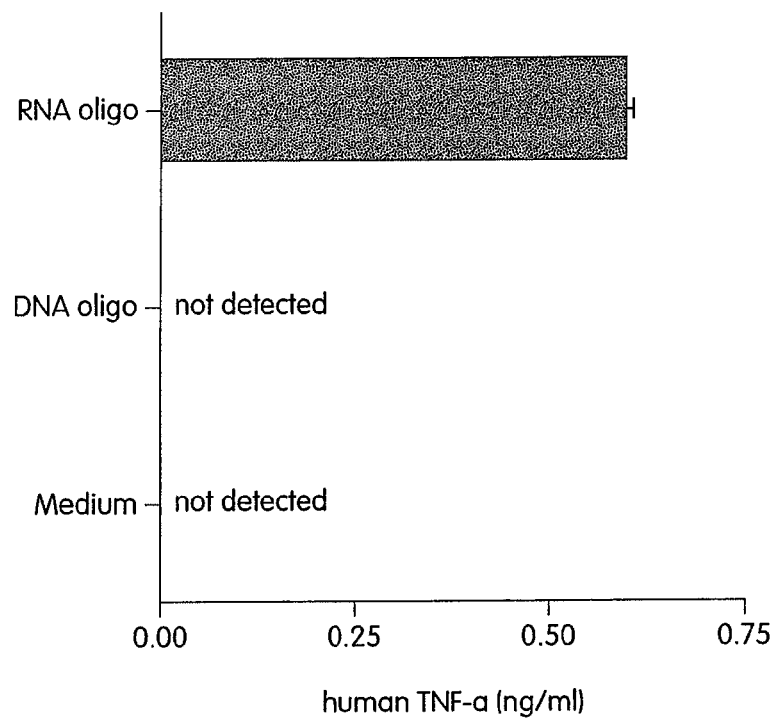
FIG. 15 is a bar graph depicting response of human PBMC to G,U-rich RNA, but not DNA, oligonucleotides.

FIG. 15 depicts how human PBMC respond to RNA G,U-rich oligonucleotides. Both RNA and DNA oligonucleotides 5'-GUUGUGGUUGUGGUUGUG-3' (SEQ ID NOs:1 and 19) were tested at 30 μM on human PBMC and TNF was monitored. Human PBMC were responsive to G,U-rich RNA oligonucleotides and not G,U-rich DNA oligonucleotides.

Example 19

Human PBMC Respond to Oxidized RNA

Figure 16:
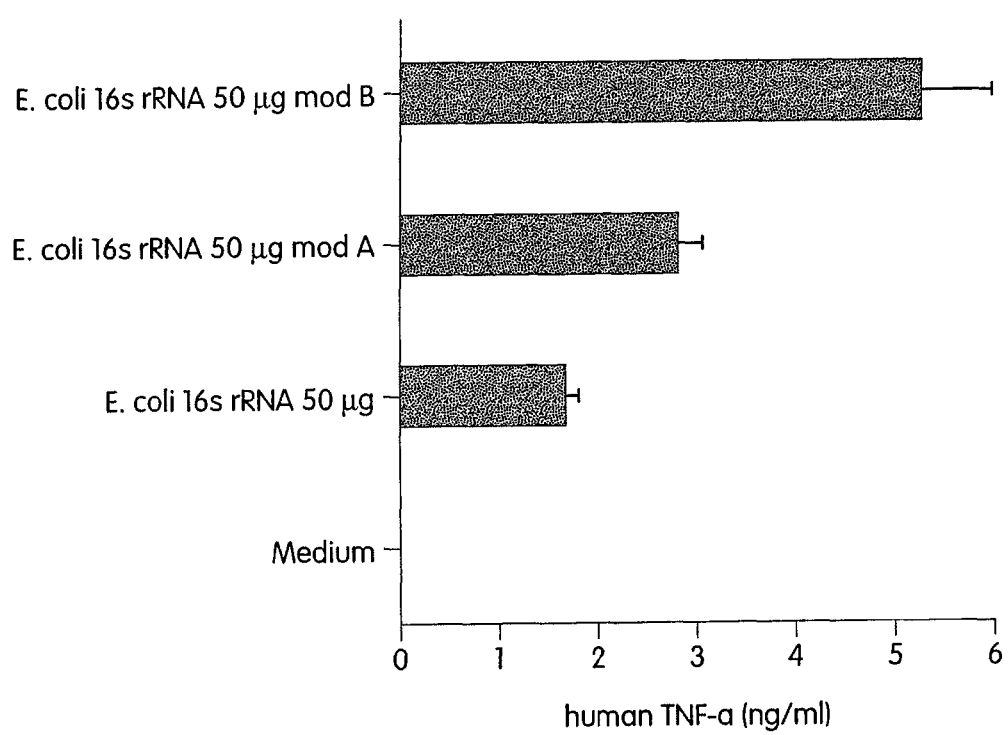
FIG. 16 is a bar graph depicting response of human PBMC to oxidized RNA.

FIG. 16 depicts the response of human PBMC to oxidized RNA. Ribosomal 16S RNA was isolated from *E. coli* and subjected to chemical oxidation. The treatments were (mod A) 0.2 mM ascorbic acid plus 0.2 mM $CuCl_2$ for 30 min at 37'C or (mod B) 0.2 mM ascorbic acid plus 0.02 mM $CuCl_2$ for 30 min at 37'C. This treatment induces oxidation at the 8 position of guanosine and also induces strand breaks 3' of the modified guanosine. It was shown that ribosomal RNA induced TNF production from human PBMC. It was also evident that oxidation of ribosomal RNA greatly potentiates the response.

Example 20

Human TLR7Responds to Oxidized Guanosine Ribonucleoside

Figure 17:
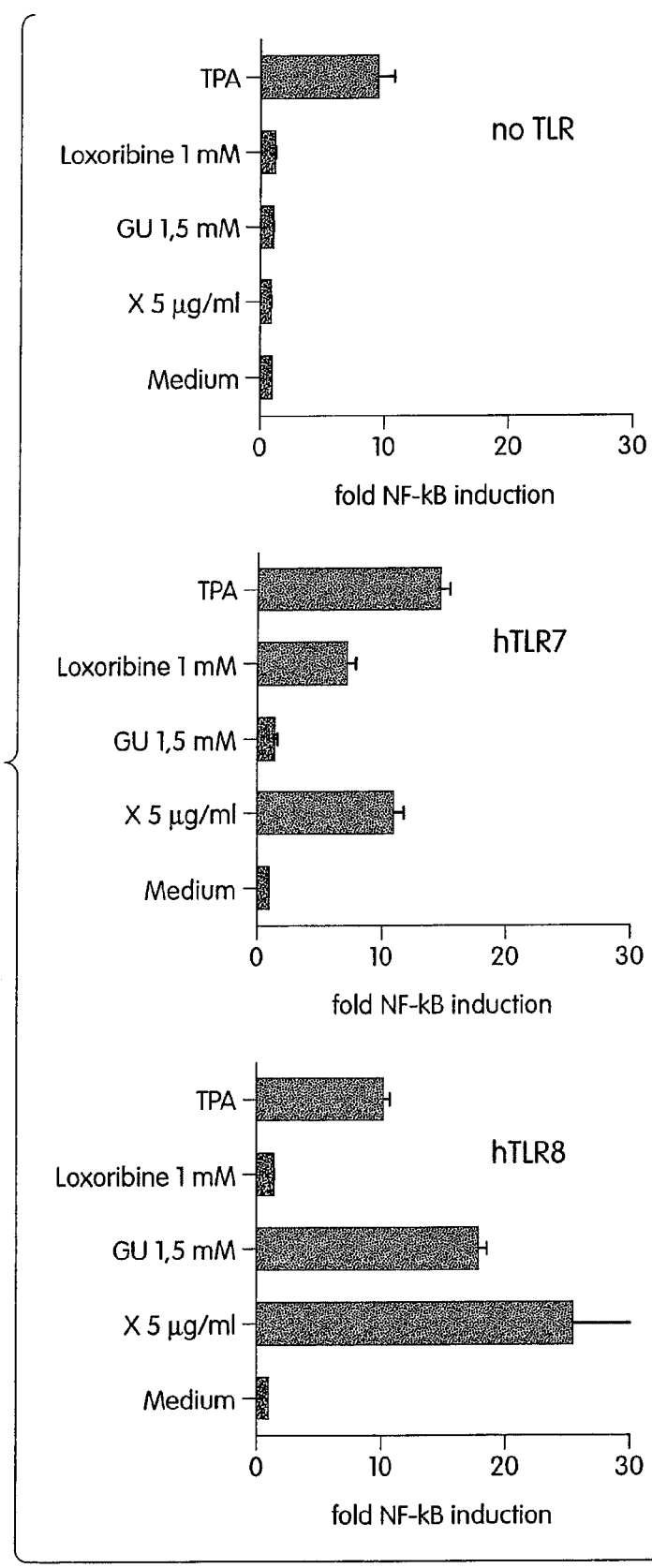
FIG. 17 is a series of three bar graphs depicting human TLR7 and TLR8 responses to oxidized guanosine ribonucleoside. X denotes resiquimod.

FIG. 17 depicts human TLR7 and TLR8 responses to the oxidized guanosine ribonucleoside. Cells mock-transfected or transfected with human TLR 7 or human TLR8, as in Example 14, were tested for responsiveness to 7-allyl-8-oxoguanosine (loxoribine) at 1 mM. It can be clearly shown that human TLR7 is responsive to 7-allyl-8-oxoguanosine. Thus it appears that a ligand for TLR 7 is oxidized nucleic acids.

Example 21

Human TLR7Responds to Other Modified Guanosine Ribonucleoside

Figure 18:
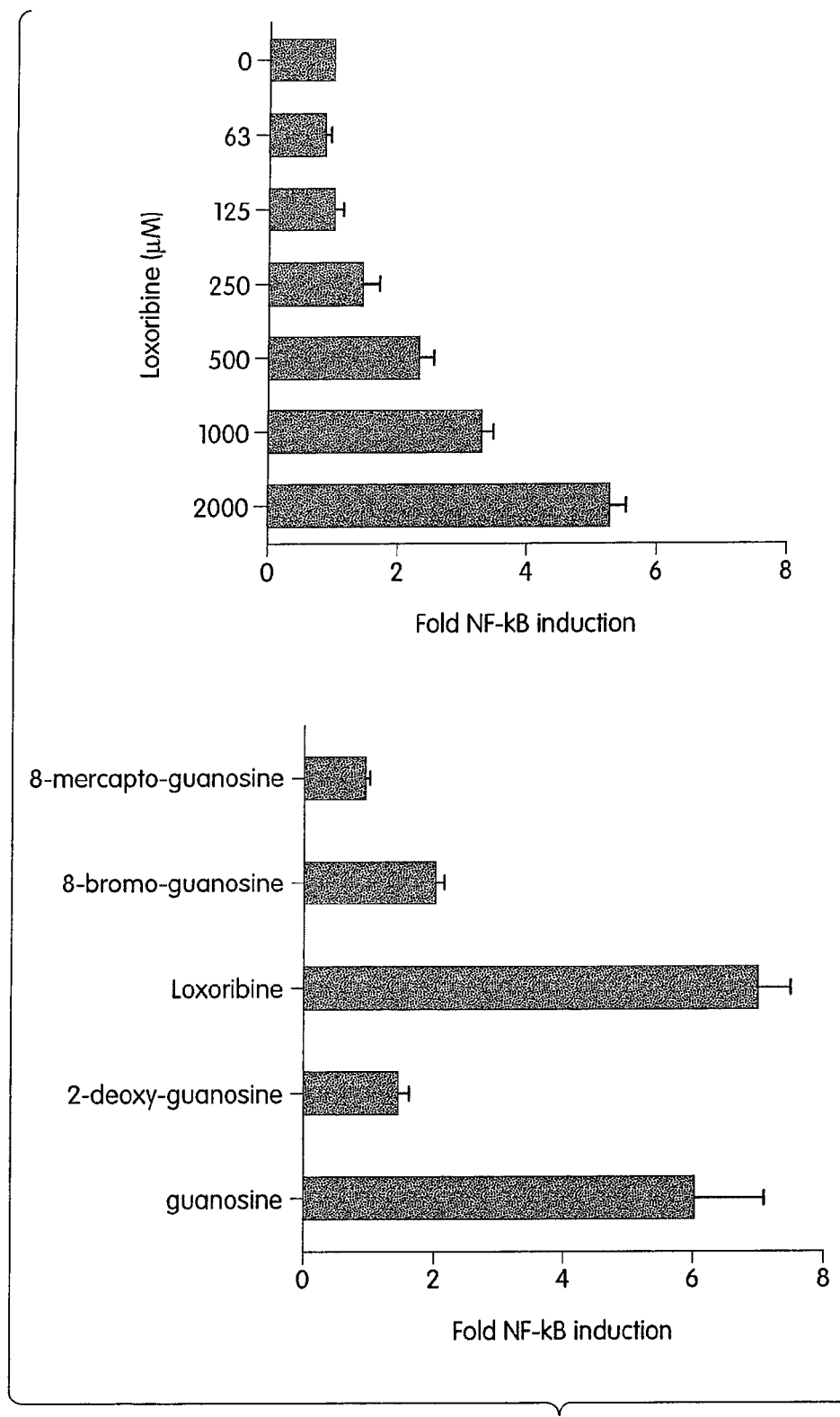
FIG. 18 is a pair of bar graphs depicting human TLR7 responses to modified guanosine ribonucleosides.

FIG. 18 depicts human TLR7 responses to the other modified guanosine ribonucleoside. Cells transfected with human TLR7, as in Example 14, were tested for a dose-dependent response to 7-allyl-8-oxoguanosine (loxoribine). Additionally other modified guanosines were tested. It can be clearly shown that human TLR 7 was responsive to 7-allyl-8-oxoguanosine in a dose-dependent manor. As shown above, human TLR7 was responsive to guanosine; however FIG. 18 also shows that human TLR7 responded mildly to the deoxy form of guanosine as well as to 8-bromo-guanosine.

Example 22

Distribution of Human TLRs

Figure 19:
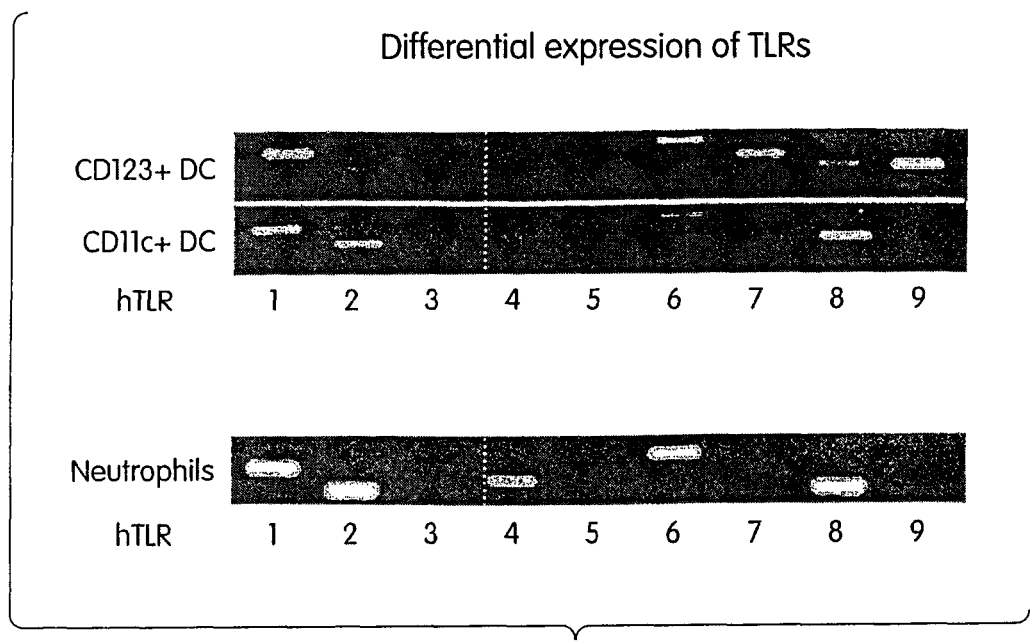
FIG. 19 is a series of aligned gel images depicting differential expression of TLR1-TLR9 on human CD123+ dendritic cells (CD123+ DC), CD11c+ DC, and neutrophils.

FIG. 19 depicts the distribution of human TLR1-TLR9. Various purified human immune cells were screened by PCR for TLR1 through 9 expression. It was shown that human lymphoid CD123+ dendritic cells (DC) were strongly positive for TLR9 and TLR7 while weaker for TLR8. The converse was shown however for myeloid CD11c+DC. This is very relevant because the two types of DC have very different functions in the immune system. Significantly, FIG. 19 also shows that human neutrophils were strongly positive for human TLR8 while very weak for TLR9 and negative for TLR7. This is also relevant because neutrophils are very often the first cells to engage infectious pathogens and thus believed to initiate responses.

Example 23

Figure 20:
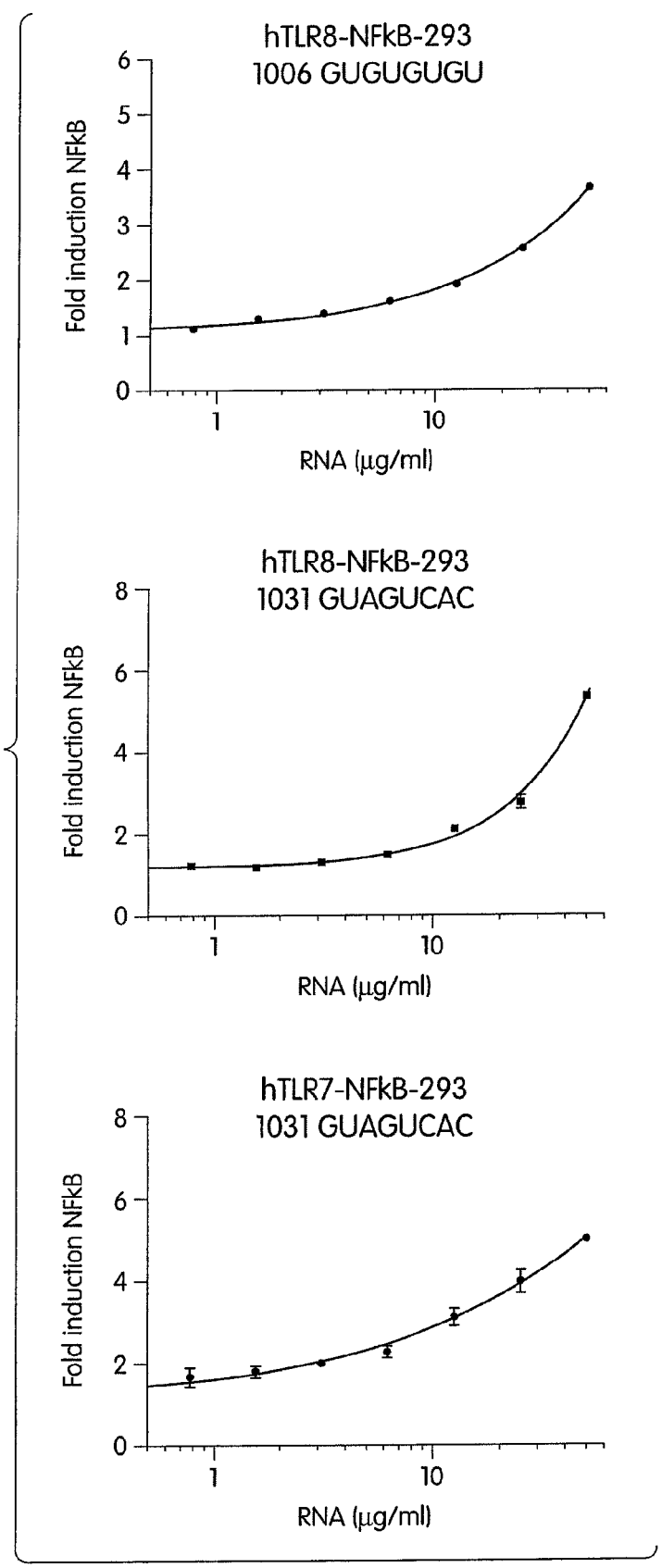
FIG. 20 is a series of three graphs depicting the ability of short, single-stranded G,U-containing RNA oligomers to induce NF-κB in HEK-293 cells stably transfected with expression plasmid for human TLR7 or human TLR8.

HEK-293 cell were stably transfected with human TLR7 or human TLR8. Additionally, the cells were stably transfected with NF-κB-luciferase reporter construct. The cells were titrated with varing amounts of RNA oligonucleotides and cultured for 16 h. Luciferase activity was measured by standard methods and normalizied versus mock-stimulated transfectants. Luciferase activity measured for the mock-stimulated transfectant was set to a value of 1-fold NF-κB induction. Results are shown in FIG. 20, where old NF-κB induced by the stimulating RNA oligonucleotide is plotted versus the concentration of test ribonucleotide. Stimulation with GUGUGUGU is shown for human TLR8. Stimulation with GUAGUCAC is shown for human TLR7 and human TLR8.

Equivalents

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A synthetic G,U-rich immunostimulatory RNA oligomer which is 15-40 nucleotides long comprising multiples of 5'-GUUGB-3', wherein B represents U, G, or C; wherein the multiples are linked through a single intervening linking nucleoside, which is selected from the group consisting of G and U.

2. The immunostimulatory RNA oligomer of claim 1 wherein B is U.

3. The immunostimulatory RNA oligomer of claim 1 or 2, wherein the intervening linking nucleoside is U.

4. An immunostimulatory RNA oligomer of claim 1, which comprises multiples of UUG.

5. An immunostimulatory RNA oligomer of claim 1, which is 15-30 nucleotides long.

6. The immunostimulatory RNA oligomer of claim 1, comprising two 5'-GUUGB-3' motifs.

7. The immunostimulatory RNA oligomer of claim 1, which is at least 90 percent guanine (G) and uracil (U).

* * * * *